United States Patent
Lamarque et al.

(10) Patent No.: US 9,920,082 B2
(45) Date of Patent: Mar. 20, 2018

(54) WATER-SOLUBLE COMPLEXING AGENTS AND CORRESPONDING LANTHANIDE COMPLEXES

(71) Applicant: CISBIO BIOASSAYS, Codolet (FR)

(72) Inventors: Laurent Lamarque, Saint Victor la Coste (FR); David Parker, Durham (GB); Stephen J. Butler, Durham (GB); Martina Delbianco, Magenta (IT)

(73) Assignee: CISBO BIOASSAYS, Codolet (FR)

( * ) Notice: Subject to any disclaimer, the term of this patent is extended or adjusted under 35 U.S.C. 154(b) by 0 days.

(21) Appl. No.: 14/760,912

(22) PCT Filed: Jan. 16, 2014

(86) PCT No.: PCT/FR2014/050085
§ 371 (c)(1),
(2) Date: Jul. 14, 2015

(87) PCT Pub. No.: WO2014/111661
PCT Pub. Date: Jul. 24, 2014

(65) Prior Publication Data
US 2015/0361116 A1    Dec. 17, 2015

(30) Foreign Application Priority Data

Jan. 16, 2013 (FR) ..................... 13 50374

(51) Int. Cl.
| | | |
|---|---|---|
| C07D 255/02 | (2006.01) |
| C07F 9/32 | (2006.01) |
| C07D 473/18 | (2006.01) |
| C07F 9/58 | (2006.01) |
| C07F 9/6558 | (2006.01) |
| C07D 213/79 | (2006.01) |
| C07F 5/00 | (2006.01) |
| C07H 23/00 | (2006.01) |
| C09K 11/06 | (2006.01) |

(52) U.S. Cl.
CPC .......... *C07F 9/3229* (2013.01); *C07D 213/79* (2013.01); *C07D 255/02* (2013.01); *C07D 473/18* (2013.01); *C07F 5/003* (2013.01); *C07F 9/587* (2013.01); *C07F 9/65583* (2013.01); *C07H 23/00* (2013.01); *C09K 11/06* (2013.01); *C09K 2211/1007* (2013.01); *C09K 2211/1074* (2013.01); *C09K 2211/182* (2013.01)

(58) Field of Classification Search
None
See application file for complete search history.

(56) References Cited

U.S. PATENT DOCUMENTS

| | | | |
|---|---|---|---|
| 4,761,481 A | 8/1988 | Hale et al. | |
| 4,859,777 A | 8/1989 | Toner | |
| 4,921,195 A | 5/1990 | Clark et al. | |
| 5,202,423 A | 4/1993 | Kankare et al. | |
| 5,216,134 A | 6/1993 | Mukkala et al. | |
| 5,324,825 A | 6/1994 | Kankare et al. | |
| 5,622,821 A | 4/1997 | Selvin et al. | |
| 2014/0336373 A1* | 11/2014 | Lamarque ............ | C07D 401/14 540/474 |

FOREIGN PATENT DOCUMENTS

| | | |
|---|---|---|
| EP | 01801492 | 5/1986 |
| EP | 0203047 | 11/1986 |
| EP | 0321353 | 6/1989 |
| FR | 2978149 * | 1/2013 |
| WO | 8901475 | 2/1989 |
| WO | 09305049 | 3/1993 |
| WO | 0196877 | 12/2001 |
| WO | 02095412 | 11/2002 |
| WO | 2005021538 | 3/2005 |
| WO | 2005058877 | 6/2005 |
| WO | 2007128874 | 11/2007 |
| WO | 2008063721 | 5/2008 |
| WO | 2013011236 | 1/2013 |

OTHER PUBLICATIONS

D'Aleo. Angewandte Communications, 2012, 51, 6622-25 and supporting documents.*
International search report for International application No. PCT/FR2014/050085, dated Mar. 25, 2014 (4 pages).
Takalo et al.: "Synthesis and Luminescence of Novel Eu Complexing Agents and Labels with 4-(Phenylethynyl) pyridine Subunits"; Helvetica Chimica Acta, 1996, vol. 79, pp. 789-802 (Cited in International Search Report).
Latva et al.: "Evaluation of solution structures of highly luminescent europium(III) chelates by using laser induced excitation of the 7F0 5D0 transition"; Inorganica Chimica Acta, 1998, pp. 63-72 (Cited in International Search Report).
D'Aleo et al.: "Ytterbium-Based Bioprobes for Near-Infrared Two-Photon Scanning Laser Microscopy Imaging"; Angewandte Chemie International Edition, 2012, vol. 51, pp. 6622-6625 (Cited in International Search Report).

(Continued)

*Primary Examiner* — Noble E Jarrell
(74) *Attorney, Agent, or Firm* — Hamre, Schumann, Mueller & Larson, P.C.

(57) ABSTRACT

The invention relates to complexing agents of formula (I):

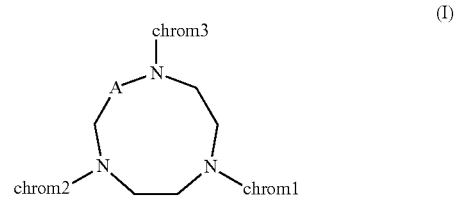

in which A, chrom1, chrom2 and chrom3 are as defined in the description. The invention also relates to the lanthanide complexes obtained from these complexing agents.

22 Claims, No Drawings

(56) References Cited

OTHER PUBLICATIONS

Placide et al.: "Design and synthesis of europium luminescent bio-probes featuring sulfobetaine"; Tetrahedron Letters, 2014, vol. 55, pp. 1357-1361 (Cited in International Search Report).
Walton et al.: "Very bright europium complexes that stain cellular mitochondria"; Chemical Communications, 2013, vol. 49, pp. 1600-1602 (Cited in International Search Report and in Specification).
Latva et al.: "Correlation between the lowest triplet state energy level of the ligand and lanthanide(III) luminescence quantum yield"; Journal of Luminescence, 1997, vol. 75, pp. 149-169 (Cited in Specification).
D'Aleo et al.: "Efficient Sensitization of Euruopium, Ytterbium, and Neodymium Fuctionalized Tris-Dipicolinate Lanthanide Complexes through Tunable Charge-Transfer Excited States"; Inorganic Chemistry, 2008, vol. 47, pp. 10258-10268 (Cited in Specification).
Cox et al.: "Synthesis of C- and N-Functionalised Derivatives of 1,4,7-Triazacyclononane-1,4,7-triyltriacetic acid (NOTA), 1 4 7 10-Tetra-azacyclododecane-1,4,7,10-tetrayltetra-acetic Acid (DOTA), and Diethylenenetriaminepenta-acetic Acid (DTPA): Bifunctional Complexing Agents for the Derivatisation of Antibodies"; J. Chem. Soc., Perkin Trans, 1990, pp. 2567-2576 (Cited in Specification).
Craig et al.: "Towards Tumour Imaging with Indium-111 Labelled Macrocyle-Antibody Conjugates"; J. Chem. Soc., Chem. Common., 1989, pp. 794-796 (Cited in Specification).
Hermanson et al.: "Bioconjugate Techniques"; Academic Press, 2008, Second Edition, pp. 169-211 (Cited in Specification).
Parker et al.: "Synthesis of C- and N-Functionalised Derivatives of 1,4,7-Triazacyclononane-1,4,7-triyltriacetic acid (NOTA), 1,4,7,10-Tetra-azacyclododecane-1,4,7,10-tetrayltetra-acetic Acid (DOTA), and Diethylenenetriaminepenta-acetic Acid (DTPA): Bifunctional Complexing Agents for the Derivatisation of Antibodies"; J. Chem. Soc., Perkin Trans, 1990, pp. 2567-2576 (Cited in Specification).
Sonogashira et al.: "A convenient synthesis of acetylenes: Catalytic substitutions of acetylenic hydrogen with Bromoalkenes, ladoarenes, and Dromopyridines"; Tetrahedron Letters, 1975, No. 50, pp. 4467-4470 (Cited in Specification).
Rossi et al.: "Palladium- and/or Copper-Mediated Cross-Coupling reactions between 1-Alkynes and Vinyl, Aryl, Alkynyl, 1,2-Propadienyl, Propargyl and Allylic Halides or related Compounds."; Organic Preparation and Procedure International, 1997, vol. 27, pp. 129-160 (Cited in Specification).
Bourdolle et al.: "Modulating the Photophysical Properties of Azamacrocyclic Europium Complexes with Charge-Transfer Antenna Chromophores"; Inorganic Chemistry, 2011, vol. 50, pp. 4987-4999 (Cited in Specification).
Ginsburg et al.: "Oximes of the Pyridine Series"; 1957, vol. 79, pp. 481-485 (Cited in Specification).
Mizrai et al.: "Enhancing Electrospray Ionization Efficiency of Peptides by Derivatization"; Analytical Chemistry, 2006, vol. 78, pp. 4175-4183 (Cited in Specification).
Burgada et al.: "Synthesis of New Phosphonated Tripod Ligands as Putative New Therapeutic Agents in the Chelation Treatment of Metal Intoxications"; European Journal of Organic Chemistry, 2001, pp. 349-352 (Cited in Specification).
Romieu et al.: "Postsynthetic Derivatization of Fluorophores with Sulfo-alanine Dipeptide Linker. Application to the Preparation of Water-Soluble Cyanine and Rhodamine Dyes"; Bioconjugate Chemistry, 2008, vol. 19, pp. 279-289 (Cited in Specification).
Machida et al.: "Bivalent Inhibitors for Disrupting Protein Surface-Substrate Interactions and for Dual Inhibition of Protein Prenyltransferases"; Journal of the American Chemical Society, 2001, vol. 113, pp. 958-963 (Cited in Specification).

* cited by examiner

WATER-SOLUBLE COMPLEXING AGENTS AND CORRESPONDING LANTHANIDE COMPLEXES

The present invention relates to water-soluble complexing agents or ligands, lanthanide complexes obtained from these complexing agents, and the use of these lanthanide complexes for labeling molecules and detecting them by time-resolved fluorescence techniques.

PRIOR ART

The use of lanthanide complexes has increased considerably over about the last twenty years in the area of the life sciences. These fluorescent compounds in fact have interesting spectroscopic characteristics, which make them markers of choice for detecting biological molecules. These fluorescent compounds are particularly suitable for use in conjunction with compatible fluorophores for performing FRET measurements (FRET: Förster Resonance Energy Transfer), application of which for studying the interactions between biomolecules is exploited commercially by several companies, including Cisbio Bioassays with its HTRF® product range. The relatively long life-time of the lanthanide complexes also allows time-resolved fluorescence measurements to be performed, i.e. with a delay after excitation of the fluorophores, which makes it possible to limit the fluorescence interferences due to the measurement medium. This last-mentioned feature is all the more useful as the measurement medium becomes closer to a biological medium, which comprises numerous proteins whose fluorescence could interfere with that of the compounds under investigation.

A great many lanthanide complexes have been described. Latva et al., for example, disclosed 41 complexes of Eu(III) and of Tb(III), whose luminescence they studied (Journal of Luminescence Volume 75, No. 2, September 1997, Pages 149-169). Compound 39, in particular, consists of a 1,4,7-triazacyclononane ring ("TACN" hereinafter), whose nitrogen atoms are substituted with chromophores derived from phenylethynylpyridine. Although the quantum yield of the complex consisting of this chromophore and Eu(III) is regarded as good by the authors, this complex is not suitable for coupling with a biomolecule. Moreover, the use of this compound in an aqueous medium may be problematic since it is very hydrophobic. Finally, the absorption of this complex is optimal at 315 nm, whereas the laser lamps often used in bioassays emit at a wavelength of 337 nm.

D'Aleo et al. described the synthesis of lanthanide complexes consisting of three ligands derived from dipicolonic acid (Inorg Chem. 2008 Nov. 17; 47(22): 10258-68). One of these ligands (L1) consists of a molecule of dipicolinic acid substituted with a phenylethynyl group, itself bearing a polyethylene glycol ("PEG" hereinafter) ether-oxide on the phenyl group. According to the authors, the PEG group endows this product with good solubility in aqueous media and in organic solvents. However, these complexes are not sufficiently stable in an aqueous medium and are not usable in a bioconjugation reaction.

Patent application WO2005/058877 relates to lanthanide complexes, some of which are based on a TACN ring in which three nitrogen atoms are substituted with chromophores consisting of a derivative of pyridine, notably of phenylpyridine. The inventors further propose to include a reactive group in these compounds so as to be able to conjugate them easily with biomolecules. Thus, it is proposed to include this reactive group via a spacer arm either at the level of a carbon of the TACN ring, or at the level of the pyridine of the chromophore.

Several other lanthanide complexes have been disclosed and some are exploited commercially: we may mention in particular the macropolycyclic cryptates of lanthanides (EP 0 180 492, EP 0 321 353, EP 0 601 113, WO2001/96877, WO2008/063721), the lanthanide complexes comprising a unit derived from coumarin bound to a diethylenetriamine penta-acid U.S. Pat. No. 5,622,821), and those comprising derivatives of pyridine (U.S. Pat. No. 4,920,195, U.S. Pat. No. 4,761,481), of bipyridine (U.S. Pat. No. 5,216,134), or of terpyridine (U.S. Pat. No. 4,859,777, U.S. Pat. No. 5,202,423, U.S. Pat. No. 5,324,825).

Patent application WO89/01475 describes the preparation of triazotized macrocycles in which one of the carbon atoms bears a group L-Z, and notably 2-(4-N-benzamidyl)butyl-1,4,7-triazacyclonane (intermediate 12). The synthesis of azotized heteromacrocycles in which one of the carbon atoms is substituted is also described by Cox et al. (J. Chem. Soc., Perkin Trans. 1, 1990, 2567-2576) and Craig et al. (J. Chem. Soc., Chem. Common, 1989, 794-796).

Patent application WO 2013/011236 describes complexing agents of formula:

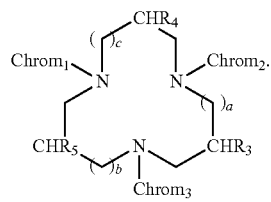

The present invention aims to overcome the drawbacks of the compounds of the prior art, and supply fluorescent lanthanide complexes having better brightness than the compounds of the prior art when they are excited at around 337 nm, good solubility in aqueous media, an emission spectrum suitable for use thereof in FRET experiments, as well as being very convenient for labeling biomolecules.

DESCRIPTION OF THE INVENTION

The problems mentioned above were solved by means of complexing agents consisting of a triazotized macrocycle (1,4,7-triazacyclononane, TACN hereinafter) whose nitrogen atoms are substituted with chromophores of the phenylethynylpyridine type, these chromophores comprising a group affecting electron density of the molecule ("O-donor" group hereinafter) bound directly to the phenyl group, and said complexing agents further comprising at least one group endowing the molecule with a relatively hydrophilic character. These compounds may also comprise a reactive group allowing them to be conjugated with a molecule to be labeled. The complexing agents according to the invention form stable complexes with the lanthanides, and can be used for producing fluorescent conjugates of molecules of interest. The lanthanide complexes according to the invention have excellent photophysical properties, especially with respect to their quantum yield, the life-time of their luminescence and their excitation spectrum, which is very suitable for laser excitation at about 337 nm. The presence of three chromophores significantly increases the molar absorption coefficient (epsilon) and consequently the brightness of the complex. The brightness (quantum yield×molar absorption coefficient) of these complexes in biological media is also better than that of the compounds of the prior art, and their solubility in aqueous media makes them very suitable for use in biological media.

Complexing Agents

The complexing agents according to the invention are the compounds of formula (I):

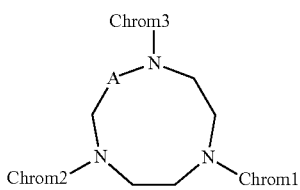

(I)

in which:

A represents —CH$_2$— or —CH(L$_2$-G)- chrom1, chrom2 are identical and are selected from the groups of formula:

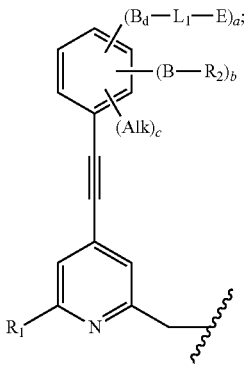

chrom3 is either identical to chrom1 and chrom2, or is a group of formula:

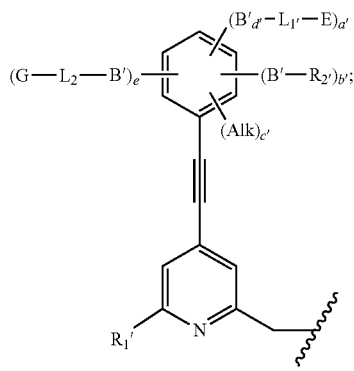

a, b, c, d, a', b', c', d', and e are each integers from 0 to 3 a+b+c≤5 and a+b≥1 a'+b'+c'+e≤5 and a'+b'+e≥1 d, d'=0 or 1

B, B' represent either an oxygen atom or the group —NHCO—

R$_2$, R$_2$', which may be identical or different, are selected from: -Alk; -phenyl; —CH$_2$—CO—NH-Alk; —CH$_2$—CO—NHAlk$_1$Alk$_2$; —CH$_2$—CO—O-Alk; —CH$_2$—CO—NH$_2$; —CH$_2$—CO—OH;

L$_1$, L$_1$', L$_2$ are divalent linkage groups, which may be identical or different;

E, E', which may be identical or different, are groups increasing the water-solubility of the complexing agent, selected from: —SO$_3$H, —PO(OH)$_2$, —COOH, —N$^+$Alk$_1$Alk$_2$Alk$_3$, a carbohydrate residue;

R$_1$, R$_1$', which may be identical or different, are selected from: —COOH, —PO(OH)R$_6$, R$_6$ being selected from the groups: phenyl, phenyl substituted with a group —SO$_3$H, preferably in the ortho or para position, benzyl, methyl, ethyl, propyl, n-butyl, sec-butyl, isobutyl, tert-butyl;

G is a reactive group;

Alk, Alk$_1$, Alk$_2$, Alk$_3$, which may be identical or different, represent a (C$_1$-C$_6$)alkyl;

provided that:

when R$_1$ or R$_1$' represent a group —COOH, E or E' do not represent a group —COOH; (and preferably when d=1, a+b≤2, and when d=0, b≤2)

the complexing agent comprises at least one group E or —SO$_3$H;

when chrom1, chrom2 and chrom3 do not comprise groups E or E', either A is a group —CH(L$_2$-G)- in which L$_2$ comprises at least one group —SO$_3$H, or R$_6$ is a phenyl group substituted with a group —SO$_3$H.

Carbohydrate means a group of formula —(CHOH)$_k$—CH$_2$OH, k being an integer in the range from 3 to 12, preferably equal to 4.

The groups —SO$_3$H, —COOH and —PO(OH)$_2$ are or are not in the deprotonated form, depending on the pH. Therefore, hereinafter, these groups also denote the groups —SO$_3^-$, —COO$^-$ and —PO(OH)O$^-$, and vice-versa.

A first subfamily of preferred complexing agents is that consisting of compounds according to formula (I), in which chrom1, chrom2 and chrom3 are identical, a=1, b=0, c=0, d=1, and the group (B$_d$-L$_1$-E) is in the ortho or para position of the phenyl ring.

A second subfamily of preferred complexing agents is that consisting of compounds according to formula (I), in which chrom1, chrom2 and chrom3 are identical, a=1, b=0, c=1, d=1, and the group (B$_d$-L$_1$-E) is in the ortho or para position of the phenyl ring.

A third subfamily of preferred complexing agents is that consisting of compounds according to formula (I), in which chrom1, chrom2 and chrom3 are identical, a=1, b=0, c=2, d=1, and the group (B$_d$-L$_1$-E) is in the ortho or para position of the phenyl ring.

A fourth subfamily of preferred complexing agents is that consisting of compounds according to formula (I), in which chrom1, chrom2 and chrom3 are identical, a=1, b=1, c=0, d=0, and the group (B—R$_2$) is in the ortho or para position of the phenyl ring.

A fifth subfamily of preferred complexing agents is that consisting of compounds according to formula (I), in which chrom1, chrom2 and chrom3 are identical, a=1, b=1, c=0, d=1, and at least one of the groups (B—R$_2$) and (B$_d$-L$_1$-E) is in the ortho or para position of the phenyl ring.

A sixth subfamily of preferred complexing agents is that consisting of compounds according to formula (I), in which chrom1, chrom2 and chrom3 are identical, a=1, b=1, c=1, d=0, and the group (B—R$_2$) is in the ortho or para position of the phenyl ring.

A seventh subfamily of preferred complexing agents is that consisting of compounds according to formula (I), in which chrom1, chrom2 and chrom3 are identical, a=1, b=1, c=1, d=1, and at least one of the groups (B—R$_2$) and (B$_d$-L$_1$-E) is in the ortho or para position of the phenyl ring.

An eighth subfamily of preferred complexing agents is that consisting of compounds according to formula (I), in which chrom1, chrom2 and chrom3 are identical, a=1, b=1, c=2, d=0, and the group (B—R$_2$) is in the ortho or para position of the phenyl ring.

A ninth subfamily of preferred complexing agents is that consisting of compounds according to formula (I), in which chrom1, chrom2 and chrom3 are identical, a=1, b=1, c=2, d=1, and at least one of the groups (B—R$_2$) and (B$_d$-L$_1$-E) is in the ortho or para position of the phenyl ring.

Among these various subfamilies of preferred complexing agents, the complexing agents are quite particularly preferred in which:

B, when it is present, is an oxygen atom,

L$_1$, when it is present, is a divalent group of formula —(CH$_2$)$_n$—, n representing an integer from 1 to 16 and preferably from 1 to 5, E represents a group —SO$_3$H, R$_2$, when it is present, represents an alkyl group, preferably a methyl group.

In one embodiment of the invention, the complexing agents correspond to formula (I'):

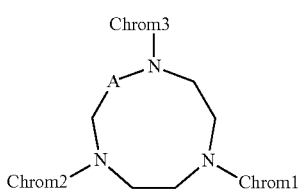

in which:

A represents —CH$_2$— or —CH(L$_2$-G)- chrom1, chrom2 are identical and are selected from the groups of formula:

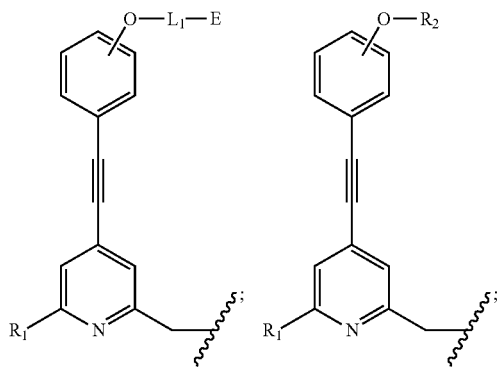

chrom3 is either identical to chrom1 and chrom2, or is a group of formula:

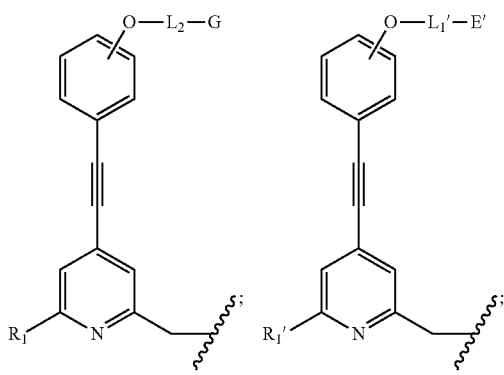

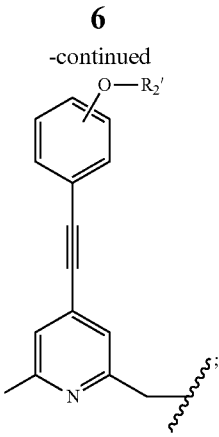

R$_2$, R$_2$', which may be identical or different, are selected from: H; -Alk; phenyl; —CH$_2$—CO—N-Alk; —CH$_2$—CO—O-Alk; —CH$_2$—CO—NH$_2$; —CH$_2$—CO—OH;

L$_1$, L$_1$', L$_2$ are divalent linkage groups, which may be identical or different;

E, E', which may be identical or different, are groups increasing the water-solubility of the complexing agent, selected from: —SO$_3$H, —P(O)(OH)$_2$, —COOH, —N$^+$Alk$_1$Alk$_2$Alk$_3$, a carbohydrate residue;

R$_1$, R$_1$', which may be identical or different, are selected from: —COOH, —PO(OH)R$_6$, R$_6$ being selected from the groups: phenyl, phenyl substituted with a group —SO$_3$H, preferably in the ortho or para position, benzyl, benzyl, methyl, ethyl, propyl, n-butyl, sec-butyl, isobutyl, tert-butyl;

G is a reactive group;

Alk, Alk$_1$, Alk$_2$, Alk$_3$, which may be identical or different, represent a (C$_1$-C$_6$)alkyl;

provided that:

when R$_1$ or R$_1$' represents a group —COOH, E or E' do not represent a group —COOH;

the complexing agent comprises at least one group E or —SO$_3$H;

when chrom1, chrom2 and chrom3 each comprise a group R$_2$ or R$_2$', A is a group —CH(L$_2$-G)- in which L$_2$ comprises at least one group —SO$_3$H or else R$_6$ is a phenyl group substituted with a group —SO$_3$H.

Carbohydrate means a group of formula —(CHOH)$_k$—CH$_2$OH, k being an integer in the range from 3 to 12, preferably equal to 4.

The groups —SO$_3$H, —COOH and —PO(OH)$_2$ are or are not in the deprotonated form, depending on the pH. Therefore, hereinafter, these groups also denote the groups —SO$_3^-$, —COO$^-$ and —PO(OH)O$^-$, and vice-versa.

This embodiment comprises several subfamilies of preferred complexing agents.

A first subfamily of preferred complexing agents is that consisting of compounds according to formula (I'), in which A is the group —CH$_2$— and chrom1, chrom2, chrom3 are identical and represent a group of formula:

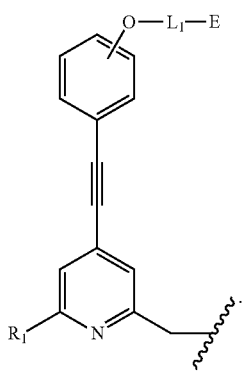

A second subfamily of preferred complexing agents is that consisting of compounds according to formula (I'), in which A is the group —CH₂— and chrom3 is different from chrom1 and chrom2.

A fourth subfamily of preferred complexing agents is that consisting of compounds according to formula (I'), in which A is the group —CH(L₂-G)- and chrom3 is different from chrom1 and chrom2.

The different combinations of chromophores chrom1, chrom2 and chrom3 belonging to these various preferred subfamilies are summarized in the following table:

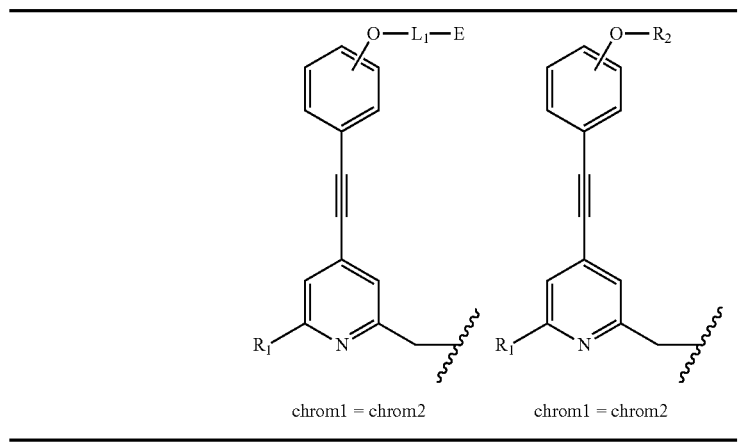

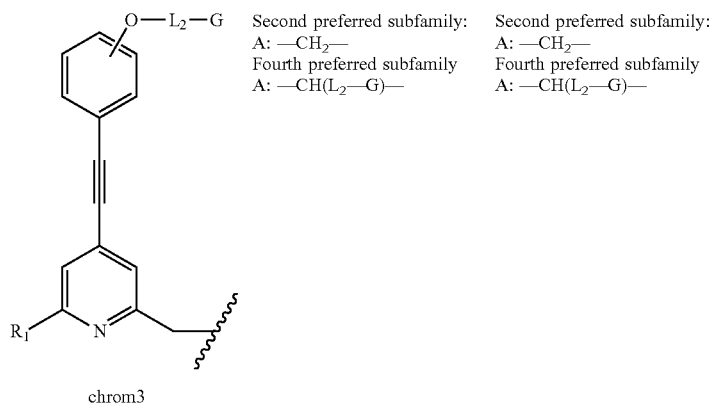

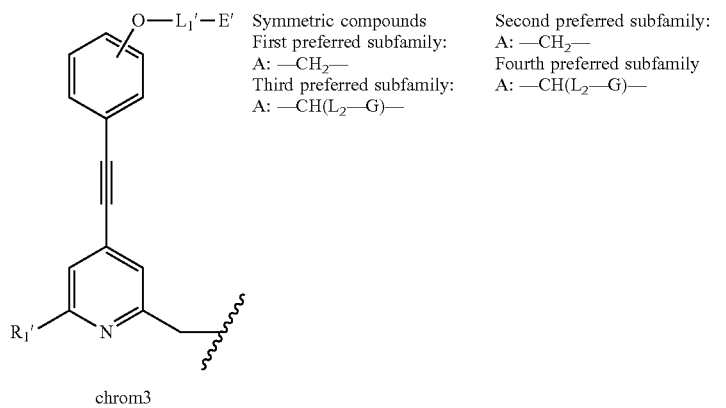

-continued

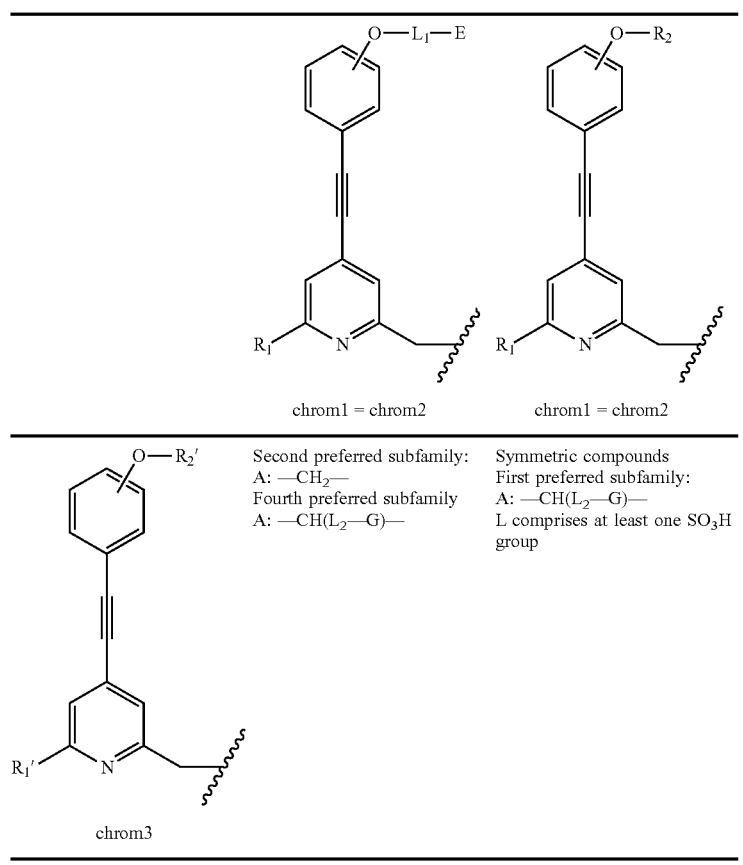

| | | |
|---|---|---|
| | Second preferred subfamily: | Symmetric compounds |
| | A: —CH₂— | First preferred subfamily: |
| | Fourth preferred subfamily | A: —CH(L₂—G)— |
| | A: —CH(L₂—G)— | L comprises at least one SO₃H group |

For each of these subfamilies of compounds according to formulas (I) and (I'), the compounds in which the groups $R_1$ or $R_1'$ are groups —COOH or —PO(OH)$R_6$ when $R_6$ represents a phenyl, benzyl, methyl, ethyl, propyl, n-butyl, sec-butyl, isobutyl, or tert-butyl group, are preferred. Among these compounds, those are quite particularly preferred whose groups $R_1$ or $R'_1$ are groups —PO(OH)$R_6$ when $R_6$ represents a methyl, ethyl, propyl, n-butyl, sec-butyl, isobutyl, or tert-butyl group, the methyl group being particularly preferred.

For each of these subfamilies of compounds according to formulas (I) and (I'), the compounds in which the group A is the group —CH(L₂-G)- and chrom1, chrom2, chrom3 are identical are preferred.

For each of these subfamilies of compounds according to formulas (I) and (I'), the compounds in which the groups E= or E' are —SO₃H groups are preferred.

The compounds according to the invention whose groups $R_1$ or $R_1'$ are groups —PO(OH)$R_6$ and whose groups E or E' are —SO₃H groups also constitute preferred compounds.

The compounds according to the invention comprising a group -L₂-G, which may be used for coupling the chelate or complex according to the invention with a molecule that we wish to label, are particularly useful and are therefore also preferred.

The reactive group G carried by a spacer arm L₂ makes it possible to couple the compounds according to the invention with a species that we wish to make fluorescent, for example an organic molecule, a peptide or a protein. The techniques of conjugation of two organic molecules are based on the use of reactive groups and form part of the general knowledge of a person skilled in the art. These conventional techniques are described for example in Bioconjugate Techniques, G. T. Hermanson, Academic Press, Second Edition 2008, p. 169-211.

Typically, the reactive group is an electrophilic or nucleophilic group that can form a covalent bond when it is brought into contact with a suitable nucleophilic or electrophilic group, respectively. The reaction of conjugation between a compound according to the invention comprising a reactive group and an organic molecule, a peptide or a protein bearing a functional group leads to the formation of a covalent bond comprising one or more atoms of the reactive group.

Preferably, the reactive group G is a group derived from one of the following compounds: an acrylamide, an activated amine (for example a cadaverine or an ethylenediamine), an activated ester, an aldehyde, an alkyl halide, an anhydride, an aniline, an azide, an aziridine, a carboxylic acid, a diazoalkane, a haloacetamide, a halotriazine, such as monochlorotriazine, dichlorotriazine, a hydrazine (including the hydrazides), an imido ester, an isocyanate, an isothiocyanate, a maleimide, a sulfonyl halide, or a thiol, a ketone, an amine, an acid halide, a hydroxysuccinimidyl ester, a hydroxysulfosuccinimidyl ester, an azidonitrophenyl, an azidophenyl, a 3-(2-pyridyldithio)-propionamide, a glyoxal, a triazine, an acetylene group, and in particular the groups of formula:

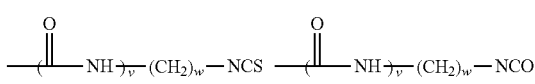

-continued in which w varies from 0 to 8 and v is equal to 0 or 1, and Ar is a saturated or unsaturated heterocycle with 5 or 6 ring members, comprising 1 to 3 heteroatoms, optionally substituted with a halogen atom.

Preferably, the reactive group G is an amine (optionally protected in the form —NHBoc), a succinimidyl ester, a haloacetamide, a hydrazine, an isothiocyanate, a maleimide group, an aliphatic amine, or a carboxylic acid (optionally protected in the form of a group —COOMe, —COOtBu). In the latter case, the acid will have to be activated in the ester form so as to be able to react with a nucleophilic species.

The reactive groups G and the solubilizing groups E and E' may be bound directly to the complexing agent by a covalent bond or else via a spacer arm advantageously consisting of a divalent organic radical. Thus, the spacer arms $L_2$, $L_1$ and $L_1'$ may be selected from:

a covalent bond;

a linear or branched $C_1$-$C_{20}$ alkylene group, optionally containing one or more double or triple bonds and optionally substituted with a number of —SO$_3$H groups between 0 and 3;

a $C_5$-$C_8$ cycloalkylene group; a $C_6$-$C_{14}$ arylene group;

said alkylene, cycloalkylene or arylene groups optionally containing one or more heteroatoms, such as oxygen, nitrogen, sulfur, phosphorus or one or more carbamoyl or carboxamido group(s), and said alkylene, cycloalkylene or arylene groups optionally being substituted with $C_1$-$C_8$ alkyl, $C_6$-$C_{14}$ aryl, sulfonate or oxo groups.

a group selected from the divalent groups of the following formulas:

in which n, m, p, q are integers from 1 to 16, preferably from 1 to 5 and e is an integer in the range from 1 to 6, preferably from 1 to 4.

Preferably, the group -$L_2$-G consists of a reactive group G selected from: a carboxylic acid (optionally protected in the form of a group —COOMe, —COOtBu), an amine (optionally protected in the form —NHBoc), a succinimidyl ester, a haloacetamide, a hydrazine, an isothiocyanate, a maleimide group, an aliphatic amine, and a spacer arm $L_2$ consisting of an alkylene chain comprising 1 to 5 carbon atoms or of a group selected from the groups of formula:

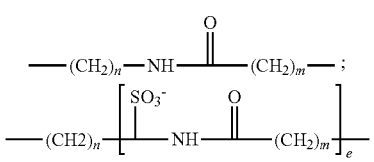

where n, m, are integers from 1 to 16, preferably from 1 to 5 and e is an integer in the range from 1 to 6, preferably from 1 to 4, the group G being bound to one or other end of these divalent groups.

In the same way, the spacer arm $L_1$ or $L_1'$, endowing the compounds according to the invention with the character of water-solubility, preferably consists of an alkylene chain comprising 1 to 5 carbon atoms or of a group selected from the groups of formula:

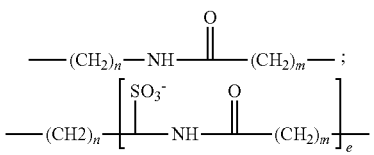

where n, m, are integers from 1 to 16, preferably from 1 to 5 and e is an integer in the range from 1 to 6, preferably from 1 to 4, the group E or E' being bound to one or other end of these divalent groups.

Complexes

The invention also relates to the lanthanide complexes consisting of a lanthanide atom complexed by a complexing agent as described above, the lanthanide being selected from: $Eu^{3+}$, $Tb^{3+}$, $Gd^{3+}$, $Dy^{3+}$, $Nd^{3+}$, $Er^{3+}$. Preferably, the lanthanide is $Tb^{3+}$ or $Eu^{3+}$ and even more preferably $Eu^{3+}$.

These complexes are prepared by contacting the complexing agents according to the invention and a lanthanide salt. Thus, the reaction between one equivalent of complexing agent and 1 to 5 equivalents of lanthanide salt (europium or terbium in the form of chlorides, acetates or triflates) in a solvent (acetonitrile, methanol or some other solvent compatible with these salts) under reflux for several hours leads to the corresponding complex.

As stated above, the fluorescent complexes obtained have excellent photophysical properties, especially with respect to their quantum yield, life-time of their luminescence and their excitation spectrum, which is very suitable for laser excitation at about 337 nm. Moreover, the distribution of the bands of their emission spectra is centered around 620 nm, thus endowing the complexes with exceptional properties that are very favorable when using FRET with acceptors of the cyanine or allophycocyanin type (such as XL665 marketed by Cisbio Bioassays). Owing to the great stability of these complexes in biological media containing divalent cations ($Mn^{2+}$, $Ca^{2+}$, $Mg^{2+}$ etc.) or EDTA, their luminescence remains excellent compared to the complexes of the prior art.

Conjugates

The complexing agents and lanthanide complexes according to the invention comprising a group -$L_2$-G are particularly suitable for labeling organic or biological molecules comprising a functional group capable of reacting with the reactive group to form a covalent bond. Thus, the invention also relates to the use of the lanthanide complexes for labeling molecules of interest (proteins, antibodies, enzymes, hormones etc.).

The invention also relates to the molecules labeled with a complex according to the invention. All the organic or biological molecules may be conjugated with a complex according to the invention if they possess a functional group capable of reacting with the reactive group. In particular, the conjugates according to the invention comprise a complex according to the invention and a molecule selected from: an amino acid, a peptide, a protein, an antibody, a sugar, a carbohydrate chain, a nucleoside, a nucleotide, an oligonucleotide, an enzyme substrate (in particular a suicide enzyme substrate such as a benzylguanine or a benzylcytosine (substrates of the enzymes marketed under the names Snaptag and Cliptag)), a chloroalkane (substrate of the enzyme marketed under the name Halotag), coenzyme A (substrate of the enzyme marketed under the name ACPtag or MCPtag).

Synthesis

Preparation of the complexing agents (ligands) and complexes according to the invention is described schematically below, and in more detail in the experimental section.

Synthesis of the Macrocycles

Scheme 1: Synthesis of substituted TACN

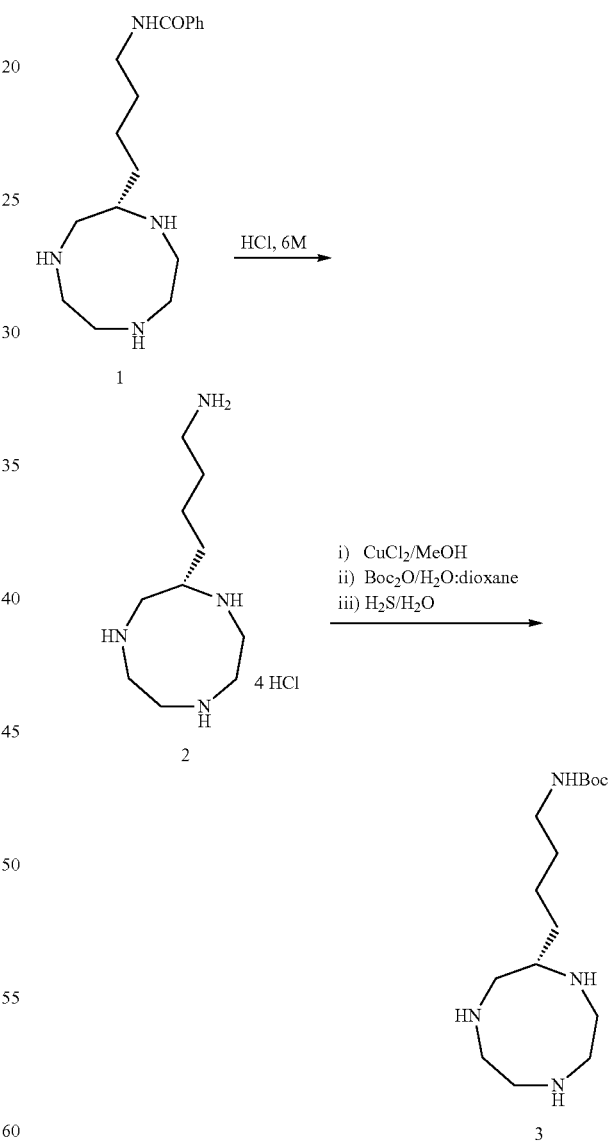

The triazacyclononane macrocycle comprising a side arm whose end is a protected NHBoc function was obtained according to the reaction sequence described in scheme 1. Compound 1, obtained using the procedures described by Parker et al. (J. Chem. Soc. Perkin Trans 1, 1990-2567), is hydrolyzed using 6 M HCl solution leading to compound 2, which is immediately complexed with copper salts. This approach allows selective protection of the endocyclic nitrogen atoms and leaves the primary amine function free, which is then protected with a Boc group. Decomplexation of the copper salts is carried out in the presence of hydrogen sulfide, thus leading to compound 3.

Scheme 2: Synthesis of protected TACN-Mono

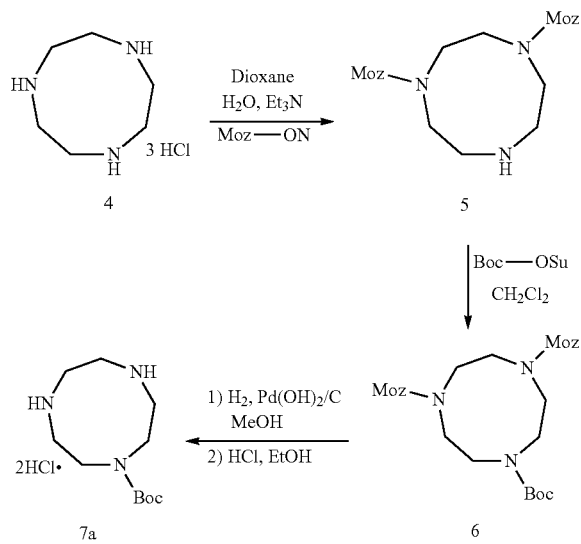

The Boc monoprotected triazacyclononane 7a is not commercially available. It was prepared according to the reaction sequence described in scheme 2. Two equivalents of Moz-ON (((2-(4-methoxybenzyloxycarbonyloxy imino)-2-phenylacetonitrile)) were condensed on the triazotized macrocycle 4 to give the disubstituted compound with suitable yields. Purification of these products proved difficult as the Moz group is sensitive to acidity. Even that of silica is sufficient to cause degradation of the products during purification on a chromatographic column. To avoid this degradation, the reaction media were purified on a neutral alumina column, which led to compound 5 with a yield of 74%. In the next step, the Boc group is introduced by means of N-(tert-butoxy carbonyloxy)succinimide (Boc-OSu) to give the trisubstituted triazotized macrocycle 6. Finally the amines bearing the Moz groups are deprotected by hydrogenolysis. The use of Pd/C at 10% as catalyst did not allow deprotection of the amines when the reaction mixture is hydrogenated for 48 h at a pressure of 3.45 bar. However, the use of the Pearlman catalyst (Pd(OH)$_2$/C) allowed the monoprotected triazotized macrocycle to be obtained. To isolate this product easily, the hydrochloride salts were formed by adding a small amount of cold hydrochloric acid, the latter being collected by precipitation in diethyl ether. This methodology makes it possible to prepare the compound monoprotected with a Boc group 7a on a scale of several grams.

Synthesis of the Alkynes

Scheme 3: Synthesis of the O-propylene-functionalized alkynes

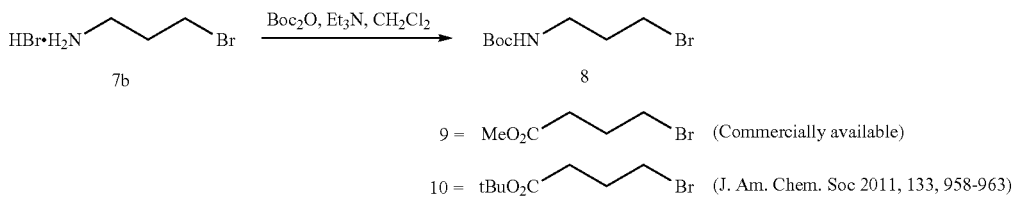

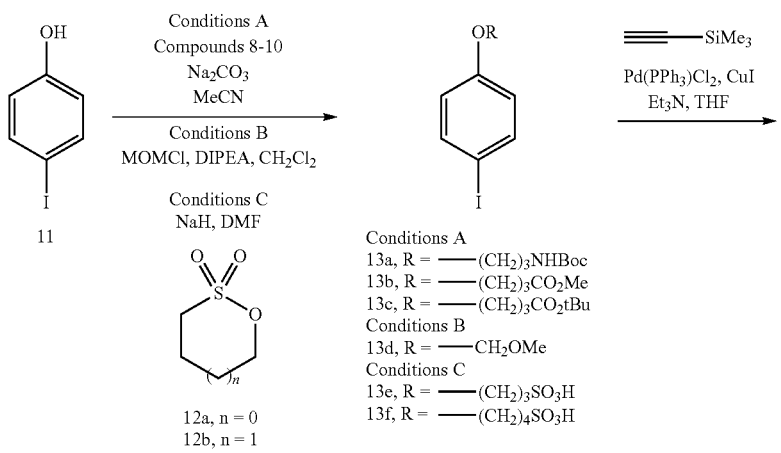

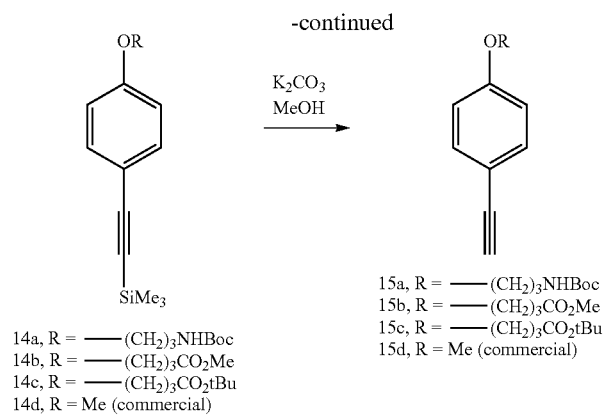

The alkynes (true or protected with a TMS group), which are not commercially available, were synthesized using Sonogashira coupling with trimethylsilylacetylene, which is described extensively in the literature (Sonogashira et al. Tetrahedron Letters, 50 (1975) 4467-4470, Rossi et al. Organic Preparation and Procedure International 27 (1995) 129-160). This reaction makes it possible to couple a true alkyne with an aromatic halide (preferably an iodinated or brominated derivative) or a tosyl group. Their synthesis is described in schemes 3 and 4 and detailed in the experimental section. Protection of the amine 7b with a Boc protective group was necessary to avoid polyalkylation. The brominated derivative 10 was prepared following the procedures described in the literature (J. Am. Chem. Soc 2011, 133, 958). The reactions of alkylation of iodophenol 11 led to the phenolic ethers 13a-c with suitable yields. The phenol 13d is protected with methylchloromethyl ether in dichloromethane in the presence of diisopropylethylamine Compounds 13e-f were obtained by carrying out a reaction between iodophenol 11 and the corresponding sultone (1,3-propane sultone 12a and 1,4-butane sultone 12b). The Sonogashira couplings were performed in the classical conditions, allowing the trimethylsilylated alkynes 14a-c to be obtained, which were then, depending on the requirements, deprotected to give the true alkynes 15a-d. The alkynes 14d and 15d are commercially available.

Scheme 4: Synthesis of the alkynes O—CH$_2$R

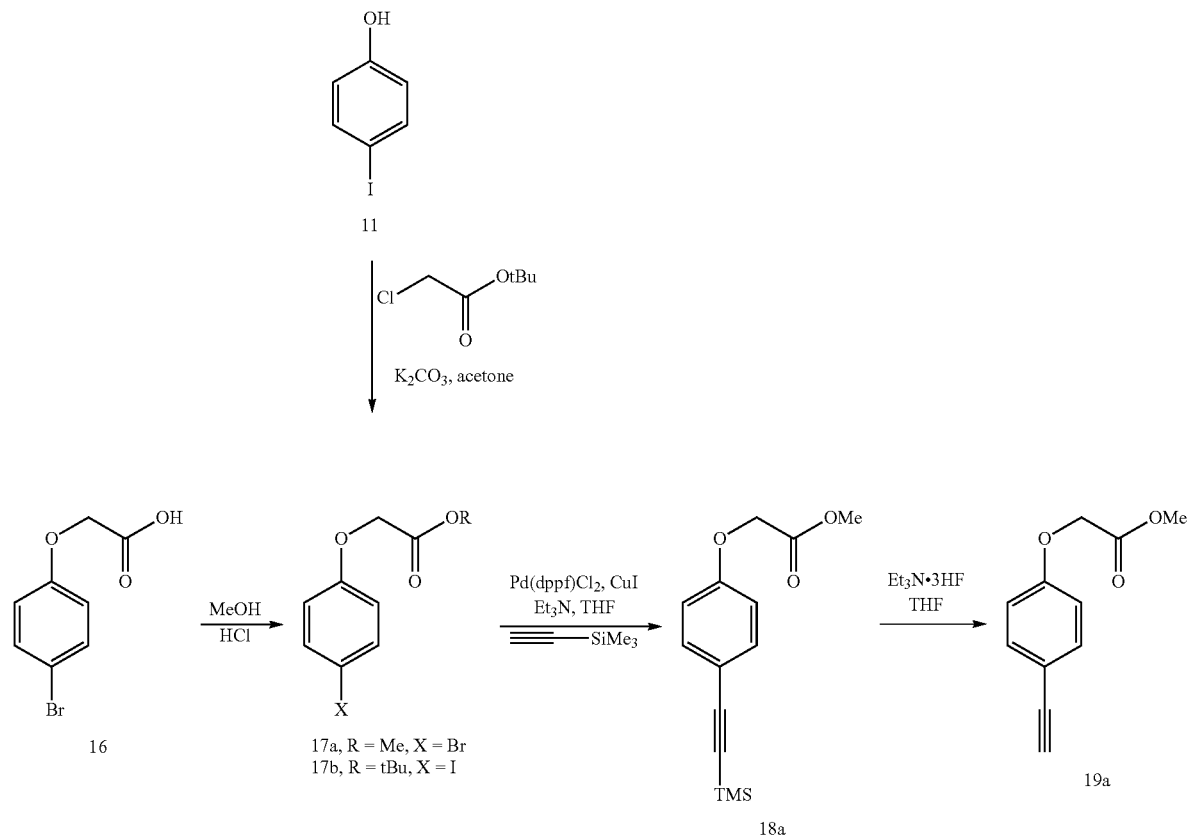

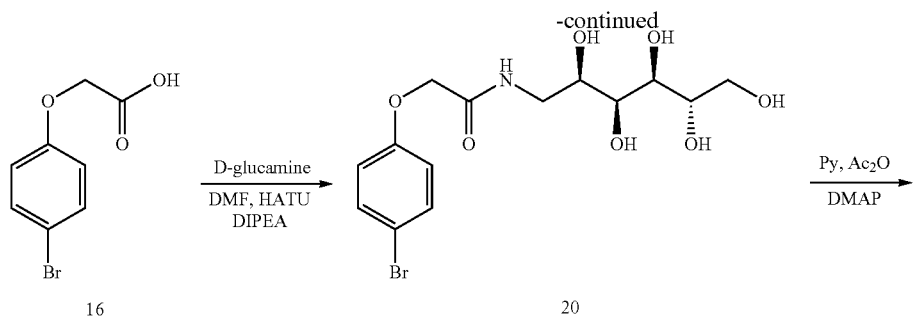

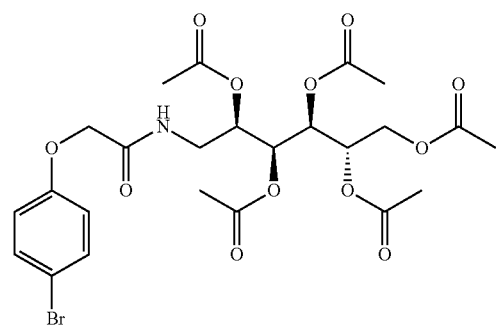

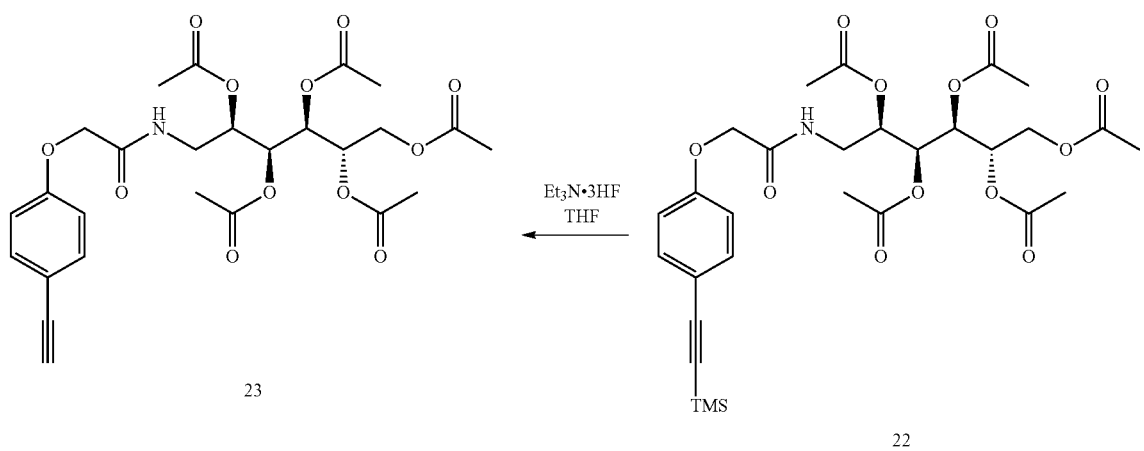 [SMILES: C#Cc1ccc(OCC(=O)NC[C@@H](OC(C)=O)[C@H](OC(C)=O)[C@@H](OC(C)=O)[C@H](COC(C)=O)OC(C)=O)cc1 ; CC(=O)OC[C@H](OC(C)=O)[C@H](OC(C)=O)[C@@H](OC(C)=O)[C@@H](CNC(=O)COc1ccc(C#C[Si](C)(C)C)cc1)OC(C)=O]

Regarding the alkynes 19a and 23, they were obtained according to the reaction sequences described in scheme 4. Compounds 17a and 17b were obtained, respectively, by an esterification reaction or an alkylation reaction starting from the precursors 16 and 11. The triple bond was introduced by Sonogashira coupling as before (see scheme 3). Regarding compound 23, it was obtained from 4-bromophenoxyacetic acid 16 via a coupling reaction with D-glucamine. The hydroxyl groups were then protected in the form of acetates to lower the polarity of the molecule, and facilitate the extractions and purifications. Introduction of the triple bond and then deprotection of TMS led to compound 23.

Synthesis of the Trisubstituted Pyridines

Scheme 5: Synthesis of pyridine 2-carbomethoxyester

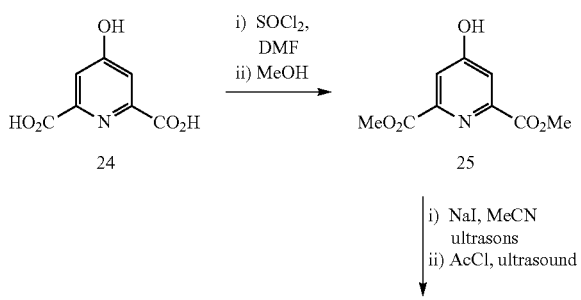

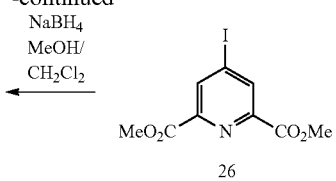

Chelidamic acid 24 was converted to chlorinated diester 25 as described by Maury et al. (Inorganic Chemistry 50 (2011) 4987-4999). Chlorine-iodine exchange was performed in the presence of sodium iodide under ultrasound, to give compound 26. Selective reduction of the diester 26 in the presence of sodium borohydride at 0° C. gave the monohydric alcohol monoester 27a with a yield of 60%.

Scheme 6: Pyridine 2-phosphinoxyester

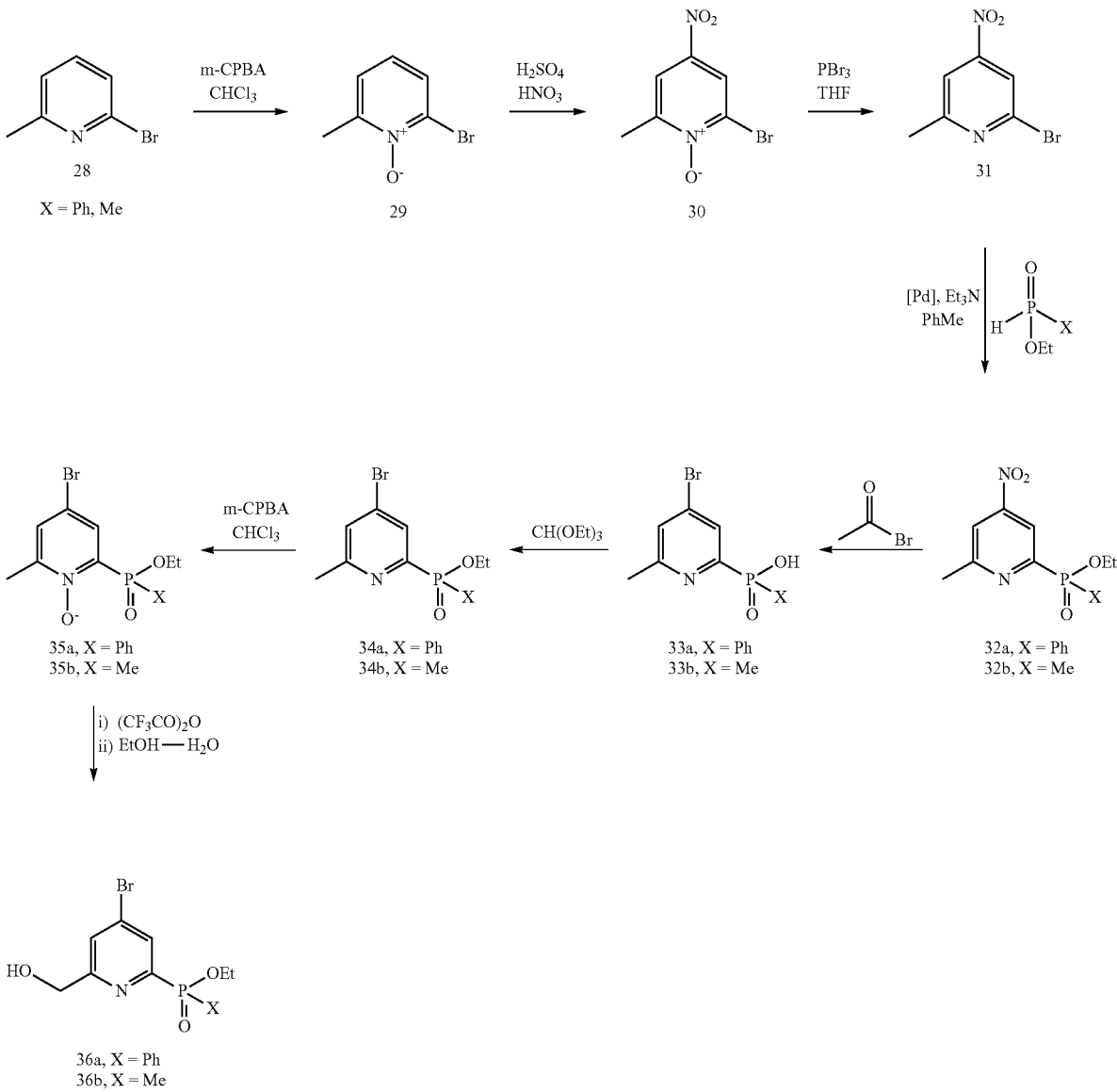

The objective of the synthesis is to obtain a pyridine derivative trisubstituted with different groups. For this, commercially available 2-bromo-6-methylpyridine was oxidized to N-oxide analog 29 simply by oxidation in the presence of metachloroperbenzoic acid (m-CPBA). Activation of this azotized heterocycle made it easy to introduce the nitro group in position 4, corresponding to the third functional group. The N-oxide was then removed using phosphorus tribromide, to lead to the free pyridinyl derivative. Introduction of the phosphinate group was performed using palladium coupling in the presence of commercial phenylphosphinic acid. Regarding pyridine methylphosphinate, it was obtained by coupling of the ethylmethyl phosphinate derivative, itself obtained by hydrolysis of diethylmethyl phosphonite using 1 equivalent of water. Development of these couplings proved particularly difficult but finally made it possible to obtain the desired compounds 32a and 32b. Substitution of the nitro group with a bromine atom was carried out in the presence of acetyl bromide. Although this reagent is effective in this reaction, it causes the formation of hydrobromic acid, which hydrolyzes the phosphinate group. The latter was reintroduced immediately afterwards using ethyl orthoformate. Functionalization of the methyl in position 6 of the pyridine was performed using a rearrangement described by Ginsburg et al. (Journal American Chemical Society 79 (1957) 481-485). The pyridine was oxidized a second time using the same conditions as those described above. This N-oxide function is sufficiently nucleophilic to react with trifluoroacetic anhydride, which undergoes an intermediate rearrangement, thus making it possible to introduce a trifluoroacetate group in position 6, leading to the corresponding acetates. The latter are not isolated, but are hydrolyzed directly, thus leading to the key synthesis intermediates 36a and 36b.

Synthesis of the Chromophores

Scheme 7: Synthesis of the chromophores of the "carboxylate" type

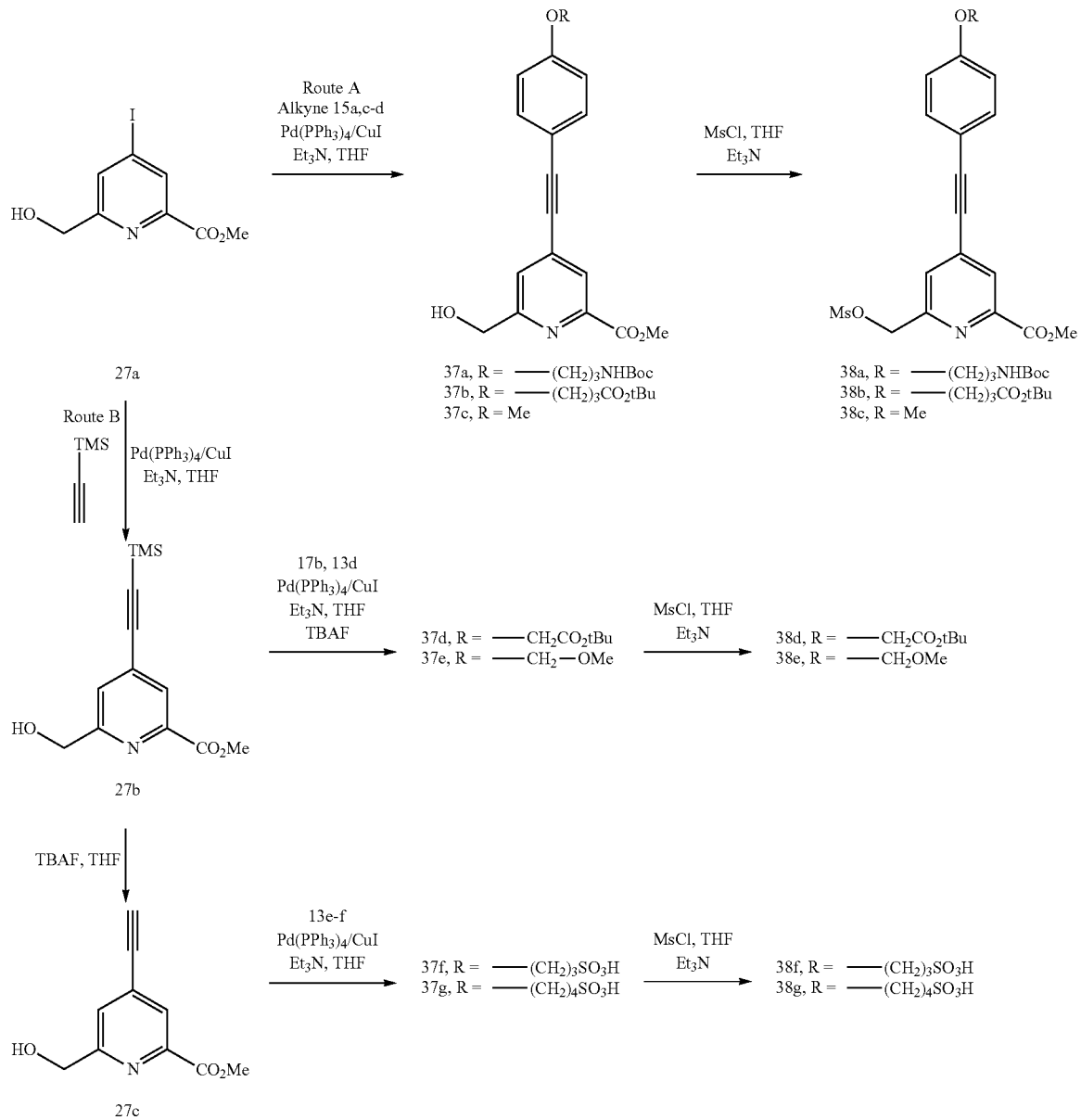

The chromophores of the carboxylate type 38a-g were synthesized according to the reaction sequences described in scheme 7. For the chromophores 38a-c (route A), a single Sonogashira reaction is involved, enabling the skeletons of the chromophores to be obtained in a single step. To avoid preparing alkynes whose substituents are O-alkyl carboxylates, O-alkyl-sulfonates or MOM, a linear synthesis strategy was used: the iodinated derivative was coupled with trimethylsilylated acetylene by Sonogashira coupling, which makes it possible to obtain the key intermediate 27b. A Sila-Sonogashira reaction (deprotection in situ of the trimethylsilyl group) led to the skeletons of the chromophores 37d-e, which were activated as before in the form of mesylated derivatives. In the case of the O-alkyl sulfonate derivatives, it proved useful to remove the TMS from 27b as the fluoride salts of tetrabutylammonium have been difficult to remove in purification by silica column chromatography or by preparative HPLC. Thus, the true alkyne 27c was coupled with the various iodophenyl sulfonates (13e-f) to lead to the compounds 37f-g, which were then mesylated conventionally.

Scheme 8: Synthesis of the chromophores of the "phosphinate" type

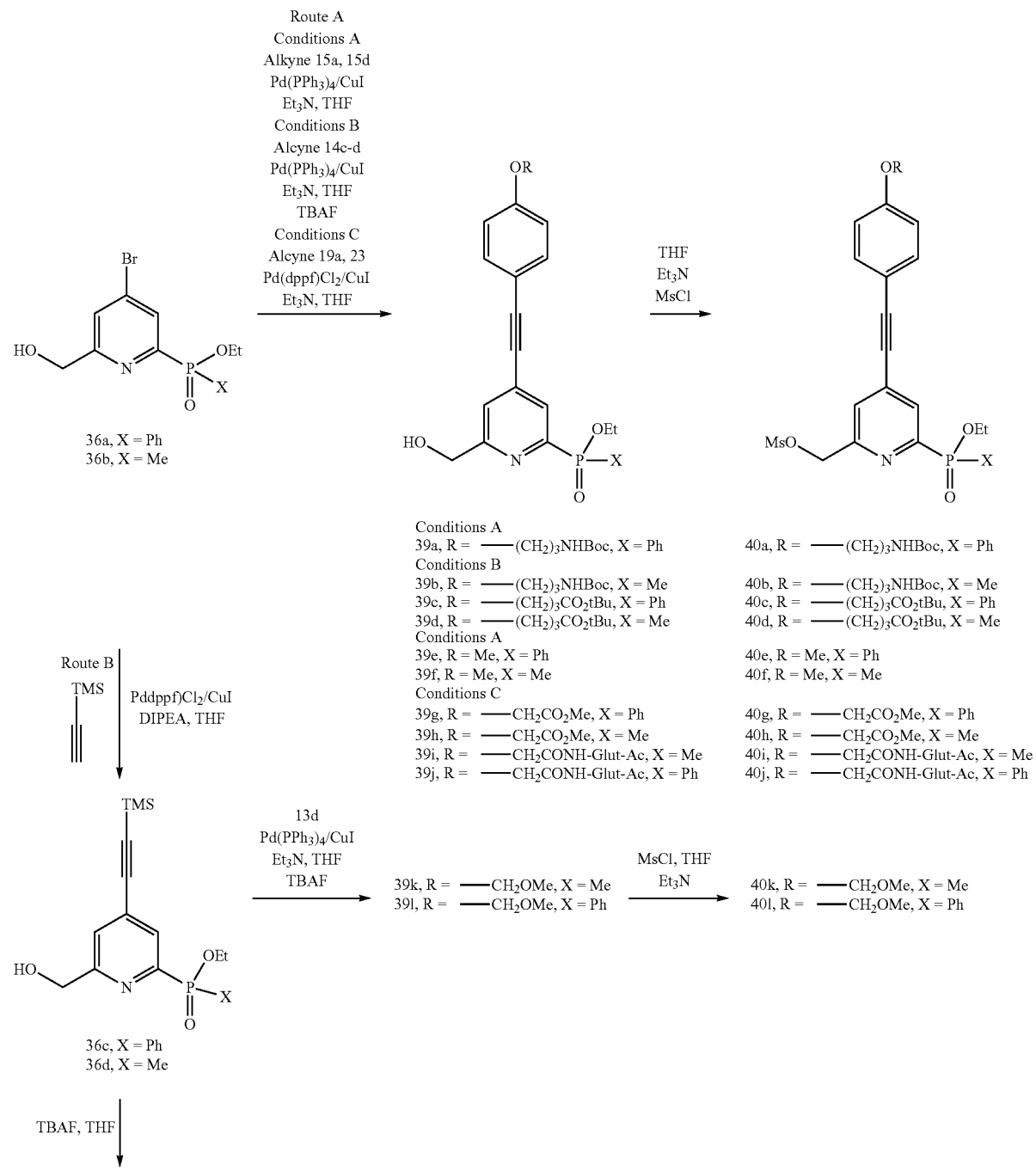

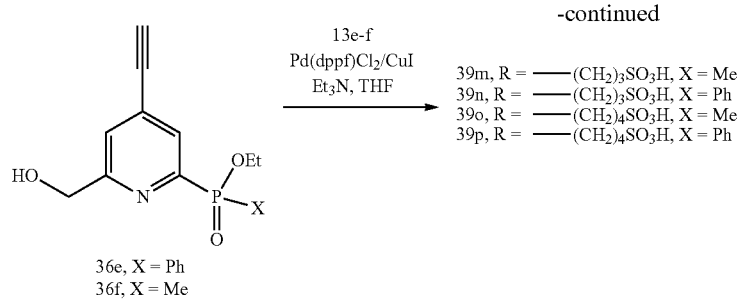
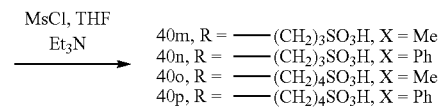

36e, X = Ph
36f, X = Me

39m, R = —(CH$_2$)$_3$SO$_3$H, X = Me
39n, R = —(CH$_2$)$_3$SO$_3$H, X = Ph
39o, R = —(CH$_2$)$_4$SO$_3$H, X = Me
39p, R = —(CH$_2$)$_4$SO$_3$H, X = Ph

40m, R = —(CH$_2$)$_3$SO$_3$H, X = Me
40n, R = —(CH$_2$)$_3$SO$_3$H, X = Ph
40o, R = —(CH$_2$)$_4$SO$_3$H, X = Me
40p, R = —(CH$_2$)$_4$SO$_3$H, X = Ph

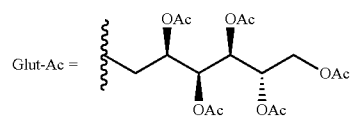

The chromophores of the phosphinate type (P-Me and P—PH) 40a-p were prepared according to the same strategies as those described for the chromophores of the carboxylate type. The reaction sequences are presented in scheme 8 and the syntheses are detailed in the experimental section.

Synthesis of the Complexes

Scheme 9: Synthesis of the symmetric complexes of the "carboxylate" type derived from TACN

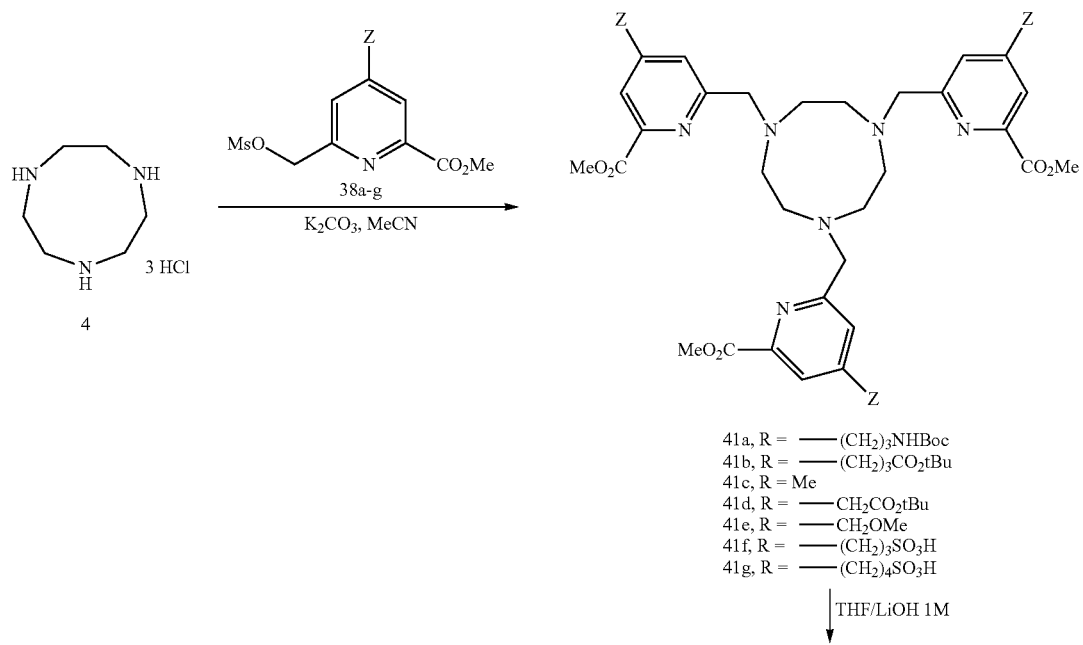

41a, R = —(CH$_2$)$_3$NHBoc
41b, R = —(CH$_2$)$_3$CO$_2$tBu
41c, R = Me
41d, R = —CH$_2$CO$_2$tBu
41e, R = —CH$_2$OMe
41f, R = —(CH$_2$)$_3$SO$_3$H
41g, R = —(CH$_2$)$_4$SO$_3$H

THF/LiOH 1M

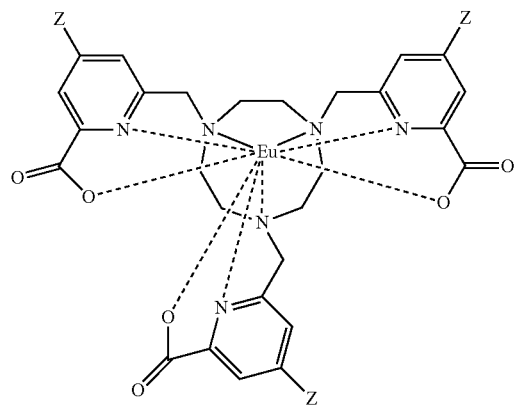
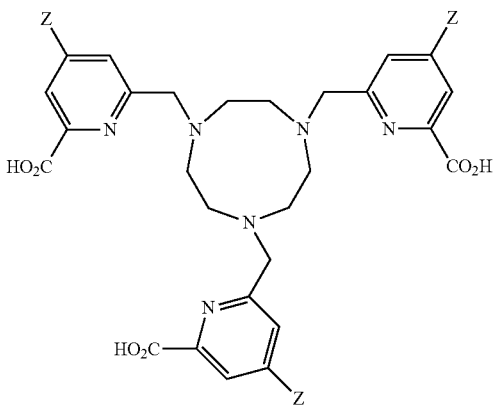

43a, R = —(CH₂)₃NHBoc
43b, R = —(CH₂)₃CO₂tBu
43c, R = Me
43d, R = —CH₂CO₂tBu
43e, R = —CH₂OMe
43f, R = —(CH₂)₃SO₃H
43g, R = —(CH₂)₄SO₃H

42a, R = —(CH₂)₃NHBoc
42b, R = —(CH₂)₃CO₂tBu
42c, R = Me
42d, R = —CH₂CO₂tBu
42e, R = —CH₂OMe
42f, R = —(CH₂)₃SO₃H
42g, R = —(CH₂)₄SO₃H

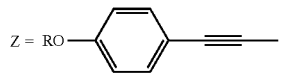

The symmetric complexes of the carboxylate type were synthesized according to the reaction sequence described in scheme 9. The first step consisted of alkylating the commercial triazacyclononane with the various mesylated chromophores 38a-g. The methyl ester functions were then hydrolyzed to give the corresponding carboxylates, and the products obtained were brought into contact with the europium salts for formation of the europium complexes 43a-g.

Scheme 10: Synthesis of the symmetric complexes of the "phosphinate" type derived from TACN

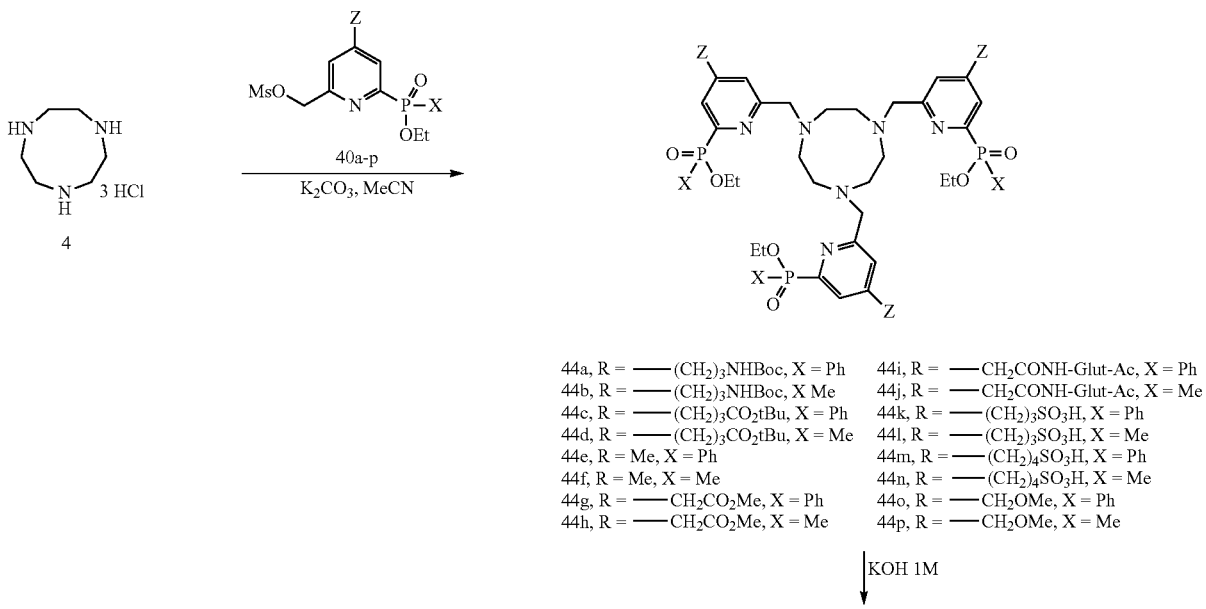

44a, R = —(CH₂)₃NHBoc, X = Ph
44b, R = —(CH₂)₃NHBoc, X Me
44c, R = —(CH₂)₃CO₂tBu, X = Ph
44d, R = —(CH₂)₃CO₂tBu, X = Me
44e, R = Me, X = Ph
44f, R = Me, X = Me
44g, R = —CH₂CO₂Me, X = Ph
44h, R = —CH₂CO₂Me, X = Me
44i, R = —CH₂CONH-Glut-Ac, X = Ph
44j, R = —CH₂CONH-Glut-Ac, X = Me
44k, R = —(CH₂)₃SO₃H, X = Ph
44l, R = —(CH₂)₃SO₃H, X = Me
44m, R = —(CH₂)₄SO₃H, X = Ph
44n, R = —(CH₂)₄SO₃H, X = Me
44o, R = —CH₂OMe, X = Ph
44p, R = —CH₂OMe, X = Me

↓ KOH 1M

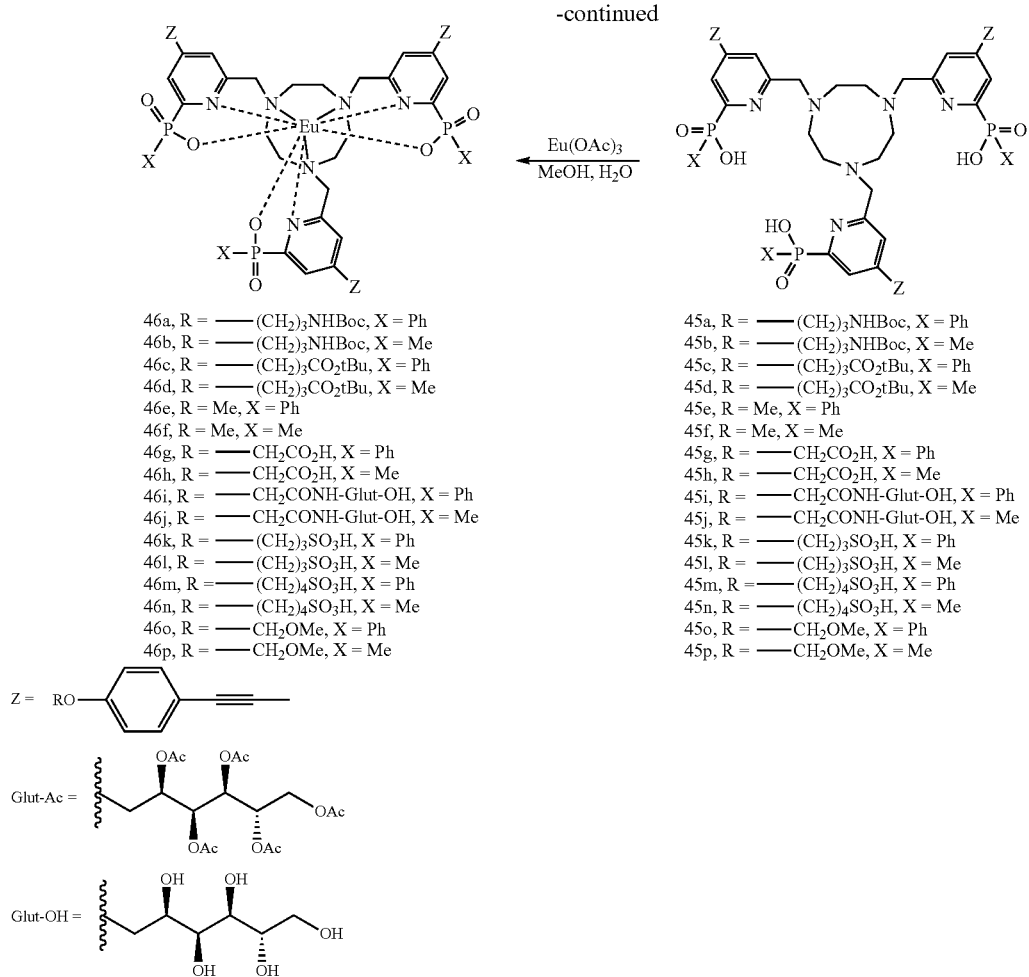

46a, R = ─(CH$_2$)$_3$NHBoc, X = Ph
46b, R = ─(CH$_2$)$_3$NHBoc, X = Me
46c, R = ─(CH$_2$)$_3$CO$_2$tBu, X = Ph
46d, R = ─(CH$_2$)$_3$CO$_2$tBu, X = Me
46e, R = Me, X = Ph
46f, R = Me, X = Me
46g, R = ─CH$_2$CO$_2$H, X = Ph
46h, R = ─CH$_2$CO$_2$H, X = Me
46i, R = ─CH$_2$CONH-Glut-OH, X = Ph
46j, R = ─CH$_2$CONH-Glut-OH, X = Me
46k, R = ─(CH$_2$)$_3$SO$_3$H, X = Ph
46l, R = ─(CH$_2$)$_3$SO$_3$H, X = Me
46m, R = ─(CH$_2$)$_4$SO$_3$H, X = Ph
46n, R = ─(CH$_2$)$_4$SO$_3$H, X = Me
46o, R = ─CH$_2$OMe, X = Ph
46p, R = ─CH$_2$OMe, X = Me 45a, R = ─(CH$_2$)$_3$NHBoc, X = Ph
45b, R = ─(CH$_2$)$_3$NHBoc, X = Me
45c, R = ─(CH$_2$)$_3$CO$_2$tBu, X = Ph
45d, R = ─(CH$_2$)$_3$CO$_2$tBu, X = Me
45e, R = Me, X = Ph
45f, R = Me, X = Me
45g, R = ─CH$_2$CO$_2$H, X = Ph
45h, R = ─CH$_2$CO$_2$H, X = Me
45i, R = ─CH$_2$CONH-Glut-OH, X = Ph
45j, R = ─CH$_2$CONH-Glut-OH, X = Me
45k, R = ─(CH$_2$)$_3$SO$_3$H, X = Ph
45l, R = ─(CH$_2$)$_3$SO$_3$H, X = Me
45m, R = ─(CH$_2$)$_4$SO$_3$H, X = Ph
45n, R = ─(CH$_2$)$_4$SO$_3$H, X = Me
45o, R = ─CH$_2$OMe, X = Ph
45p, R = ─CH$_2$OMe, X = Me The symmetric complexes of the phosphinate type were synthesized according to the reaction sequence described in scheme 10. The first step consisted of alkylating triazacyclononane with the various mesylated chromophores 40a-p. The phosphinate esters were then hydrolyzed to give the corresponding phosphinic acids and the products obtained were contacted, without prior purification, with the europium salts, leading to formation of the europium complexes 46a-p.

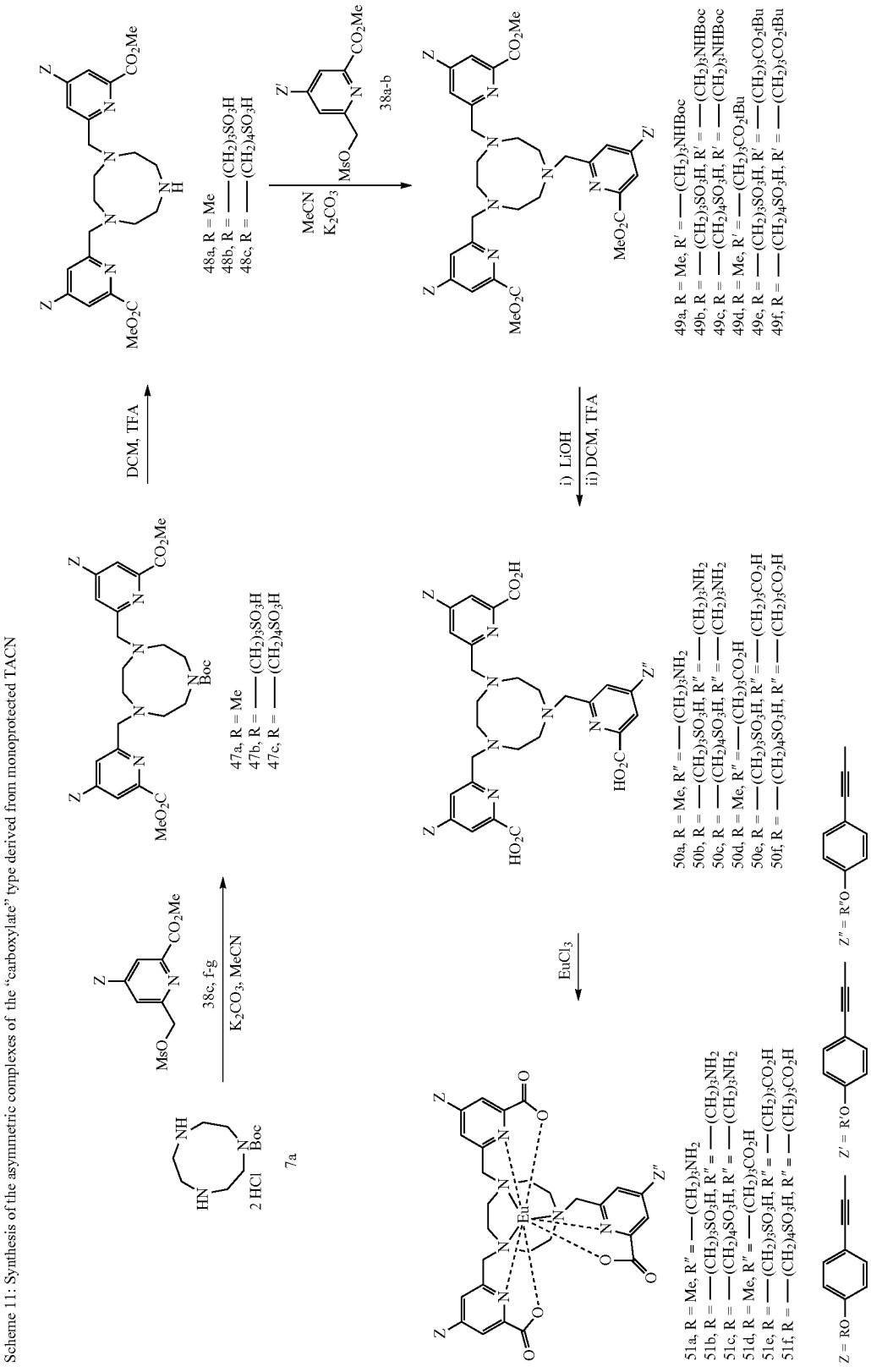

The europium complexes were prepared according to schemes 11 and 12. Starting from the monosubstituted macrocycle, two "carboxylate chromophore" or "phosphinate" units were condensed to give the derivatives 47a-c or 52a-f. The Boc protective group was removed in the presence of trifluoroacetic acid, and the third chromophore comprising a masked amino or carboxyl group was alkylated to allow subsequent conjugation to a biomolecule. The three methyl (carboxylate) or ethyl (phosphinate) ester functions were then hydrolyzed and the Boc or tBu group was removed in an acid medium. The lanthanide complex was formed by reacting the ligands 50 and 55 with the corresponding lanthanide salts, in this particular case europium chloride or acetate, to give the complexes 51 and 56.

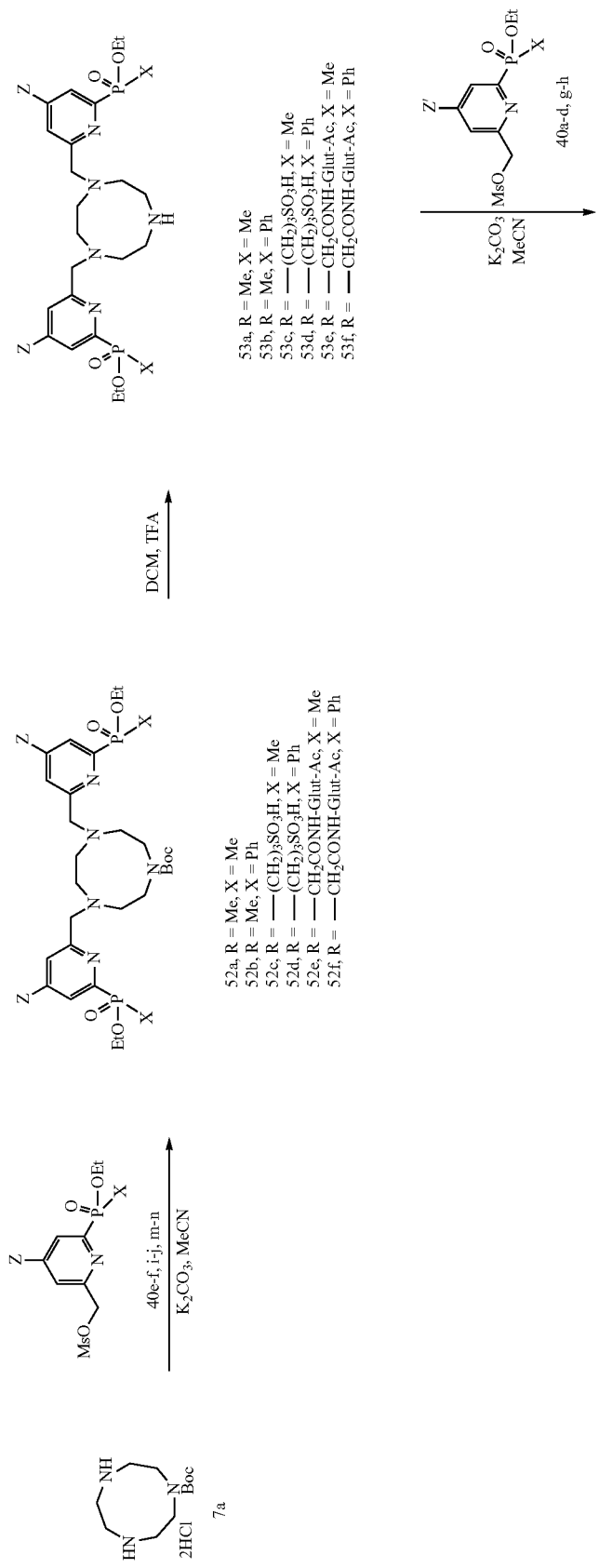

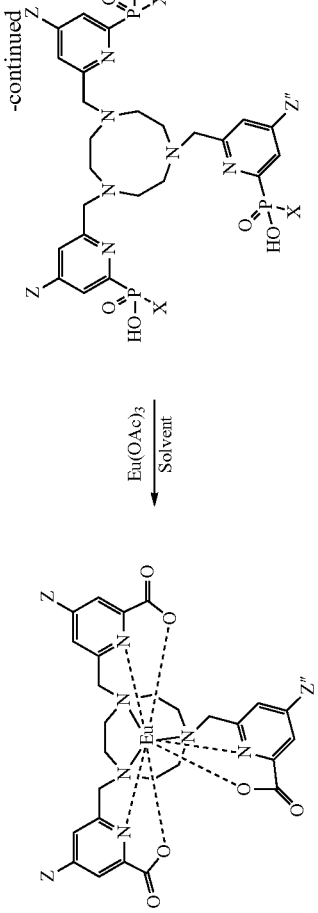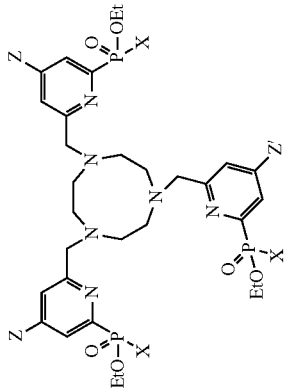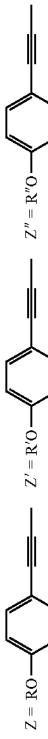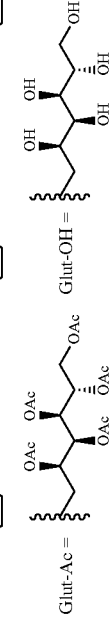

Conditions A

55a, R = Me, X = Me, R″ = —(CH$_2$)$_3$—NH$_2$
55b, R = Me, X = Ph, R″ = —(CH$_2$)$_3$—NH$_2$
55c, R = Me, X = Me, R″ = —(CH$_2$)$_3$CO$_2$H
55d, R = Me, X = Ph, R″ = —(CH$_2$)$_3$CO$_2$H

55e, R = Me, X = Me, R″ = —CH$_2$—CO$_2$H
55f, R = Me, X = Ph, R″ = —CH$_2$—CO$_2$H

Conditions A

55g, R = —(CH$_2$)$_3$SO$_2$H, X = Me, R″ = —(CH$_2$)$_3$—NH$_2$
55h, R = —(CH$_2$)$_3$SO$_2$H, X = Ph, R″ = —(CH$_2$)$_3$—NH$_2$
55i, R = —(CH$_2$)$_3$SO$_2$H, X = Me, R″ = —(CH$_2$)$_3$—CO$_2$H
55j, R = —(CH$_2$)$_3$SO$_2$H, X = Ph, R″ = —(CH$_2$)$_3$—CO$_2$H

Conditions B

55k, R = —(CH$_2$)$_3$SO$_2$H, X = Me, R″ = —CH$_2$—CO$_2$H
55l, R = —(CH$_2$)$_3$SO$_2$H, X = Ph, R″ = —CH$_2$—CO$_2$H

Conditions A

55m, R = —CH$_2$CONH-Glut-OH, X = Me, R″ = —(CH$_2$)$_3$—NH$_2$
55n, R = —CH$_2$CONH-Glut-OH, X = Ph, R″ = —(CH$_2$)$_3$—NH$_2$
55o, R = —CH$_2$CONH-Glut-OH, X = Me, R″ = —(CH$_2$)$_3$—CO$_2$H
55p, R = —CH$_2$CONH-Glut-OH, X = Ph, R″ = —(CH$_2$)$_3$—CO$_2$H Conditions B 55q, R = —CH$_2$CONH-Glut-OH X = Ph, R″ = —(CH$_2$)$_3$—CO$_2$H
55r, R = —CH$_2$CONH-Glut-OH, X = Ph, R″ = —CH$_2$—CO$_2$H 54a, R = Me, X = Me, R′ = —(CH$_2$)$_3$—NHBoc
54b, R = Me, X = Ph, R′ = —(CH$_2$)$_3$—NHBoc
54c, R = Me, X = Me, R′ = —(CH$_2$)$_3$CO$_2$tBu
54d, R = Me, X = Ph, R′ = —(CH$_2$)$_3$CO$_2$tBu 54e, R = Me, X = Me, R′ = —CH$_2$—CO$_2$Me
54f, R = Me, X = Ph, R′ = —CH$_2$—CO$_2$Me 54g, R = —(CH$_2$)$_3$SO$_3$H, X = Me, R′ = —(CH$_2$)$_3$—NHBoc
54h, R = —(CH$_2$)$_3$SO$_3$H, X = Ph, R′ = —(CH$_2$)$_3$—NHBoc
54i, R = —(CH$_2$)$_3$SO$_3$H, X = Me, R′ = —(CH$_2$)$_3$—CO$_2$tBu
54j, R = —(CH$_2$)$_3$SO$_3$H, X = Ph, R′ = —(CH$_2$)$_3$—CO$_2$tBu 54k, R = —(CH$_2$)$_3$SO$_3$H, X = Me, R′ = —CH$_2$—CO$_2$Me
54l, R = —(CH$_2$)$_3$SO$_3$H, X = Ph, R′ = —CH$_2$—CO$_2$Me 54m, R = —CH$_2$CONH-Glut-Ac, X = Me, R′ = —(CH$_2$)$_3$—NHBoc
54n, R = —CH$_2$CONH-Glut-Ac, X = Ph, R′ = —(CH$_2$)$_3$—NHBoc
54o, R = —CH$_2$CONH-Glut-Ac, X = Me, R′ = —(CH$_2$)$_3$—CO$_2$tBu
54p, R = —CH$_2$CONH-Glut-Ac, X = Ph, R′ = —(CH$_2$)$_3$—CO$_2$tBu 54q, R = —CH$_2$CONH-Glut-Ac, X = Me, R′ = —CH$_2$—CO$_2$Me
54r, R = —CH$_2$CONH-Glut-Ac, X = Ph, R′ = —CH$_2$—CO$_2$Me 56a, R = Me, X = Me, R″ = —(CH$_2$)$_3$—NH$_2$
56b, R = Me, X = Ph, R″ = —(CH$_2$)$_3$—NH$_2$
56c, R = Me, X = Me, R″ = —(CH$_2$)$_3$—CO$_2$H
56d, R = Me, X = Ph, R″ = —(CH$_2$)$_3$—CO$_2$H 56e, R = Me, X = Me, R″ = —CH$_2$—CO$_2$H
56f, R = Me, X = Ph, R″ = —CH$_2$—CO$_2$H 56g, R = —(CH$_2$)$_3$SO$_2$H, X = Me, R″ = —(CH$_2$)$_3$—NH$_2$
56h, R = —(CH$_2$)$_3$SO$_2$H, X = Ph, R″ = —(CH$_2$)$_3$—NH$_2$
56i, R = —(CH$_2$)$_3$SO$_2$H, X = Me, R″ = —(CH$_2$)$_3$—CO$_2$H
56j, R = —(CH$_2$)$_3$SO$_2$H, X = Ph, R″ = —(CH$_2$)$_3$—CO$_2$H 56k, R = —(CH$_2$)$_3$SO$_2$H, X = Me, R″ = —CH$_2$—CO$_2$H
56l, R = —(CH$_2$)$_3$SO$_2$H, X = Ph, R″ = —CH$_2$—CO$_2$H 56m, R = —CH$_2$CONH-Glut-Ac, X = Me, R″ = —(CH$_2$)$_3$—NH$_2$
56n, R = —CH$_2$CONH-Glut-Ac, X = Ph, R″ = —(CH$_2$)$_3$—NH$_2$
56o, R = —CH$_2$CONH-Glut-Ac, X = Me, R″ = —(CH$_2$)$_3$—CO$_2$H
56p, R = —CH$_2$CONH-Glut-Ac, X = Ph, R″ = —(CH$_2$)$_3$—CO$_2$H 56q, R = —CH$_2$CONH-Glut-Ac, X = Me, R″ = —(CH$_2$)$_3$—CO$_2$H
56r, R = —CH$_2$CONH-Glut-Ac, X = Ph, R″ = —(CH$_2$)$_3$—CO$_2$H

Z = RO
Z′ = R′O
Z″ = R″O

Glut-OH =
Glut-Ac =

Scheme 13: Synthesis of the symmetric complexes of the "carboxylate" type derived from C-substituted TACN

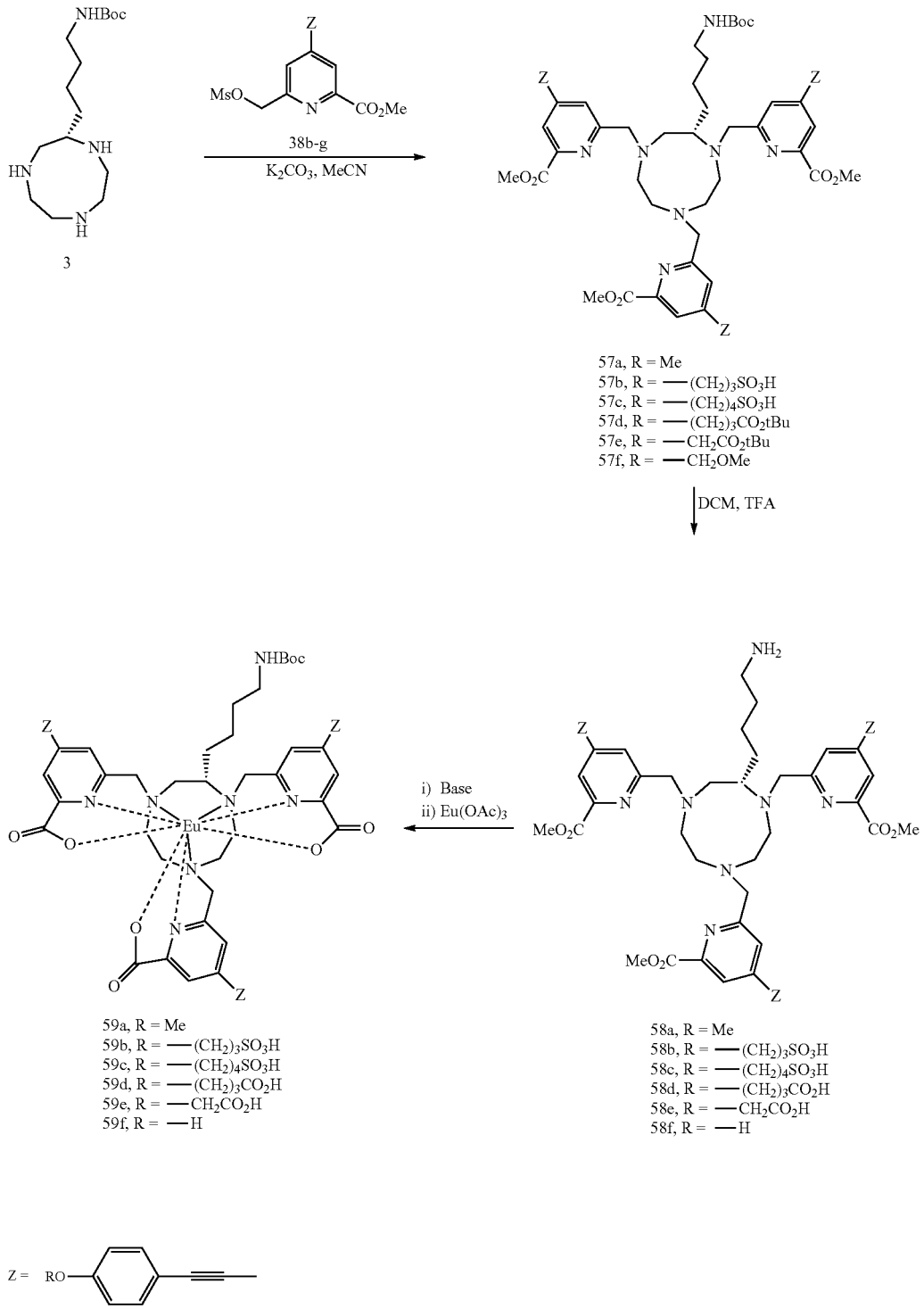

The syntheses of the symmetric complexes comprising the Boc alkyl chain on the macrocycle were described in schemes 13 (carboxylate version) and 14 (phosphinate version). This time the functional group allowing bioconjugation is put on the macrocycle. This new system makes the synthesis easier, as the three chromophores may be identical.

As described in the synthesis of the carboxylate or phosphinate symmetric complexes, triazacyclononane 3 was alkylated by the different chromophores 38 and 40, and then the ester functions (carboxylates and phosphinates) were hydrolyzed. Finally complexation with the europium salts led to the complexes 59a-f and 62a-l.

Scheme 14: Synthesis of the symmetric complexes of the "phosphinate" type derived from C-substituted TACN
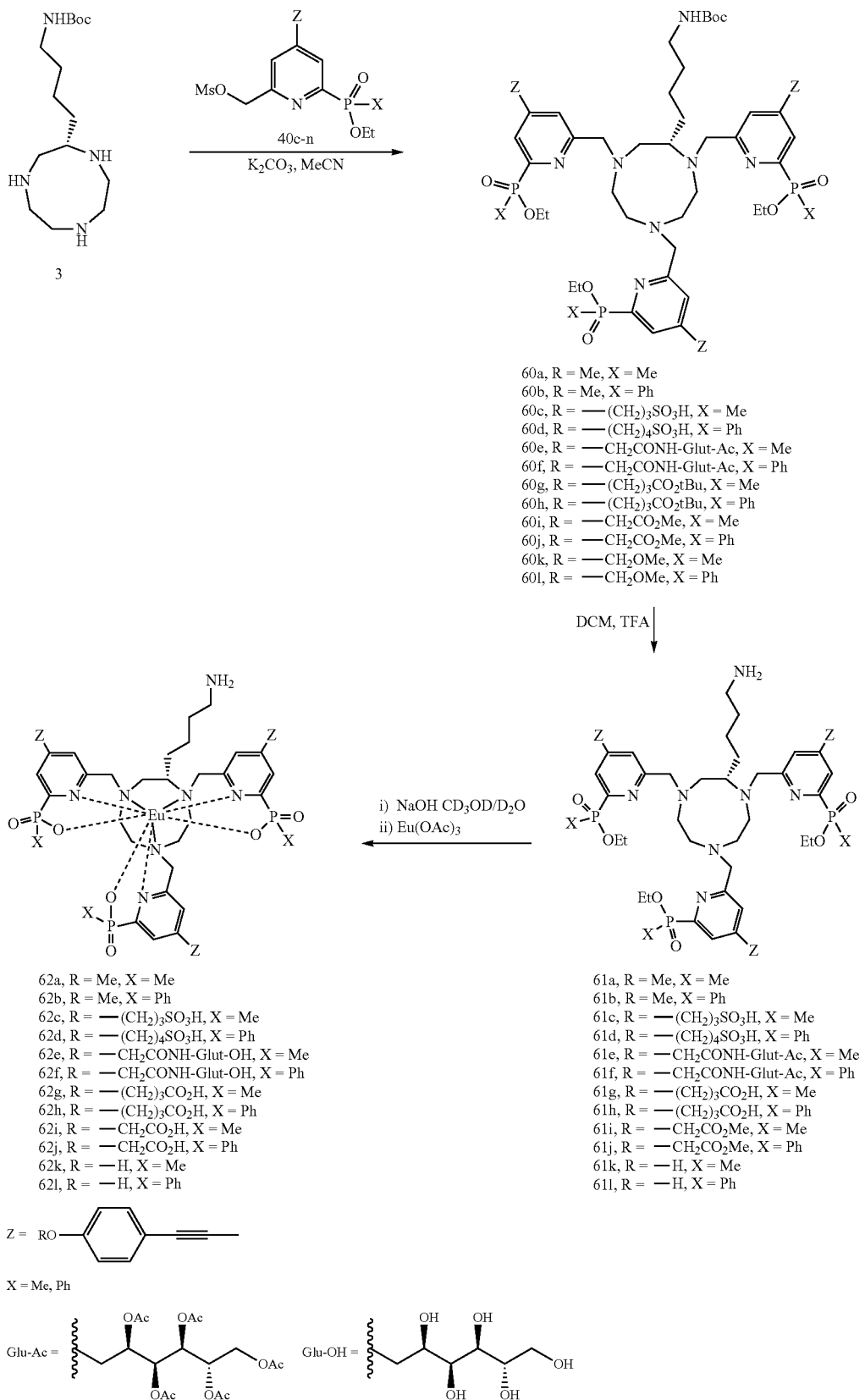

Scheme 15: Synthesis of the asymmetric complexes of the "carboxylate" type derived from C-substituted TACN
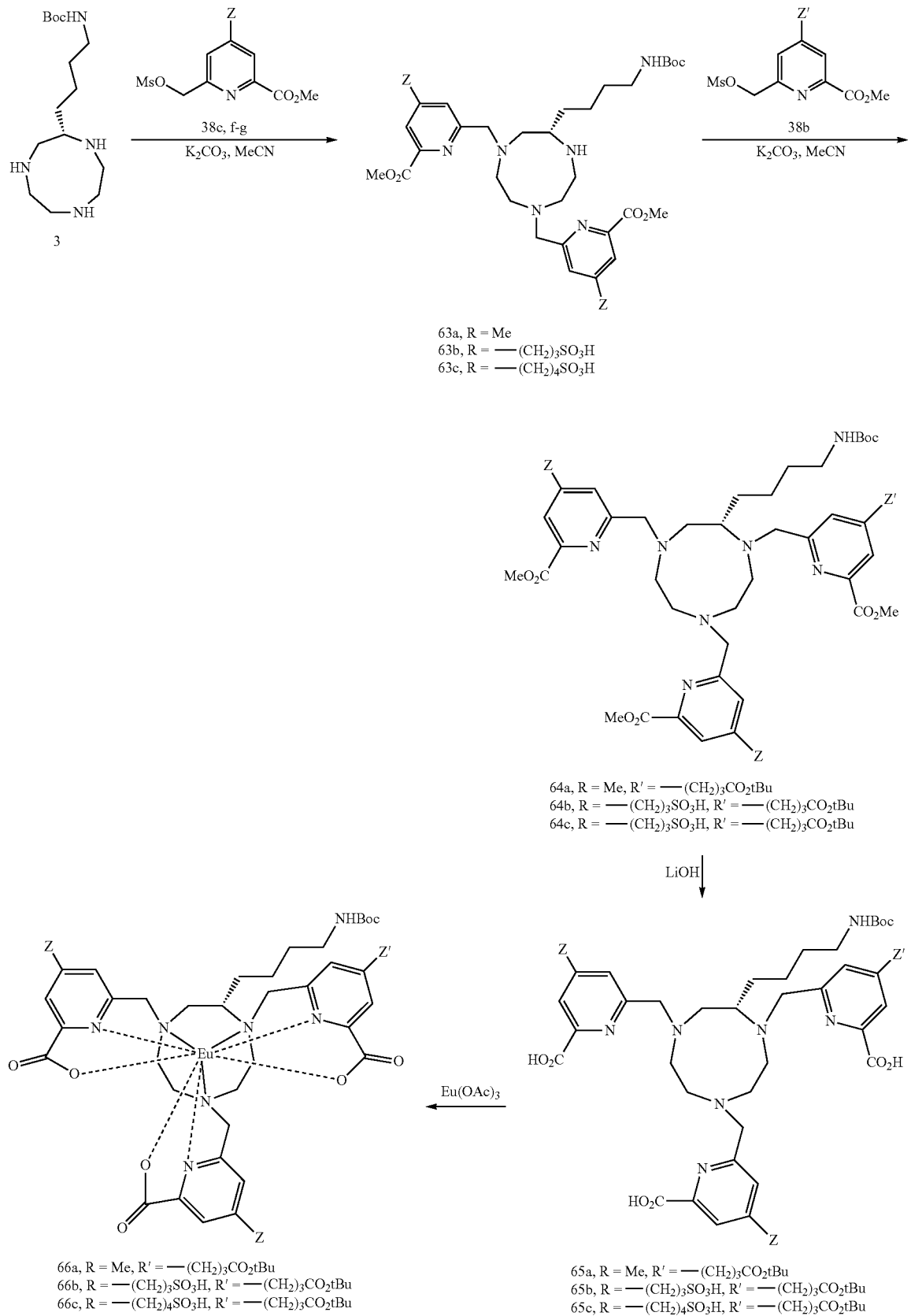

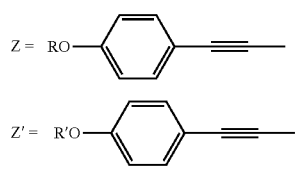

Steric hindrance (presence of a methylene) around the nitrogen atom in the alpha position of the substituent of triazacyclononane ring 3 lowers the reactivity of this atom. Thus, when triazacyclononane 3 is alkylated in the classical conditions ($K_2CO_3$, MeCN), the first two nitrogen atoms are alkylated in less than 24h. However, the third substitution is kinetically longer, which makes it possible, from a practical standpoint, to isolate the disubstituted compounds 63a-c and 67a-f by purification. This result makes it possible to obtain macrocycles bearing two types of chromophores (two chromophores identical and a third one different) without using orthogonal protective groups as described in the preceding experiments (schemes 11 and 12). The third chromophores chosen were substituents whose deprotection is orthogonal to the Boc group. The third chromophores were introduced in the presence of $K_2CO_3$ into the acetonitrile, which led after 48 h to the trialkylated compounds. The reaction sequence is identical to that described in the preceding experiments, namely hydrolysis of the ester functions (carboxylate or phosphinate) and then treatment of the ligand with europium salts, leading to the various complexes 66a-c and 70a-l (schemes 15 and 16).

Scheme 16: Synthesis of the asymmetric complexes of the "phosphinate" type derived from C-substituted TACN

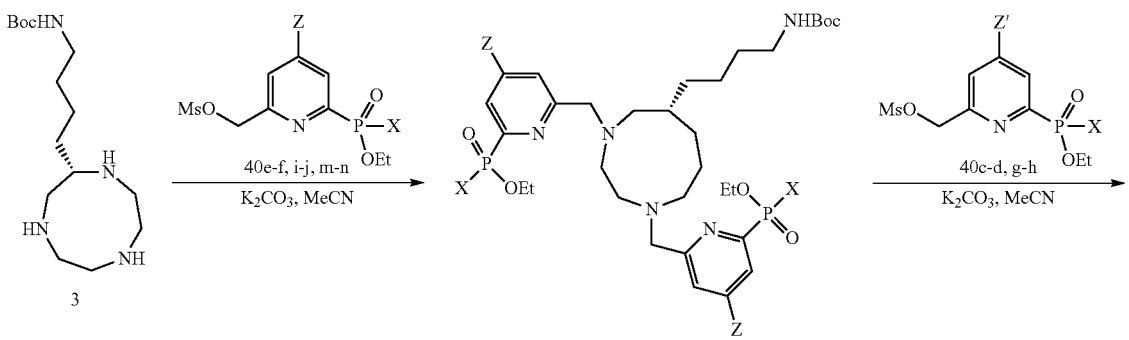

67a, R = Me, X = Me
67b, R = Me, X = Ph
67c, R = —(CH₂)₃SO₃H, X = Me
67d, R = —(CH₂)₄SO₃H, X = Ph
67e, R = —CH₂CONH-Glut-Ac, X = Me
67f, R = —CH₂CONH-Glut-Ac, X = Ph

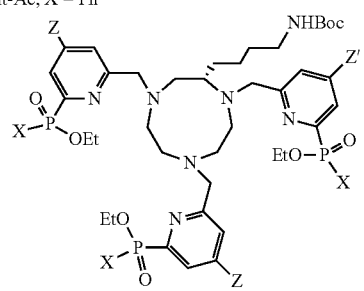

68a, R = Me, X = Me, R' = —(CH₂)₃—CO₂tBu
68b, R = Me, X = Ph, R' = —(CH₂)₃—CO₂tBu
68c, R = Me, X = Me, R' = —CH₂—CO₂Me
68d, R = Me, X = Ph, R' = —CH₂—CO₂Me
68e, R = —(CH₂)₃SO₃H, X = Me, R' = —(CH₂)₃—CO₂tBu
68f, R = —(CH₂)₃SO₃H, X = Ph, R' = —(CH₂)₃—CO₂tBu
68g, R = —(CH₂)₃SO₃H, X = Me, R' = —CH₂—CO₂Me
68h, R = —(CH₂)₃SO₃H, X = Ph, R' = —CH₂—CO₂Me
68i, R = —CH₂CONH-Glut-Ac, X = Me, R' = —(CH₂)₃—CO₂tBu
68j, R = —CH₂CONH-Glut-Ac, X = Ph, R' = —(CH₂)₃—CO₂tBu
68k, R = —CH₂CONH-Glut-Ac, X = Me, R' = —(CH₂)₃—CO₂Me
68l, R = —CH₂CONH-Glut-Ac, X = Ph, R' = —(CH₂)₃—CO₂Me

-continued

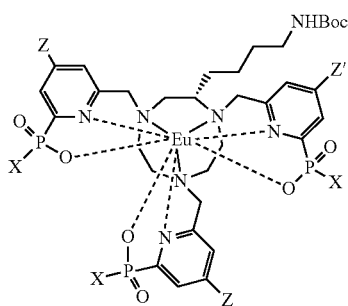

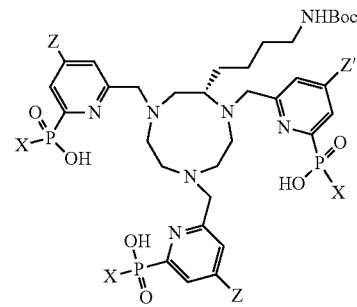

70a, R = Me, X = Me, R' = —(CH$_2$)$_3$—CO$_2$tBu
70b, R = Me, X = Ph, R' = —(CH$_2$)$_3$—CO$_2$tBu
70c, R = Me, X = Me, R' = —CH$_2$—CO$_2$H
70d, R = Me, X = Ph, R' = —CH$_2$—CO$_2$H
70e, R = —(CH$_2$)$_3$SO$_3$H, X = Me, R' = —(CH$_2$)$_3$—CO$_2$tBu
70f, R = —(CH$_2$)$_3$SO$_3$H, X = Ph, R' = —(CH$_2$)$_3$—CO$_2$tBu
70g, R = —(CH$_2$)$_3$SO$_3$H, X = Me, R' = —CH$_2$—CO$_2$H
70h, R = —(CH$_2$)$_3$CO$_2$H, X = Ph, R' = —CH$_2$—CO$_2$H
70i, R = —CH$_2$CONH-Glut-OH, X = Me, R' = —(CH$_2$)$_3$—CO$_2$tBu
70j, R = —CH$_2$CONH-Glut-OH, X = Ph, R' = —(CH$_2$)$_3$—CO$_2$tBu
70k, R = —CH$_2$CONH-Glut-OH, X = Me, R' = —(CH$_2$)$_3$—CO$_2$H
70l, R = —CH$_2$CONH-Glut-OH, X = Ph, R' = —(CH$_2$)$_3$—CO$_2$H 69a, R = Me, X = Me, R' = —(CH$_2$)$_3$—CO$_2$tBu
69b, R = Me, X = Ph, R' = —(CH$_2$)$_3$—CO$_2$tBu
69c, R = Me, X = Me, R' = —CH$_2$—CO$_2$H
69d, R = Me, X = Ph, R' = —CH$_2$—CO$_2$H
69e, R = —(CH$_2$)$_3$SO$_3$H, X = Me, R' = —(CH$_2$)$_3$—CO$_2$tBu
69f, R = —(CH$_2$)$_3$SO$_3$H, X = Ph, R' = —(CH$_2$)$_3$—CO$_2$tBu
69g, R = —(CH$_2$)$_3$SO$_3$H, X = Me, R' = —CH$_2$—CO$_2$H
69h, R = —(CH$_2$)$_3$CO$_2$H, X = Ph, R' = —CH$_2$—CO$_2$H
69i, R = —CH$_2$CONH-Glut-OH, X = Me, R' = —(CH$_2$)$_3$—CO$_2$tBu
69j, R = —CH$_2$CONH-Glut-OH, X = Ph, R' = —(CH$_2$)$_3$—CO$_2$tBu
69k, R = —CH$_2$CONH-Glut-OH, X = Me, R' = —(CH$_2$)$_3$—CO$_2$H
69l, R = —CH$_2$CONH-Glut-OH, X = Ph, R' = —(CH$_2$)$_3$—CO$_2$H X = Me, Ph

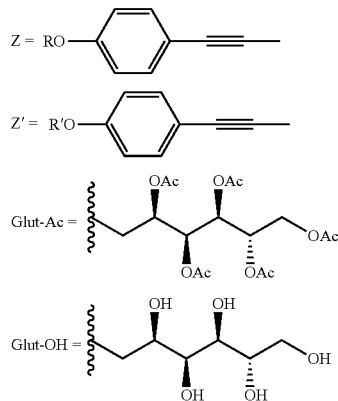

Characteristics of the Europium Complexes:

The characteristics of the various europium complexes prepared above are specified in the following Table 1:

TABLE 1

| Comp. | Has one or more solubilizing groups | The water-soluble complex has a group (amine or COOH) allowing conjugation with another molecule | To improve solubility, must be modified by introduction of groups that solubilize via an amine, COOH (after activation) or phenol group | Can be conjugated with another molecule, by introduction of an arm bearing a solubilizing group AND a reacting group, via an amine group, COOH (after activation) |
|---|---|---|---|---|
| 43a | − | − | + | − |
| 43b | + | − | − | − |
| 43c | − | − | − | − |
| 43d | + | − | − | − |
| 43e | − | − | + | − |
| 43f | + | − | − | − |
| 43g | + | − | − | − |
| 51a | − | − | + | + |
| 51b | + | + | − | − |
| 51c | + | + | − | − |
| 51d | + | − | + | + |
| 51e | + | + | − | − |
| 51f | + | + | − | − |
| 59a | − | − | + | + |

TABLE 1-continued

| Comp. | Has one or more solubilizing groups | The water-soluble complex has a group (amine or COOH) allowing conjugation with another molecule | To improve solubility, must be modified by introduction of groups that solubilize via an amine, COOH (after activation) or phenol group | Can be conjugated with another molecule, by introduction of an arm bearing a solubilizing group AND a reacting group, via an amine group, COOH (after activation) |
|---|---|---|---|---|
| 59b | + | + | − | − |
| 59c | + | + | − | − |
| 59d | + | + | − | − |
| 59e | + | + |  |  |
| 59f | − | + | + | − |
| 66a | + | + | − | − |
| 66b | + | + | − | − |
| 66c | + | + | − | − |
| 46a | − | − | + | − |
| 46b | − | − | + | − |
| 46c | + | − | − | − |
| 46d | + | − | − | − |
| 46e | − | − | − | − |
| 46f | − | − | − | − |
| 46g | + | − | − | − |
| 46h | + | − | − | − |
| 46i | + | − | − | − |
| 46j | + | − | − | − |
| 46k | + | − | − | − |
| 46l | + | − | − | − |
| 46m | + | − | − | − |
| 46n | + | − | − | − |
| 46o | − | − | + | − |
| 46p | − | − | + | − |
| 56a | − | − | + | + |
| 56b | − | − | + | + |
| 56c | + | − | − | + |
| 56d | + | − | − | + |
| 56e | + | − | − | + |
| 56f | + | − | − | + |
| 56g | + | + | − | − |
| 56h | + | + | − | − |
| 56i | + | + | − | − |
| 56j | + | + | − | − |
| 56k | + | + | − | − |
| 56l | + | + | − | − |
| 56m | + | + | − | − |
| 56n | + | + | − | − |
| 56o | + | + | − | − |
| 56p | + | + | − | − |
| 56q | + | + | − | − |
| 56r | + | + | − | − |
| 62a | − | − | + | + |
| 62b | − | − | + | + |
| 62c | + | + | − | − |
| 62d | + | + | − | − |
| 62e | + | + | − | − |
| 62f | + | + | − | − |
| 62g | + | + | − | − |
| 62h | + | + | − | − |
| 62i | + | + | − | − |
| 62j | + | + | − | − |
| 62k | − | + | + | − |
| 62l | − | + | + | − |
| 70a | + | + | − | − |
| 70b | + | + | − | − |
| 70c | + | + | − | − |
| 70d | + | + | − | − |
| 70e | + | + | − | − |
| 70f | + | + | − | − |
| 70g | + | + | − | − |
| 70h | + | + | − | − |
| 70i | + | + | − | − |
| 70j | + | + | − | − |
| 70k | + | + | − | − |
| 70l | + | + | − | − |

The compounds satisfying (+) the criterion of the first column are compounds according to the invention comprising groups that increase their water-solubility. They cannot be conjugated to another molecule but can be used as conventional fluorescent compounds.

The compounds satisfying (+) the criterion of the second column possess a reactive group allowing conjugation of the europium complex with a molecule that we wish to label. In the examples in this table, these reactive groups are amine groups, protected or not, or carboxylate groups, protected or not, the latter having to be activated, for example in the form of N-hydroxysuccinimide ester. A person skilled in the art may employ the classical techniques of chemistry in order to use these amine or carboxylate groups for conjugating these complexes with a molecule of interest. When the reactive group is an amine, coupling reagents may be used, for example DCC (dicyclohexylcarbodiimide) and NHS (N-hydroxysuccinimide), to form a species capable of reacting with an amine present on a molecule that we wish to label. Other reagents known by a person skilled in the art may be used, such as TSTU (O—(N-succinimidyl)-1,1,3,3-tetramethyluronium tetrafluoroborate), HATU or else TBTU.

The compounds satisfying (+) the criterion of the third column are not compounds according to the invention but intermediates that lead to these compounds: in fact they possess carboxylate reactive groups (which must be activated, e.g. in the form of NHS esters), amines or phenols (each optionally protected) allowing introduction of groups that will increase the water-solubility of the complexes in question. After deprotection of the Boc, CO$_2$tBu or MOM groups, a person skilled in the art can use classical techniques to obtain the compounds according to the invention starting from these europium complexes. In particular, when the reacting groups are amines, he will be able to react them for example with the following electrophilic compounds, comprising an NHS ester function and a group that increases the hydrophilic character (quaternary ammonium, phosphonate or sulfonate):

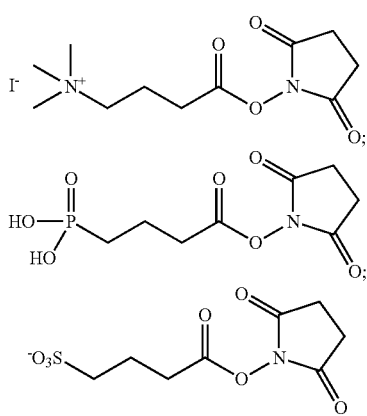

The synthesis of the first compound is described in Analytical Chemistry, 2006, 78, 4175-4183, that of the second compound is described in European Journal of Chemistry, 2001, 349-352, and that of the third compound is described in patent application WO 02/095412.

When the reacting groups are carboxylates activated in the form of NHS ester, the following nucleophilic groups may for example be used for introducing the groups conferring better solubility:

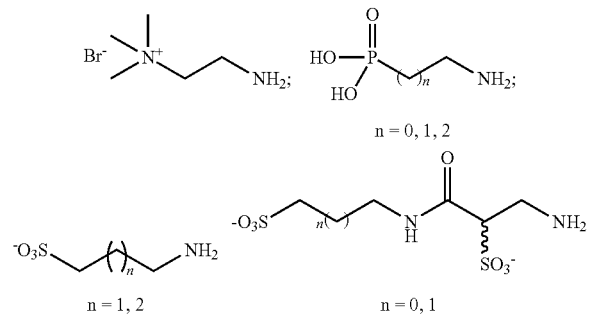

The first reagent is commercially available (Toronto Research Chemicals), as are the second and the third (Sigma). The fourth was synthesized according to the following scheme by condensing the NHS ester prepared according to the procedures described in Bioconjugate Chemistry, 2008, 19, 279-289, on taurine (n=0) or homotaurine (n=1). These last-mentioned compounds were then deprotected (Fmoc group) in the classical conditions known by a person skilled in the art.

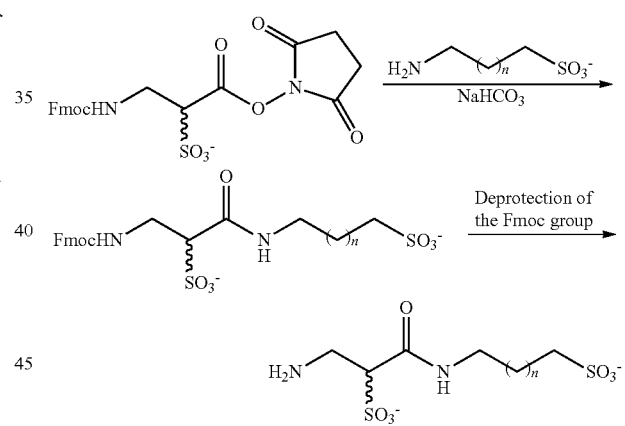

Finally, when the reacting group is a phenol or a primary, secondary or tertiary amine, a sulfonate group can be introduced on the complex by reaction with a sultone of the following formula (commercially available, Sigma):

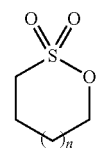

n = 0, 1

The complexes satisfying (+) the criterion of the fourth column only comprise a single amine or carboxylate reactive group, protected or not. Complexes according to the invention with improved water-solubility and which can be conjugated to another molecule may be prepared by reacting the complexes comprising an amine (optionally after deprotection of the Boc groups) with compounds of the formula:

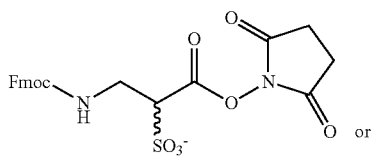

or

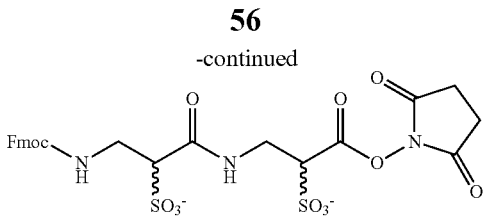

The synthesis of these two compounds is described in Bioconjugate Chemistry, 2008, 19, 279-289.

These various aspects are represented in schemes 17 and 18.

Scheme 17: Synthesis of the water-soluble functionalized asymmetric complexes of the "carboxylate" type

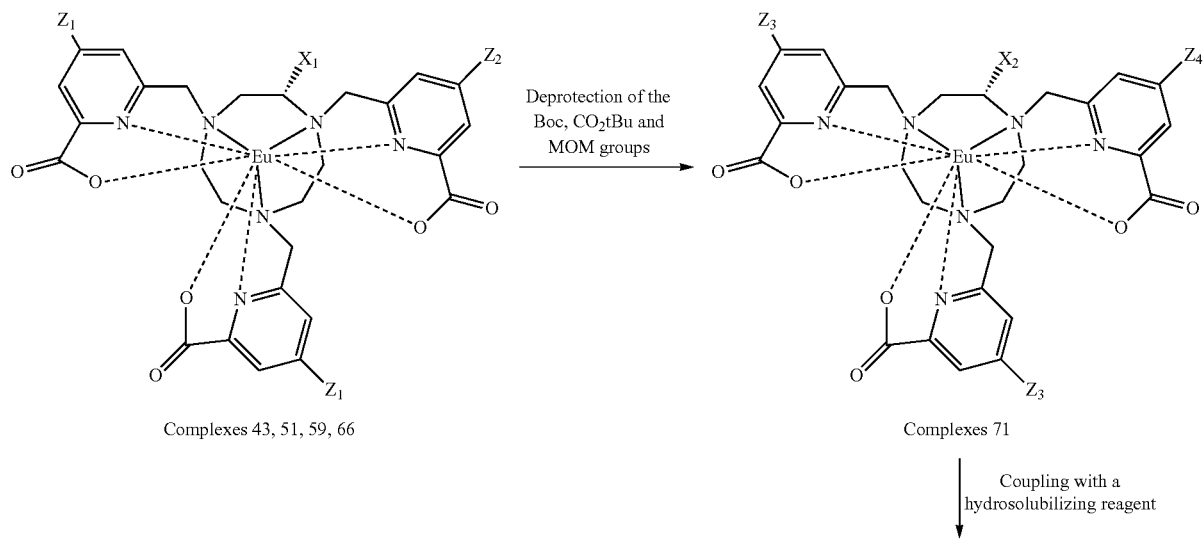

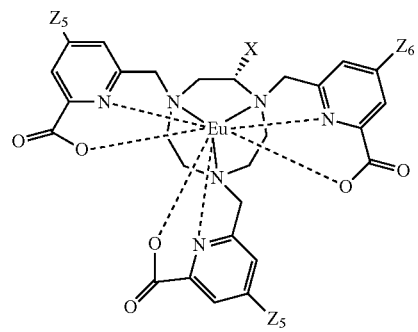

Water-soluble complexes 72

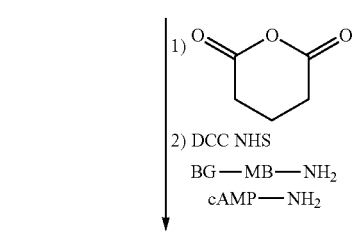

Water-soluble functionalized complexes 73

-continued

NHS hydrosolubilizing reagents or electrophilic species

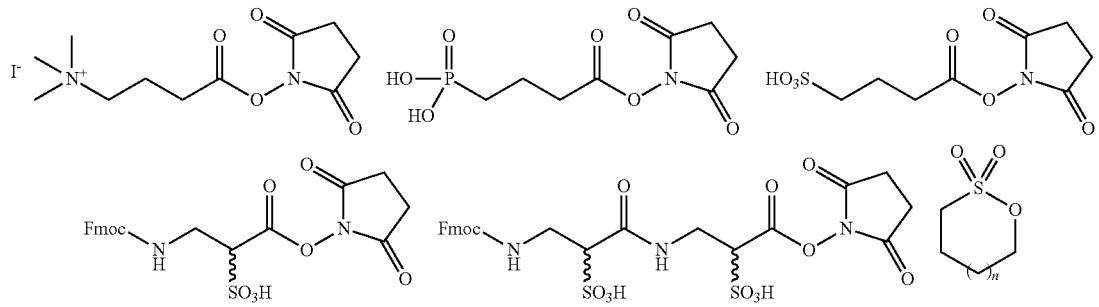

NH2 hydrosolubilizing reagents or nucleophilic species

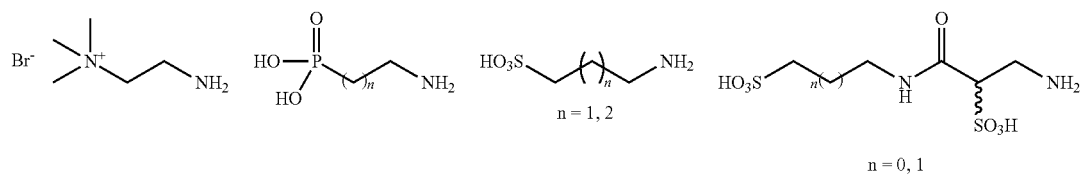

n = 0, 1

$X_1 =$ H, —(CH$_2$)$_4$—NHBoc,
$X_2 =$ —(CH$_2$)$_4$—NH$_2$

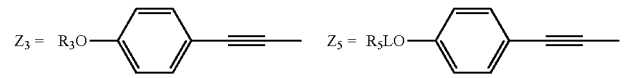

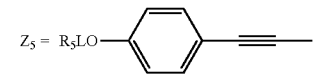

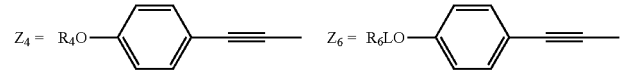

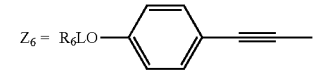

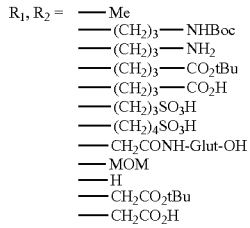

$R_1, R_2 =$ —Me
—(CH$_2$)$_3$—NHBoc
—(CH$_2$)$_3$—NH$_2$
—(CH$_2$)$_3$—CO$_2$tBu
—(CH$_2$)$_3$—CO$_2$H
—(CH$_2$)$_3$SO$_3$H
—(CH$_2$)$_4$SO$_3$H
—CH$_2$CONH-Glut-OH
—MOM
—H
—CH$_2$CO$_2$tBu
—CH$_2$CO$_2$H

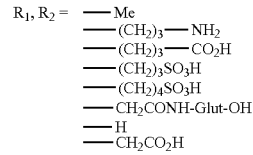

$R_3, R_4 =$ —Me
—(CH$_2$)$_3$—NH$_2$
—(CH$_2$)$_3$—CO$_2$H
—(CH$_2$)$_3$SO$_3$H
—(CH$_2$)$_4$SO$_3$H
—CH$_2$CONH-Glut-OH
—H
—CH$_2$CO$_2$H

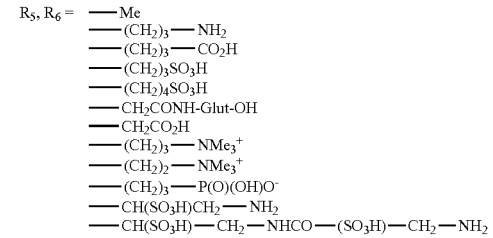

$R_5, R_6 =$ —Me
—(CH$_2$)$_3$—NH$_2$
—(CH$_2$)$_3$—CO$_2$H
—(CH$_2$)$_3$SO$_3$H
—(CH$_2$)$_4$SO$_3$H
—CH$_2$CONH-Glut-OH
—CH$_2$CO$_2$H
—(CH$_2$)$_3$—NMe$_3^+$
—(CH$_2$)$_2$—NMe$_3^+$
—(CH$_2$)$_3$—P(O)(OH)O$^-$
—CH(SO$_3$H)CH$_2$—NH$_2$
—CH(SO$_3$H)—CH$_2$—NHCO—(SO$_3$H)—CH$_2$—NH$_2$ Scheme 18: Synthesis of the water-soluble functionalized asymmetric complexes of the "phosphinate" type

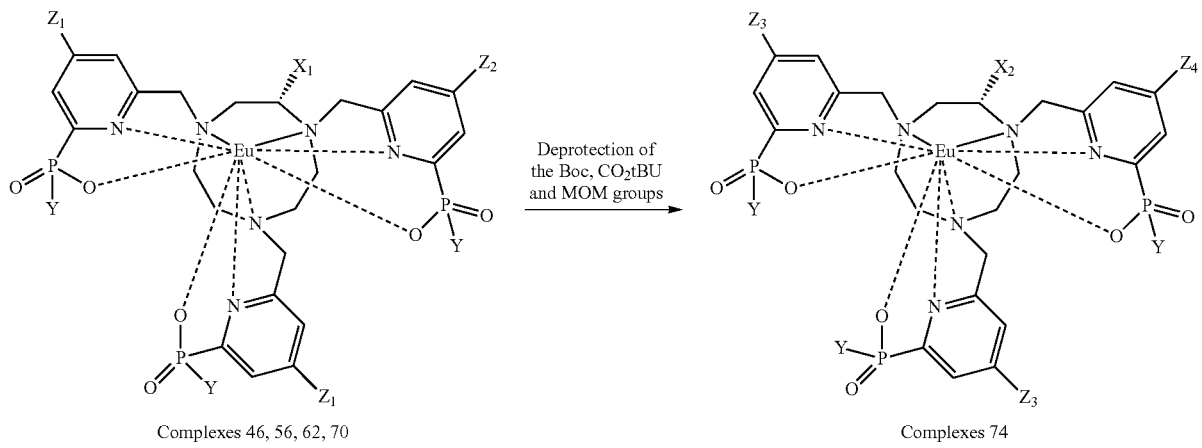

Complexes 46, 56, 62, 70

Deprotection of the Boc, CO$_2$tBU and MOM groups

Complexes 74

$X_1 =$ H, —(CH$_2$)$_4$—NHBoc,
$X_2 =$ —(CH$_2$)$_4$—NH$_2$

Coupling with a hydrosolubilizing reagent

59

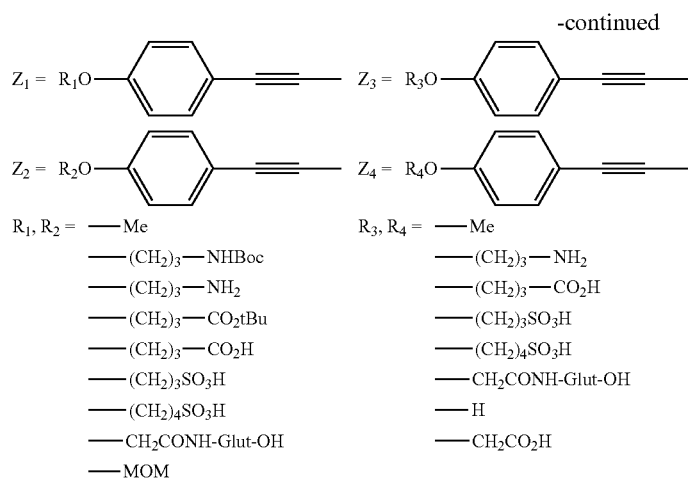

$Z_1 = R_1O-C_6H_4-C\equiv C-$
$Z_2 = R_2O-C_6H_4-C\equiv C-$ $R_1, R_2 =$
— Me
— $(CH_2)_3$—NHBoc
— $(CH_2)_3$—$NH_2$
— $(CH_2)_3$—$CO_2tBu$
— $(CH_2)_3$—$CO_2H$
— $(CH_2)_3SO_3H$
— $(CH_2)_4SO_3H$
— $CH_2CONH$-Glut-OH
— MOM $Z_3 = R_3O-C_6H_4-C\equiv C-$
$Z_4 = R_4O-C_6H_4-C\equiv C-$ $R_3, R_4 =$
— Me
— $(CH_2)_3$—$NH_2$
— $(CH_2)_3$—$CO_2H$
— $(CH_2)_3SO_3H$
— $(CH_2)_4SO_3H$
— $CH_2CONH$-Glut-OH
— H
— $CH_2CO_2H$ — H
— $CH_2CO_2tBu$
— $CH_2CO_2H$ Y = Ph, Me

60

-continued

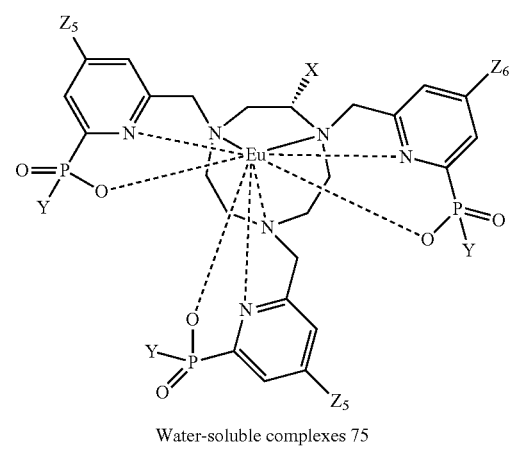

Water-soluble complexes 75

1) 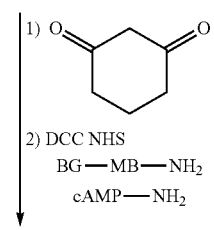

2) DCC NHS
BG—MB—$NH_2$
cAMP—$NH_2$

Water-soluble functionalized complexes 76

$Z_5 = R_5LO-C_6H_4-C\equiv C-$
$Z_6 = R_6LO-C_6H_4-C\equiv C-$ $R_5, R_6 =$ — Me NHS hydrosolubilizing reagents or electrophilic species

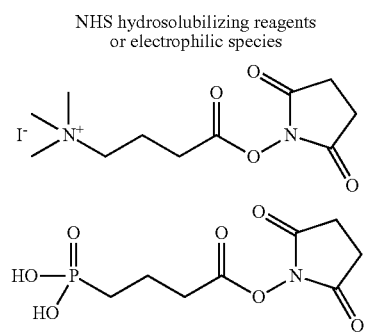

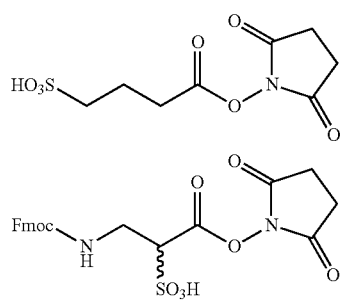

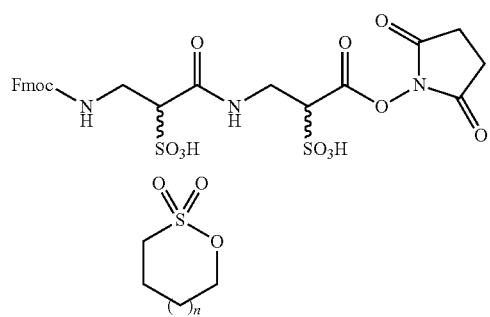

— $(CH_2)_3$—$NH_2$
— $(CH_2)_3$—$CO_2H$
— $(CH_2)_3SO_3H$
— $(CH_2)_4SO_3H$
— $CH_2CONH$-Glut-OH
— $CH_2CO_2H$
— $(CH_2)_3$—$NMe_4^+$
— $(CH_2)_2$—$NMe_4^+$
— $(CH_2)_3$—$P(O)(OH)O^-$
— $CH(SO_3H)CH_2$—$NH_2$
— $CH(SO_3H)$—$CH_2$—NHCO—$(SO_3H)$—$CH_2$—$NH_2$

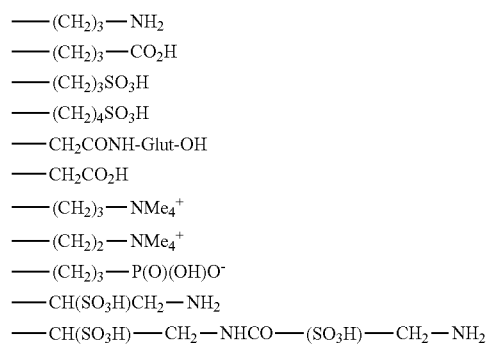

NH₂ hydrosolubilizing reagents or nucleophilic species

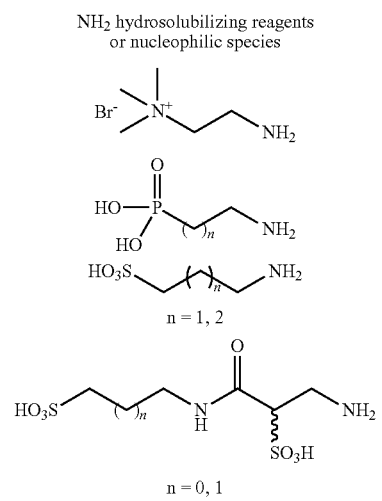

n = 1, 2 n = 0, 1

In a particular embodiment of the invention, the spacer arm L (L₁, L₁' or L₂) comprises one or more sulfonate units. Preparation of these compounds starting from europium complexes described above, as well as that of conjugates of these complexes with cyclic AMP or a benzylguanine derivative, is summarized in schemes 19 and 20.

Scheme 19: Examples of functionalization with mono- and disulfonate linkers

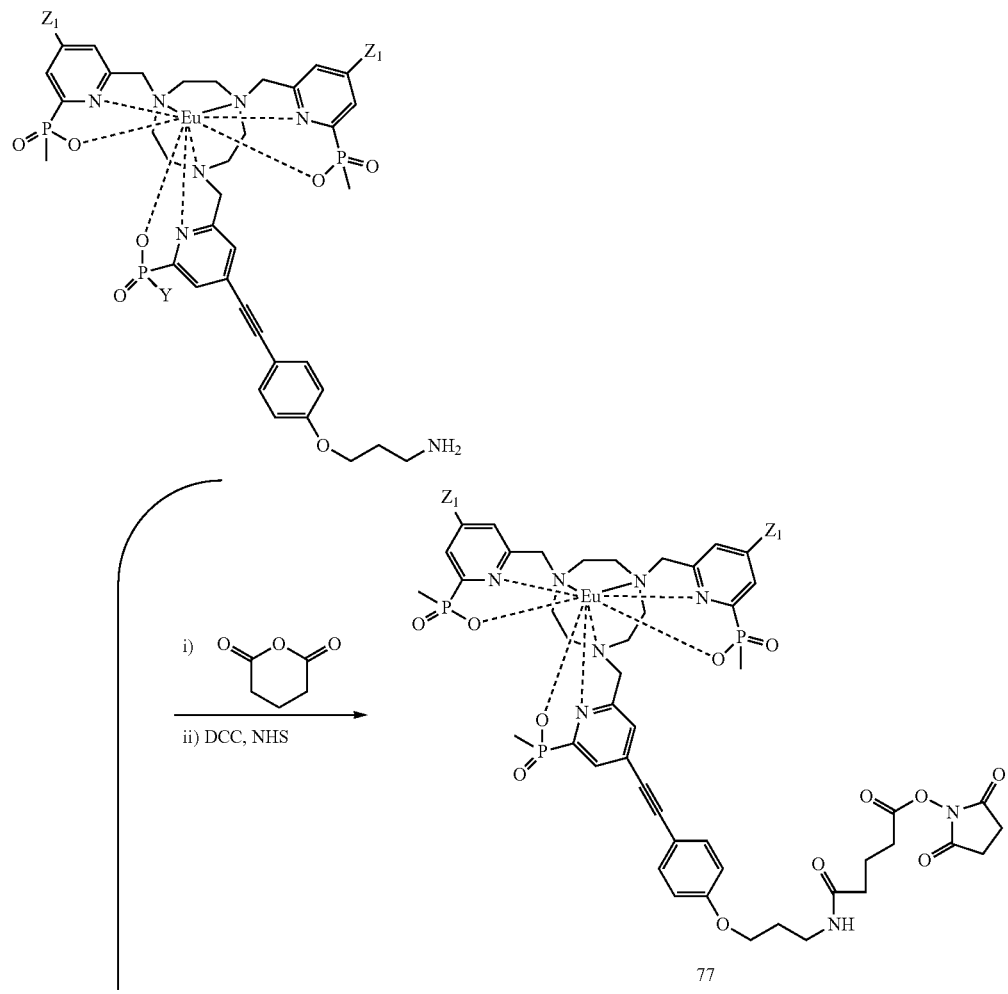

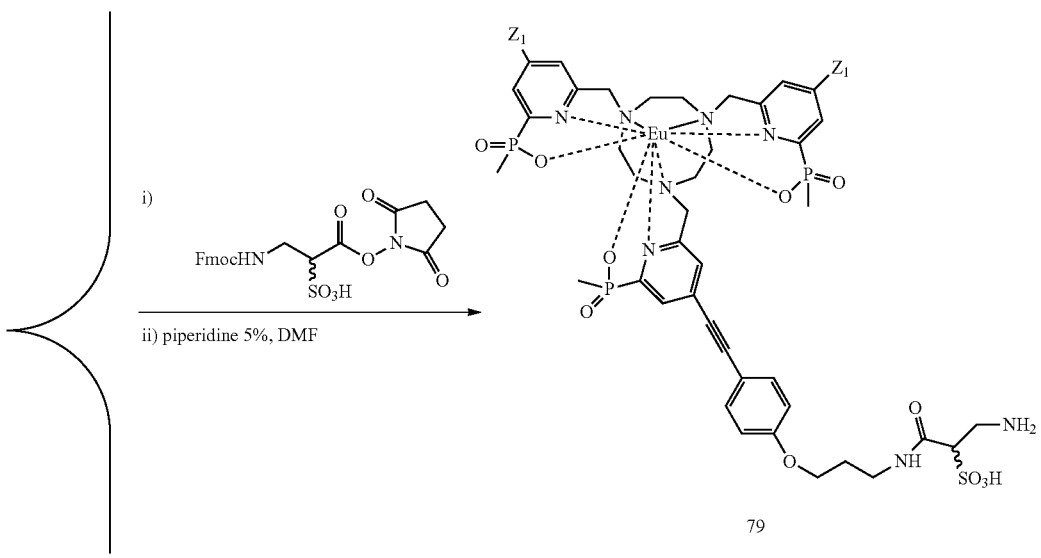
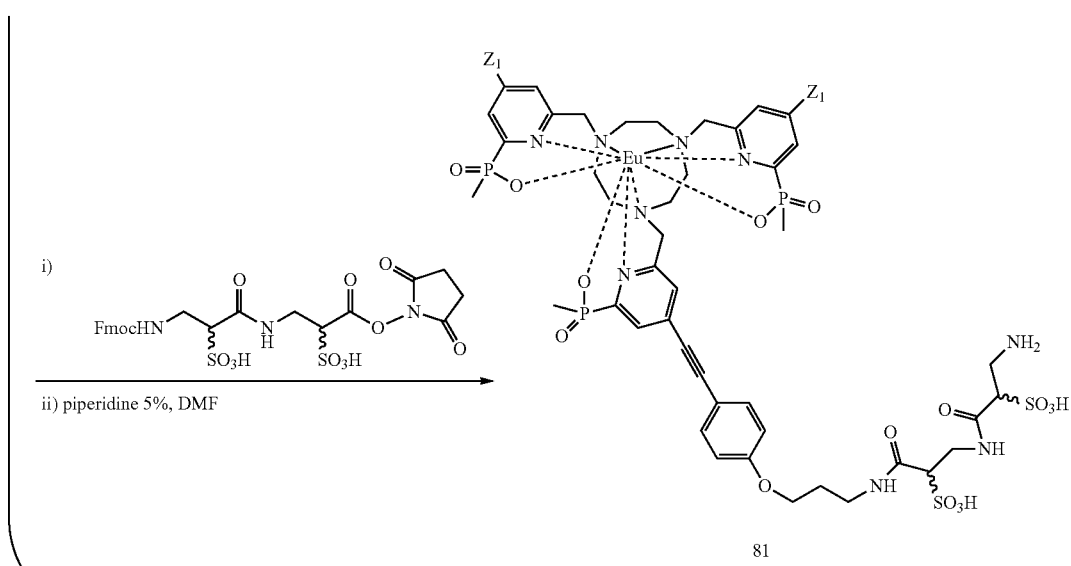
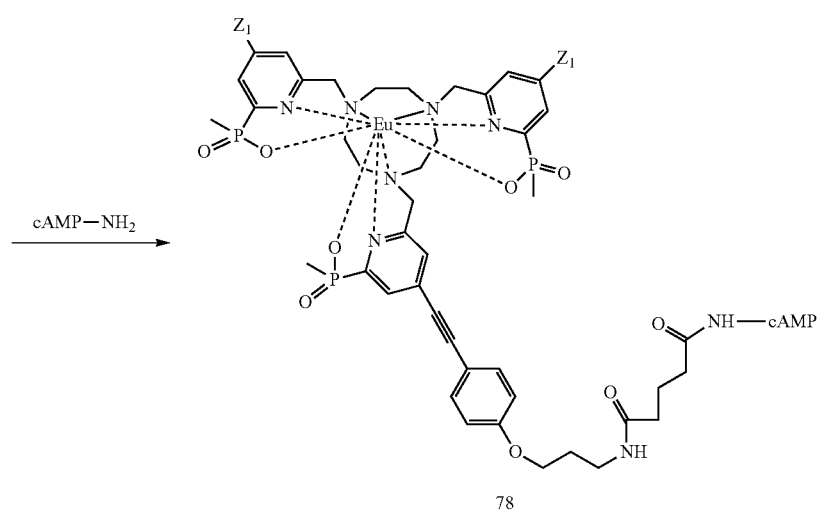

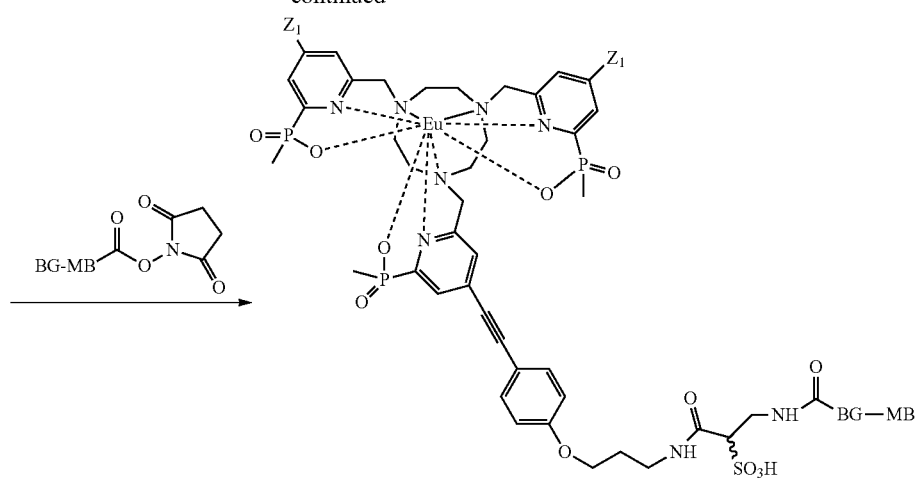
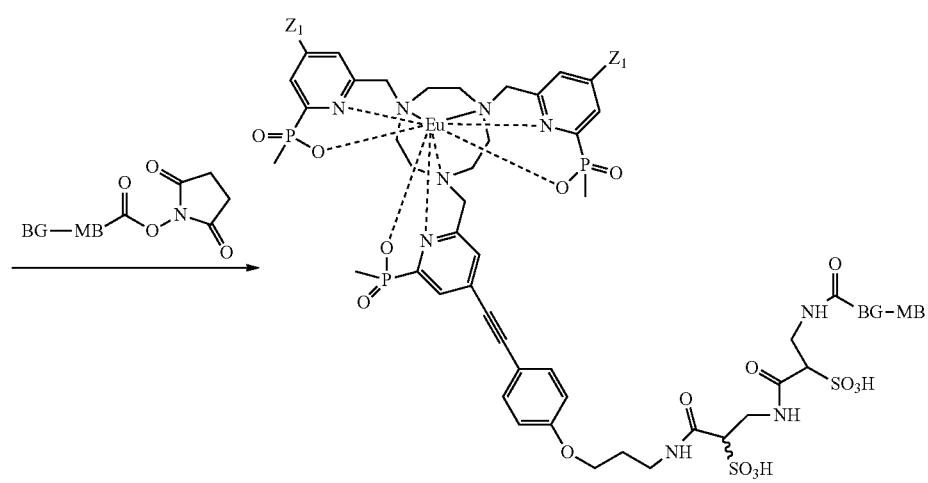
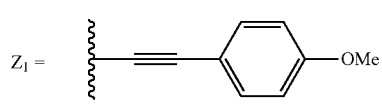
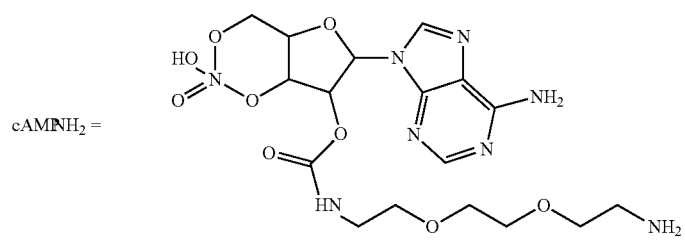
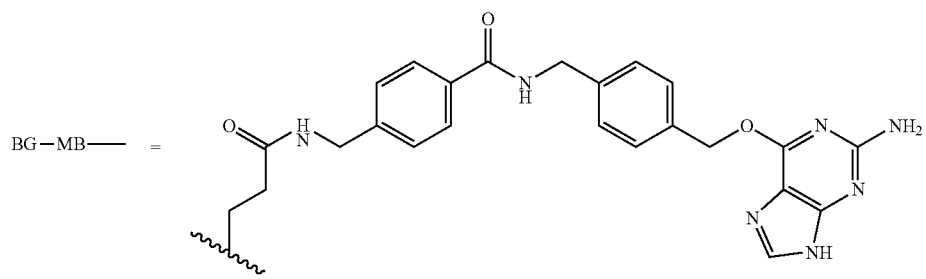

Scheme 20: examples of functionalization with mono- and disulfonate linkers
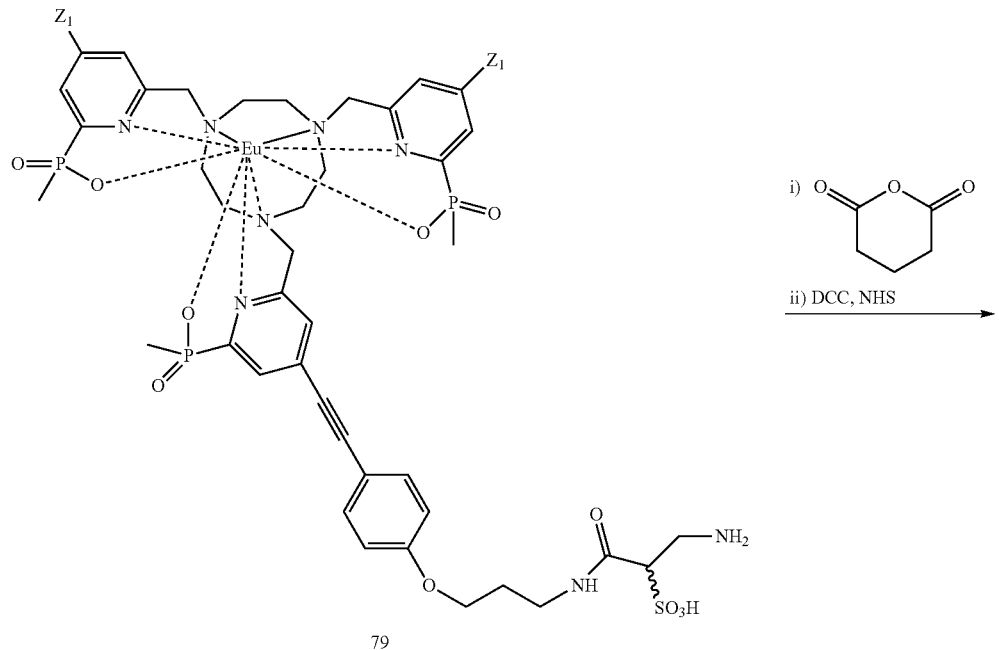
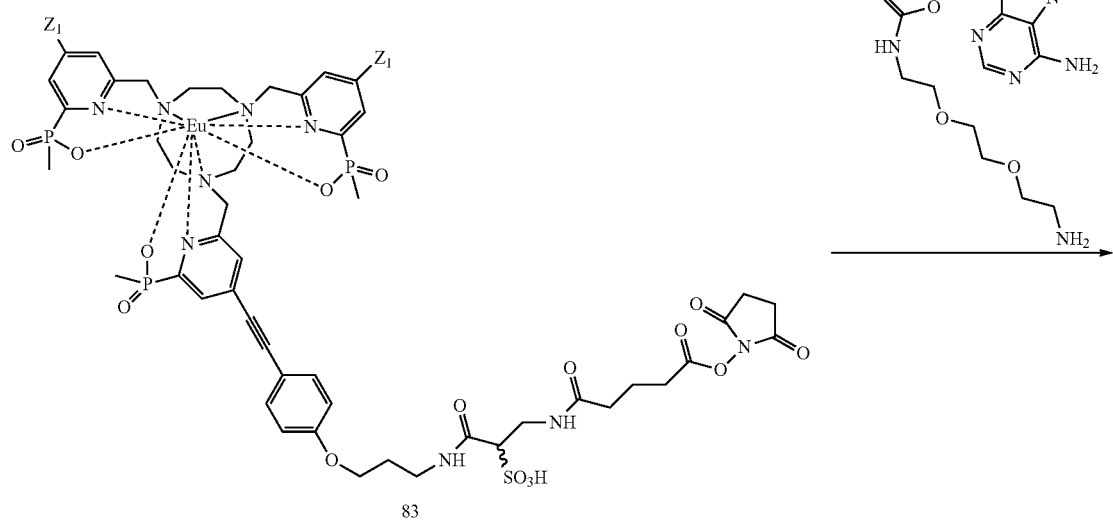

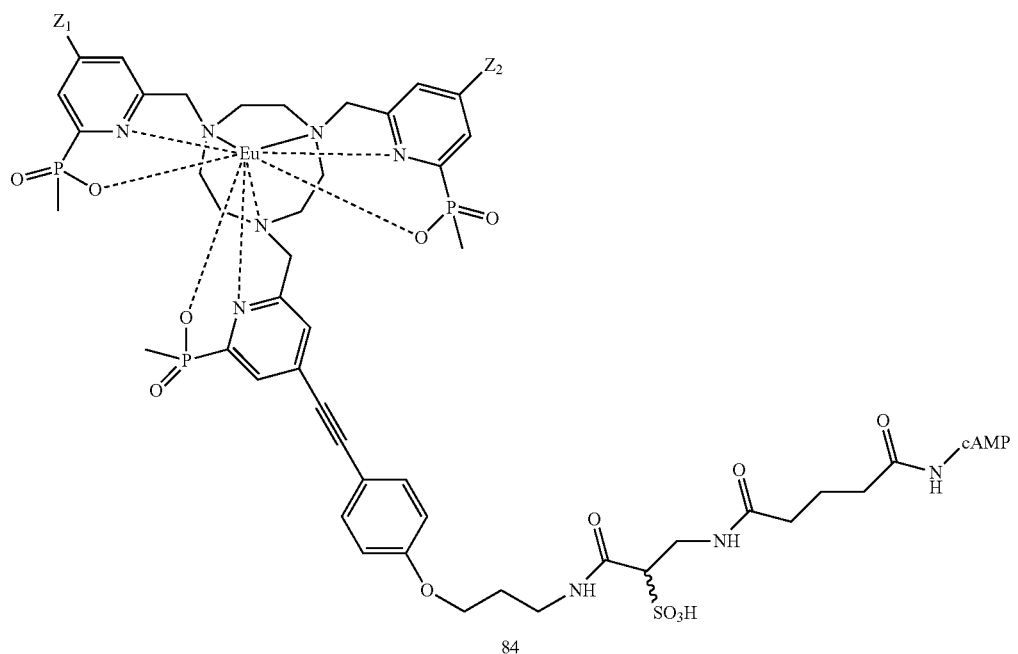
84
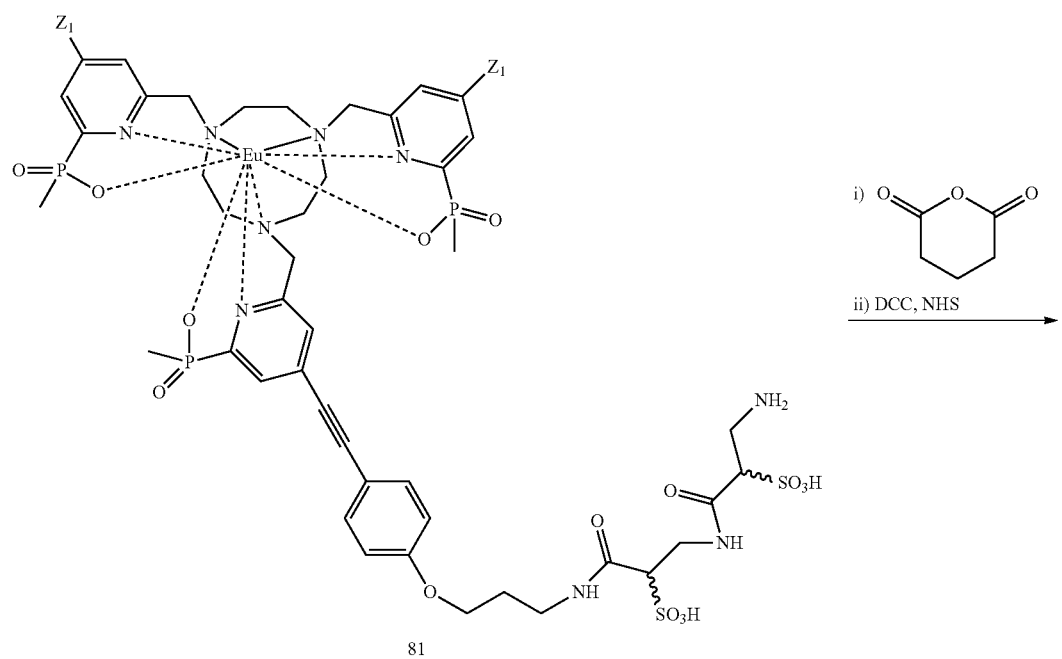
81
i) 
ii) DCC, NHS

-continued
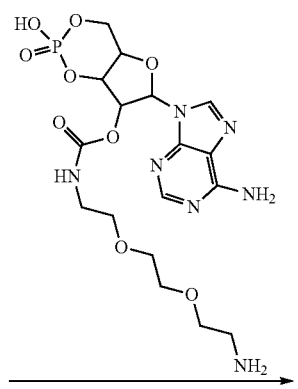
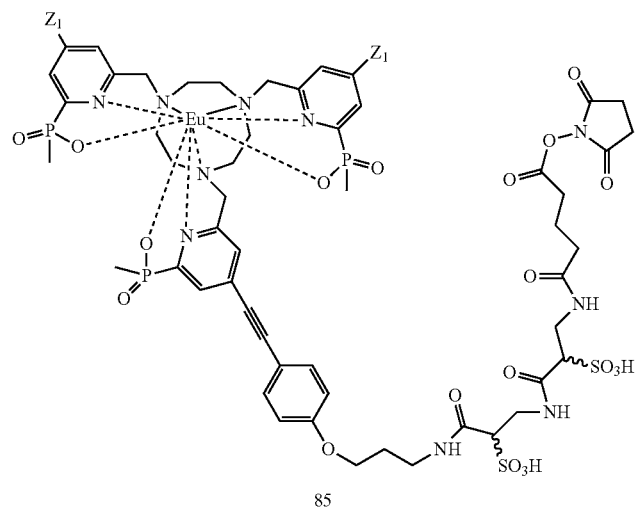
85
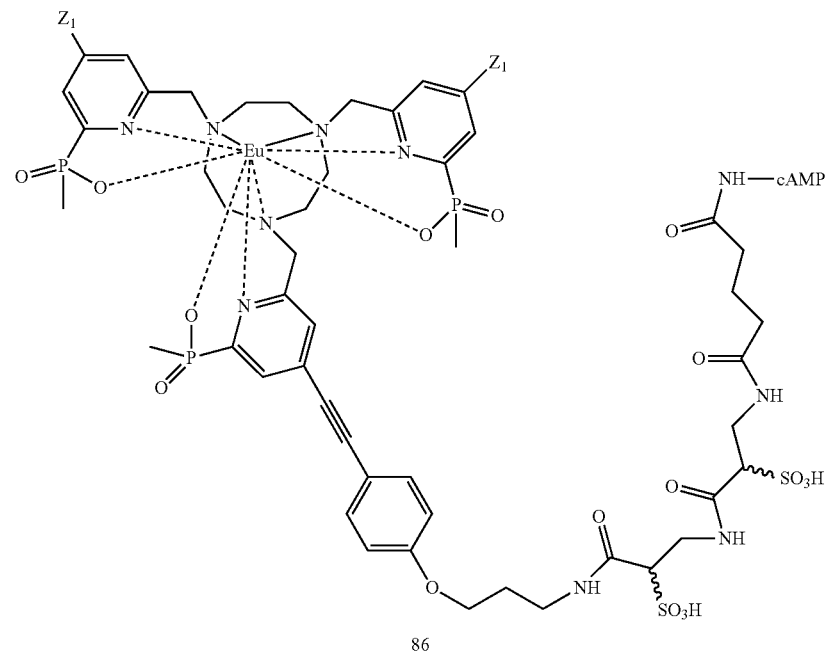
86
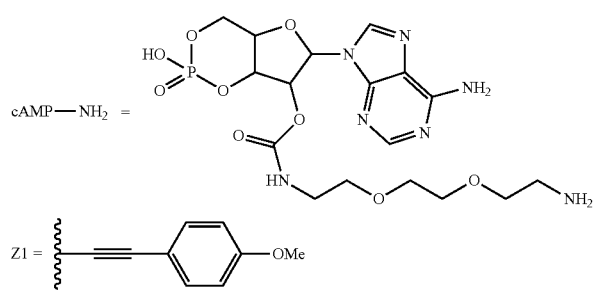

Scheme 21: Examples of maleimide, biotin and peptide functionalization
The preparation of conjugates of europium complexes according to the invention with cationic peptides (polyarginine or polylysine) and with biotin is represented in scheme 21.
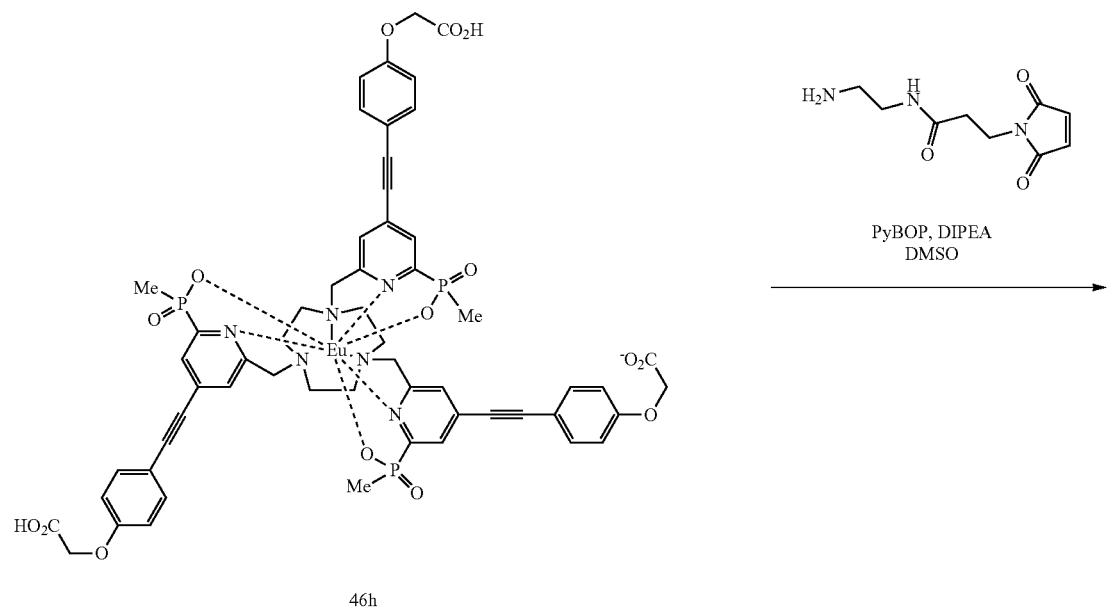
46h
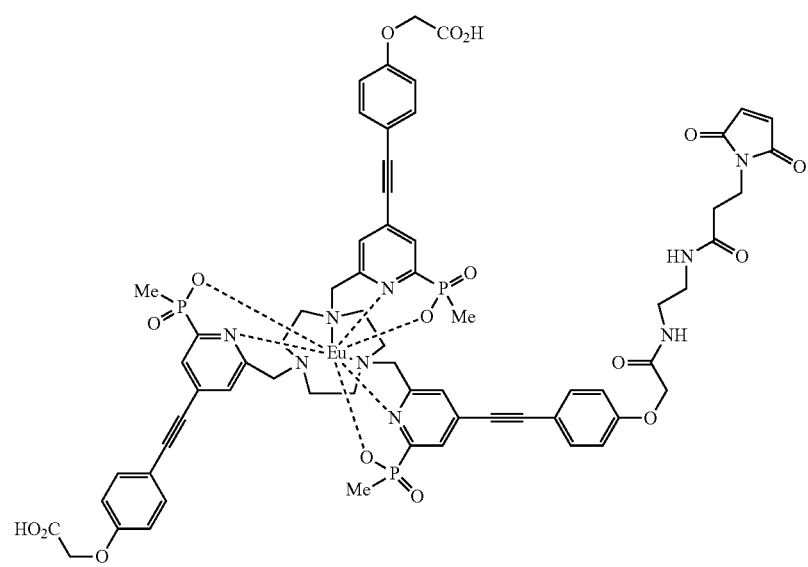
87
DMF, H$_2$N—CGPKKKRKVCO$_2$H
Phosphate buffer -continued
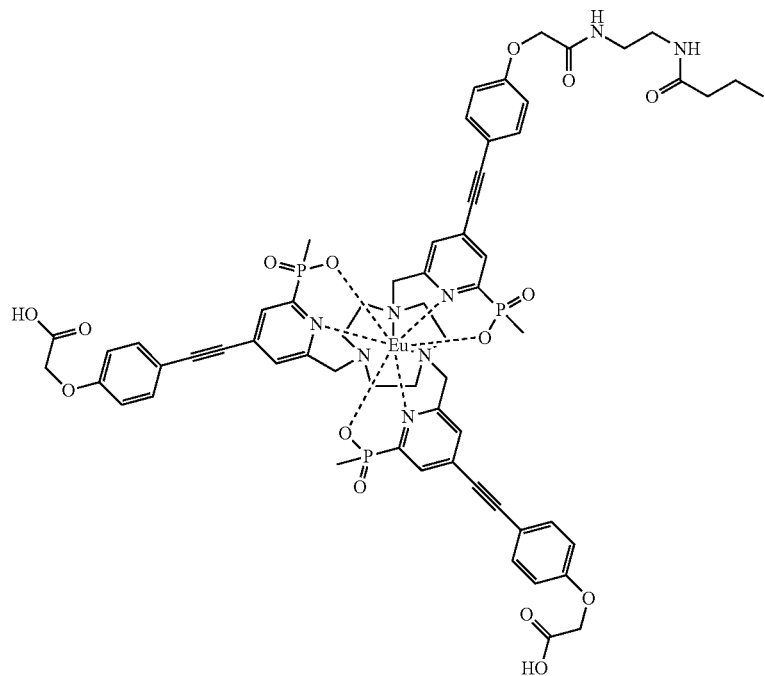
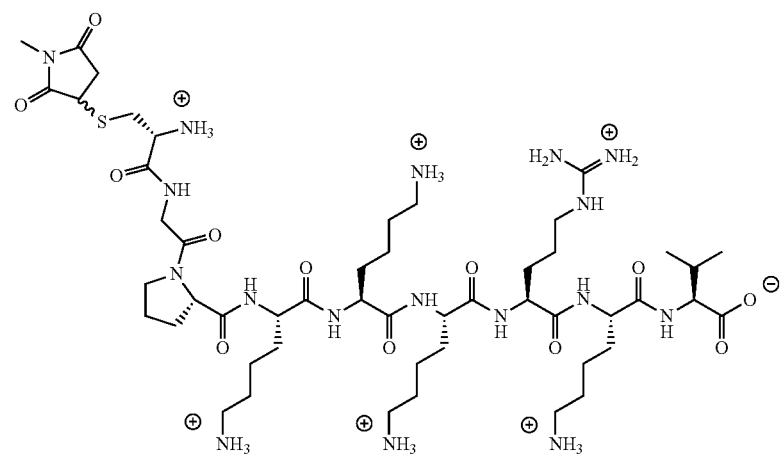

-continued
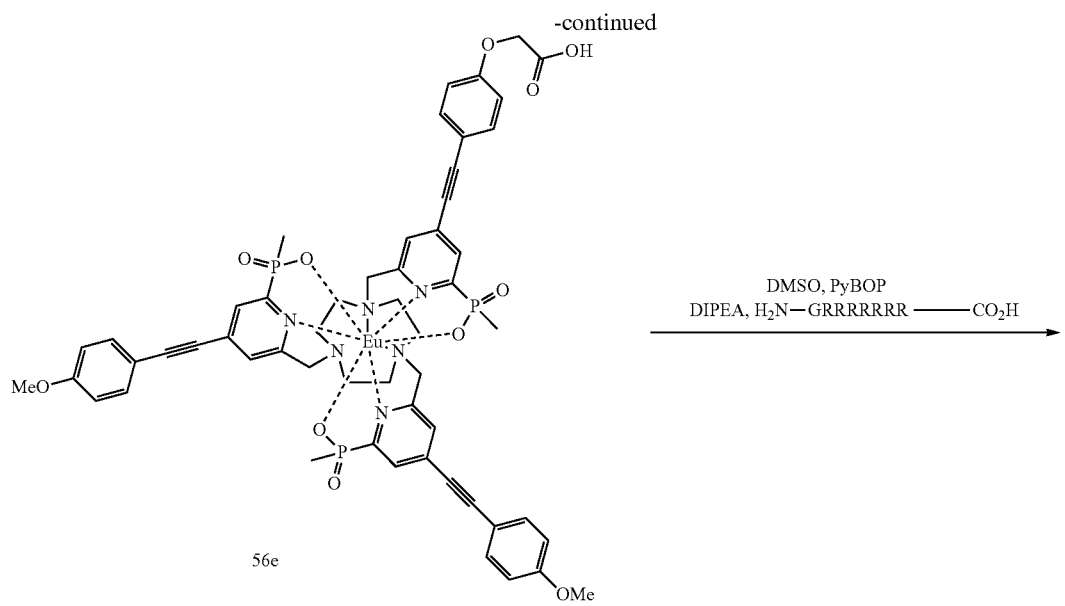
56e
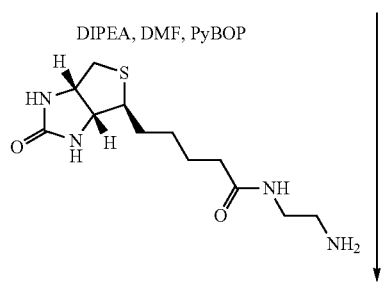
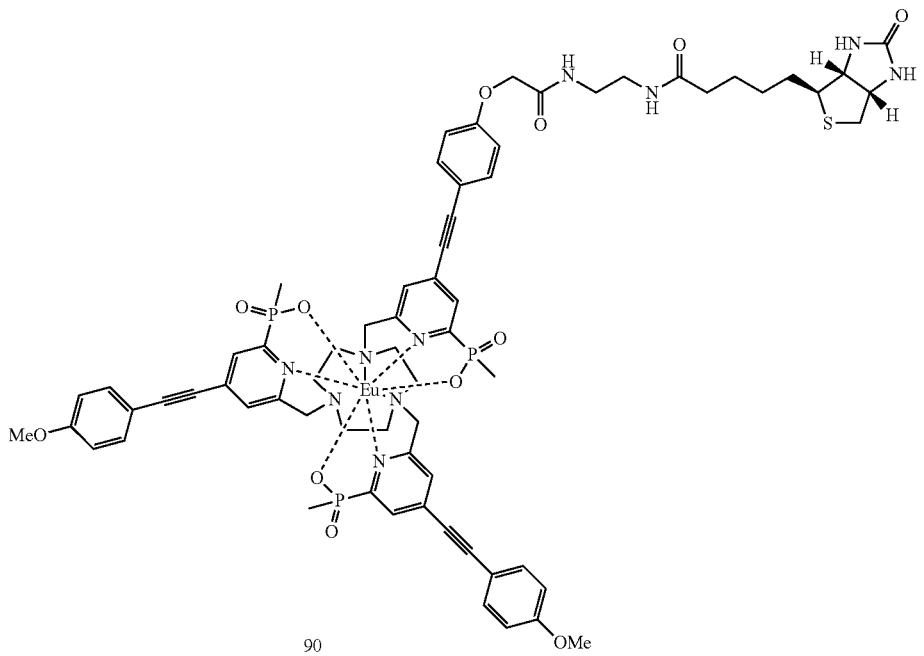
90

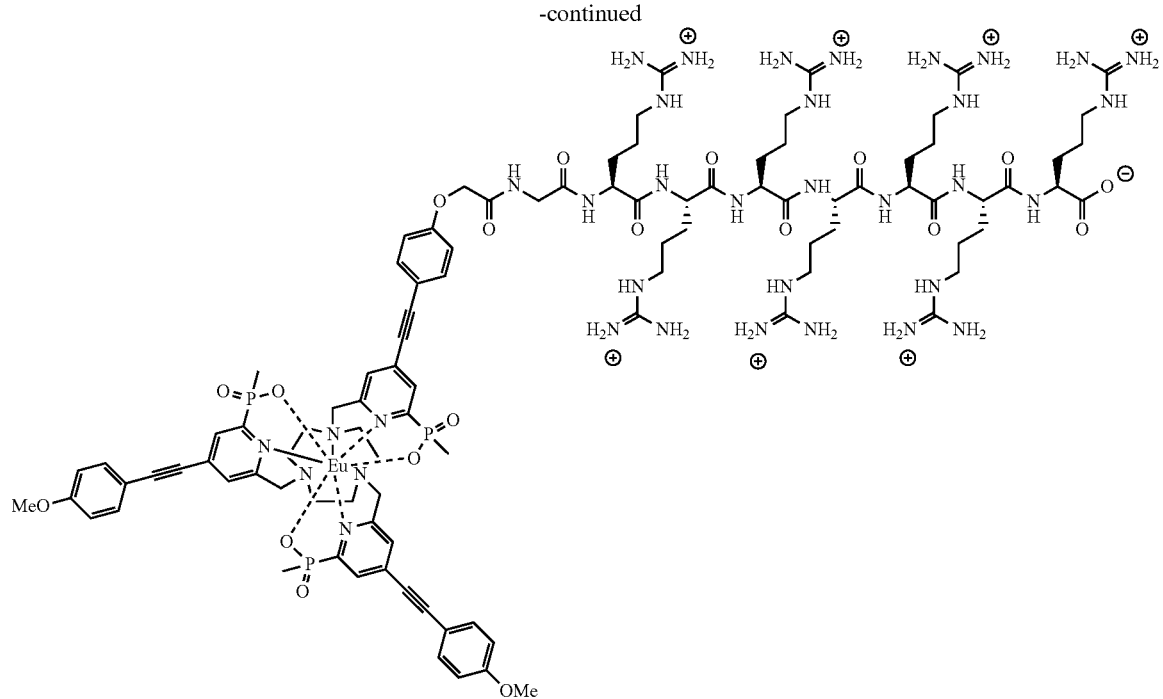
89

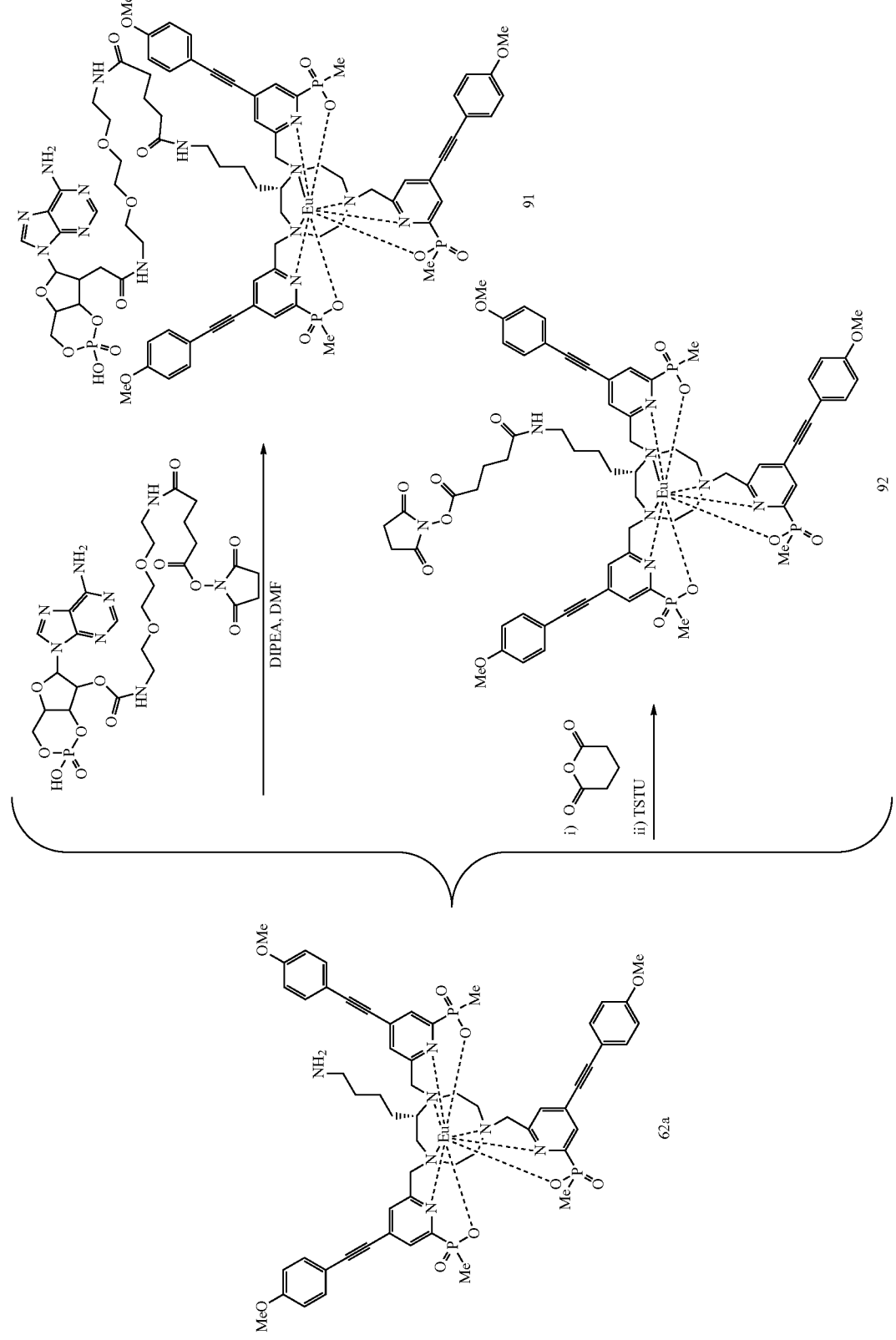
Scheme 22: example of functionalization with a substituted TACN structure
The use of complexes according to the invention bearing group LG at the level of the TACN macrocycle for preparing conjugates is illustrated in scheme 22, with the example of a conjugate with cAMP.

-continued
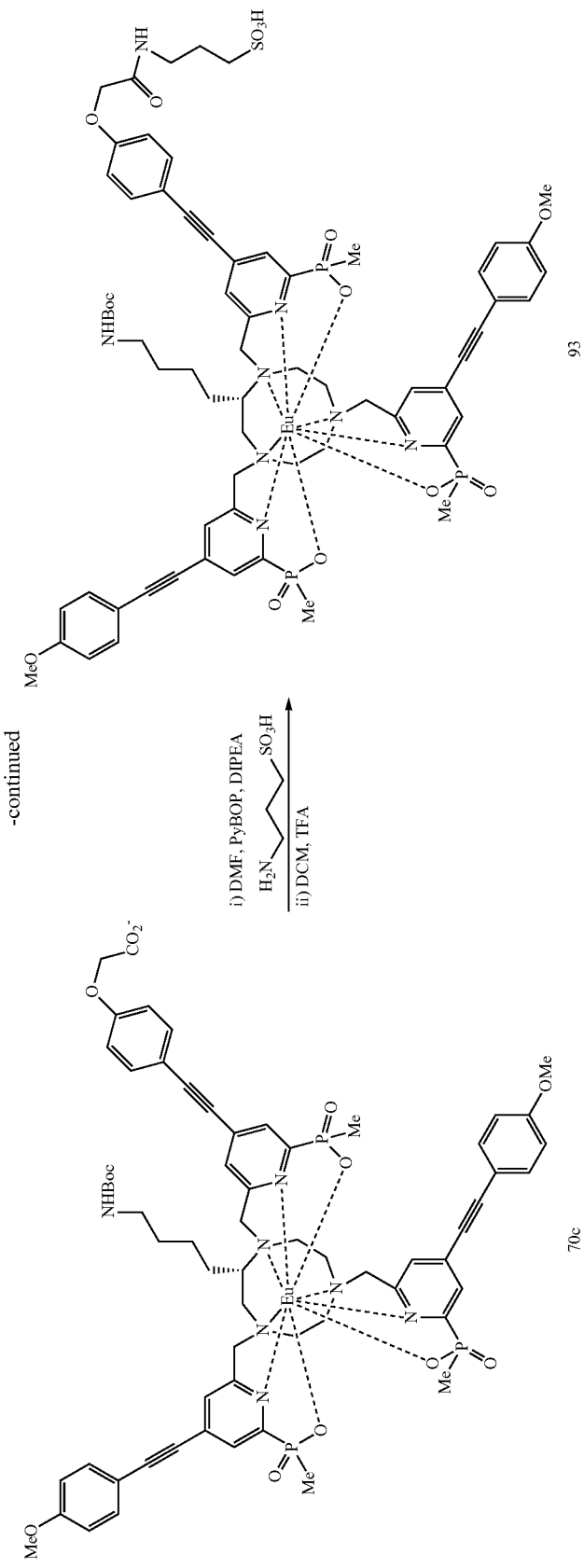

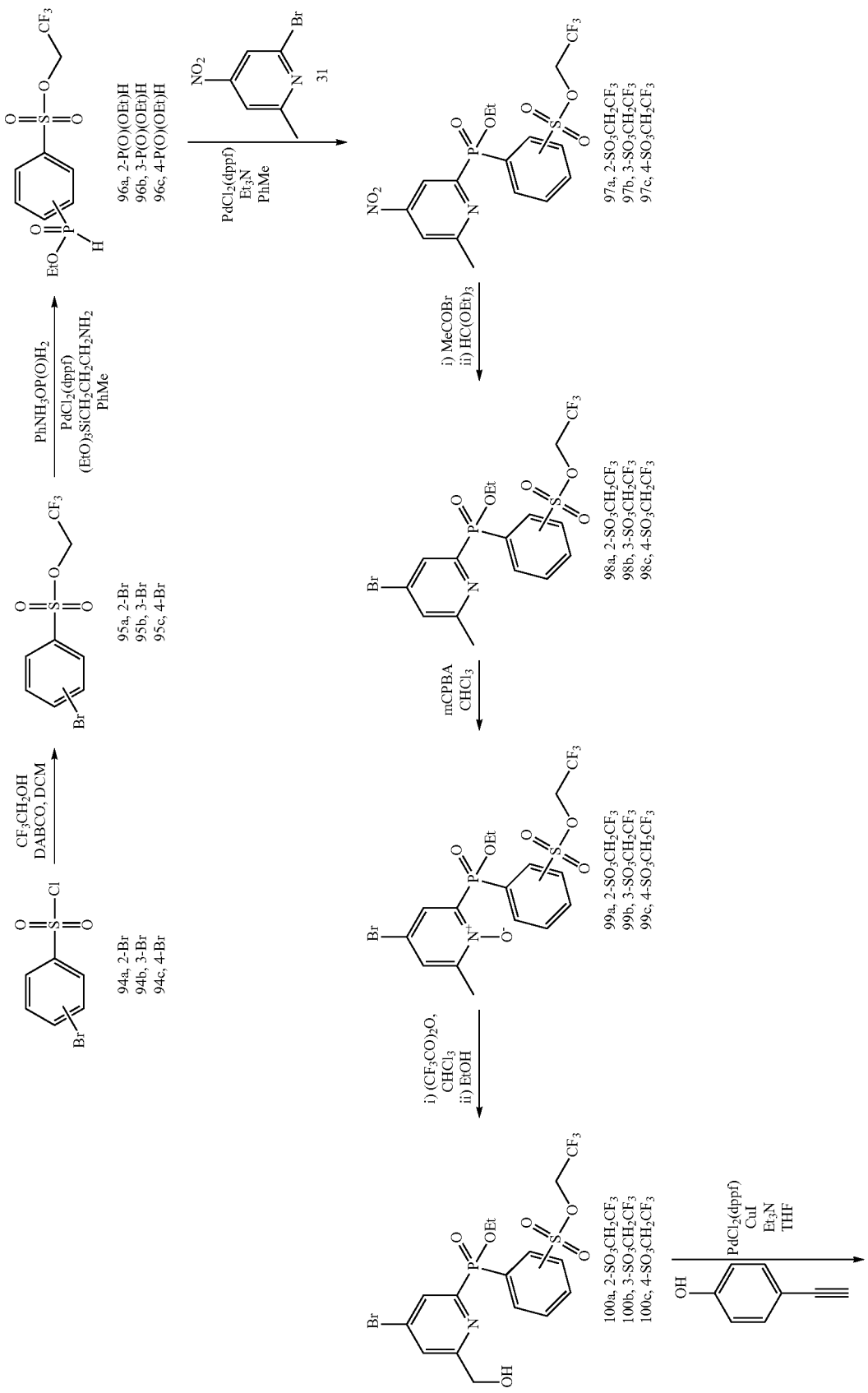

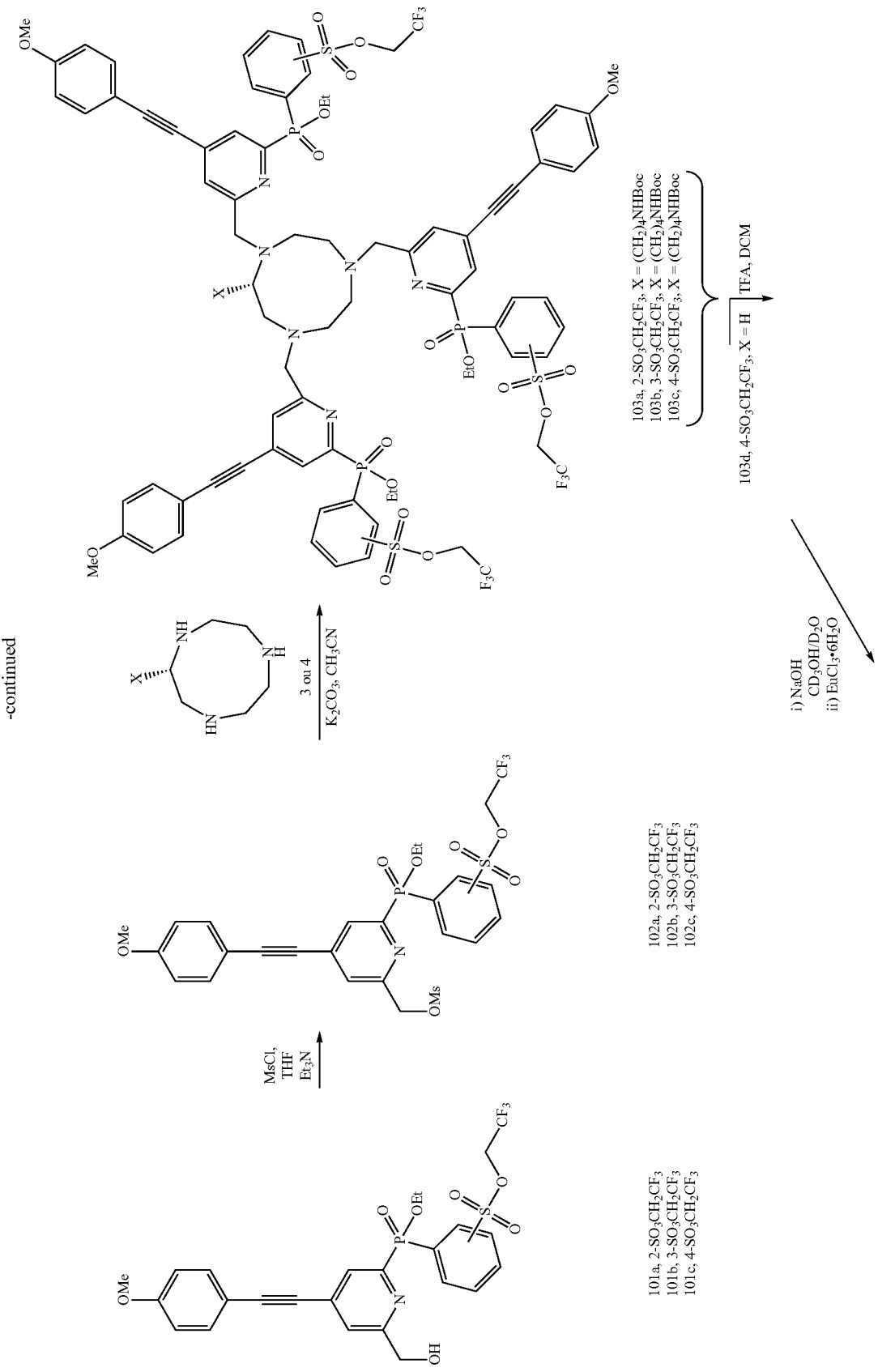

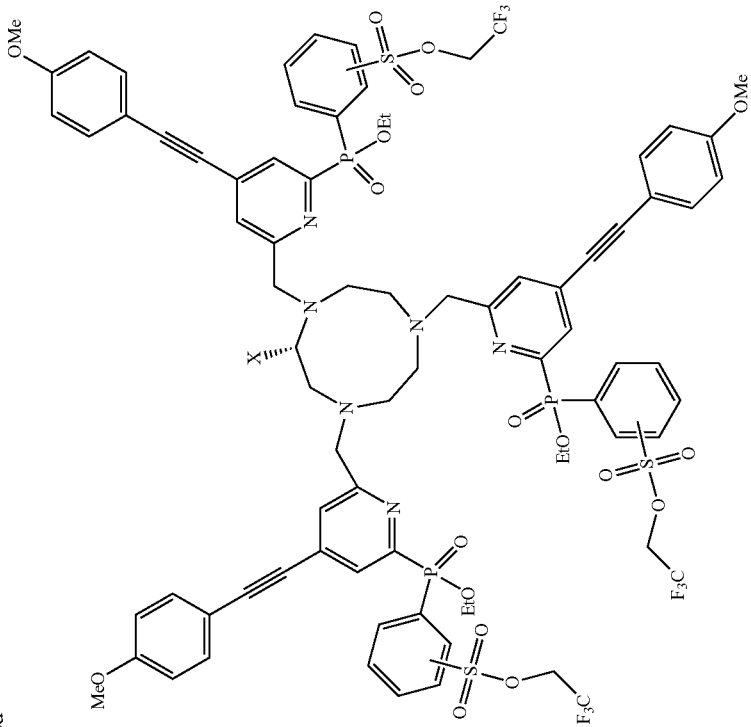
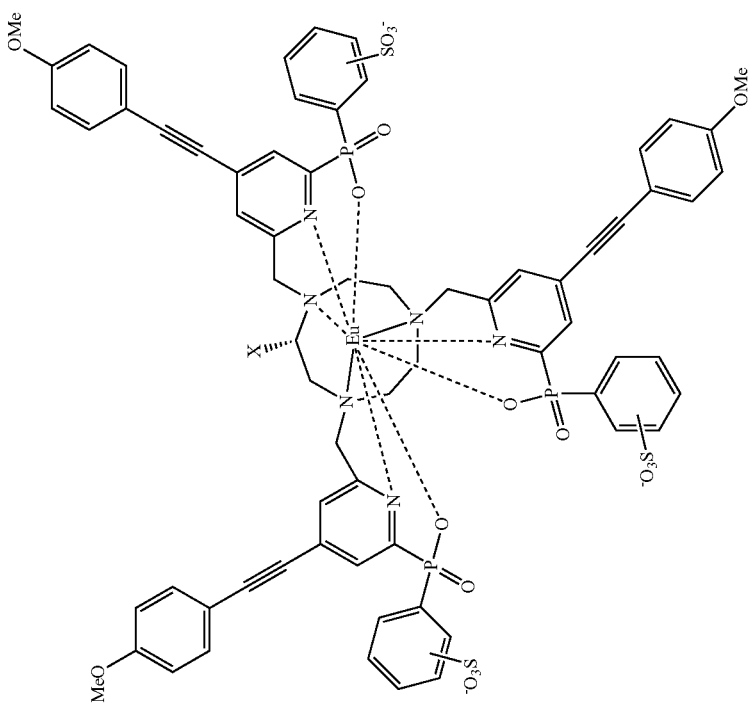

The syntheses of the complexes 105 are described in scheme 23. The commercial derivatives 94 (sulfonyl chlorides) are protected using trifluoroethanol. A first coupling using palladium salts allows the phosphinate function to be introduced on the aromatic ring and then this phosphinate function is coupled on the pyridine unit 31 whose synthesis was described above. The rest of the synthesis is identical to the complexes of the phosphinate type: substitution of the nitro group with a bromine atom using acetyl bromide and re-esterification of the corresponding phosphinic acid leading to compounds 98, functionalization of the methyl group to hydroxyl-methylene via the N-oxide intermediate, preparation of chromophores 101 by Sonogashira coupling, activation of the alcohol function to mesylated derivatives 102 which are then condensed on the macrocycle 3 or 4 (7a may also be envisaged), then depending on the macrocycle used, deprotection of the orthogonal Boc protective group in an acid medium, allowing functionalization, deprotection of the sulfonate and phosphinate groups in a basic medium and finally formation of the complexes using the europium salts.

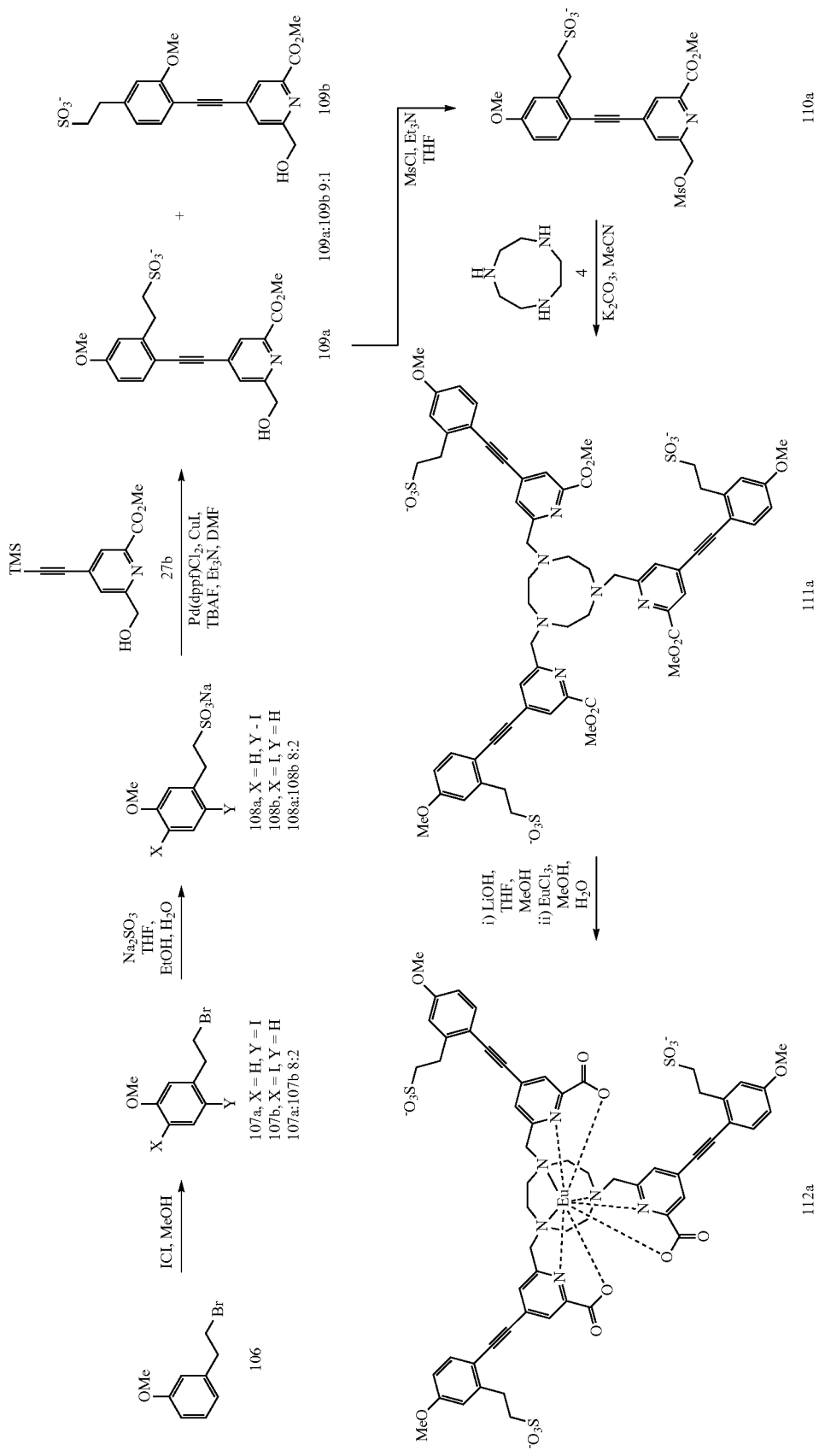
Scheme 24: synthesis of the symmetric complexes of the "alkylsulfonate carboxylate" type For introducing the sulfonate group on the aromatic ring, giving rise to a series of complexes 112a, the commercial compound 106 is first iodinated in the presence of iodine chloride in methanol (mixture of positional isomers 107a-b) and then sulfonated by treating compounds 107 with sodium sulfite. The synthesis is then identical to the preceding syntheses, namely Sonogashira reaction between compound 27b and 108, activation of the alcohol in the form of mesylated derivative, alkylation of macrocycle 4, hydrolysis and formation of complex 112a. The example of scheme 24 illustrates the methodology, allowing a sulfonate group to be introduced on an aliphatic chain carried by the aromatic ring of the chromophore. It should be noted that similar complexes can be obtained with derivatives whose aliphatic chain comprises one or three carbon atoms, without changing the photophysical properties.

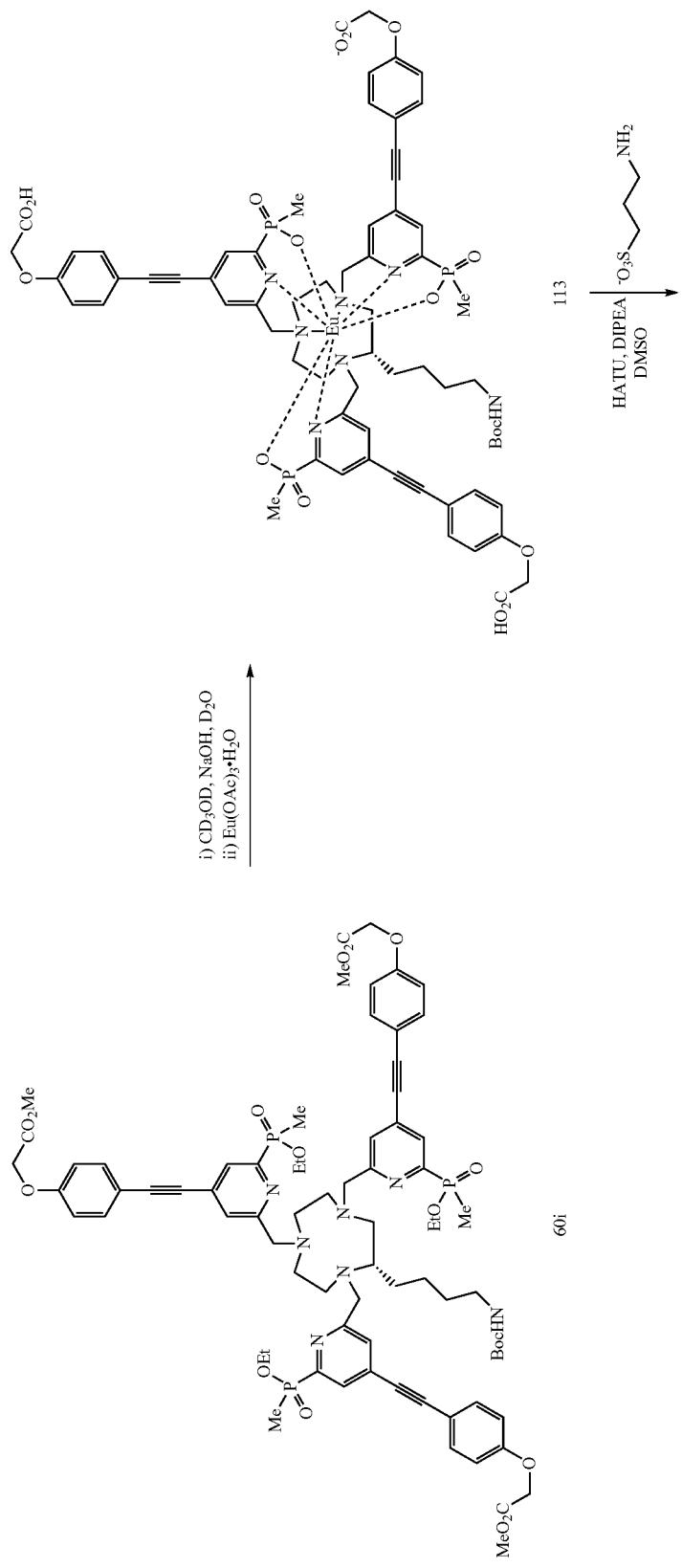
Scheme 25: synthesis of the symmetric complexes of the "methyl-phosphinate" type derived from C-substituted TACN -continued
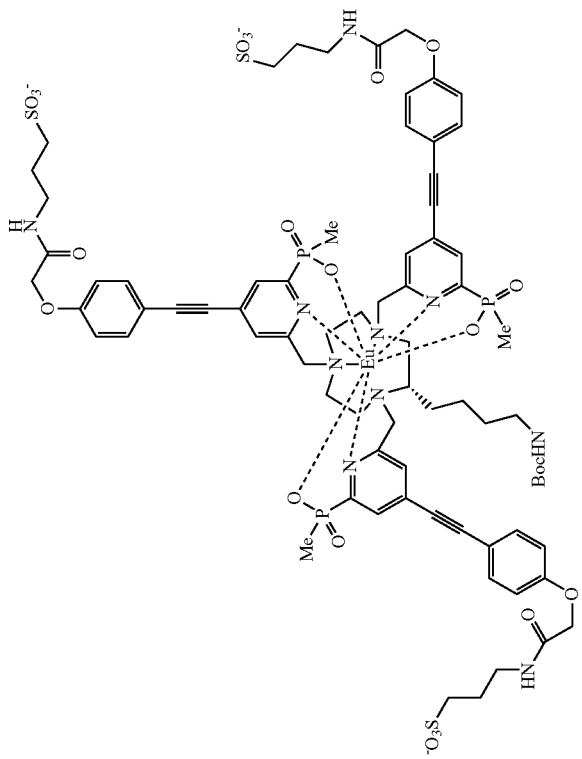
114
DCM, TFA
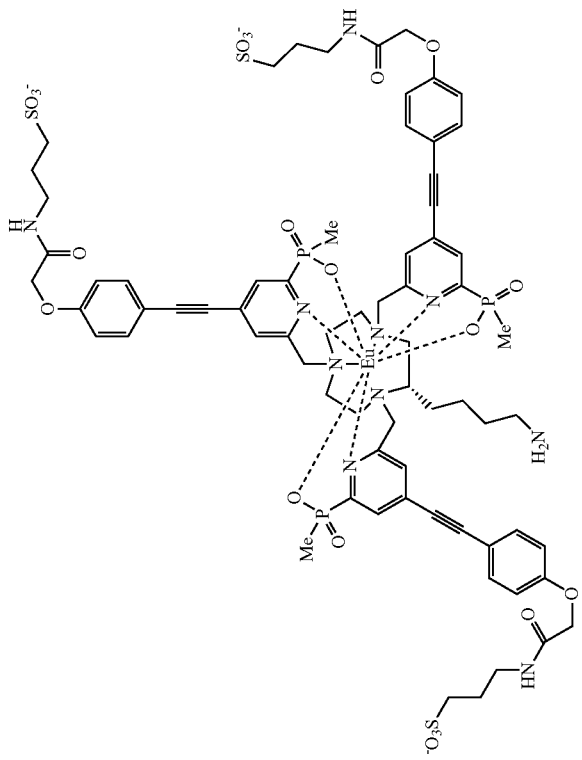
115

The synthesis of complex 115 comprising three sulfonate groups is represented in scheme 25. The ligand 60i is saponified and then complexed with europium salts. The carboxylate groups are then free and can be condensed with homotaurine using HATU as coupling agent. Finally, deprotection of the Boc group allows the amine to be released, which can then be used in a reaction of bioconjugation.

EXPERIMENTAL SECTION

Abbreviations Used

Boc: tert-butyloxycarbonyl
Boc-OSu: N-(tert-butoxycarbonyloxy)succinimide
cAMP: cyclic adenosyl monophosphate
TLC: thin-layer chromatography
δ: chemical shift
DABCO: 1,4-diazabicyclo[2.2.2]octane
DCC: dicyclohexylcarbodiimide
DCM: dichloromethane
DCU: dicyclohexylurea
DIPEA: diisopropylethylamine
DMAP: dimethylaminopyridine
DMF: dimethylformamide
DMSO: dimethylsulfoxide
ESI−: negative mode electrospray ionization
ESI+: positive mode electrospray ionization
EtOH: ethanol
h: hour
HATU: (O-(7-azabenzotriazol-1-yl)-N,N,N',N'-tetramethyluronium hexafluorophosphate)
HPLC: high-performance liquid chromatography
HRMS: high-resolution mass spectroscopy
HTRF: homogeneous time-resolved fluorescence
Hz: Hertz
LC-MS: high-performance liquid chromatography coupled to mass spectrometry
LRMS: low-resolution mass spectrum
m-CPBA: meta-chloroperbenzoic acid
MeCN: acetonitrile
MeOH: methanol
min: minute
MOM: methyl methyl ether
Mops: 3-(N-morpholino)propanesulfonic acid
Moz: p-methoxybenzyloxycarbonyl
Moz-ON: ((2-(4-methoxybenzyloxycarbonyloxy imino)-2-phenylacetonitrile)
Ms: mesyl
NBS: N-bromosuccinimide
NHS: N-hydroxysuccinimide
NIS: N-iodosuccinimide
Pd(dppf)Cl$_2$: bis(diphenylphosphino)ferrocene]dichloropalladium(II)
PEG: polyethylene glycol
Ph: phenyl
ppm: parts per million
M.p.: melting point
Py: pyridine
PyBOP: benzotriazol-1-yl-oxytripyrrolidinophosphonium hexafluorophosphate
NMR: nuclear magnetic resonance
MS: mass spectrometry
TBAF: tetrabutylammonium fluoride
TEA/Et$_3$N: triethylamine
TEAAc: triethylammonium acetate buffer
TFA: trifluoroacetic acid
THF: tetrahydrofuran
TMS=trimethylsilyl
Ts: tosyl
TSTU: O—(N-succinimidyl)-1,1,3,3-tetramethyluronium tetrafluoroborate
Chromatography
Thin-layer chromatography (TLC) was performed on Merck 60 F$_{254}$ silica gel plates on aluminum foil or on Merck 60 F$_{254}$ neutral aluminum oxide plates (type E) on aluminum foil.
Analytical and preparative high-performance liquid chromatography (HPLC) was carried out on two instruments:
Analytical HPLC: ThermoScientific, quaternary pump P4000, UV 1000 Detector with deuterium lamp (190-350 nm), analytical column Waters XBridge C18, 3.5 μm, 4.6×100 mm.
Preparative HPLC: Shimadzu, two LC-8A pumps, UV detector with diode array Varian ProStar, preparative column Waters XBridge prep. C18, 5 μm: 19×100 mm or 50×150 mm.
Spectroscopy
Nuclear Magnetic Resonance (NMR)
The NMR spectra ($^1$H, $^{13}$C and $^{31}$P) were obtained using a Bruker Avance 400 MHz NanoBay spectrometer (9.4 tesla magnet), equipped with a BBFO measuring probe, multicore with diameter of 5 mm, with gradient Z and lock $^2$H. The chemical shifts (δ) are expressed in parts per million (ppm). The following abbreviations are used:
s: singlet, bs: broad singlet, s app: apparent singlet, d: doublet, t: triplet, q: quadruplet, m: multiplet, dd: doublet of doublets, td: triplet of doublets, qd: quadruplet of doublets, ddd: doublet of doublets of doublets, AB: system AB.
Mass Spectrometry (LRMS)
The mass spectra (LC-MS) were obtained using a Waters ZQ 2000 spectrometer, single quadrupole with ESI/APCI multimode source equipped with Waters XBridge C18 column, 3.5 μm, 4.6×100 mm.
High-Resolution Mass Spectrometry (HRMS)
The analyses were performed with a QStar Elite mass spectrometer (Applied Biosystems SCIEX) equipped with a pneumatically assisted atmospheric pressure ionization source (API). The sample was ionized in positive mode electrospray in the following conditions: electrospray voltage (ISV): 5500 V; orifice voltage (OR): 20 V; pressure of the spraying gas (air): 20 psi. The high-resolution mass spectrum (HRMS) was obtained with a time-of-flight (TOF) analyzer. Exact measurement of mass was performed in triplicate with double internal calibration.
Melting Point
Melting point apparatus: the melting points were determined using BUCHI melting point B-540 apparatus.
Compound 2

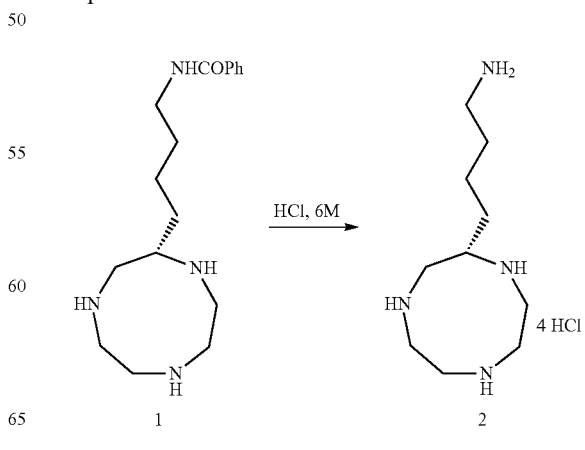

Compound 1 (182 mg, 0.6 mmol) (J. Chem. Soc Perkin Trans 1, 1990, 2567) was dissolved in 6 M aqueous hydrochloric acid solution (3 mL), which was then stirred at 100° C. for 72 h. The progress of the reaction was monitored by TLC. After this time the reaction was complete. The solution was cooled to room temperature and diluted with water (3 mL) and was then extracted with diethyl ether (3×10 mL). The aqueous phase was concentrated under reduced pressure to give compound 2 in the form of hydrochloride salts (100 mg, quantitative). $^1$H NMR (400 MHz, D$_2$O) δ: 3.42-3.13 (m, 10H), 3.96-2.87 (m, 3H), 1.64-1.37 (m, 6H). $^{13}$C NMR (100 MHz, D$_2$O) δ: 53.3, 46.1, 43.2, 41.8, 39.2, 39.1, 39.0, 30.6, 26.5, 22.1. HRMS (ESI+) calculated for C$_{10}$H$_{25}$N$_4$ [M+H]$^+$, m/z 201.2079. found: 201.2068.

Compound 3

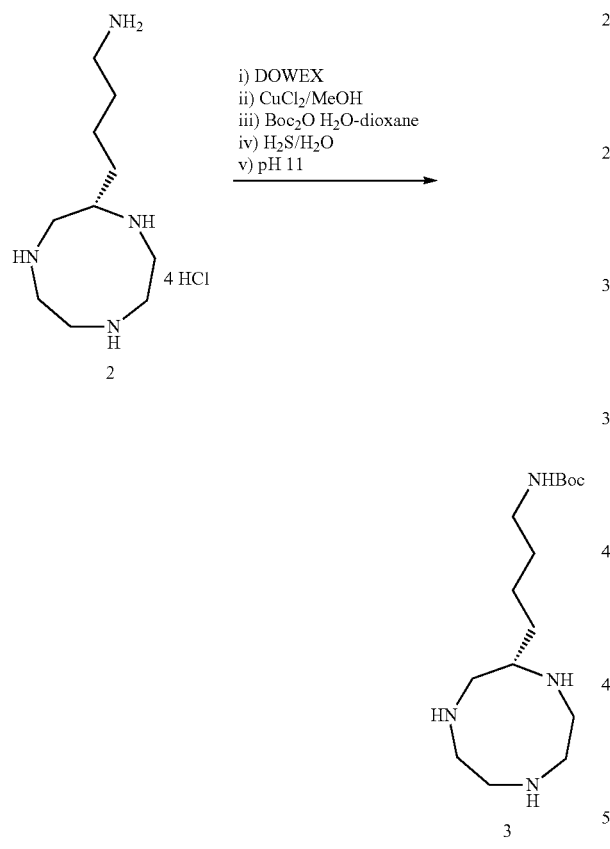

Tetramine 2 was converted to free amine (66 mg, 0.33 mmol) by ion-exchange chromatography using DOWEX 1×2-200 resin. The free amine was dissolved in methanol (4 mL) and copper chloride monohydrate (56 mg, 1.33 mmol) was added to this solution. The solution, initially colorless, turned deep green. The mixture was stirred at room temperature for 2 h and then the solvent was removed under reduced pressure to give a greenish solid, which was dissolved in water again (2 mL). A solution of di-tert-butyl dicarbonate (140 mg, 0.66 mmol) in dioxane (2 mL) was added to this solution and it was then stirred at room temperature for 3 h. After this time, the reaction was not complete. A second addition of a solution of di-tert-butyl dicarbonate (70 mg, 0.33 mmol) in dioxane (1 mL) was carried out and then this solution was stirred at room temperature for an additional 16 h. The progress of the reaction was monitored by LC-MS. After this time the reaction was complete. The green solution was treated by bubbling with hydrogen sulfide for a period of 5 min and the mixture was centrifuged to remove the black precipitate. The supernatant was washed with dichloromethane and then the aqueous solution was adjusted to pH 11 before performing intensive extraction with dichloromethane (8×10 mL). The organic phases were combined and dried over magnesium sulfate and then filtered and concentrated under reduced pressure to give a colorless oil (27 mg, 27%). $^1$H NMR (400 MHz, CDCl$_3$) δ: 6.46 (bs, 1H), 3.13 (m, 2H), 2.89-2.67 (m, 10H), 2.47 (m, 1H), 2.35 (bs, 3H), 1.47 (s, 9H), 1.49-1.35 (m, 6H); $^{13}$C NMR (100 MHz, CDCl$_3$) δ: 156.3, 79.3, 55.2, 49.9, 46.2, 45.3, 44.3, 40.6, 40.3, 33.9, 30.4, 23.7, 28.6. HRMS (ESI+) calculated for C$_{15}$H$_{33}$N$_4$O$_2$ [M+H]$^+$, m/z 301.2604. found: 301.2603.

Compound 5

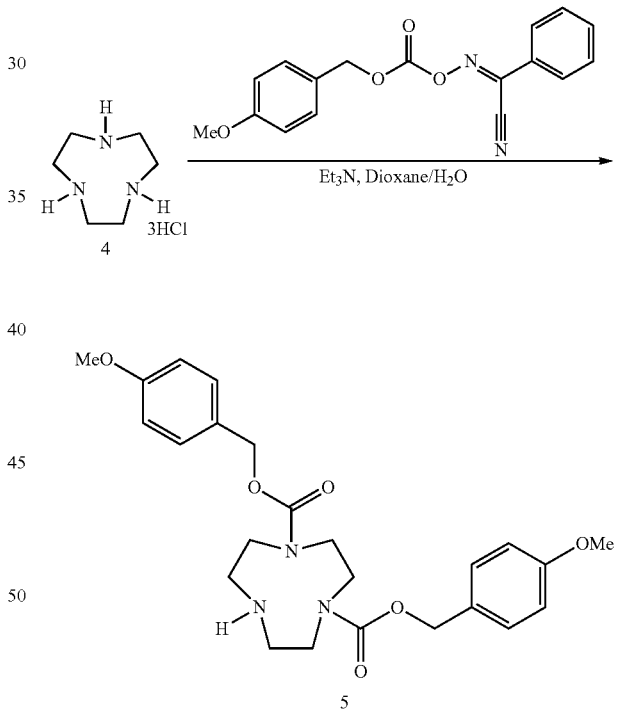

2-(4-Methoxybenzyloxycarbonyloxyimino)-2-phenylacetonitrile (Moz-ON) (477 mg, 1.5 mmol) was added to a solution of 1,4,7-triazacyclononane hydrochloride 4 (188 mg, 0.78 mmol) in a dioxane/water mixture (10 mL, 8:2). The reaction mixture was homogenized by stirring vigorously and then a solution of triethylamine (540 µL, 3.8 mmol) in a dioxane/water mixture (10 mL, 8:2) was added to this mixture. The progress of the reaction was monitored by TLC. After 24 h, reaction was complete. The solvent was removed under reduced pressure. The residue was dissolved in dichloromethane. This solution was washed with water saturated with sodium chloride (3×10 mL). The organic phase was dried over magnesium sulfate, filtered and concentrated under reduced pressure. The crude reaction product was purified by alumina column chromatography (dichloromethane/methanol 98:2 to 90:10 in increments of 1%) to give the desired compound 5 in the form of an oil (266 mg, 74%). $^1$H NMR (400 MHz, CDCl$_3$) δ: 7.32-7.25 (m, 4H), 6.88-6.85 (m, 4H), 5.09 (m, 4H), 3.80 (s, 6H), 3.56-3.47 (m, 4H), 3.31-3.25 (m, 4H), 2.87 (m, 4H). $^{13}$C NMR (100 MHz, CDCl$_3$) δ: 159.68, 156.76, 130.05, 128.92, 114.03, 67.15, 55.41, 52.20, 51.98, 51.26, 50.31, 50.07, 49.19, 48.18, 47.73, 47.66. LRMS (ESI+) calculated for C$_{24}$H$_{32}$N$_3$O$_6$ [M+H]$^+$, m/z 458.2291. found: 458.08. R$_f$=0.48 (silica, dichloromethane-methanol 90:10).

Compound 6

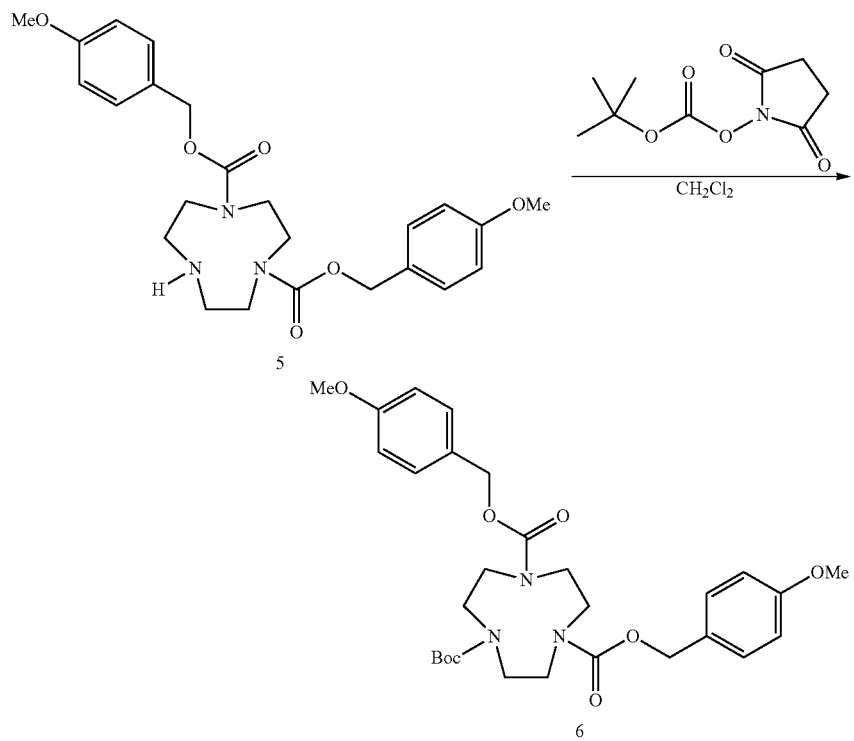

N-(tert-Butoxycarbonyloxy)succinimide (Boc-OSu) (36 mg, 0.15 mmol) was added to a solution of diprotected macrocycle 5 (50 mg, 0.1 mmol) in dichloromethane (7 mL). The solution was stirred at room temperature under inert atmosphere. The progress of the reaction was monitored by TLC. After 24 h, reaction was complete. The solution was washed directly with water saturated with sodium chloride (3×10 mL). The organic phase was dried over magnesium sulfate, filtered and concentrated under reduced pressure. The crude product was purified by alumina column chromatography (dichloromethane/methanol 90:10 to 70:30 in increments of 5%) to give compound 6 in the form of a brown-colored oil (44 mg, 72%). $^1$H NMR (400 MHz, CDCl$_3$) δ: 7.30-7.19 (m, 4H), 6.88-6.83 (m, 4H), 5.06-4.92 (m, 4H), 3.77 (s, 6H), 3.46-3.39 (m, 12H), 1.55 (s, 9H). $^{13}$C NMR (100 MHz, CDCl$_3$) δ: 159.65, 156.56, 155.76, 130.04, 128.98, 114.00, 80.01, 67.15, 55.38, 49.74, 49.64, 49.47, 49.37, 49.12, 48.92, 48.80, 28.53, 27.75, 25.60. HRMS (ESI+) calculated for C$_{29}$H$_{39}$N$_3$O$_8$ [M+H]$^+$, m/z 558.2815. found: 558.2808. R$_f$=0.28 (silica; cyclohexane-ethyl acetate 50:50).

Compound 7a

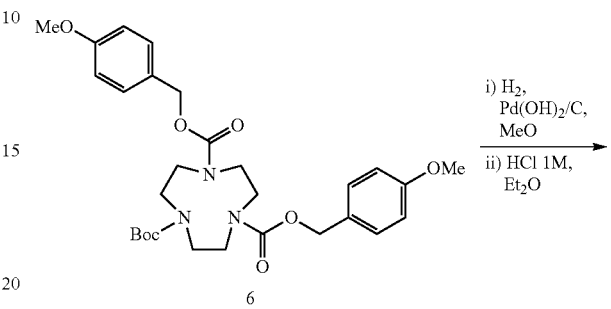

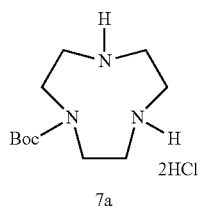

Palladium hydroxide adsorbed on charcoal (about 100 mg) was added to a solution of diMOZ-monoBoc macro cycle 6 (300 mg, 0.5 mmol) in methanol (25 mL). The reaction mixture was put in a hydrogenator and was stirred vigorously under a hydrogen atmosphere (3.45 bar or 50 PSI). The progress of the reaction was monitored by TLC on alumina. After being left overnight, reaction was complete. The reaction mixture was filtered on Celite and then concentrated under reduced pressure. The colorless oil obtained was dissolved in methanol (3 mL). A 1 M aqueous solution of hydrochloric acid (pH 2-3) was added to this solution. The mixture was concentrated under reduced pressure and was dissolved again in a minimum of methanol (2 mL). Diethyl ether (35 mL) was added to this solution. The white precipitate obtained was collected by filtration to give a white solid corresponding to the hydrochloride 7a (102 mg, 62%). M.p.: 172-174° C. $^1$H NMR (500 MHz, D$_2$O) δ: 3.74 (t, J=4.5 Hz, 4H), 3.63 (s, 4H), 3.48 (t, J=4.5 Hz, 4H), 1.47 (s, 9H). $^{13}$C NMR (125 MHz, CDCl$_3$) δ: 136.0, 62.9, 25.9, 22.2, 21.7, 6.7. HRMS (ESI+) calculated for C$_{11}$H$_{23}$N$_3$O$_2$ [M+H]$^+$, m/z 230.1869. found: 230.1863. R$_t$=10.92 min (Waters XBridge RP-C18 column, 3.5 μm, 4.6×100 mm) with 0.2% aqueous solution of trifluoroacetic acid (pH 1-MeCN (v/v)) as eluent, linear gradient from 15 to 100% MeCN (19 min), with a flow rate of 1 mL min$^{-1}$ and UV detection of 280 nm.

Compound 8

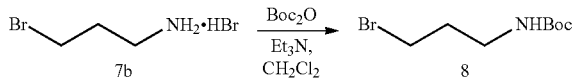

di-tert-Butyl dicarbonate (3.71 g, 16.9 mmol) and triethylamine (10 mL) were added to a solution of 3-bromopropylamine hydrobromide 7b (3.72 g, 16.9 mmol) in dichloromethane (100 mL). The reaction mixture was stirred at room temperature for 12 h. The progress of the reaction was monitored by TLC. After this time, reaction was complete. The solvent was removed under reduced pressure. A saturated solution of sodium chloride (100 mL) was added to this residue and the mixture was extracted with diethyl ether (2×50 mL). The organic phases were combined, washed with a saturated solution of sodium chloride (3×50 mL) and dried over sodium sulfate. After filtration, the solvent was removed under reduced pressure to give compound 8 in the form of a slightly brown solid. The compound was sufficiently pure to be used in the rest of the synthesis without additional purification (3.50 g, 87%). M.p.: 32-33° C. $^1$H NMR (200 MHz, CDCl$_3$) δ: 4.63 (s, 1H), 3.42 (t, J=6.5 Hz, 2H), 3.26 (td, J=6.5; 6.5 Hz, 2H), 2.03 (m, J=6.5 Hz, 2H), 1.43 (s, 9H); $^{13}$C NMR (125 MHz, CDCl$_3$) δ: 156.09, 79.54, 39.96, 32.82, 30.90, 28.48. HRMS (ESI+) calculated for C$_8$H$_{16}$NO$_2$Br [M+H]$^+$, m/z 255.0703. found: 255.0695. R$_f$=0.59 (silica; cyclohexane-ethyl acetate 50:50).

Compound 10

The synthesis of this compound was described by S. Machida et al. (Journal American Chemical Society 2011-133-958-963, supplementary material).

Compound 13a

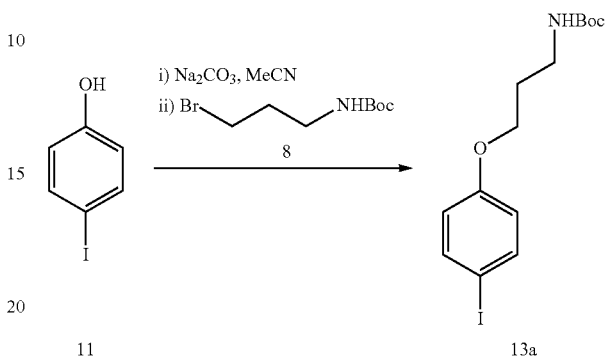

Sodium carbonate (5.65 g, 40.9 mmol) was added to a solution of 4-iodophenol 11 (3.00 g, 13.6 mmol) in anhydrous acetonitrile (100 mL). The reaction was heated under reflux for 1 h and then the brominated derivative 8 (2.60 g, 10.9 mmol) was added to this suspension. The reaction mixture was heated under reflux for 12 h. The progress of the reaction was monitored by TLC. After this time, reaction was complete. The reaction mixture was cooled to room temperature and the solvent was removed under reduced pressure. Water (100 mL) was added to this residue and the mixture was extracted with dichloromethane (2×50 mL). The organic phases were combined, dried over magnesium sulfate and filtered. The solvent was removed under reduced pressure and the residue was purified by silica column chromatography using dichloromethane to give compound 13a in the form of a white solid (3.10 g, 75%). M.p.: 79-80° C. $^1$H NMR (500 MHz, CDCl$_3$) δ: 7.52 (d, J=8.9 Hz, 2H), 6.64 (d, J=8.9 Hz, 2H), 4.69 (s, 1H), 3.95 (t, J=6.2 Hz, 2H), 3.29 (td, J=6.2; 6.2 Hz, 2H), 1.94 (m, J=6.2 Hz, 2H), 1.41 (s, 9H), $^{13}$C NMR (125 MHz, CDCl$_3$) δ: 158.7, 155.9, 138.2, 116.9, 82.9, 65.9, 37.9. HRMS (ESI+) calculated for C$_{14}$H$_{20}$NO$_3$I [M+H]$^+$, m/z 378.0561. found: 378.0559. R$_f$=0.58 (silica; cyclohexane-ethyl acetate 50:50).

Compounds 13b and 13c

These compounds were synthesized according to the same procedure as that used for preparing compound 13a.

Compound 13d

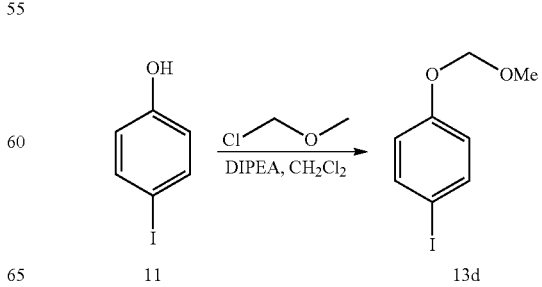

Diisopropylethylamine (1.045 mL, 6 mmol), and then dropwise chloro(methoxy)methane (MOMCl) (607 μL, 8 mmol), in the space of 5 min, were added to a solution of iodophenol 11 (606 mg, 3 mmol) in dichloromethane (8 mL) cooled to 5° C. After addition, the mixture was heated at room temperature and then at 60° C. for 4 h. The progress of the reaction was monitored by TLC. After this time, reaction was complete. The mixture was cooled to room temperature and then dichloromethane (20 mL) was added to this solution. The organic phase was washed with water (2×20 mL), dried with magnesium sulfate, filtered and concentrated under reduced pressure. The residue was purified by silica column flash chromatography with dichloromethane as eluent to give the desired product 13d (605 mg, 76%). $^1$H NMR (400 MHz, CDCl$_3$) δ: 7.57 (d, J=8.9 Hz, 2H), 6.83 (d, J=8.9 Hz, 2H), 5.14 (s, 2H), 3.46 (s, 3H). $^{13}$C NMR (100 MHz, CDCl$_3$) δ: 157.09, 138.28, 118.61, 94.33, 84.39, 56.05. LRMS (ESI+) calculated for C$_8$H$_{10}$IO$_2$ [M+H]$^+$, m/z 264.97. found: 264.03. R$_f$=0.73 (silica; cyclohexane-ethyl acetate 30:70).

Compound 13e

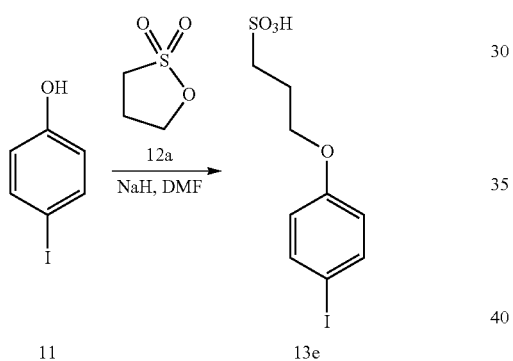

Sodium hydride at 60% dispersion in mineral oil was added in small portions (52 mg, 2.1 mmol) in the space of 5 min and under a nitrogen stream, to a solution of iodophenol 11 (200 mg, 1 mmol) in anhydrous dimethylformamide (3 mL). The mixture was stirred at room temperature for 30 min and then 1,3-propane sultone 12a (115 μL, 1.3 mmol) was added to this suspension. The mixture was then stirred for 2.5 h at room temperature under inert atmosphere. The progress of the reaction was monitored by HPLC. After this time the reaction was complete. The suspension was filtered, and the solid was washed with dichloromethane (30 mL) and then dried under reduced pressure to give a white solid, which was sufficiently pure to be used in the next step without additional purification (309 mg, 91%). M.p.: 350° C. (dec). $^1$H NMR (400 MHz, DMSO-d$_6$) δ: 7.56 (d, J=8.8 Hz, 2H), 6.76 (d, J=8.8 Hz, 2H), 4.03 (t, J=6.5 Hz, 2H), 2.59 (t, J=7.4 Hz, 2H), 2.00 (q, J=6.5 Hz, 7.4 Hz, 2H). $^{13}$C NMR (100 MHz, DMSO-d$_6$) δ: 158.55, 137.96, 117.33, 82.86, 66.81, 47.81, 25.11. HRMS (ESI+) calculated for C$_9$H$_{15}$NO$_4$IS [M+NH$_4$]$^+$, m/z 359.9766. found: 359.9760. R$_t$=12.28 min (Waters XBridge RP-C18 column, 3.5 μm, 4.6×100 mm) with 0.2% aqueous solution of trifluoroacetic acid (pH 1-MeCN (v/v)) as eluent, [isocratic 5% MeCN (2 min)], linear gradient from 5 to 100% MeCN (19 min), with a flow rate of 1 mL min$^{-1}$ and UV detection of 280 nm.

Compound 13f

This compound was synthesized according to the same procedure as that used for preparing compound 13e, using sultone 12b.

Compound 14a

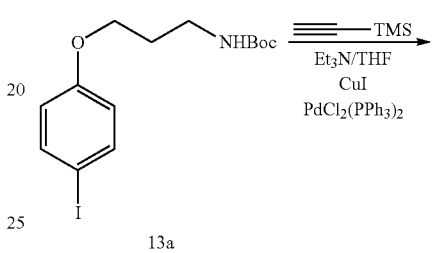

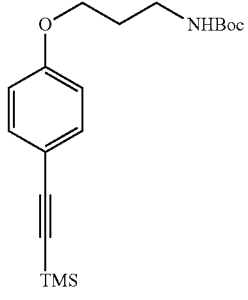

A solution of iodinated derivative 13a (2.50 g, 6.6 mmol) in a solvent mixture of tetrahydrofuran (20 mL) and triethylamine (20 mL) was degassed with stirring for 20 min. Trimethylsilylacetylene (1.95 g, 19.8 mmol) was added to this solution, followed by palladium(II) bis-chloride bis-triphenylphosphine (46 mg, 0.06 mmol) and copper(I) iodide (25 mg, 0.13 mmol). The reaction was stirred at room temperature for 12 h. The progress of the reaction was monitored by TLC. After this time, reaction was complete. The solvents were removed under reduced pressure. A saturated solution of ammonium chloride (50 mL) was added to the residue and the mixture was extracted with dichloromethane (2×25 mL). The organic phases were combined and washed with a saturated solution of ammonium chloride (50 mL) and then with a saturated solution of sodium chloride (2×50 mL) and then dried over sodium sulfate. After filtration, the solvent was removed under reduced pressure and the residue was purified by silica column chromatography (dichloromethane/pentane 1/1 then dichloromethane) to give compound 14a in the form of a white solid (1.50 g, 65%). M.p.: 92-93° C. $^1$H NMR (200 MHz, CDCl$_3$) δ: 7.37 (d, J=8.7 Hz, 2H), 6.78 (d, J=8.7 Hz, 2H), 4.69 (s, 1H), 3.99 (t, J=6.2 Hz, 2H), 3.29 (td, J=6.2; 6.2 Hz, 2H), 1.95 (m, J=6.2 Hz, 2H), 1.42 (s, 9H), 0.22 (s, 9H). $^{13}$C NMR (100 MHz, CDCl$_3$) δ: 159.08, 156.13, 133.61, 115.54, 114.44, 105.28, 92.63, 79.41, 65.92, 38.06, 29.66, 28.54, 0.20. HRMS (ESI+) calculated for C$_{19}$H$_{29}$NO$_3$Si [M+H]$^+$, m/z 348.1989. found: 348.1993. R$_f$=0.77 (silica; dichloromethane-methanol 95:5).

Compounds 14b and 14c

These compounds were synthesized according to the same procedure as that used for preparing compound 14a, using the corresponding precursors.

Compound 15a

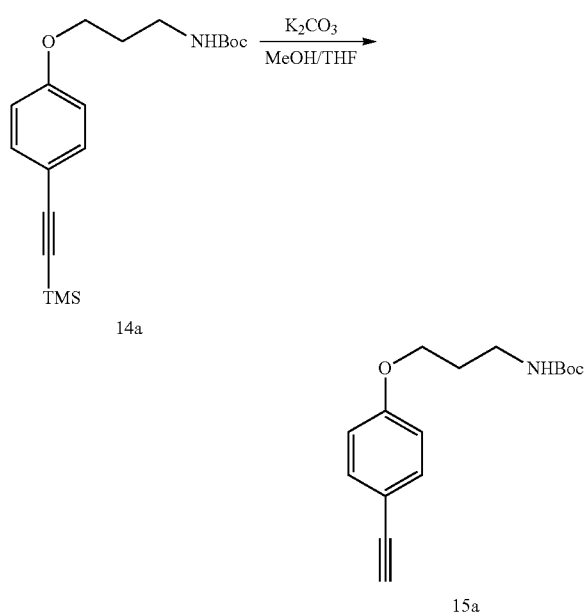

Potassium carbonate (1.52 g, 11.0 mmol) was added to a solution of silylated derivative 14a (1.27 g, 3.7 mmol) in a mixture of tetrahydrofuran (30 mL) and methanol (30 mL). The reaction mixture was stirred at room temperature for 2 h. The progress of the reaction was monitored by TLC. After this time, reaction was complete. The reaction mixture was filtered and the filtrate was concentrated under reduced pressure. The residue was purified by silica column chromatography (pentane/dichloromethane 50/50 up to 100% in increments of 10%) to give compound 15a in the form of a white solid (0.86 g, 85%). $^1$H NMR (200 MHz, CDCl$_3$) δ: 7.39 (d, J=8.7 Hz, 2H), 6.81 (d, J=8.7 Hz, 2H), 4.69 (s, 1H), 3.99 (t, J=6.2 Hz, 2H), 3.29 (td, J=6.2 Hz and J=6.2 Hz, 2H), 2.97 (s, 1H), 1.95 (t, J=6.2 Hz, 2H), 1.42 (s, 9H). LRMS (ESI+) calculated for C$_{16}$H$_{22}$NO$_3$ [M+H]$^+$, m/z 276.1600. found: 276.18. R$_f$=0.90 (silica; dichloromethane-methanol 90:10).

Compounds 15b and 15c

These compounds were synthesized according to the same procedure as that used for preparing compound 15a using the corresponding precursors.

Compound 17a

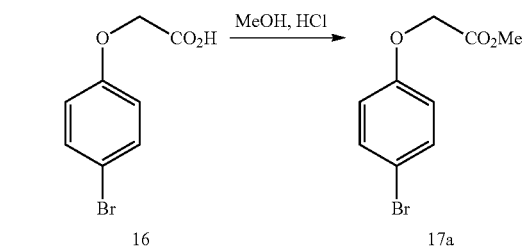 [SMILES: O=C(O)COc1ccc(Br)cc1 ; COC(=O)COc1ccc(Br)cc1]

2-(4-Bromophenoxy)-acetic acid 16 (1.0 g, 4.3 mmol) was added to a 3 M methanolic solution of hydrochloride (3 mL). The mixture was stirred for 20 h at room temperature under inert atmosphere. The solvent was removed under reduced pressure and the residual oil was dissolved in dichloromethane (15 mL) and was washed successively with water (10 mL), a saturated bicarbonate solution (10 mL) and then again with water (10 mL). The organic phase was dried over magnesium sulfate, filtered and then concentrated under reduced pressure to give compound 17a in the form of a colorless oil, which was sufficiently pure to be used in the rest of the synthesis without additional purification (1 g, 95%). $^1$H NMR (400 MHz, CDCl$_3$) δ: 7.31 (d, J=8.5 Hz, 2H), 6.78 (d, J=8.5 Hz, 2H), 4.55 (s, 2H), 3.80 (s, 3H); $^{13}$C NMR (176 MHz, CDCl$_3$) δ: 169.3, 157.1, 132.7, 116.7, 114.3, 65.6, 52.6; HRMS (ESI+) calculated for C$_9$H$_9$O$_3$BrNa [M+Na]$^+$, m/z 266.9633. found: 266.9622; R$_f$=0.65 (silica; cyclohexane-ethyl acetate 1:1).

Compound 17b

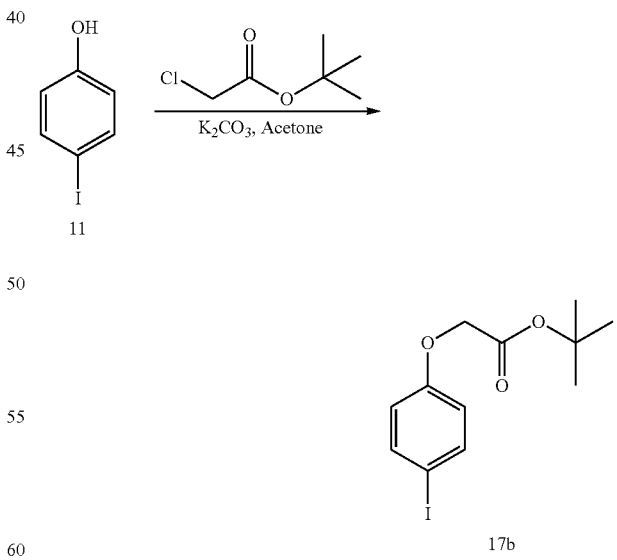

Potassium carbonate (6.3 g, 45 mmol) and tert-butyl chloroacetate (2.37 mL, 16.5 mmol) were added to a solution of iodophenol 11 (3.0 g, 15 mmol) in acetone (100 mL). The suspension was heated under reflux for 12 h. The progress of the reaction was monitored by TLC. After this time, reaction was complete. The mixture was cooled to room temperature and the solvent was removed under reduced pressure. The residue was dissolved in dichloromethane (60 mL) and was washed with water (2×40 mL). The organic phase was dried over magnesium sulfate, filtered and concentrated under reduced pressure. The crude product was purified by silica column chromatography using dichloromethane as eluent to give a yellowish oil identified as the desired compound 17b (4.8 g, 81%). $^1$H NMR (400 MHz, CDCl$_3$) δ: 7.55 (d, J=9.0 Hz, 2H), 6.66 (d, J=9.0 Hz, 2H), 4.47 (s, 2H), 1.47 (s, 9H). $^{13}$C NMR (100 MHz, CDCl$_3$) δ: 167.70, 157.91, 138.36, 117.06, 83.89, 82.66, 65.73, 28.13. HRMS (ESI+) calculated for $C_{12}H_{19}INO_3$ [M+NH$_4$]$^+$, m/z 352.0410. found: 352.0400. R$_f$=0.57 (silica; dichloromethane 100%).

Compound 19a

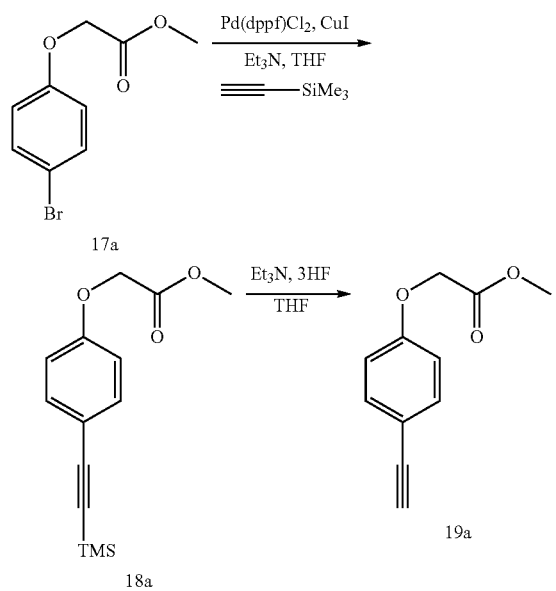

Ethynyltrimethylsilane (0.83 mL, 5.87 mmol) and triethylamine (3.40 mL, 24.5 mmol) were added to a solution of compound 17a (1.20 g, 4.89 mmol) in anhydrous tetrahydrofuran (2 mL) degassed beforehand by three cycles of freezing-thawing under vacuum. The mixture was degassed again by three cycles of freezing-thawing under vacuum and then [1,1-bis(diphenylphosphino)ferrocene]dichloropalladium(II) (41 mg, 0.49 mmol) and copper iodide (93 mg, 0.49 mmol) were added. The brown solution was heated at 65° C. for 24 h under inert atmosphere. The progress of the reaction was monitored by TLC. After this time, reaction was complete. The solvent was removed under reduced pressure and the brown oil was purified by silica column chromatography using a gradient of eluent (cylohexane-ethyl acetate 30-70 to 50-50 in increments of 5%) leading to compound 18a in the form of yellowish oil (760 mg, 60%). R$_f$=0.47 (silica; cyclohexane-ethyl acetate 75:25). This compound was used directly in the rest of the synthesis. Triethylamine trihydrofluoride (0.87 mL, 5.35 mmol) was added to this oil (140 mg, 0.53 mmol) dissolved in anhydrous tetrahydrofuran (2 mL) and then it was heated at 35° C. for 24 h under inert atmosphere. The progress of the reaction was monitored by TLC. After this time, reaction was complete. The solvent was removed under reduced pressure and the crude reaction product was purified by silica column chromatography using a cyclohexane-ethyl acetate 70-30 eluent to give, after evaporation of the fractions, a colorless oil identified as compound 19a (89 mg, 87%). $^1$H NMR (600 MHz, CDCl$_3$) δ: 7.43 (d, J=8.9 Hz, 2H), 6.85 (d, J=8.9 Hz, 2H), 4.64 (s, 2H), 3.80 (s, 3H), 3.00 (s, 1H); $^{13}$C NMR (151 MHz, CDCl$_3$) δ: 169.1, 158.2, 133.8, 115.6, 114.7, 83.4, 76.3, 65.3, 52.5. LRMS (ESI+) calculated for $C_{11}H_9O_3$ [M–H]$^+$, m/z 189.06. found: 189.00. R$_f$=0.39 (silica; cyclohexane-ethyl acetate 75:25).

Compound 21

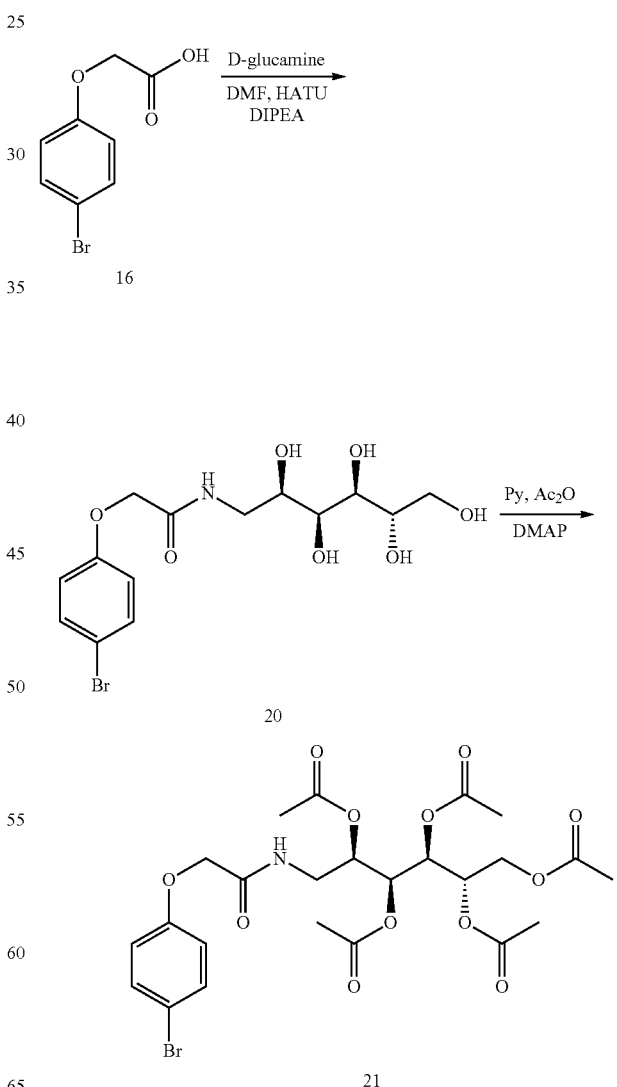

D-Glucamine (282 mg, 1.56 mmol), O-(7-azabenzotriazol-1-yl)-1,1,3,3-tetramethyluronium hexafluorophosphate (HATU) (592 mg, 1.56 mmol) and diisopropylethylamine (0.542 mL, 3.90 mmol) were added successively to a solution of 4-bromophenoxyacetic acid 16 (300 mg, 1.30 mmol) in anhydrous dimethylformamide (20 mL). The mixture was stirred at room temperature for 16 h under inert atmosphere. The progress of the reaction was monitored by TLC. After this time, reaction was complete. A 0.1 M aqueous solution of hydrochloric acid (10 mL) was added to this mixture and then the solvent was removed under reduced pressure a pale yellow solid corresponding to compound 20. Acetic anhydride (6.18 mL, 64.9 mmol) and 4-dimethylaminopyridine (16 mg, 0.13 mmol) were added to this solid dissolved in anhydrous pyridine (40 mL). The solution was stirred at 35° C. for 16 h under inert atmosphere. The progress of the reaction was monitored by TLC. After this time, reaction was complete. The solvent was removed under reduced pressure and the last traces of reagents were removed by azeotropic distillation to give a yellow oil, which was distributed in dichloromethane (30 mL) and 0.5 M aqueous solution of sodium bicarbonate (30 mL). The aqueous phase was extracted with dichloromethane (3×30 mL) and the organic phases were combined, washed with water (100 mL), dried over magnesium sulfate, filtered and concentrated under reduced pressure to give yellow oil. The crude product was purified by silica column chromatography using dichloromethane as eluent to give compound 22 in the form of white solid (481 mg, 60%). M.p.: 125-126° C. $^1$H NMR (700 MHz, CDCl$_3$) δ: 7.42 (d, J=9.0 Hz, 2H), 6.85 (t, J=6.0 Hz, 1H), 6.81 (d, J=9.0 Hz, 2H), 5.49 (dd, J=6.5; 4.7 Hz, 1H), 5.32 (dd, J=5.8; 4.7 Hz, 1H), 5.17 (m, 1H), 5.02 (ddd, J=6.5; 5.5; 3.3 Hz, 1H), 4.45 (q AB, 2H), 4.24 (dd, J=12.5; 3.3 Hz, 1H), 4.11 (dd, J=12.5; 5.5 Hz, 1H), 3.55 (m, 2H), 2.13 (s, 3H), 2.09 (s, 3H), 2.07 (s, 3H), 2.04 (s, 3H), 2.03 (s, 3H); $^{13}$C NMR (176 MHz, CDCl$_3$) δ 170.7, 170.5, 170.2, 170.0, 169.9, 168.3, 156.4, 132.8, 116.7, 114.7, 70.2, 69.2, 69.1, 69.0, 67.6, 61.6, 39.4, 20.9, 20.8, 20.8, 20.7. HRMS (ESI+) calculated for C$_{24}$H$_{30}$BrNNaO$_{12}$ [M+Na]$^+$, m/z 626.0849. found: 626.0848. R$_f$=0.29 (silica, dichloromethane).

Compound 22

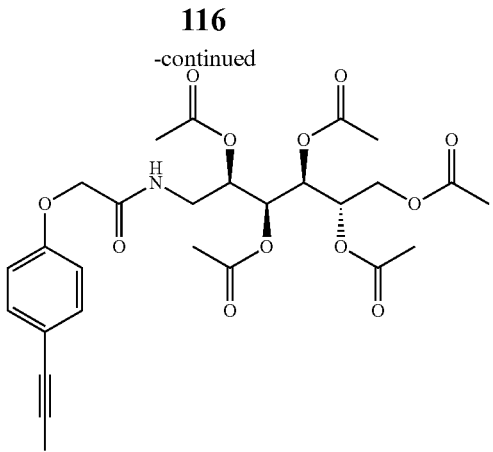

22

Ethynyltrimethylsilane (82 mg, 0.58 mmol) and triethylamine (0.67 mL, 4.81 mmol) were added to a solution of compound 21 (290 mg, 0.48 mmol) in anhydrous tetrahydrofuran (6 mL) degassed beforehand by three cycles of freezing-thawing under vacuum. The mixture was degassed again by three cycles of freezing-thawing under vacuum and then [1,1-bis(diphenylphosphino)ferrocene]dichloropalladium(II) (39 mg, 0.048 mmol) and copper iodide (9 mg, 0.048 mmol) were added. The brown solution was heated at 65° C. for 18 h under inert atmosphere. The progress of the reaction was monitored by TLC. After this time, reaction was complete. The solvent was removed under reduced pressure and the brown oil was purified by silica column chromatography using an eluent (cylohexane-ethyl acetate 30-70) leading to compound 22 as a white solid (182 mg, 63%). M.p.: 152-154° C. $^1$H NMR (700 MHz, CDCl$_3$) δ: 7.42 (d, J=8.9 Hz, 2H), 6.86 (t, J=6.1 Hz, 1H), 6.84 (d, J=8.9 Hz, 2H), 5.48 (dd, J 6.5; 4.8 Hz, 1H), 5.33 (dd, J=5.8; 4.8 Hz, 1H), 5.17 (ddd, J=6.8; 5.8; 4.8 Hz, 1H), 5.02 (ddd, J=6.5; 5.5; 3.4 Hz, 1H), 4.47 (q, AB, 2H), 4.25 (dd, J=12.5; 3.4 Hz, 1H), 4.11 (dd, J=12.5; 5.5 Hz, 1H), 3.55 (m, 2H), 2.09 (s, 3H), 2.08 (s, 3H), 2.07 (s, 3H), 2.04 (s, 3H), 2.03 (s, 3H), 0.24 (s, 9H); $^{13}$C NMR (176 MHz, CDCl$_3$) δ: 170.7, 170.5, 170.2, 170.0, 169.9, 168.3, 157.2, 133.9, 117.2, 114.7, 104.6, 93.5, 70.2, 69.2, 69.1, 69.0, 67.3, 61.6, 39.4, 20.9, 20.8 (4), 20.8 (3), 20.7, 0.15. HRMS (ESI+) calculated for C$_{29}$H$_{39}$NNaO$_{12}$Si [M+Na]$^+$, m/z 644.2139. found: 644.2158. R$_f$=0.63 (silica; cyclohexane-ethyl acetate 75:25).

Compound 23

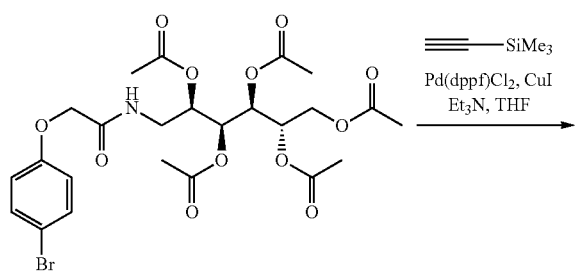 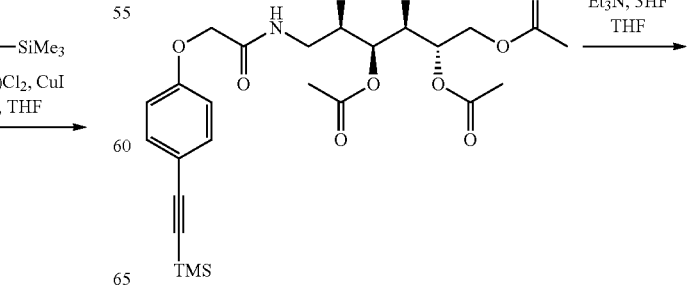

21 → 22

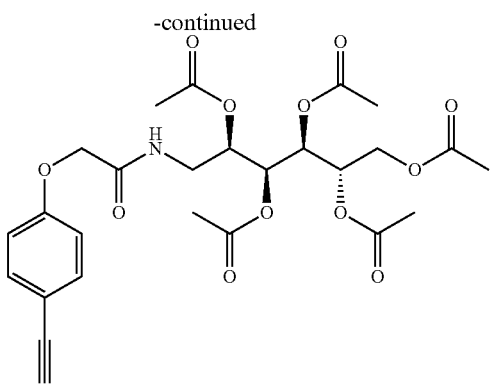

23

Triethylamine trihydrofluoride (0.29 mL, 0.17 mmol) was added to a solution of compound 22 (109 mg, 0.17 mmol) in anhydrous tetrahydrofuran (2 mL), which was then heated at 35° C. for 24 h under inert atmosphere. The progress of the reaction was monitored by TLC. After this time, reaction was complete. The solvent was removed under reduced pressure and the crude product was purified by silica column chromatography using a cyclohexane-ethyl acetate 50-50 eluent to give, after evaporation of the fractions, a white solid identified as compound 23 (75 mg, 78%). M.p.: 148-150° C. HRMS (ESI+) calculated for $C_{26}H_{31}NO_{12}Na$ [M+Na]$^+$, m/z 572.1744. found: 572.1757. $R_f$=0.45 (silica, cyclohexane-ethyl acetate 70:30).

Compound 25

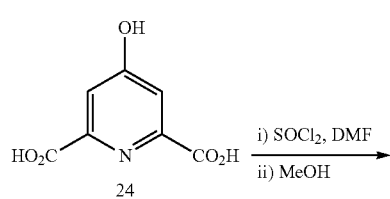

24

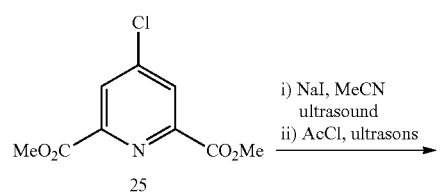

25

A few drops of anhydrous dimethylformamide were added to a solution of chelidamic acid 24 (17 g, 93 mmol) in thionyl chloride (95 mL). This solution was heated at 100° C. for 48 h. The thionyl chloride was removed under reduced pressure. Dichloromethane (50 mL) was added to this residue and the mixture was cooled to 0° C. Anhydrous methanol (40 mL) was added dropwise to this mixture in the space of 10 min and the mixture was heated at room temperature and then was stirred overnight. The solvents were removed under reduced pressure and saturated solution of sodium bicarbonate (100 mL) was added to this residue. The mixture was filtered and the filtrate was extracted with dichloromethane (3×50 mL), the organic phases were combined, dried over magnesium sulfate, filtered and evaporated under reduced pressure to give a white solid identified as compound 25. The product was sufficiently pure to be used in the rest of the synthesis without additional purification (13.3 g, 63%). M.p.: 141-142° C. $^1$H NMR (300 MHz, CDCl$_3$) δ: 8.32 (s, 2H), 4.06 (s, 6H). $^{13}$C NMR (75 MHz, CDCl$_3$) δ: 163.59, 149.06, 145.45, 127.78, 52.95. HRMS (ESI+) calculated for $C_9H_9NO_4Cl$ [M+H]$^+$, m/z 230.0215. found: 230.0216. $R_f$=0.75 (silica, dichloromethane-methanol 90:10).

Compound 26

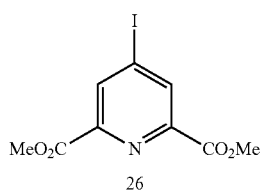

26

Sodium iodide (39 g, 262 mmol) was added to a solution of compound 25 (6.0 g, 26.2 mmol) in anhydrous acetonitrile (140 mL) and the mixture was sonicated for 20 min. Acetyl chloride (5.55 mL, 78.6 mmol) was added to this mixture, and the mixture was sonicated for 5 h. A saturated solution of sodium bicarbonate (75 mL) and then water (100 mL) were added to this solution cooled to 0° C. The mixture was extracted with ethyl acetate (2×50 mL), and the organic phases were combined, washed with a 0.2 M solution of thiosulfate and finally dried over magnesium sulfate, filtered and then concentrated under reduced pressure. Methanol (40 mL) was added to this residue, the mixture was stirred for 20 min and was then filtered to give a white solid identified as compound 26. The product was sufficiently pure to be used in the rest of the synthesis without additional purification (6.9 g, 82%). M.p.: 165-167° C. $^1$H NMR (300 MHz, CDCl$_3$) δ: 8.68 (s, 2H), 4.05 (s, 6H). $^{13}$C NMR (75 MHz, CDCl₃) δ 163.48, 149.06, 147.83, 136.29, 108.76, 52.86. HRMS (ESI+) calculated for $C_9H_9NO_4I$ [M+H]⁺, m/z 321.9571. found: 321.9567. $R_f$=0.36 (silica, cyclohexane-ethyl acetate 50:50).

Compound 27a

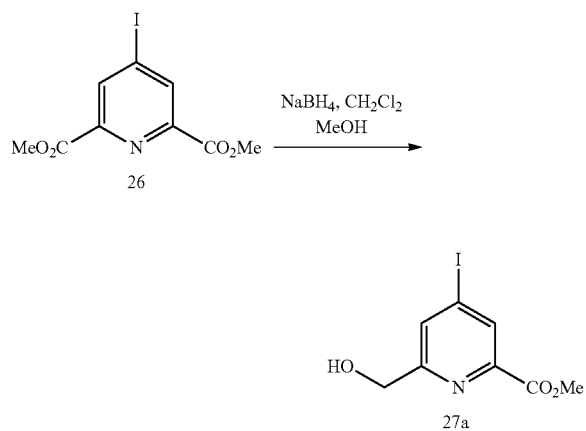

Methanol (35 mL) and then sodium borohydride (540 mg, 14.2 mmol) were added to a solution of diester 26 (7.0 g, 21.8 mmol) in dichloromethane (50 mL) cooled to 0° C. The mixture was stirred for 2 h at 0° C. The progress of the reaction was monitored by TLC. After this time, reaction was complete. A 1 M aqueous solution of hydrochloric acid (20 mL) was added to this mixture. The solvent was removed under reduced pressure and a saturated solution of sodium bicarbonate (100 mL) was added to the residue, then the mixture was extracted with ethyl acetate (4×30 mL). The organic phases were combined, dried over magnesium sulfate, filtered and concentrated under reduced pressure. The residue was purified by silica column chromatography (cyclohexane/ethyl acetate 60/40 to 0/100 in increments of 10%) to give compound 27a as a white solid (3.8 g, 60%). M.p.: 119-122° C. ¹H NMR (300 MHz, CDCl₃) δ: 8.41 (s, 1H), 7.99 (s, 1H), 4.85 (s, 2H), 4.02 (s, 3H). ¹³C NMR (75 MHz, CDCl₃) δ: 164.44, 161.44, 147.31, 133.34, 133.06, 106.97, 64.31, 53.29. HRMS (ESI+) calculated for $C_8H_9NO_3I$ [M+H]⁺, m/z 293.9622. found: 293.9615. $R_f$=0.54 (silica, dichloromethane-methanol 90:10).

Compound 27b

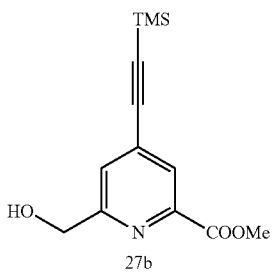

Anhydrous tetrahydrofuran (10 mL) was added to iodinated pyridine 27a (3.22 g, 11 mmol) and the solution was degassed by three cycles of freezing-thawing. Trimethylsilyl acetylene (7.8 mL, 55 mmol) and diisopropylethylamine (9.6 mL, 50 mmol) were added to this solution and the solution was degassed again. Tetrakis(triphenylphosphine)palladium(0) (385 mg, 0.55 mmol) and copper iodide (209 mg, 0.11 mmol) were added to this solution. This new solution was degassed again three times and then was stirred at room temperature under inert atmosphere. A color change from very light yellow to dark brown was observed and the mixture was stirred at 65° C. under inert atmosphere. The progress of the reaction was monitored by TLC. After 3 h, reaction was complete. The reaction mixture was cooled to room temperature and the solvent was removed under reduced pressure. The crude product was purified by silica column chromatography (dichloromethane/methanol 0 to 4% in increments of 0.5%) to obtain compound 27b (2.61 g, 90%); ¹H NMR (400 MHz, CDCl₃) δ: 8.01 (s, 1H), 7.56 (s, 1H), 4.82 (s, 2H), 3.97 (s, 3H), 0.25 (s, 9H); ¹³C NMR (100 MHz, CDCl₃) δ: 165.2, 160.8, 147.2, 133.4, 126.2, 126.0, 101.9, 101.3, 64.6, 53.1, 0.3. HRMS (ESI+) calculated for $C_{13}H_{18}NO_3Si$ [M+H]⁺, m/z 264.1056 found: 264.1050. Rf=0.68 (silica, dichloromethane-methanol, 90:10).

Compound 27c

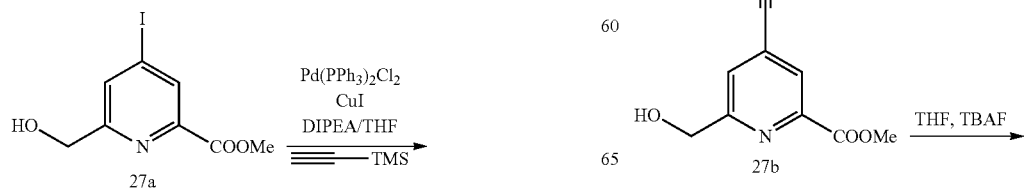

Compound 30

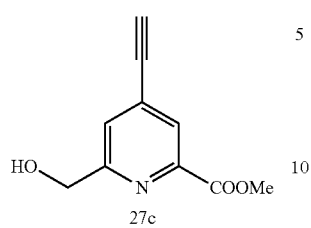

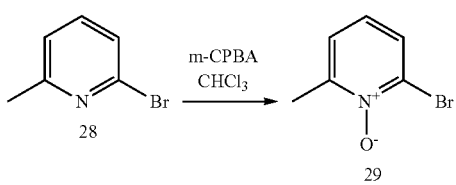

A 1 M solution of tetrabutylammonium fluoride in THF (1 mL) was added to a solution of compound 27b (263 mg, 1 mmol) in tetrahydrofuran (10 mL). The mixture was stirred at room temperature for 1 h. The progress of the reaction was monitored by TLC. After this time, reaction was complete. The solvent was removed under reduced pressure. The residue was dissolved in dichloromethane (20 mL) and the organic phase was washed with water (4×10 mL), dried over magnesium sulfate, filtered and concentrated under reduced pressure to give compound 27c (162 mg, 85%).

Compound 29

At room temperature, m-chloroperbenzoic acid (82 g, 475 mmol) was added to a solution of 2-bromo-6-methyl-pyridine 28 (40 g, 232.5 mmol) in chloroform (400 mL). The mixture was heated at 65° C. for 20 h and then was cooled to 0° C. for 3 h. After filtration of the precipitate, the filtrate was concentrated under reduced pressure. An aqueous solution of sodium hydroxide 2 M (100 mL) was added to this residue and this solution was extracted with dichloromethane (4×100 mL). The organic phases were combined, dried over magnesium sulfate, filtered and concentrated under reduced pressure to give compound 29 in the form of a yellow solid, which was used in the rest of the synthesis without additional purification (35.48 g, 81%). M.p.: 48-55° C. $^1$H NMR (400 MHz, CDCl$_3$) δ: 7.55 (dd, J=7.9; 1.6 Hz, 1H), 7.23 (dd, J=7.9; 1.6 Hz, 1H), 7.01 (t, J=7.9 Hz, 1H), 2.57 (s, 3H); $^{13}$C NMR (100 MHz, CDCl$_3$) δ: 151.2, 133.5, 128.7, 125.3, 125.2, 19.3. HRMS (ESI+) calculated for C$_6$H$_7$NOBr [M+H]$^+$, m/z 187.9711. found: 187.9698. R$_f$=0.33 (silica, dichloromethane-methanol 96:4).

52.5% fuming nitric acid (13.6 mL, 329.5 mmol) was added dropwise to a solution of N-oxide compound 29 (13.2 g, 69.8 mmol) in 96% concentrated sulfuric acid (18.5 mL, 347.7 mmol) cooled to 0° C. The mixture was stirred at room temperature for 15 min and then was heated at 85° C. for 16 h. The solution was then cooled to room temperature and was poured into crushed ice (80 g). After stirring for 15 min, the precipitate was filtered and was washed with water (50 mL). The yellow solid was dissolved in dichloromethane and the solution was dried over magnesium sulfate, filtered and concentrated under reduced pressure to give compound 30 in the form of a yellow solid, which was used in the rest of the synthesis without additional purification (15 g, 92%). M.p.: 137-138° C. $^1$H NMR (400 MHz, CDCl$_3$) δ: 8.40 (d, J=2.8 Hz, 1H), 8.09 (d, J=2.8 Hz, 1H), 2.62 (s, 3H); $^{13}$C NMR (100 MHz, CDCl$_3$) δ: 151.8, 140.7, 134.0, 122.8, 118.9, 19.6. HRMS (ESI+) calculated for C$_6$H$_6$BrN$_2$O$_3$ [M+H]$^+$, m/z 232.9562. found: 232.9564. Rf=0.53 (silica, dichloromethane-methanol 98:2).

Compound 31

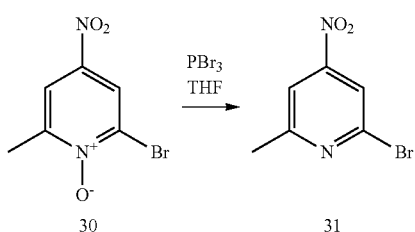

Phosphorus tribromide (22 mL, 234 mmol) was added to a solution of N-oxide compound 30 (16 g, 68.66 mmol) in anhydrous tetrahydrofuran (500 mL), and the mixture was heated at 60° C. under inert atmosphere for 16 h. The solution was cooled to room temperature and was concentrated under reduced pressure and then was poured into iced 2 M solution of sodium hydroxide (300 mL). The mixture was extracted with dichloromethane (3×100 mL), the organic phases were combined, dried over mag nesium sulfate and concentrated under reduced pressure. The resultant oil was purified by silica column chromatography using dichloromethane as eluent, thus leading to compound 31 in the form of a yellow solid (5.4 g, 36%). M.p. 51-52° C. $^1$H NMR (400 MHz, CDCl$_3$) δ: 8.02 (d, J=2.8 Hz, 1H), 7.83 (d, J=2.8 Hz, 1H), 2.70 (s, 3H); $^{13}$C NMR (100 MHz, CDCl$_3$) δ: 162.9, 154.9, 142.4, 118.4, 115.0, 24.6. HRMS (ESI+) calculated for C$_6$H$_6$BrN$_2$O$_2$ [M+H]$^+$, m/z 216.9613. found: 232.9621. Rf=0.75 (silica, dichloromethane-methanol 98:2).

Compound 32a

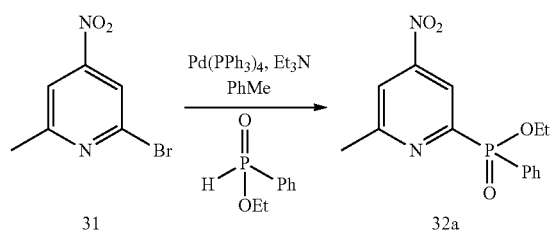

Ethyl phenylphosphinate (0.95 g, 5.60 mmol) and triethylamine (2.6 mL, 19.0 mmol) were added to a solution of 2-bromo-6-methyl-4-nitropyridine 31 (1.01 g, 4.68 mmol) in anhydrous toluene (10 mL). The mixture was degassed by three cycles of freezing-thawing. Tetrakis(triphenylphosphine)palladium(0) (83 mg, 0.07 mmol) was added to this solution and the mixture was degassed again three times before it was stirred under reflux for 16 h under inert atmosphere. The progress of the reaction was monitored by TLC. After this period, reaction was complete. The solution was cooled and was diluted with dichloromethane (20 mL). The mixture was washed with 1 M aqueous solution of hydrochloric acid (2×15 mL) followed by washing with water (3×15 mL). The organic phase was dried over magnesium sulfate, filtered and the solvent was removed under reduced pressure to obtain a dark residue, which was purified by silica column chromatography (dichloromethane/methanol 0.5%), thus leading to compound 32a in the form of a yellow oil (645 mg, 45%). $^1$H NMR (400 MHz, CDCl$_3$) δ: 8.55 (dd, J=5.6; 1.4 Hz, 1H), 7.97 (ddd, J=11.2; 7.7 Hz, 1.4 Hz, 2H), 7.90 (d, J=1.4 Hz, 1H), 7.55 (td, J=7.7; 1.4 Hz, 1H), 7.46 (td, J=7.7; 3.5 Hz, 2H), 4.15 (qd, J=7.0; 4.2 Hz, 2H), 2.72 (s, 3H), 1.38 (t, J=7.0 Hz, 3H); $^{13}$C NMR (100 MHz, CDCl$_3$) δ: 163.0 (d, J=21 Hz), 158.1 (d, J=167 Hz), 154.0 (d, J=13 Hz), 132.9 (d, J=3 Hz), 132.5 (d, J=10 Hz), 129.1 (d, J=140 Hz), 128.5 (d, J=13 Hz), 117.6 (d, J=24 Hz), 117.5 (d, J=3 Hz), 62.2 (d, J=6 Hz), 24.9, 16.4; $^{31}$P NMR (162 MHz, CDCl$_3$) δ: 23.7. HRMS (ESI+) calculated for C$_{14}$H$_{16}$N$_2$O$_4$P [M+H]$^+$, m/z 307.0848. found: 307.0851. Rf=0.47 (silica, dichloromethane-methanol 95:5).

Compound 32b

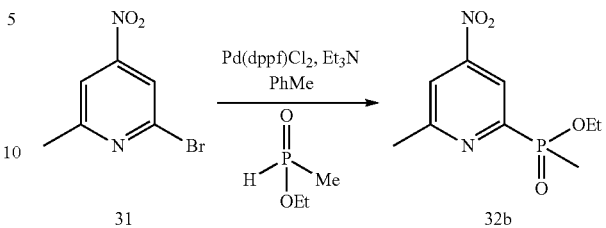

Water (264 μL, 14.7 mmol) was added at 0° C. to diethylmethyl phosphonite (2 g, 14.7 mmol), without any particular precautions. The reaction mixture was heated to room temperature in 1 h and was then stirred for 16 h at room temperature. A solution of 2-bromo-6-methyl-4-nitropyridine 31 (2.65 g, 12.3 mmol) in anhydrous toluene (35 mL) and then triethylamine (6 mL, 43.0 mmol) were added to this mixture. The mixture was degassed by three cycles of freezing-thawing. bis(Diphenylphosphino)ferrocene]dichloropalladium(II) (800 mg, 1.1 mmol) was added to this solution and the mixture was degassed again three times before it was stirred under reflux for 16 h under inert atmosphere. The progress of the reaction was monitored by TLC. After this period, reaction was complete. The solution was cooled and concentrated under reduced pressure and was then diluted with dichloromethane (20 mL). The mixture was washed with 1 M aqueous solution of hydrochloric acid (2×15 mL) and then with water (3×15 mL). The organic phase was dried over magnesium sulfate, filtered and the solvent was removed under reduced pressure to obtain a dark residue, which was purified by silica column chromatography (dichloromethane/methanol 1.6% in increments of 0.1%), thus leading to compound 32b in the form of a colorless oil (2.1 g, 59%). $^1$H NMR (400 MHz, CDCl$_3$) δ: 8.54-8.56 (m, 1H), 7.96-8.01 (m, 1H), 3.68-4.44 (m, 2H), 2.79 (s, 3H), 1.83 (d, J=15 Hz, 3H), 1.31 (t, J=7.1 Hz, 3H); $^{13}$C NMR (100 MHz, CDCl$_3$) δ: 163.2 (d, J=21 Hz), 158.1 (d, J=157 Hz), 154.3 (d, J=157 Hz), 117.9 (d, J=3 Hz), 117.2 (d, J=23 Hz), 61.6 (d, J=7 Hz), 24.9; 16.6 (d, J=6 Hz), 13.5 (d, J=105 Hz); $^{31}$P NMR (162 MHz, CDCl$_3$) δ: +37.2. HRMS (ESI+) calculated for C$_9$H$_{13}$N$_2$O$_4$P [M+H]$^+$, m/z 244.0613. found: 244.0607. R$_f$=0.26 (silica, dichloromethane-methanol 95:5).

Compound 33a

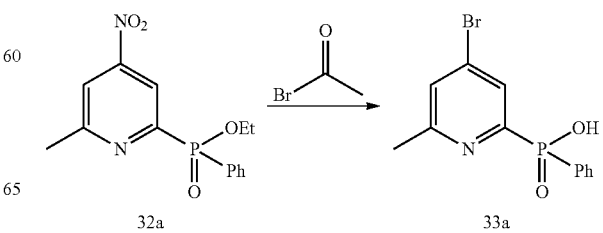

Acetyl bromide (15 mL, 0.2 mol) was added to the nitrated derivative 32a (2.00 g, 6.54 mmol) and the mixture was stirred at 70° C. for 16 h under argon. During this time, a pale brown precipitate formed. The suspension was poured slowly into methanol (100 mL) cooled to 0° C. in the space of 10 min. The mixture was stirred for 10 min at room temperature. The solvent was removed under reduced pressure to give the desired compound in the form of a pale brown solid, which was used directly in the rest of the synthesis without purification (1.81 g, 90%); $^1$H NMR (400 MHz, CD$_3$OD) δ: 8.33 (dd, J=7.2 Hz, 2.0 Hz, 1H), 8.23 (d, J=2.0 Hz, 1H), 7.95 (ddd, J=13.2 Hz, 7.6 Hz, 1.6 Hz, 2H), 7.63 (1H, td, J=7.6 Hz, 1.6 Hz, 1H), 7.55 (2H, td, J=7.6 Hz, 3.6 Hz), 2.77 (3H, s); $^{13}$C NMR (100 MHz, CD$_3$OD) δ: 159.4 (d, J=20 Hz), 151.7 (d, J=160 Hz), 145.1 (d, J=10 Hz), 134.8 (d, J=3 Hz), 133.3 (d, J=10 Hz), 131.0 (d, J=24 Hz), 130.6 (d, J=3 Hz), 130.2 (d, J=140 Hz), 129.6 (d, J=12 Hz), 20.4; $^{31}$P NMR (162 MHz, CD$_3$OD) δ: 14.3. HRMS (ESI+) calculated for C$_{12}$H$_{10}$NO$_2$P [M+H]$^+$, m/z 309.9633. found: 309.9648. R$_f$=0.01 (silica, dichloromethane-methanol 95:5).
Compound 33b

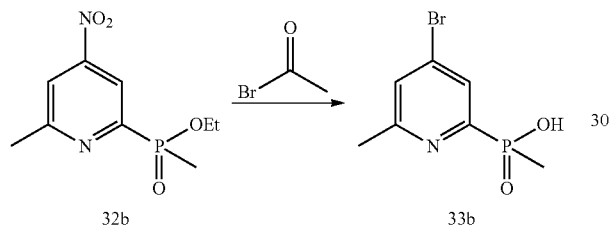

Acetyl bromide (40 mL, 541 mmol) was added to the nitrated derivative 32b (5 g, 20.5 mmol) and the mixture was stirred at 70° C. for 16 h under argon. During this time, a pale brown precipitate formed. The suspension was poured slowly into methanol (100 mL) cooled to 0° C. in the space of 10 min. The mixture was stirred at room temperature for 10 min. The solvent was removed under reduced pressure to give the desired compound in the form of a pale brown solid, which was used directly in the rest of the synthesis without purification (4.57 g, 90%); $^1$H NMR (400 MHz, CD$_3$OD) δ: 8.25-8.28 (m, 1H), 8.17-8.18 (m, 1H), 2.76 (s, 3H), 1.80 (d, J=16 Hz, 3H); $^{31}$P NMR (162 MHz, CD$_3$OD) δ: +28.6. HRMS (ESI+) calculated for C$_7$H$_{10}$BrNO$_2$P [M+H]$^+$, m/z 249.9633. found: 249.9627. R$_f$=0.01 (silica, dichloromethane-methanol 95:5).
Compound 34a

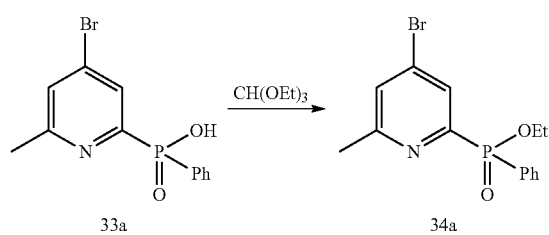 [SMILES: Cc1cc(Br)cc(P(=O)(O)c2ccccc2)n1 ; CCOP(=O)(c1ccccc1)c1cc(Br)cc(C)n1 ; "CH(OEt)3"]

Ethyl orthoformate (50 mL) was added to phosphinic acid 33a (1.80 g, 5.80 mmol) and the mixture was stirred at 140° C. for 72 h under inert atmosphere. The progress of the reaction was monitored by TLC. After this period, reaction was complete. The solution was cooled to room temperature and the solvent was removed under reduced pressure. The residue was purified by silica column chromatography (dichloromethane/methanol 0.5%) to give compound 34a in the form of a yellow oil (1.08 g, 55%). $^1$H NMR (400 MHz, CDCl$_3$) δ: 8.04 (dd, J=6.3 Hz, 1.4 Hz, 1H), 7.95 (ddd, J=11.2; 7.0; 1.4 Hz, 2H), 7.51 (1H, td, 7.0; 1.4 Hz, 1H), 7.43 (td, J=7.0; 3.5 Hz, 2H), 7.37 (d, J=1.4 Hz, 1H), 4.11 (qd, J=7.0; 4.2 Hz, 2H), 2.52 (s, 3H), 1.34 (t, J=7.0 Hz, 3H); $^{13}$C NMR (100 MHz, CDCl$_3$) δ: 161.2 (d, J=22 Hz), 155.7 (d, J=165 Hz), 133.5 (d, J=15 Hz), 132.7 (d, J=3 Hz), 132.6 (d, J=10 Hz), 130.0 (d, J=139 Hz), 128.5 (d, J=3 Hz), 128.4 (d, J=23 Hz), 128.3 (d, J=13 Hz), 62.1 (d, J=6 Hz), 24.5, 16.7; $^{31}$P NMR (162 MHz, CDCl$_3$) δ: 25.5. HRMS (ESI+) calculated for C$_{14}$H$_{16}$NO$_2$BrP [M+H]$^+$, m/z 340.0102. found: 340.0102. R$_f$=0.3 (silica, cyclohexane-ethyl acetate 30:70).

Compound 34b

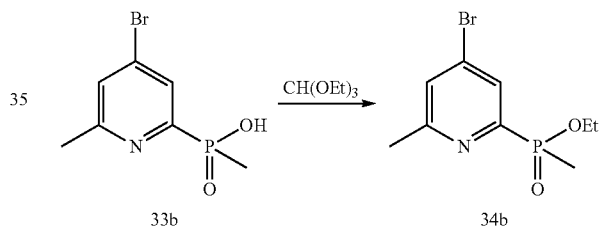

Ethyl orthoformate (46 mL) was added to phosphinic acid 33b (4.54 g, 18.4 mmol) and the mixture was stirred at 140° C. for 42 h under argon. The progress of the reaction was monitored by TLC. After this period, reaction was complete. The solution was cooled to room temperature and the solvent was removed under reduced pressure. The residue was purified by silica column chromatography (dichloromethane/methanol 1%) to give compound 34b in the form of a yellow oil (3.9 g, 68%); $^1$H NMR (400 MHz, CDCl$_3$) δ 8.04 (dd, J=5.9; 1.8 Hz, 1H), 7.46 (s app, 1H), 3.82-4.16 (m, 2H), 2.59 (s, 3H), 1.77 (d, J=15 Hz, 3H), 1.28 (t, J=7.1 Hz, 3H); $^{13}$C NMR (100 MHz, CDCl$_3$) δ: 161.1 (d, J=21 Hz), 155.4 (d, J=156 Hz), 133.6 (d, J=14 Hz), 128.9 (d, J=3 Hz), 128.2 (d, J=22 Hz), 61.3 (d, J=6 Hz), 24.4; 16.5 (d, J=6 Hz), 13.6 (d, J=104 Hz); $^{31}$P NMR (162 MHz, CDCl$_3$) δ: +38.0; HRMS (ESI+) calculated for C$_9$H$_{13}$NO$_2$BrP [M+H]$^+$, m/z 276.9867. found: 276.9862. R$_f$=0.52 (silica, dichloromethane-methanol 95:5).

Compound 35a

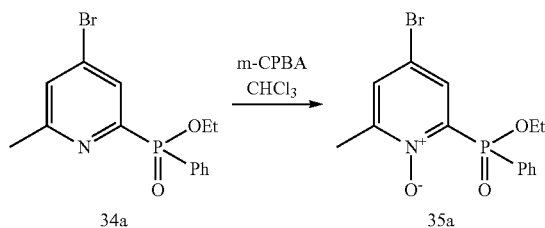 [SMILES: CCOP(=O)(c1ccccc1)c1cc(Br)cc(C)n1 ; "m-CPBACHCl3" ; CCOP(=O)(c1ccccc1)c1cc(Br)cc(C)[n+]1[O-]]

meta-Chloroperbenzoic acid (1.27 g, 7.35 mmol) was added to a solution of pyridinyl derivative 34a (1.25 g, 3.68 mmol) in chloroform (20 mL). The resultant solution was stirred at 65° C. for 16 h under inert atmosphere. The progress of the reaction was monitored by TLC. After this period, reaction was complete. The mixture was cooled to room temperature and the solvent was removed under reduced pressure to obtain a yellow oil. This oil was dissolved in dichloromethane (50 mL) and was washed with 0.5 M aqueous solution of sodium bicarbonate (50 mL). The phases were separated and the aqueous phase was extracted with dichloromethane (3×30 mL). The organic phases were combined, dried over magnesium sulfate, filtered and the solvent was removed under reduced pressure. The resultant yellow oil was purified by silica column chromatography (dichloromethane/methanol 0 to 2% in increments of 0.1%) to obtain a yellow oil corresponding to compound 35a (1.11 g, 75%). $^1$H NMR (400 MHz, CDCl$_3$) δ: 8.05 (dd, J=7.7 Hz, 2.1 Hz, 1H), 7.98 (dd, J=7.7 Hz, 13.3 Hz, 2H), 7.50 (t, 7.7 Hz, 1H), 7.44 (d, J=2.1 Hz, 1H), 7.41 (td, J=7.7 Hz, 4.2 Hz, 2H), 4.13 (qd, J=5.6 Hz, 4.9 Hz, 2H), 2.32 (s, 3H), 1.34 (t, J=5.6 Hz, 3H); $^{13}$C NMR (100 MHz, CDCl$_3$) δ: 151.0 (d, J=4 Hz), 144.2 (d, J=149 Hz), 133.2 (d, J=11 Hz), 133.1 (d, J=4 Hz), 133.0 (d, J=11 Hz), 132.2 (d, J=4 Hz), 129.0 (d, J=152 Hz), 128.4 (d, J=14 Hz), 117.4 (d, J=12 Hz), 62.3 (d, J=6 Hz), 17.5, 16.7; $^{31}$P NMR (162 MHz, CDCl$_3$) δ: +21.2. HRMS (ESI+) calculated for C$_{14}$H$_{16}$NO$_3$BrP [M+H]$^+$, m/z 356.0051. found: 356.0061. R$_f$=0.5 (silica, dichloromethane-methanol 90:10).

Compound 35b

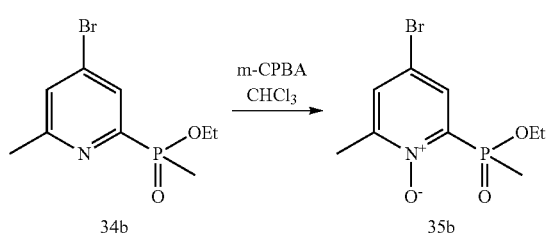

meta-Chloroperbenzoic acid (4.1 g, 23.8 mmol) was added to a solution of pyridinyl derivative 34b (3.5 g, 11.87 mmol) in chloroform (40 mL). The resultant solution was stirred at 65° C. for 2 h under argon. The progress of the reaction was monitored by TLC. After this period, reaction was complete. The mixture was cooled to room temperature and the solvent was removed under reduced pressure to obtain a yellow oil. This oil was dissolved in dichloromethane (50 mL) and was washed with 0.5 M solution of sodium bicarbonate (100 mL). The phases were separated and the aqueous phase was extracted with dichloromethane (3×100 mL). The organic phases were combined and were dried over magnesium sulfate and the solvent was removed under reduced pressure. The resultant yellow oil was purified by silica column chromatography (dichloromethane/methanol 0 to 2% in increments of 0.1%) to obtain a yellow oil corresponding to compound 35b (2.6 g, 75%). $^1$H NMR (400 MHz, CDCl$_3$) δ 8.04 (dd, J=7.9; 2.9 Hz, 1H), 7.54 (dd, J=2.9 Hz, 1H), 3.89-4.22 (m, 2H), 2.48 (s, 3H), 1.97 (d, J=17 Hz, 3H), 1.31 (t, J=7.1 Hz, 3H); $^{13}$C NMR (100 MHz, CDCl$_3$) δ: 151.1 (d, J=4 Hz), 143.8 (d, J=136 Hz), 133.4 (d, J=11 Hz), 132.3 (d, J=2 Hz), 118.0 (d, J=12 Hz), 62.1 (d, J=7 Hz), 17.5; 16.6 (d, J=6 Hz), 14.5 (d, J=111 Hz); $^{31}$P NMR (162 MHz, CDCl$_3$) δ: +32.2; m/z HRMS (ESI+) calculated for C$_9$H$_{13}$BrNO$_3$P [M+H]$^+$, m/z 292.9816. found: 292.9811. R$_f$=0.27 (silica, dichloromethane-methanol 95:5).

Compound 36a

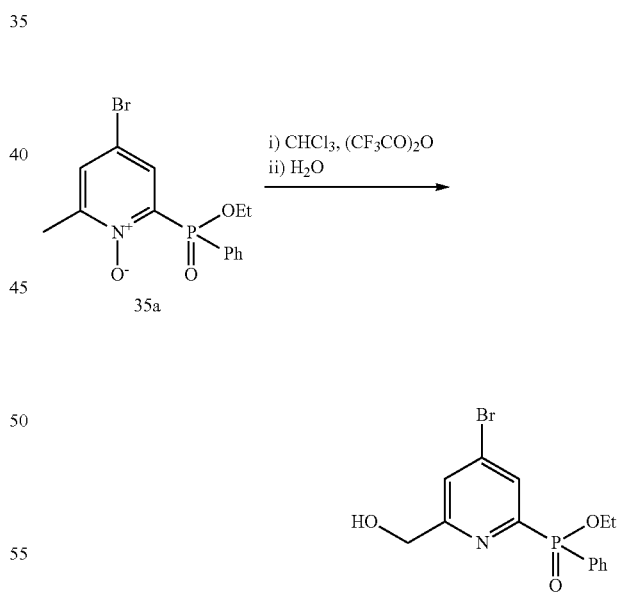

Chloroform (35 mL) and trifluoroacetic anhydride (25 mL) were added to the pyridinyl N-oxide derivative 35a (1.7 g, 4.8 mmol). The solution was heated at 60° C. for 2 h with stirring. The progress of the reaction was monitored by TLC. After this period, reaction was complete. The solution was cooled to room temperature and the solvent was removed under reduced pressure. The residue was purified by silica column chromatography (dichloromethane/methanol from 0 to 5% in increments of 1%) to obtain a white solid corresponding to compound 36a (1.6 g, 97%). M.p. 98-100° C. $^1$H NMR (400 MHz, CDCl$_3$) δ: 8.16 (dd, J=6.0; 1.3 Hz, 1H), 7.95 (ddd, J=12.3; 8.3; 1.4 Hz, 2H), 7.62 (s, 1H); 7.60-7.56 (m, 1H); 7.53-7.46 (m, 2H); 4.78 (s, 2H); 4.67 (bs, 1H); 4.24-4.10 (m, 2H); 1.40 (t, J=7.0 Hz, 3H). HRMS (ESI+) calculated for C$_{14}$H$_{16}$NO$_3$BrP [M+H]$^+$, m/z 356.0051. found: 356.0049. R$_f$=0.44 (silica, dichloromethane-methanol 90:10).

Compound 36b

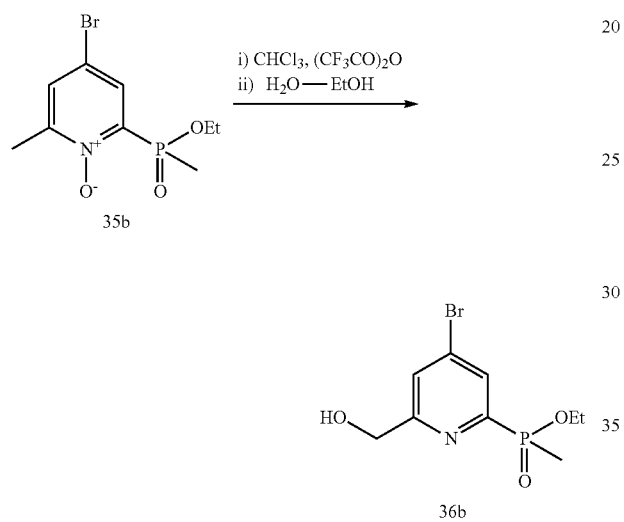

Chloroform (60 mL) and trifluoroacetic anhydride (28 mL) were added to the pyridinyl N-oxide derivative 35b (3.0 g, 10.23 mmol). The solution was heated at 60° C. for 2 h with stirring. The progress of the reaction was monitored by TLC. After this period, reaction was complete. The solution was cooled to room temperature and the solvent was removed under reduced pressure. Ethanol (5 mL) and water (5 mL) were added to this residue. The solution was stirred at room temperature for 12 h and then was concentrated under reduced pressure. Dichloromethane (70 mL) and water (70 mL) were added to this residue. The organic phase was separated and then was dried over magnesium sulfate, filtered and evaporated under reduced pressure to give the crude compound, which was purified by silica column chromatography (dichloromethane/methanol from 0 to 5% in increments of 1%) to obtain a yellowish oil corresponding to compound 36b (2.2 g, 67%). $^1$H NMR (400 MHz, CDCl$_3$) δ: 8.13 (dd J=5.9; 1.8 Hz, 1H), 7.63 (s app, 1H), 4.80 (s, 2H), 3.70-4.20 (m, 2H), 3.26 (bs, 1H), 1.76 (d, J=15 Hz, 3H), 1.27 (t, J=7.1 Hz, 3H); $^{13}$C NMR (100 MHz, CDCl$_3$) δ: 162.8 (d, J=20 Hz), 154.8 (d, J=154 Hz), 134.5 (d, J=13 Hz), 129.5 (d, J=22 Hz), 126.3 (d, J=3 Hz), 64.2; 61.5 (d, J=6 Hz), 16.5 (d, J=6 Hz), 13.6 (d, J=105 Hz); $^{31}$P NMR (162 MHz, CDCl$_3$) δ: +38.0; HRMS (ESI+) calculated for C$_9$H$_{13}$NO$_3$BrP [M+H]$^+$, m/z 292.9816. found: 292.9813. R$_f$=0.24 (silica, dichloromethane-methanol 95:5).

Compound 36c

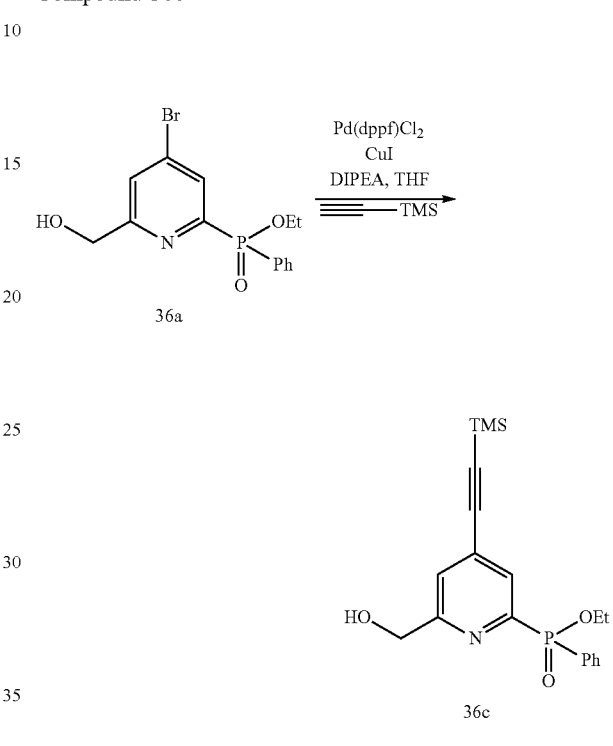

Anhydrous tetrahydrofuran (5 mL) was added to brominated pyridine 36a (178 mg, 0.5 mmol) and the solution was degassed by three cycles of freezing-thawing. Trimethylsilyl acetylene (355 µL, 2.5 mmol) and diisopropylethylamine (227 µL, 2.5 mmol) were added to this solution and the solution was degassed again. [1,1-bis (Diphenylphosphino)ferrocene]dichloropalladium(II) (37 mg, 0.05 mmol) and copper iodide (10 mg, 0.05 mmol) were added to this solution. This new solution was degassed again three times and then was stirred under inert atmosphere. A color change from very light yellow to dark brown was observed and the mixture was stirred at 65° C. under inert atmosphere. The progress of the reaction was monitored by TLC. After 1 h, reaction was complete. The reaction mixture was cooled to room temperature and the solvent was removed under reduced pressure. The residue was diluted in dichloromethane (60 mL) and was washed with a saturated aqueous solution of ammonium chloride (60 mL) and then with water (60 mL). The organic phase was dried over magnesium sulfate, filtered and then concentrated under reduced pressure to give a residue. The crude product was purified by silica column chromatography (dichloromethane/methanol 0 to 6% in increments of 1%) to obtain compound 36c (163 mg, 87%). HMRS (ESI+) calculated for $C_{19}H_{25}NO_3PSi$ [M+H]$^+$, m/z 374.1336 found: 374.1336. $R_f$=0.44 (silica; dichloromethane-methanol: 90:10).

Compound 36d

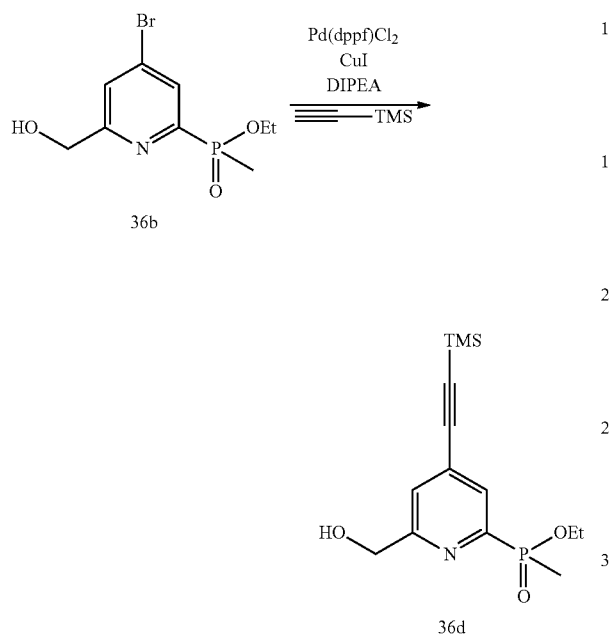

36b

36d

Anhydrous tetrahydrofuran (5 mL) was added to brominated pyridine 36b (250 mg, 0.85 mmol) and the solution was degassed by three cycles of freezing-thawing. Trimethylsilyl acetylene (600 µL, 4.3 mmol) and diisopropylethylamine (750 µL, 4.3 mmol) were added to this solution and the solution was degassed again. [1,1-bis(Diphenylphosphino)ferrocene]dichloropalladium(II) (63 mg, 0.85 mmol) and copper iodide (16 mg, 0.085 mmol) were added to this solution. This new solution was degassed again three times and then was stirred under inert atmosphere and the mixture was stirred at 65° C. The progress of the reaction was monitored by TLC. After 1 h, reaction was complete. The reaction mixture was cooled to room temperature and the solvent was removed under reduced pressure. The residue was diluted in dichloromethane (50 mL) and was washed with a saturated aqueous solution of ammonium chloride (50 mL) and then with water (50 mL). The organic phase was dried over magnesium sulfate, filtered and then concentrated under reduced pressure to give a residue. The crude product was purified by silica column chromatography (dichloromethane/methanol 0 to 4% in increments of 1%) to obtain compound 36d (265 mg, 98%). LMRS (ESI+) calculated for $C_{14}H_{23}NO_3PSi$ [M+H]$^+$, m/z 312.1185 found: 312.30. $R_f$=0.48 (silica; dichloromethane-methanol: 90:10).

Compound 36e

This compound was prepared according to the same procedure as that used for compound 36f, using the corresponding precursor.

Compound 36f

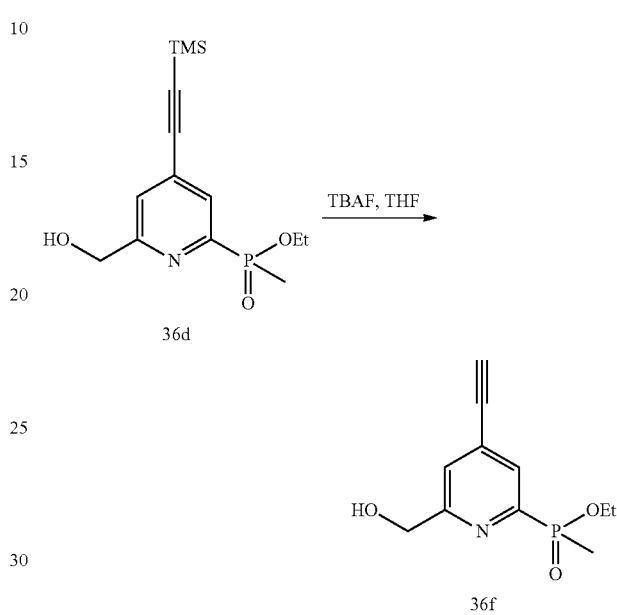

36d

36f

A solution of tetrabutyl ammonium fluoride in anhydrous tetrahydrofuran 1 M (500 µL, 643 µmol) was added to a solution of the silylated derivative 36d (200 mg, 643 µmol) in anhydrous tetrahydrofuran (10 mL). The solution was stirred at room temperature for 1 h under inert atmosphere. The progress of the reaction was monitored by TLC. After this time, reaction was complete. The solvent was removed under reduced pressure and the residue was diluted in dichloromethane (50 mL) and was washed with water (2×50 mL). The organic phase was dried over magnesium sulfate and was filtered and then concentrated under reduced pressure to give the desired compound 36f, which was used in the rest of the synthesis without additional purification (146 mg, 95%). LRMS (ESI+) calculated for $C_{11}H_{15}NO_3P$ [M+H]$^+$, m/z 240.0790 found: 240.33. $R_f$=0.42 (silica; dichloromethane-methanol 90:10).

Compound 37a

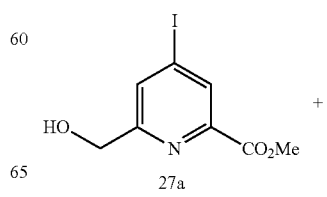

27a

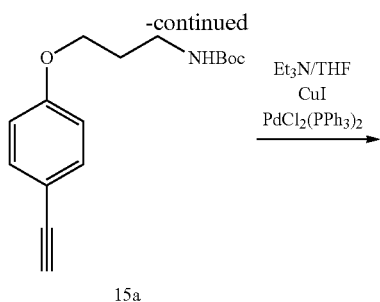

15a

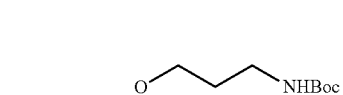

37a

A solution of acetylenic derivative 15a (0.864 g, 3.1 mmol) and of iodinated derivative 27a (0.735 g, 2.5 mmol) in a mixture of anhydrous tetrahydrofuran (20 mL) and triethylamine (20 mL) was degassed with stirring for 20 min. Palladium(II) bis-chloride bis-triphenylphosphine (22 mg, 0.031 mmol) and copper(I) iodide (12 mg, 0.063 mmol) were added to this solution. The reaction was stirred at room temperature for 12 h. The progress of the reaction was monitored by TLC. After this time, reaction was complete. The solvents were removed under reduced pressure. A saturated solution of ammonium chloride (50 mL) was added to the residue and the mixture was extracted with dichloromethane (2×25 mL). The organic phases were combined, washed with a saturated solution of ammonium chloride (50 mL) and then with a saturated solution of sodium chloride (2×50 mL) and then dried over magnesium sulfate. After filtration, the solvent was removed under reduced pressure and the residue was purified by silica column chromatography (dichloromethane/methanol 98/2) to give compound 37a in the form of a white solid (0.91 g, 82%). M.p.: 143-144° C. $^1$H NMR (500 MHz, CDCl$_3$) δ: 8.04 (s, 1H), 7.58 (s, 1H), 7.45 (d, J=8.7 Hz, 2H), 6.86 (d, J=8.7 Hz, 2H), 4.83 (d, J=5.4 Hz, 2H), 4.75 (s, 1H), 4.01 (t, J=6.1 Hz, 2H), 3.97 (s, 3H), 3.31 (td, J=6.1; 6.1 Hz, 2H), 1.96 (m, J=6.1 Hz, 2H), 1.41 (s, 9H). $^{13}$C NMR (125 MHz, CDCl$_3$) δ: 165.4, 160.8, 160.1, 156.2, 147.3, 134.1, 133.8, 125.8, 125.4, 114.9, 113.9, 95.9, 85.4, 66.1, 64.8, 53.2, 38.1, 29.7, 28.6. HRMS (ESI+) calculated for C$_{24}$H$_{28}$N$_2$O$_6$ [M+H]$^+$, m/z 441.2020. found: 441.2021. R$_f$=0.32 (silica, dichloromethane-methanol 96:4).

Compound 37b

This compound was prepared according to the same procedure as that used for compound 37c using the corresponding precursor.

Compound 37c

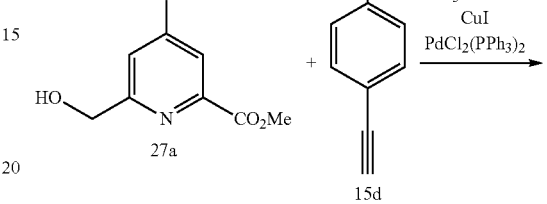

37c

A solution of acetylenic derivative 15d (133 mg, 1 mmol) and of iodinated derivative 27a (294 mg, 1 mmol) in a mixture of anhydrous tetrahydrofuran (8 mL) and triethylamine (5 mL) was degassed with stirring for 20 min. Palladium(II) bis-chloride bis-triphenylphosphine (68 mg, 0.1 mmol) and copper(I) iodide (37 mg, 0.2 mmol) were added to this solution. The reaction was stirred at 75° C. for 12 h. The progress of the reaction was monitored by TLC. After this time, reaction was complete. The solvents were removed under reduced pressure. A saturated solution of ammonium chloride (50 mL) was added to the residue and the mixture was extracted with dichloromethane (2×25 mL). The organic phases were combined, washed with a saturated solution of ammonium chloride (50 mL) and then with a saturated solution of sodium chloride (2×50 mL) and then dried over magnesium sulfate. After filtration, the solvent was removed under reduced pressure and the residue was purified by silica column chromatography using a gradient of eluent (dichloromethane/methanol 100/0 to 95/5 in increments of 0.5%) to give compound 37c (241 mg, 68%). $^1$H NMR (400 MHz, CDCl$_3$) δ: 8.07 (s, 1H), 7.59 (s, 1H), 7.49

(d, J=8.9 Hz, 2H), 6.90 (d, J=8.9 Hz, 2H), 4.85 (s, 2H), 4.00 (s, 3H), 3.84 (s, 3H). $^{13}$C NMR (100 MHz, CDCl$_3$) δ: 165.4, 160.7, 160.6, 147.3, 134.0, 133.8, 125.8, 125.4, 114.4, 113.8, 96.0, 85.3, 64.7, 55.5, 53.1. HRMS (ESI+) calculated for C$_{17}$H$_{16}$NO$_4$ [M+H]$^+$, m/z 298.1079. found: 298.1075. Rf=0.6 (silica, dichloromethane-methanol, 90:10).

Compound 37d

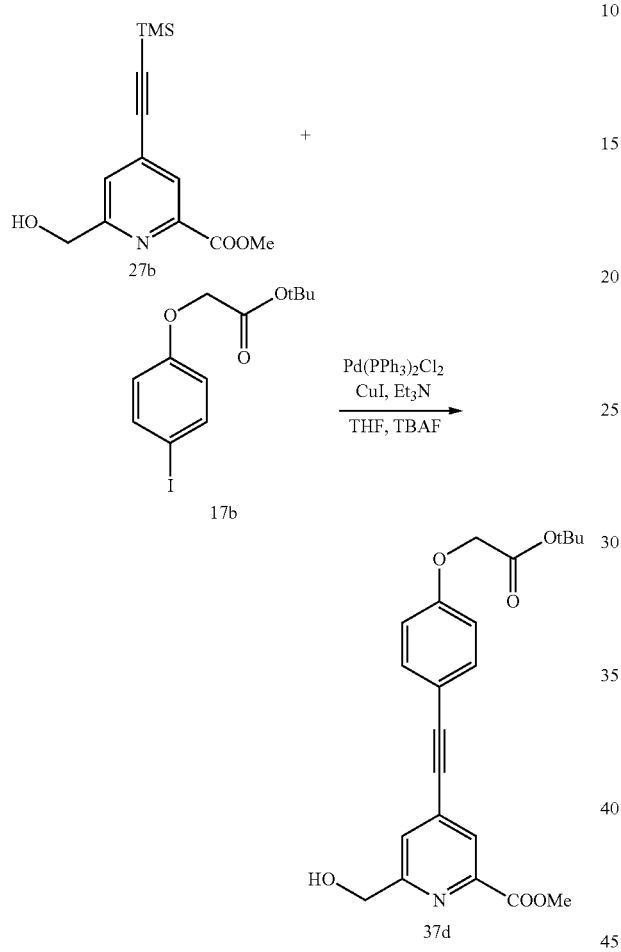

Iodinated derivative 17b (370 mg, 1 mmol) was added to a solution of acetylene derivative 27b (263 mg, 1 mmol) in anhydrous tetrahydrofuran (10 mL) and anhydrous triethylamine (5 mL). The mixture was degassed with stirring for 1 h. A solution of tetrabutylammonium fluoride in tetrahydrofuran 1 M (1.5 mL, 1.5 mmol), palladium(II) bis-chloride bis-triphenylphosphine (72 mg, 0.1 mmol) and copper(I) iodide (40 mg, 0.2 mmol) were added to this solution. The reaction mixture was stirred at 75° C. for 3 h away from the light. The progress of the reaction was monitored by TLC. After this time, reaction was complete. The solvents were removed under reduced pressure. Water (10 mL) was added to the black residue and the mixture was extracted with dichloromethane (3×20 mL). The organic phases were combined and dried over magnesium sulfate. After filtration, the solvent was removed under reduced pressure. The crude product obtained was purified by silica column flash chromatography (dichloromethane/methanol 0.5% to 5% in increments of 1%) to give compound 37d in the form of a yellowish oil (203 mg, 54%). $^1$H NMR (400 MHz, CDCl$_3$) δ: 7.95 (s, 1H), 7.59 (s, 1H), 7.40 (d, J=8.8 Hz, 2H), 6.81 (d, J=8.8 Hz, 2H), 4.80 (s, 2H), 4.47 (s, 2H), 3.89 (s, 3H), 1.41 (s, 9H). $^{13}$C NMR (100 MHz, CDCl$_3$) δ: 167.47, 165.16, 161.32, 158.69, 133.54, 131.93, 131.83, 128.43, 125.31, 114.72, 114.56, 95.26, 85.41, 82.61, 65.43, 65.54, 52.87, 27.91. HRMS (ESI+) calculated for C$_{18}$H$_{18}$NO$_5$ [M+H]$^+$, m/z 398.1604 found: 398.1597. Rf=0.74 (silica, dichloromethane-methanol, 90:10).

Compound 37e

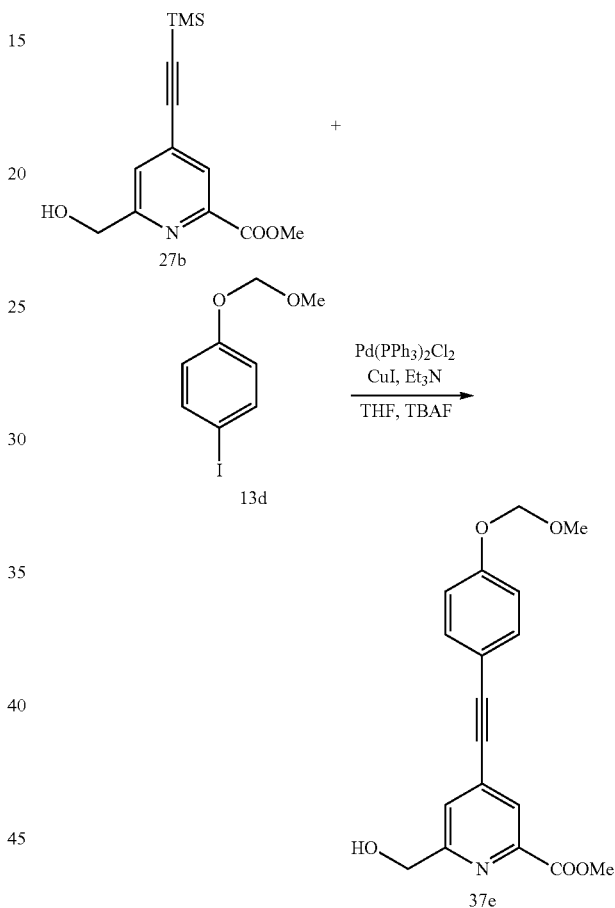

Iodinated derivative 13d (105 mg, 0.4 mmol) was added to a solution of acetylene derivative 27b (124 mg, 0.4 mmol) in anhydrous tetrahydrofuran (8 mL) and anhydrous triethylamine (5 mL). The mixture was degassed with stirring for 1 h. A solution of tetrabutylammonium fluoride in tetrahydrofuran 1 M (600 μL, 0.6 mmol), palladium(II) bis-chloride bis-triphenylphosphine (28 mg, 0.04 mmol) and copper(I) iodide (15 mg, 0.1 mmol) were added to this solution. The reaction mixture was stirred at 75° C. for 2.5 h away from the light. The progress of the reaction was monitored by TLC. After this time, reaction was complete. The solvents were removed under reduced pressure. Water (10 mL) was added to the black residue and the mixture was extracted with dichloromethane (3×20 mL). The organic phases were combined and dried over magnesium sulfate. After filtration, the solvent was removed under reduced pressure. The crude product obtained was purified by silica column flash chromatography (dichloromethane/methanol 0.5% to 5% in increments of 1%) to give compound 37e in the form of a yellowish oil (137 mg, quantitative). $^1$H NMR (400 MHz, CDCl$_3$) δ: 8.05 (s, 1H), 7.22 (s, 1H), 7.47 (d, J=8.8 Hz, 2H), 7.02 (d, J=8.8 Hz, 2H), 5.19 (s, 2H), 4.86 (s, 2H), 3.98 (s, 3H), 3.47 (s, 3H). HRMS (ESI+) calculated for C$_{18}$H$_{18}$NO$_5$ [M+H]$^+$, m/z 328.1185 found: 328.1177. Rf=0.66 (silica, dichloromethane-methanol, 90:10).

Compound 37f

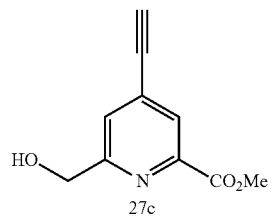

mmol) were added to this mixture. The reaction mixture was stirred at 65° C. for 3 h. The progress of the reaction was monitored by HPLC and TLC. After this time, reaction was complete. The solvents were removed under reduced pressure. The crude product obtained was purified by silica column flash chromatography (dichloromethane/methanol 0% to 10% in increments of 1%) to give compound 37f in the form of a yellowish oil (122 mg, 40%). LRMS (ESI+) calculated for C$_{19}$H$_{20}$NO$_7$S [M+H]$^+$, m/z 406.0960 found: 406.30. R$_f$=0.24 (silica, dichloromethane-methanol-triethylamine 96:3:1). R$_t$=11.1 min (Waters XBridge RP-C18 column, 3.5 μm, 4.6×100 mm) with 0.2% aqueous solution of trifluoroacetic acid (pH 1-MeCN (v/v) as eluent [linear gradient from 5 to 100% MeCN (21 min), with a flow rate of 1 mL min$^{-1}$ and UV detection at 320 nm.

Compound 37g

This compound was prepared according to the same procedure as that used for compound 37f using the corresponding precursor.

Compound 38a

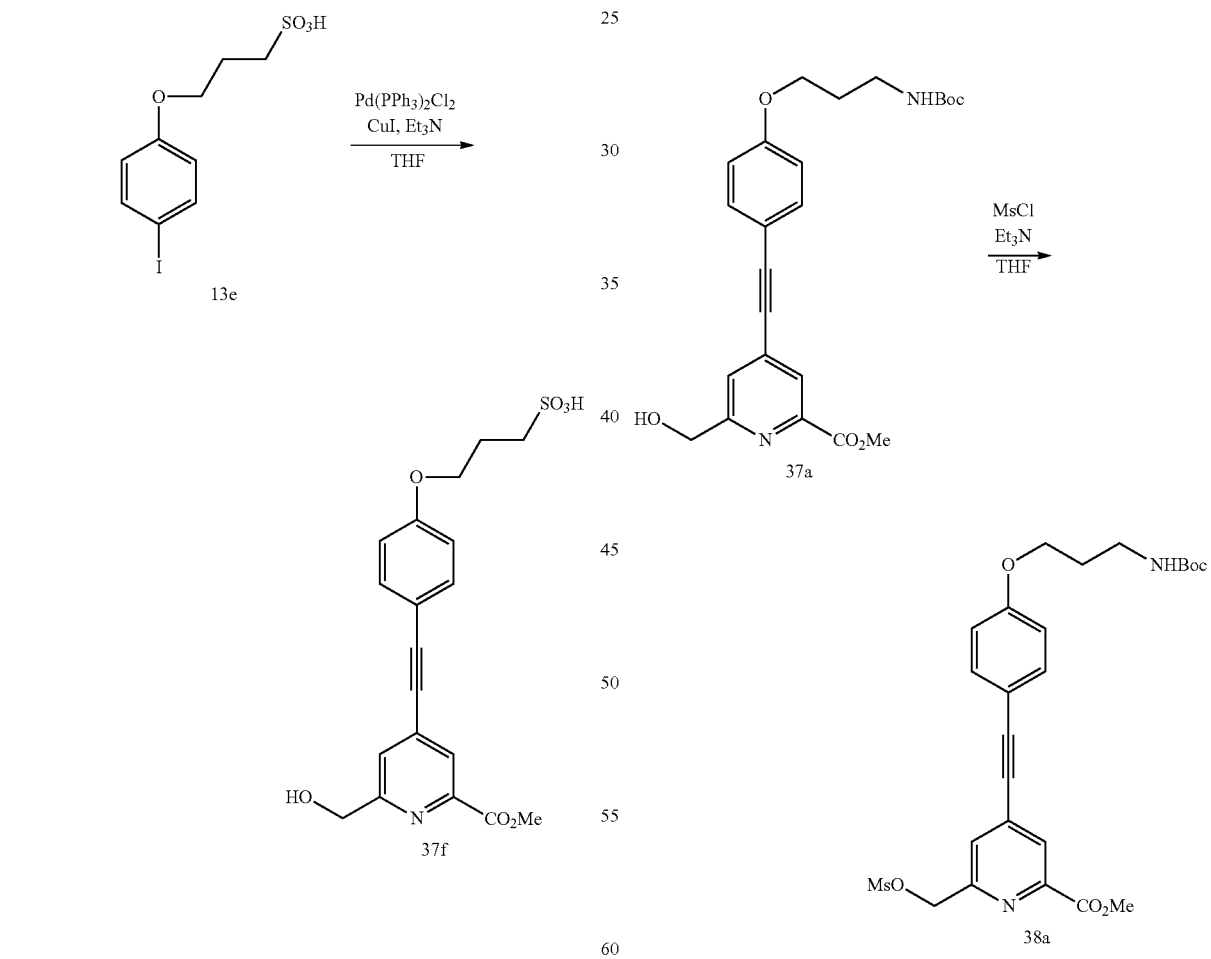

Iodinated derivative 13e (273 mg, 0.8 mmol) was added to a solution of acetylene derivative 27c (145 mg, 0.76 mmol) in anhydrous tetrahydrofuran (20 mL) and anhydrous triethylamine (3.5 mL). The mixture was degassed with stirring for 1 h. Palladium(II) bis-chloride bis-triphenylphosphine (68 mg, 0.1 mmol) and copper(I) iodide (36 mg, 0.2

Triethylamine (0.2 mL, 148 μmol) was added dropwise under inert atmosphere to a solution of alcohol 37a (195 mg, 0.44 mmol) in anhydrous tetrahydrofuran (7 mL). Mesyl chloride (67 μL, 0.84 mmol) was added dropwise to this mixture cooled to 4° C. The progress of the reaction was monitored by TLC. After 5 min, reaction was complete. The solvent was removed under reduced pressure. The residue was dissolved in dichloromethane (10 mL) and this solution was washed with water (2×10 mL). The organic phase was dried over magnesium sulfate, filtered and concentrated under reduced pressure to give an oil of a yellowish-green color (240 mg, quantitative). The product 38a was sufficiently pure to be used in the rest of the synthesis without additional purification. LRMS (ESI+) calculated for $C_{25}H_{31}N_2O_8S$ [M+H]$^+$, m/z 519.1801. found: 519.13. Rf=0.6 (silica, dichloromethane-methanol 96:4).

Compound 38b

This compound was prepared according to the same procedure as that used for compound 38a using the corresponding precursor.

Compound 38c cooled to 4° C. The progress of the reaction was monitored by TLC. After 20 min, reaction was complete. The solvent was removed under reduced pressure. The residue was dissolved in dichloromethane (20 mL) and this solution was washed with water (3×10 mL). The organic phase was dried over magnesium sulfate, filtered and concentrated under reduced pressure to give an oil of a yellowish-green color (314 mg, quantitative). The product 38c was sufficiently pure to be used in the rest of the synthesis without additional purification. $^1$H NMR (400 MHz, CDCl$_3$) δ: 8.16 (d, J=1.3 Hz, 1H); 7.72 (d, J=1.3 Hz, 1H); 7.53 (d, J=8.9 Hz, 2H); 6.93 (d, J=8.9 Hz, 2H); 5.43 (s, 2H); 4.03 (s, 3H); 3.86 (s, 3H); 3.18 (s, 3H). $^{13}$C NMR (100 MHz, CDCl$_3$) δ: 165.00, 160.88, 154.68, 147.95, 134.75, 133.86, 126.77, 126.46, 114.40, 113.54, 96.98, 84.97, 70.76, 55.49, 53.25, 38.16. LRMS (ESI+) calculated for $C_{18}H_{18}NO_6S$ [M+H]$^+$, m/z 376.0855. found: 376.04. Rf=0.52 (silica, cyclohexane-ethyl acetate 30:70).

Compound 38d

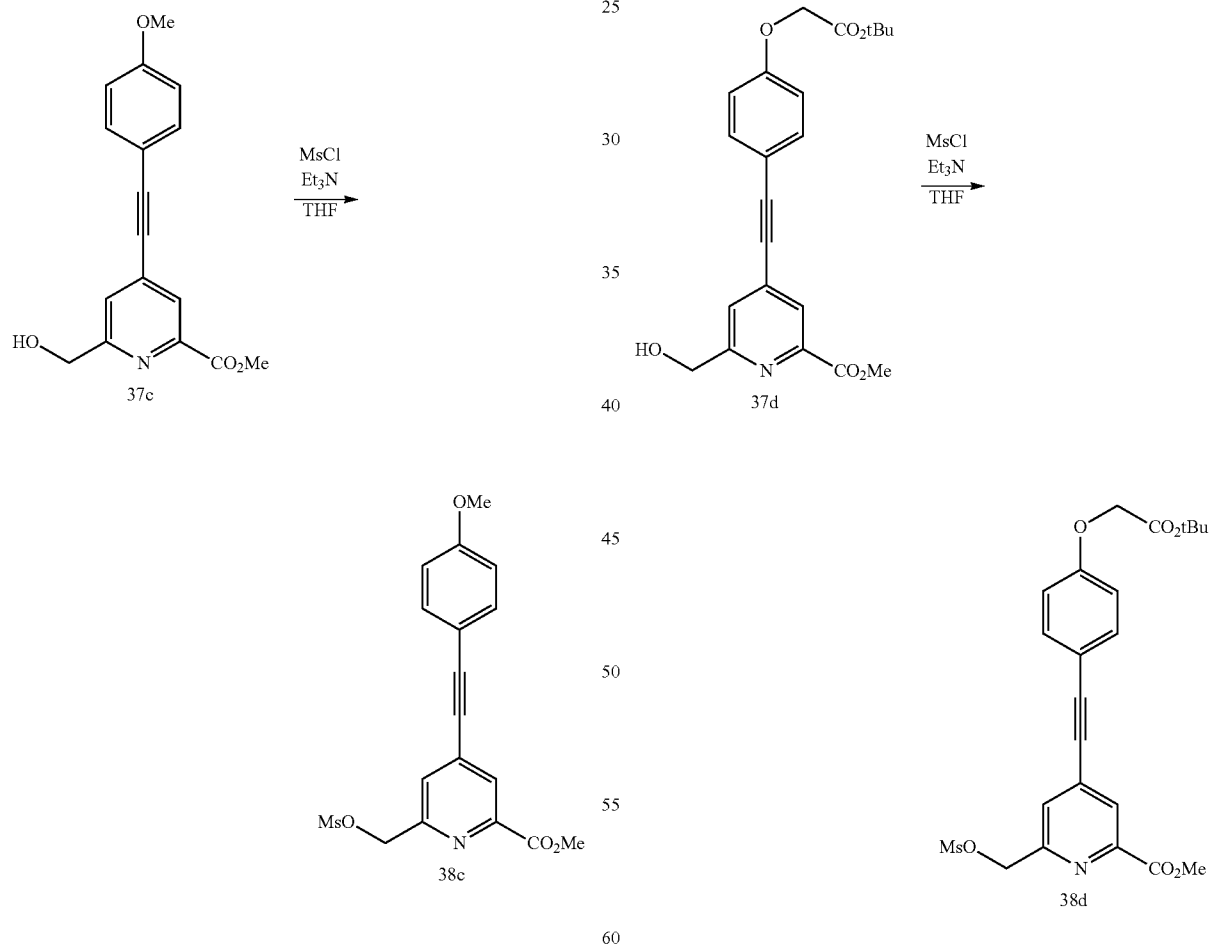

Triethylamine (339 mg, 2.8 mmol) was added dropwise under inert atmosphere to a solution of alcohol 37c (241 mg, 0.8 mmol) in anhydrous tetrahydrofuran (10 mL). A solution of mesyl chloride (94 μL, 1.2 mmol) in anhydrous tetrahydrofuran (0.2 mL) was added dropwise to this mixture Triethylamine (120 μL, 0.86 mmol) was added dropwise under inert atmosphere to a solution of alcohol 37d (114 mg, 0.29 mmol) in anhydrous tetrahydrofuran (5 mL). A solution of mesyl chloride (33 μL, 0.43 mmol) in anhydrous tetrahydrofuran (1 mL) was added dropwise to this mixture cooled to 4° C. The progress of the reaction was monitored by TLC. After 10 min, reaction was complete. The solvent was removed under reduced pressure. The residue was dissolved in dichloromethane (15 mL) and this solution was washed with water (3×5 mL). The organic phase was dried over magnesium sulfate, filtered and concentrated under reduced pressure to give an oil of a yellowish-green color (138 mg, quantitative). The product 38d was sufficiently pure to be used in the rest of the synthesis without additional purification. $^1$H NMR (400 MHz, CDCl$_3$) δ: 8.14 (s, 1H), 7.70 (s, 1H), 7.50 (d, J=8.8 Hz, 2H), 6.90 (d, J=8.8 Hz, 2H), 5.40 (s, 2H), 4.55 (s, 2H), 4.00 (s, 3H), 3.16 (s, 3H), 1.48 (s, 9H). $^{13}$C NMR (100 MHz, CDCl$_3$) δ: 167.56, 164.98, 159.12, 154.71, 147.97, 133.62, 133.85, 126.79, 126.46, 114.99, 114.49, 96.60, 85.13, 82.85, 70.73, 65.67, 53.26, 38.17, 27.91. LRMS (ESI+) calculated for $C_{23}H_{26}NO_8S$ [M+H]$^+$, m/z 476.14 found: 476.19. Rf=0.74 (neutral alumina oxide, cyclohexane-ethyl acetate 30:70).
Compound 38e cooled to 4° C. The progress of the reaction was monitored by TLC. After 10 min, reaction was complete. The solvent was removed under reduced pressure. The residue was dissolved in dichloromethane (15 mL) and this solution was washed with water (3×5 mL). The organic phase was dried over magnesium sulfate, filtered and concentrated under reduced pressure to give an oil of a yellowish-green color (152 mg, quantitative). The product 38e was sufficiently pure to be used in the rest of the synthesis without additional purification. $^1$H NMR (400 MHz, CDCl$_3$) δ: 8.14 (s, 1H), 7.70 (s, 1H), 7.50 (d, J=8.8 Hz, 2H), 6.90 (d, J=8.8 Hz, 2H), 5.40 (s, 2H), 4.55 (s, 2H), 4.00 (s, 3H), 3.16 (s, 3H), 1.48 (s, 9H). $^{13}$C NMR (100 MHz, CDCl$_3$) δ: 167.56, 164.98, 159.12, 154.71, 147.97, 133.62, 133.85, 126.79, 126.46, 114.99, 114.49, 96.60, 85.13, 82.85, 70.73, 65.67, 53.26, 38.17, 27.91. HRMS (ESI+) calculated for $C_{19}H_{20}NO_7S$ [M+H]$^+$, m/z 406.0960 found: 406.0954. Rf=0.61 (neutral alumina oxide, cyclohexane-ethyl acetate, 30:70).
Compound 38f

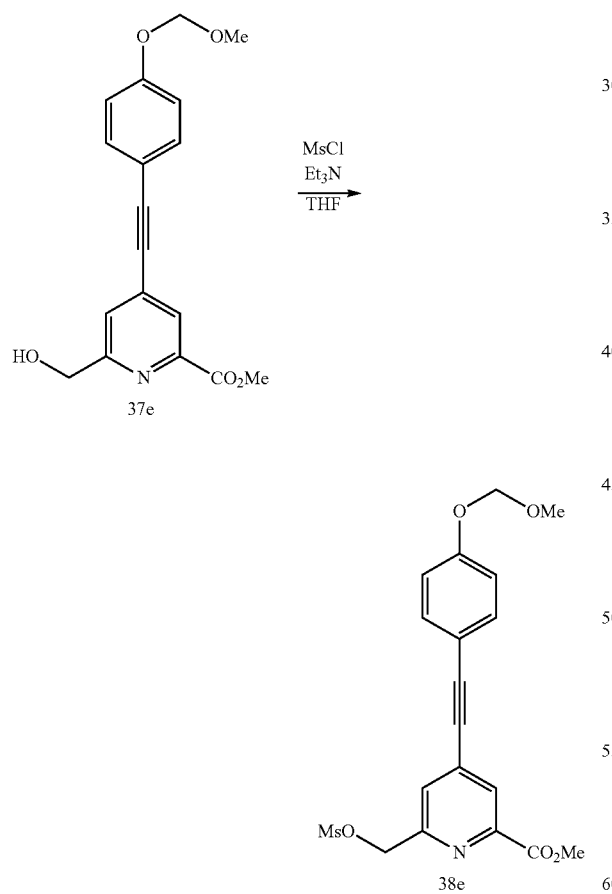

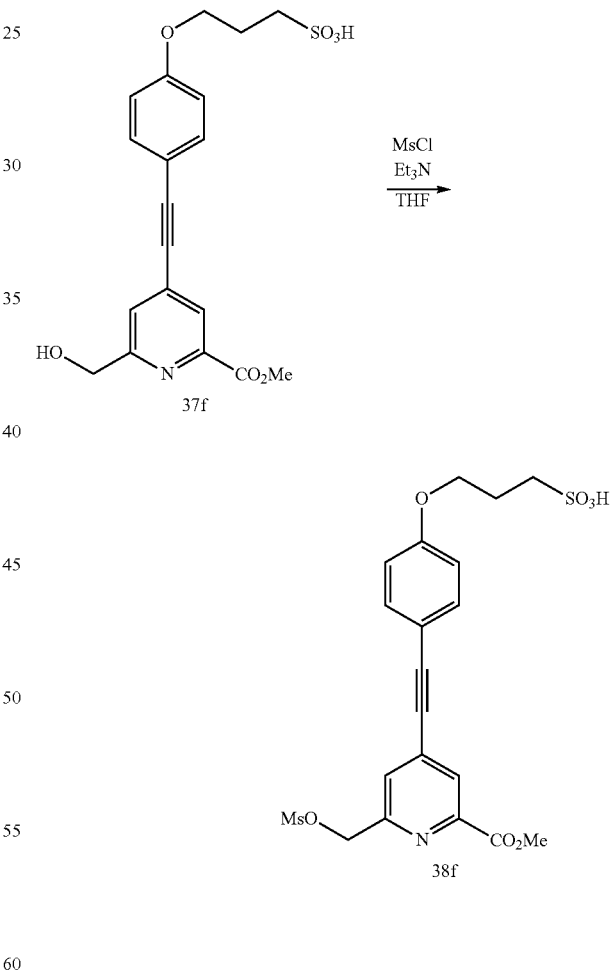

Triethylamine (132 μL, 0.95 mmol) was added dropwise under inert atmosphere to a solution of alcohol 37e (140 mg, 0.25 mmol) in anhydrous tetrahydrofuran (4 mL). A solution of mesyl chloride (37 μL, 0.48 mmol) in anhydrous tetrahydrofuran (1 mL) was added dropwise to this mixture Triethylamine (40 μL, 0.29 mmol) was added dropwise under inert atmosphere to a solution of alcohol 37f (39 mg, 84 μmol) in anhydrous tetrahydrofuran (4 mL). A solution of mesyl chloride (14 μL, 0.17 mmol) in anhydrous tetrahydrofuran (1 mL) was added dropwise to this mixture cooled to 4° C. The progress of the reaction was monitored by HPLC. After 10 min, reaction was complete. The solvent was removed under reduced pressure and the residue was dissolved in aqueous buffer of triethylammonium acetate 25 mM pH 6 (5 mL) and this solution was purified by preparative HPLC using the following gradient: Waters XBridge RP-C18 column, 5 μm, 50×150 mm) with aqueous buffer of triethylammonium acetate 25 mM pH 6-MeCN (v/v) as eluent [isocratic 5% MeCN (2 min)], linear gradient from 5 to 100% MeCN (18 min) with a flow rate of 100 mL min$^{-1}$ and UV detection at 320 nm to give the desired mesylated product 38f (41 mg, quantitative). LRMS (ESI+) calculated for $C_{20}H_{22}NO_9S_2$ [M+H]$^+$, m/z 484.0736. found: 484.34. $R_t$=11.05 min (Waters XBridge RP-C18 column, 3.5 μm, 4.6×100 mm) with 0.2% aqueous solution of trifluoroacetic acid (pH 1-MeCN (v/v) as eluent [linear gradient from 5 to 80% MeCN (25 min)], with a flow rate of 1 mL min$^{-1}$ and UV detection at 320 nm.

Compound 38g

This compound was prepared according to the same procedure as that used for compound 38f using the corresponding precursor.

Compound 39a

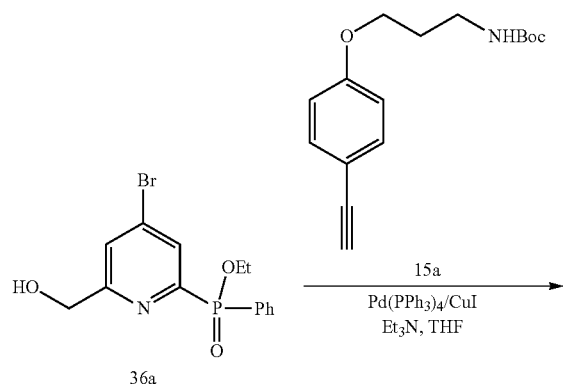

Anhydrous tetrahydrofuran (10 mL) was added to the brominated derivative 36a (142 mg, 0.4 mmol) and the solution was degassed by three cycles of freezing-thawing. The acetylene derivative 15a (147 mg, 0.4 mmol) and triethylamine (5 mL) were added to this solution, and the solution was degassed again. Tetrakis(triphenylphosphine) palladium(0) (46 mg, 0.04 mmol) and copper iodide (7.6 mg, 0.04 mmol) were added to this solution. This new solution was degassed again three times and then was stirred at 65° C. under inert atmosphere. The progress of the reaction was monitored by TLC. After 1 h, reaction was complete. The reaction mixture was cooled to room temperature and the solvent was removed under reduced pressure. The residue was diluted in dichloromethane (25 mL) and was washed with a saturated aqueous solution of ammonium chloride (25 mL) and then with water (25 mL). The organic phase was dried over magnesium sulfate, filtered and then concentrated under reduced pressure to give a residue, which was purified by silica column chromatography (dichloromethane/methanol 0 to 3% in increments of 0.5%) to obtain a yellow oil corresponding to compound 39a (154 mg, 70%). $^1$H NMR (400 MHz, CDCl$_3$) δ: 8.01 (dd, J=6.4; 2.0 Hz, 1H), 7.89 (dd, J=8.4; 12.4 Hz, 2H), 7.48 (t, J=8.4 Hz, 1H), 7.40 (d, J=8.8 Hz, 2H), 7.39 (td, J=8.4; 4.2 Hz, 2H), 7.33 (d, J=2.0 Hz, 1H), 6.81 (d, J=8.8 Hz, 2H), 4.73 (s, 1H), 4.69 (s, 2H), 4.08 (qd, J=5.6; 4.8 Hz, 2H), 3.97 (t, J=6 Hz, 2H), 3.26 (m, 2H), 1.92 (q, J=6 Hz, 2H), 1.37 (s, 9H, 1.31 (t, J=5.6 Hz, 3H); $^{13}$C NMR (100 MHz, CDCl$_3$) δ: 160.3 (d, J=18 Hz), 159.8; 156.0; 153.2 (d, J=164 Hz); 133.7; 133.0 (d, J=11 Hz); 132.6 (d, J=5 Hz); 132.3 (d, J=10 Hz); 129.6 (d, J=138 Hz); 128.6 (d, J=18 Hz); 128.5 (d, J=9 Hz); 123.8 (d, J=3 Hz); 114.7, 113.8, 96.0, 85.3 (d, J=2 Hz); 79.3, 65.9, 63.8, 61.9 (d, J=6 Hz); 37.9, 29.5, 28.4, 16.6; $^{31}$P NMR (162 MHz, CDCl$_3$) δ: +25.6. HRMS (ESI+) calculated for $C_{30}H_{36}N_2O_6P$ [M+H]$^+$, m/z 551.2306 found: 551.2305. Rf=0.24 (silica, dichloromethane-methanol, 95:5).

Compound 39b

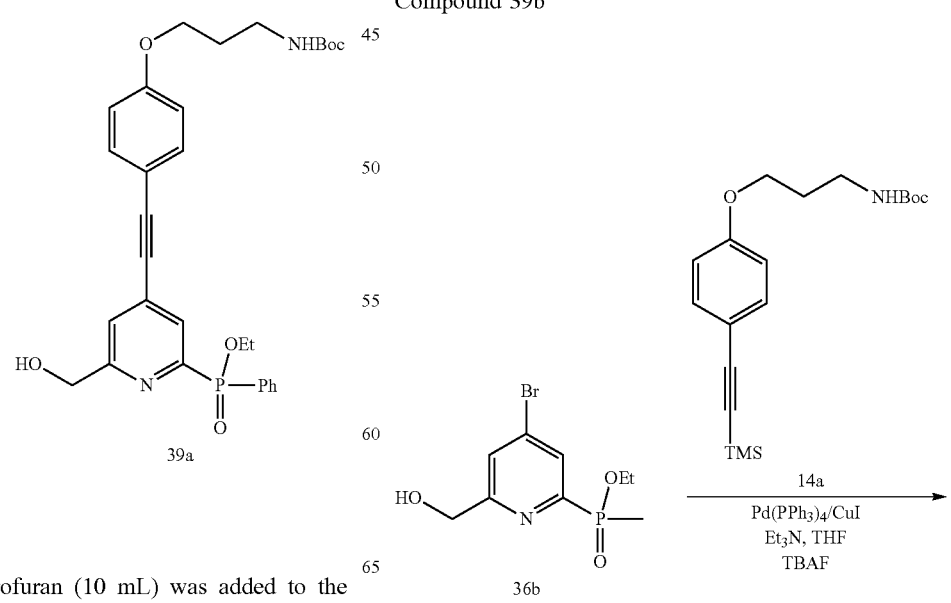

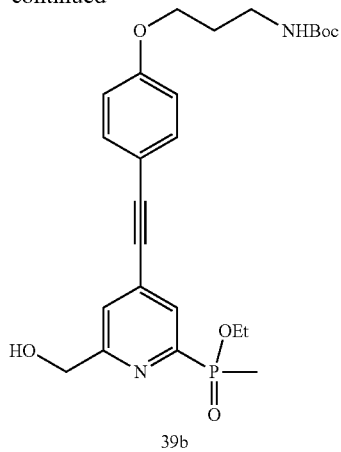

39b

Anhydrous tetrahydrofuran (10 mL) was added to the brominated derivative 36b (200 mg, 0.68 mmol) and the solution was degassed by three cycles of freezing-thawing. The acetylene derivative 14a (260 mg, 0.75 mmol) and triethylamine (5 mL) were added to this solution, and the solution was degassed again. Tetrakis(triphenylphosphine)palladium(0) (79 mg, 0.068 mmol) and copper iodide (13 mg, 0.068 mmol) were added to this solution. This new solution was degassed again three times and then was stirred at 65° C. under inert atmosphere. The progress of the reaction was monitored by TLC. After 1 h, reaction was complete. The reaction mixture was cooled to room temperature and the solvent was removed under reduced pressure. The residue was diluted in dichloromethane (25 mL) and was washed with a saturated aqueous solution of ammonium chloride (25 mL) and then with water (25 mL). The organic phase was dried over magnesium sulfate, filtered and then concentrated under reduced pressure to give a residue, which was purified by silica column chromatography (dichloromethane/methanol 0 to 5% in increments of 1%) to obtain a yellow oil corresponding to compound 39b (220 mg, 66%). HRMS (ESI+) calculated for $C_{25}H_{34}N_2O_6P$ $[M+H]^+$, m/z 489.2149 found: 489.2152. Rf=0.35 (silica, dichloromethane-methanol, 95:5).

Compounds 39c-d

These compounds were prepared according to the same procedure as that used for compound 39b using the corresponding precursors.

Compound 39f

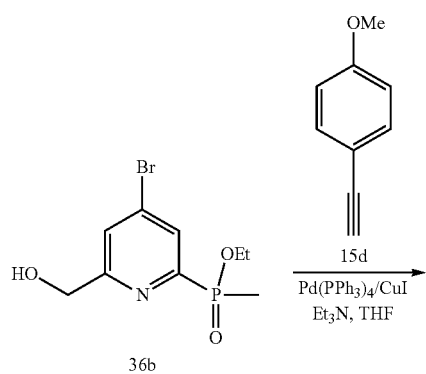

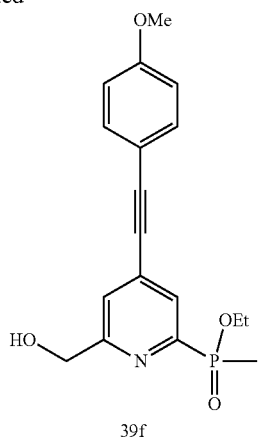

39f

Anhydrous tetrahydrofuran (10 mL) was added to the brominated derivative 36b (400 mg, 1.36 mmol) and the solution was degassed by three cycles of freezing-thawing. Ethynylanisole 15d (180 mg, 1.36 mmol) and triethylamine (5 mL) were added to this solution, and the solution was degassed again. Tetrakis(triphenylphosphine)palladium(0) (158 mg, 0.136 mmol) and copper iodide (26 mg, 0.136 mmol) were added to this solution. This new solution was degassed again three times and then was stirred at 65° C. under argon. The progress of the reaction was monitored by TLC. After 1 h, reaction was complete. The reaction mixture was cooled to room temperature and the solvent was removed under reduced pressure. The residue was diluted in dichloromethane (40 mL) and was washed with a saturated aqueous solution of ammonium chloride (40 mL) and then with water (40 mL). The organic phase was dried over magnesium sulfate, filtered and then concentrated under reduced pressure. The crude product was purified by silica column chromatography (dichloromethane/methanol 0 to 8% in increments of 1%) to obtain an oil corresponding to compound 39f (480 mg, 96%). $^1$H NMR (400 MHz, CDCl$_3$) δ: 7.95 (bs, 1H), 7.51 (bs, 1H), 7.42 (d, J=8.8 Hz, 2H), 6.84 (d, J=8.8 Hz, 2H), 4.78 (s, 2H), 4.10-4.04 (m, 1H), 3.86-3.81 (m, 1H), 3.78 (s, 3H), 1.73 (d, J=14.9 Hz, 3H), 1.23 (t, J=7 Hz, 3H); $^{13}$C NMR (100 MHz, CDCl$_3$) δ: 161.2 (d, J=18 Hz), 160.6, 153.1 (d, J=156 Hz), 133.6, 132.9 (d, J=12 Hz), 127.7 (d, J=19 Hz), 124.1 (d, J=4 Hz), 114.2, 114.0, 96.0, 85.3, 64.2, 61.2 (d, J=6 Hz), 55.3, 16.4 (d, J=6 Hz), 13.4 (d, J=104 Hz); $^{31}$P NMR (162 MHz, CDCl$_3$) δ: +38.6. HRMS (ESI+) calculated for $C_{18}H_{21}NO_4P$ $[M+H]^+$, m/z 346.1203 found: 346.1202. R$_f$=0.26 (neutral alumina oxide, dichloromethane-methanol 95:5).

Compound 39g

This compound was prepared according to the same procedure as that used for compound 39h using the corresponding precursor.

Compound 39h

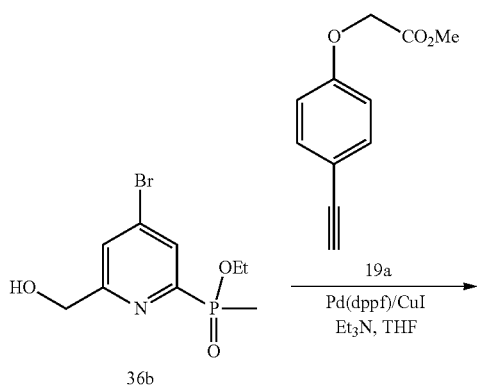

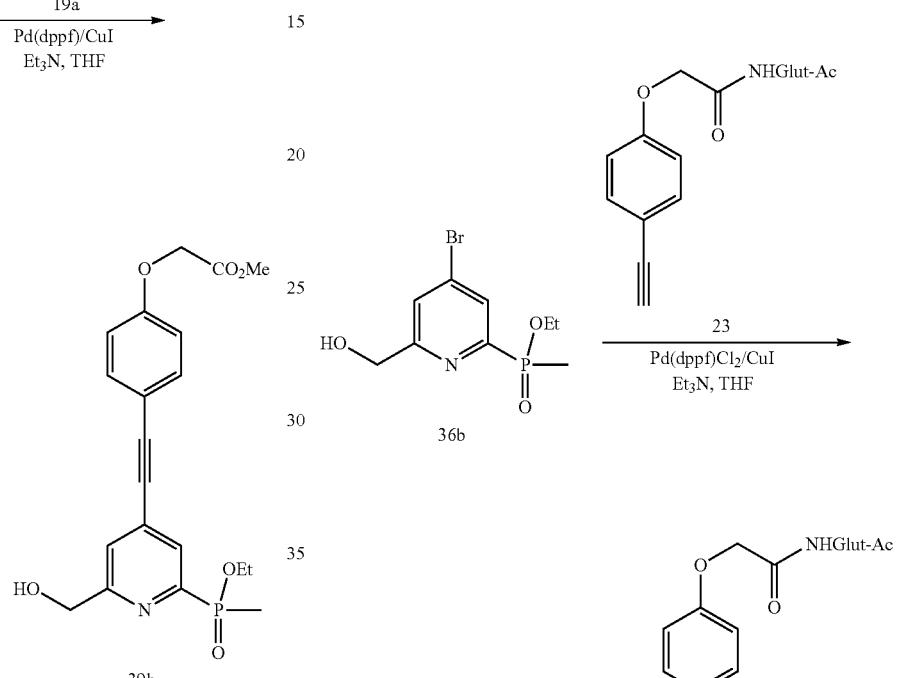

Anhydrous tetrahydrofuran (1 mL) was added to the brominated derivative 36b (103 mg, 0.35 mmol) and the solution was degassed by three cycles of freezing-thawing. The acetylene derivative 19a (80 mg, 0.42 mmol) and triethylamine (0.24 mL, 1.75 mmol) were added to this solution, and the solution was degassed again. [1,1-bis(Diphenylphosphino)ferrocene]dichloropalladium(II) (30 mg, 0.035 mmol) and copper iodide (7 mg, 0.035 mmol) were added to this solution. This new solution was degassed again three times and then was stirred at 65° C. under inert atmosphere. The progress of the reaction was monitored by TLC. After 18 h, reaction was complete. The reaction mixture was cooled to room temperature and the solvent was removed under reduced pressure. The crude product was purified by silica column chromatography (dichloromethane/methanol 0 to 3% in increments of 0.1%) to obtain a yellow oil corresponding to compound 39h (122 mg, 87%). $^1$H NMR (400 MHz, CDCl$_3$) δ 7.98 (bs, 1H), 7.50 (bs, 1H), 7.45 (d, J=8.9 Hz, 2H), 6.88 (d, J=8.9 Hz, 2H), 4.80 (s, 2H), 4.65 (s, 2H), 4.09 (m, 1H), 3.99 (bs, 1H), 3.86 (m, 1H), 3.79 (s, 3H), 1.76 (d, J=14.9 Hz, 3H), 1.26 (t, J=6.9 Hz, 3H); $^{13}$C NMR (100 MHz, CDCl$_3$) δ 168.9, 161.0 (d, J=19 Hz), 158.8, 153.3 (d, J=155 Hz), 133.8, 132.9 (d, J=12 Hz), 128.1 (d, J=22 Hz), 124.2, 115.1, 115.0, 95.7, 85.6, 65.2, 64.3, 61.3 (d, J=5 Hz), 52.5, 16.5 (d, J=4 Hz), 13.5 (d, J=104 Hz); $^{31}$P NMR (162 MHz, CDCl$_3$) δ: +39.5. HRMS (ESI+) calculated for C$_{20}$H$_{22}$NNaO$_6$P [M+Na]$^+$, m/z 426.1082 found: 426.1063. R$_f$=0.44 (silica; dichloromethane-methanol 90:10).

Compound 39i

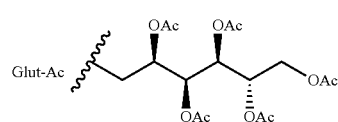

The acetylene derivative 23 (75 mg, 0.14 mmol) and triethylamine (0.19 mL, 1.36 mmol) were added to a solution of derivative 36b (40 mg, 0.14 mmol) in anhydrous tetrahydrofuran (1 mL) degassed by three cycles of freezing-thawing under vacuum, and the solution was degassed again. [1,1-bis(Diphenylphosphino)ferrocene]dichloropalladium (II) (11 mg, 0.014 mmol) and copper iodide (2.6 mg, 0.014 mmol) were added to this solution. This new solution was stirred at 65° C. under argon. The progress of the reaction was monitored by TLC. After 16 h, reaction was complete. The reaction mixture was cooled to room temperature and the solvent was removed under reduced pressure. The crude product was purified by silica column chromatography (dichloromethane/methanol 0 to 3% in increments of 0.5%) to obtain a colorless oil corresponding to compound 39i (71 mg, 68%). $^1$H NMR (700 MHz, CDCl$_3$) δ 8.02 (d, J=4.6 Hz, 1H), 7.56 (m, 1H), 7.49 (d, J=8.6 Hz, 2H), 7.38 (t, J=6.9 Hz, 1H), 6.93 (d, J=8.6 Hz, 2H), 5.48 (dd, J=6.4; 4.8 Hz, 1H), 5.32 (dd, J=5.8; 4.8 Hz, 1H), 5.17 (m, 1H), 5.02 (ddd, J=6.5; 5.6; 3.4 Hz, 1H), 4.81 (s, 2H), 4.50 (q AB, 2H), 4.25 (dd, J=12.4; 3.4 Hz, 1H), 4.11 (dd, J=12.4; 5.5 Hz, 1H), 3.86 (m, 2H), 3.79 (bs, 1H), 3.55 (m, 2H), 2.12 (s, 3H), 2.09 (s, 3H), 2.05 (s, 3H), 2.04 (s, 3H), 2.02 (s, 3H), 1.77 (d, J=14.9 Hz, 3H), 1.27 (t, J=6.9 Hz, 3H); $^{13}$C NMR (176 MHz, CDCl$_3$) δ 170.7, 170.5, 170.2, 170.0, 169.9, 168.1, 160.9 (d, J=19 Hz), 158.1, 153.5 (d, J=156 Hz), 134.0, 132.9 (d, J=12 Hz), 127.7 (d, J=10 Hz), 128.4 (d, J=12 Hz), 115.5, 115.1, 95.4, 85.8, 70.2, 69.2, 69.1, 69.0, 67.3, 64.2, 61.6, 61.3 (d, J=6 Hz), 39.4, 20.8 (4); 20.8 (3); 20.8 (0); 20.7 (9); 20.6 (6); 16.6 (d, J=6 Hz), 13.6 (d, J=105 Hz); $^{31}$P NMR (284 MHz, CDCl$_3$) δ +39.0; HRMS (ESI+) calculated for C$_{35}$H$_{43}$N$_2$NaO$_{15}$P [M+Na]$^+$, m/z 785.2299 found: 785.2285. R$_f$=0.24 (silica; dichloromethane-methanol 95:5).

Compound 39j: This compound was prepared according to the same procedure as that used for compound 39i using the corresponding precursor.

Compound 39m

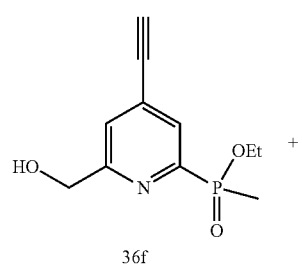
36f

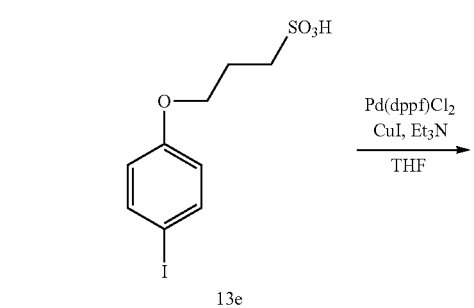
13e

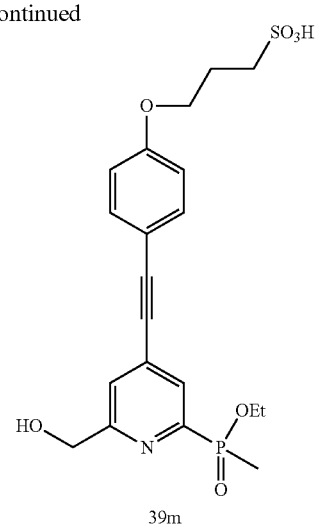
39m

Iodinated derivative 13e (208 mg, 610 μmol) was added to a solution of acetylene derivative 36f (146 mg, 610 μmol) in anhydrous tetrahydrofuran (12 mL) and anhydrous triethylamine (6 mL). The mixture was degassed with stirring for 1 h. bis(Diphenylphosphino)ferrocene]dichloropalladium(II) (45 mg, 61 μmol) and copper(I) iodide (12 mg, 61 μmol) were added to this solution. The reaction mixture was stirred at 65° C. for 2 h away from the light. The progress of the reaction was monitored by TLC. After this time, reaction was complete. The solvents were removed under reduced pressure. The crude product obtained was purified by: Waters XBridge RP-C18 column, 5 μm, 50×150 mm) with aqueous buffer of triethylammonium acetate 25 mM pH 6-MeCN (v/v) as eluent [isocratic 5% MeCN (2 min), linear gradient from 5 to 100% MeCN (18 min) with a flow rate of 100 mL min$^{-1}$ and UV detection at 320 nm compound 39m. LRMS (ESI+) calculated for C$_{20}$H$_{25}$NNaO$_7$PS [M+H+Na]$^+$, m/z 477.0987 found: 477.21. R$_t$=6.55 min (Waters XBridge RP-C18 column, 3.5 μm, 4.6×100 mm) with 0.1% aqueous solution of formic acid (pH 2-MeCN (v/v)) as eluent, [isocratic 5% MeCN (1 min)], linear gradient from 5 to 100% MeCN (14 min), with a flow rate of 1 mL min$^{-1}$.

Compound 39n

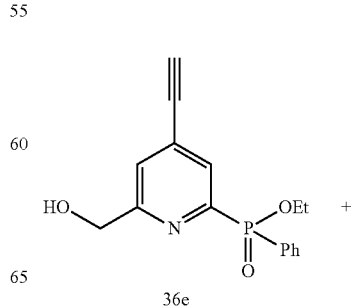
36e

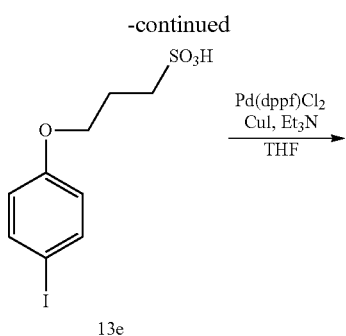

13e nol) to give compound 39n in the form of a yellowish oil (9 mg, 13%). LRMS (ESI+) calculated for $C_{25}H_{27}NO_7PS$ [M+H]$^+$, m/z 516.1246 found: 516.34. $R_f$=0.51 (silica, dichloromethane-methanol-triethylamine 99:9:1). $R_t$=7.6 min (Waters XBridge RP-C18 column, 3.5 μm, 4.6×100 mm) with 0.1% aqueous solution of formic acid (pH 2-MeCN (v/v) as eluent [isocratic 5% MeCN (1 min)], linear gradient from 5 to 100% MeCN (14 min), with a flow rate of 1 mL min$^{-1}$.

Compounds 39o-p

These compounds were prepared according to the same procedure as that used for compounds 39m-n respectively using the corresponding precursors.

Compound 40a

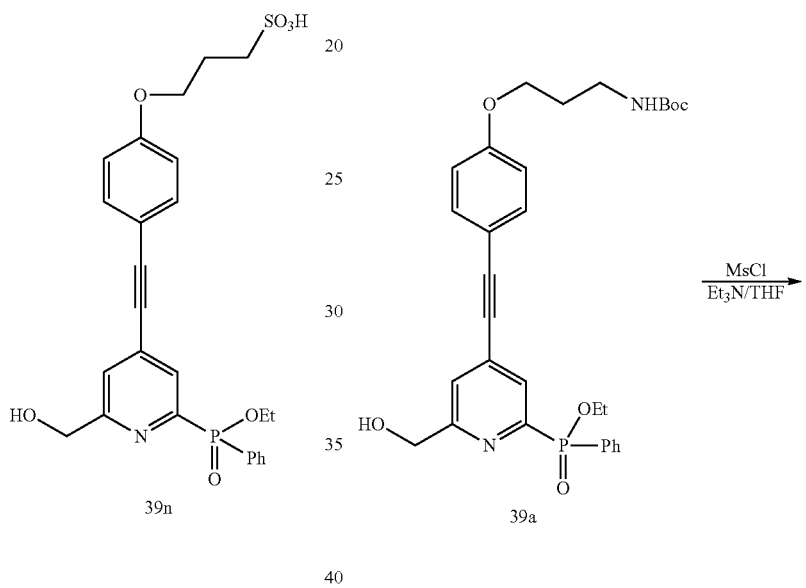

39n

39a

Iodinated derivative 13e (50 mg, 147 μmol) was added to a solution of acetylene derivative 36e (50 mg, 134 μmol) in anhydrous tetrahydrofuran (10 mL) and anhydrous triethylamine (5 mL). The mixture was degassed with stirring for 1 h. bis(Diphenylphosphino)ferrocene]dichloropalladium(II) (10 mg, 13 μmol) and copper(I) iodide (2.5 mg, 13 μmol) were added to this solution. The reaction mixture was stirred at 65° C. for 1 h away from the light and under inert atmosphere. The progress of the reaction was monitored by LC-MS. After this time, reaction was complete. The solvents were removed under reduced pressure. A saturated solution of ammonium chloride (40 mL) was added to the black residue, and the mixture was extracted with dichloromethane (2×40 mL). The organic phases were combined and dried over magnesium sulfate. After filtration, the solvent was removed under reduced pressure. The crude product obtained was purified by silica column flash chromatography (dichloromethane-methanol-triethylamine: 99.75:0:0.25 to 89.75:10:0.25 in increments of 1% of metha-

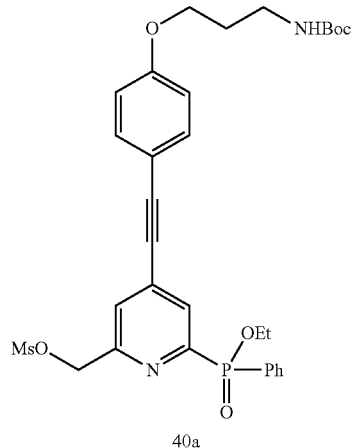

40a

Triethylamine (87 μL, 0.64 mmol) and then mesyl chloride (24 μL, 0.32 mmol) were added under inert atmosphere to a solution of alcohol 39a (118 mg 0.21 mmol) in anhydrous tetrahydrofuran (7 mL) cooled to 5° C. The reaction mixture was stirred at room temperature for 15 min. The progress of the reaction was monitored by TLC. After this period, reaction was complete. The solvent was removed under reduced pressure. Water saturated with sodium chloride (30 mL) was added to the residue and the mixture was extracted with dichloromethane (2×30 mL). The organic phases were combined and dried over magnesium sulfate. After filtration, the solvent was removed under reduced pressure to give a brown oil corresponding to compound 40a (125 mg, 95%), which was sufficiently pure to be used in the next step without additional purification. HRMS (ESI+) calculated for $C_{31}H_{38}N_2O_8PS$ [M+H]$^+$, m/z 629.2081 found: 629.2081. Rf=0.15 (neutral alumina oxide, cyclohexane-ethyl acetate 30:70).
Compound 40b tetrahydrofuran (5 mL) cooled to 5° C. The reaction mixture was stirred at 5° C. for 5 min. The progress of the reaction was monitored by TLC. After this period, reaction was complete. The solvent was removed under reduced pressure. Water (50 mL) was added to the residue and the mixture was extracted with dichloromethane (2×50 mL). The organic phases were combined and dried over magnesium sulfate. After filtration, the solvent was removed under reduced pressure to give a brown oil corresponding to compound 40b (97 mg, 95%), which was sufficiently pure to be used in the next step without additional purification. HRMS (ESI+) calculated for $C_{26}H_{36}N_2O_8PS$ [M+H]$^+$, m/z 567.1925 found: 567.1939. Rf=0.13 (neutral alumina oxide, cyclohexane-ethyl acetate 30:70).
Compound 40f

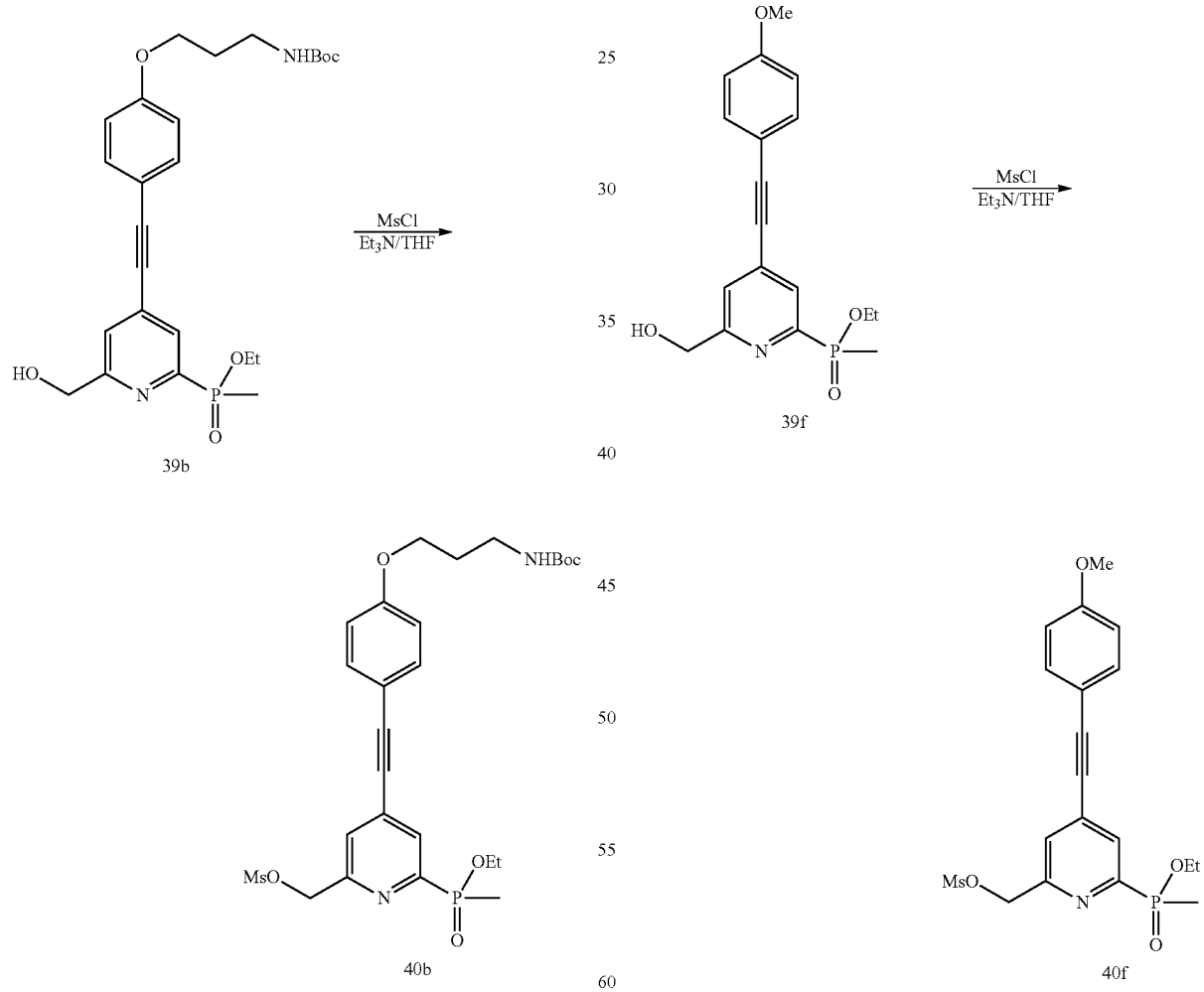

Triethylamine (77 µL, 0.55 mmol) and then mesyl chloride (21 µL, 0.27 mmol) were added under inert atmosphere to a solution of alcohol 39b (90 mg 0.18 mmol) in anhydrous Triethylamine (0.26 mL, 1.86 mmol) and then mesyl chloride (71 µL, 0.93 mmol) were added under inert atmosphere to a solution of alcohol 39f (214 mg, 0.62 mmol) in anhydrous tetrahydrofuran (5 mL) cooled to 5° C. The reaction mixture was stirred at room temperature for 15 min. The progress of the reaction was monitored by TLC. After this period, reaction was complete. The solvent was removed under reduced pressure. Water saturated with sodium chloride (30 mL) was added to the residue and the mixture was extracted with dichloromethane (2×30 mL). The organic phases were combined and dried over magnesium sulfate. After filtration, the solvent was removed under reduced pressure to give a colorless oil corresponding to compound 40f (213 mg, 81%), which was sufficiently pure to be used in the next step without additional purification. $^1$H NMR (400 MHz, CDCl$_3$) δ: 8.11 (dd, J=6.0; 1.5 Hz, 1H), 7.65 (bs, 1H), 7.52 (d, J=8.9 Hz, 2H), 6.93 (d, J=8.9 Hz, 2H), 5.39 (s, 2H), 4.20-4.10 (m, 1H), 3.95-3.88 (m, 1H), 3.86 (s, 3H), 3.16 (s, 3H), 1.80 (d, J=15.1 Hz, 3H), 1.31 (t, J=7.1 Hz, 3H); HRMS (ESI+) calculated for $C_{19}H_{23}NO_6PS$ [M+H]$^+$, m/z 424.0978 found: 424.0975. R$_f$=0.17 (neutral alumina oxide, cyclohexane-ethyl acetate 30:70).

Compound 40h

Triethylamine (0.15 mL, 1 mmol) and then mesyl chloride (35 μL, 0.45 mmol) were added under inert atmosphere to a solution of alcohol 39h (122 mg 0.3 mmol) in anhydrous tetrahydrofuran (3 mL) cooled to 5° C. The reaction mixture was stirred at room temperature for 15 min. The progress of the reaction was monitored by TLC. After this period, reaction was complete. The solvent was removed under reduced pressure. Water saturated with sodium chloride (30 mL) was added to the residue and the mixture was extracted with dichloromethane (2×30 mL). The organic phases were combined and dried over magnesium sulfate. After filtration, the solvent was removed under reduced pressure to give a colorless oil corresponding to compound 40h (115 mg, 80%), which was sufficiently pure to be used in the next step without additional purification. $^1$H NMR (400 MHz, CDCl$_3$) δ: 8.08 (bs, 1H), 7.63 (bs, 1H), 7.48 (d, J=8.9 Hz, 2H), 6.90 (d, J=8.9 Hz, 2H), 5.35 (s, 2H), 4.66 (s, 2H), 4.12 (m, 1H), 3.87 (m, 1H), 3.80 (s, 3H), 3.10 (s, 3H), 1.76 (d, J=14.9 Hz, 3H), 1.26 (t, J=7.0 Hz, 3H); $^{31}$P NMR (162 MHz, CDCl$_3$) δ: +38.2. HRMS (ESI+) calculated for $C_{21}H_{24}NO_8NaPS$ [M+Na]$^+$, m/z 504.0858 found: 504.0859. R$_f$=0.56 (silica; dichloromethane-methanol 90:10).

Compound 40i

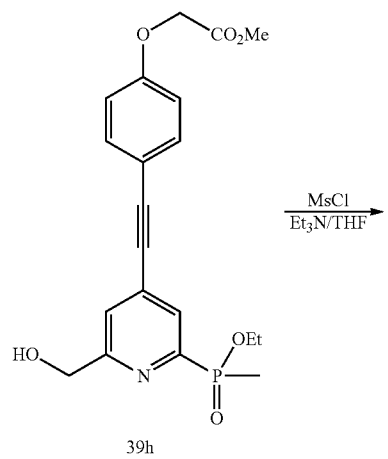

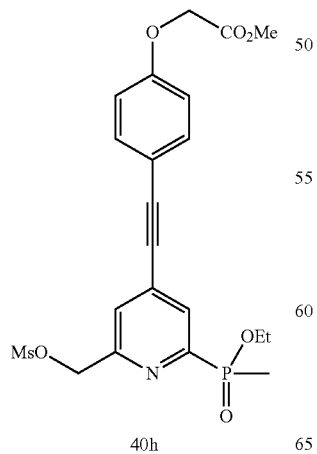

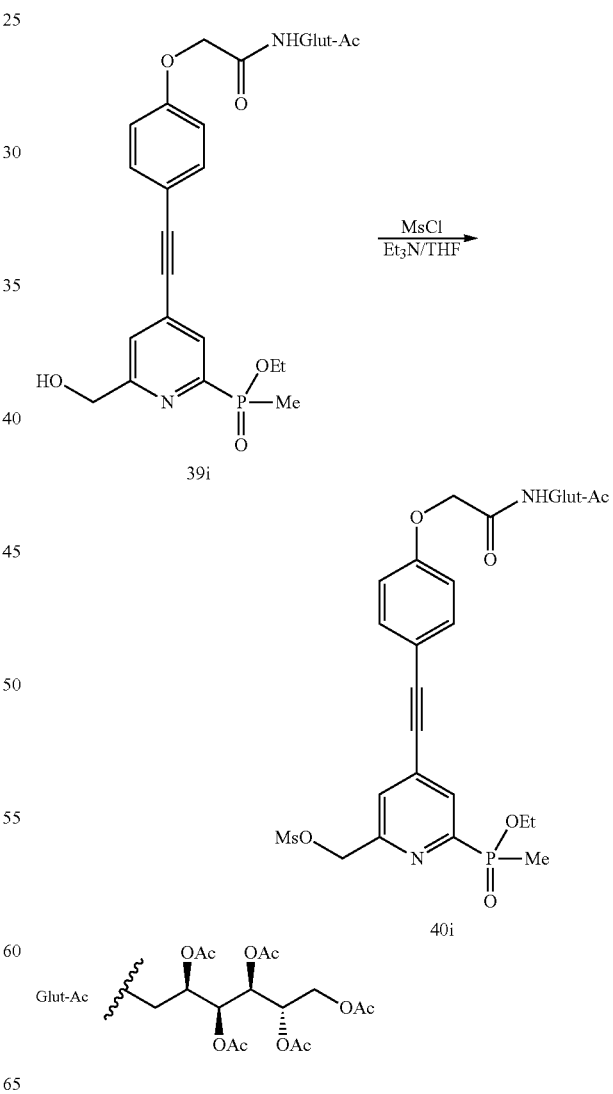

Triethylamine (0.26 μL, 0.19 mmol) and then mesyl chloride (11 μL, 0.14 mmol) were added under inert atmosphere to a solution of alcohol 39i (71 mg, 93 μmol) in anhydrous tetrahydrofuran (1.5 mL) cooled to 5° C. The reaction mixture was stirred at room temperature for 1 h. The progress of the reaction was monitored by TLC. After this period, reaction was complete. The solvent was removed under reduced pressure. Water saturated with sodium chloride (10 mL) was added to the residue and the mixture was extracted with dichloromethane (3×10 mL). The organic phases were combined and dried over magnesium sulfate. After filtration, the solvent was removed under reduced pressure to give a colorless oil corresponding to compound 40i (78 mg, quantitative), which was sufficiently pure to be used in the next step without additional purification. $^1$H NMR (400 MHz, CDCl$_3$) δ 8.01 (d, J=5.6 Hz, 1H), 7.64 (m, 1H), 7.52 (d, J=8.6 Hz, 2H), 7.38 (m, 1H), 6.94 (d, J=8.6 Hz, 2H), 5.49 (dd, J=6.4; 4.8 Hz, 1H), 5.38 (m, 2H), 5.33 (dd, J=5.8; 4.6 Hz, 1H), 5.17 (m, 1H), 5.02 (ddd, J=6.6; 5.6; 3.4 Hz, 1H), 4.50 (m, 2H), 4.25 (dd, J=12.5; 3.4 Hz, 1H), 4.11 (dd, J=12.5; 5.6 Hz, 1H), 3.87 (m, 2H), 3.55 (m, 2H), 3.14 (s, 3H), 2.13 (s, 3H), 2.09 (s, 3H), 2.06 (s, 3H), 2.05 (s, 3H), 2.02 (s, 3H), 1.77 (d, J=15 Hz, 3H), 1.28 (t, J=7.0 Hz, 3H); LRMS (ESI+) calculated for C$_{36}$H$_{46}$N$_2$O$_{17}$PS [M+H]$^+$, m/z 841.2255 found: 841.31. R$_f$=0.44 (silica; dichloromethane-methanol: 90:10).

Compound 40j

This compound was prepared according to the same procedure as that used for compound 40i using the corresponding precursor.

Compounds 40m-p

These compounds were prepared according to the same procedure as that used for compound 38f using the corresponding precursors.

Compound 41a

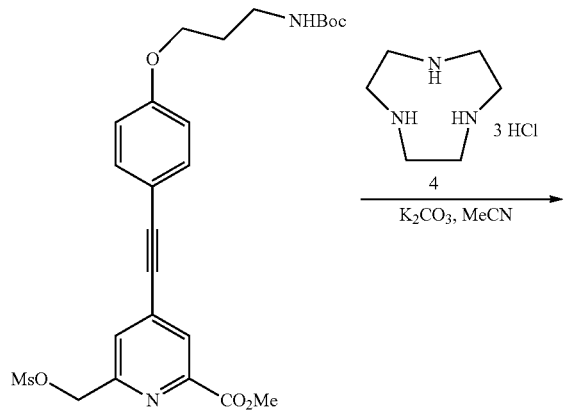

38a

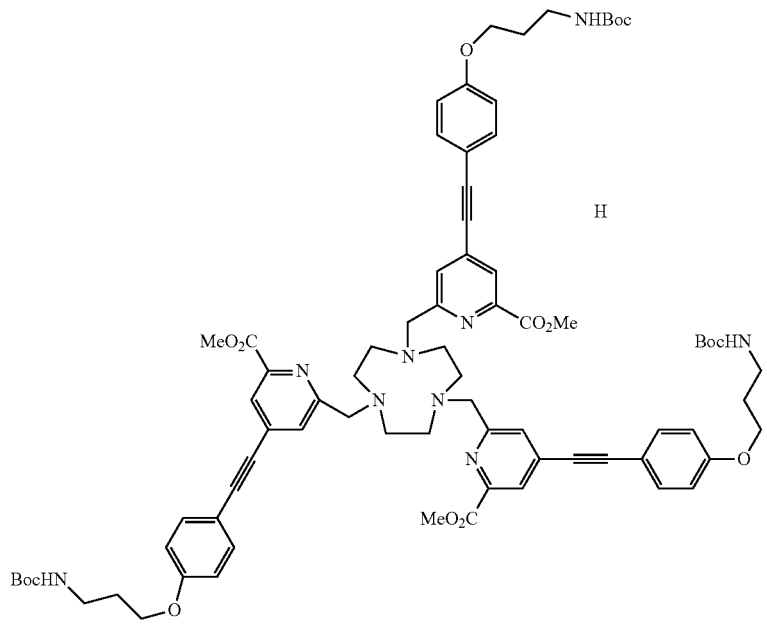

41a

Potassium carbonate (65 mg, 0.471 mmol) and 1,4,7-triazacyclononane 4 (30 mg, 0.126 mmol) were added under inert atmosphere to a solution of mesylated derivative 38a (235 mg, 0.454 mmol) in anhydrous acetonitrile (10 mL). The reaction mixture was heated at 65° C. for 18 h. The progress of the reaction was monitored by LC-MS. After this period, reaction was complete. The reaction mixture was cooled to room temperature and the solvent was removed under reduced pressure. The residue was purified by preparative HPLC using the following gradient: Waters XBridge RP-C18 column, 5 μm, 50×150 mm) with a solution of formic acid 0.1% pH 2-MeCN (v/v) as eluent [isocratic 5% MeCN (3 min)], linear gradient from 5 to 100% MeCN (25 min) with a flow rate of 100 mL min$^{-1}$ and UV detection at 320 nm to give compound 41a (52.7 mg, 30%). LMRS (ESI+) calculated for $C_{78}H_{94}N_9O_{15}$ [M+H]$^+$, m/z 1396.6869. found: 1396.31. $R_t$=14.03 min (Waters XBridge RP-C18 column, 3.5 μm, 4.6×100 mm) with 0.1% aqueous solution of formic acid (pH 2-MeCN (v/v) as eluent [isocratic 5% MeCN (1 min)], linear gradient from 5 to 100% MeCN (14 min), with a flow rate of 1 mL min$^{-1}$.

Compound 41b

This compound was prepared according to the same procedure as that used for compound 41a using the corresponding precursor.

Compound 41c

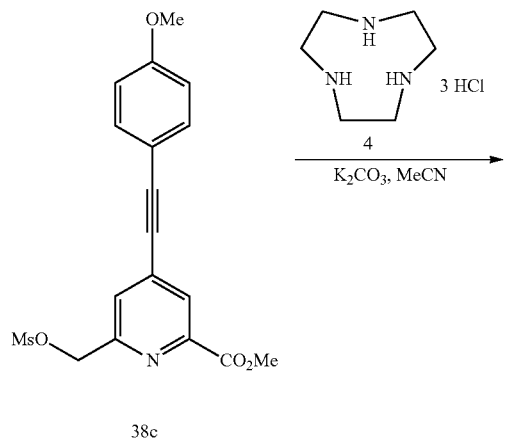

38c

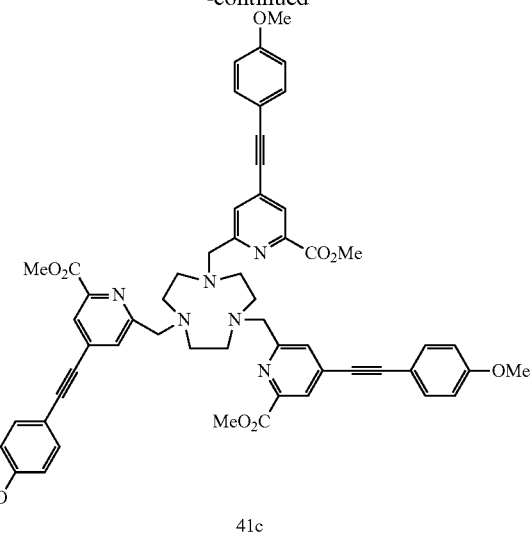

41c

Potassium carbonate (34.7 mg, 250 μmol) and 1,4,7-triazacyclononane 4 (9.6 mg, 40 μmol) were added under inert atmosphere to a solution of mesylated derivative 38c (46.8 mg, 120 μmol) in anhydrous acetonitrile (5 mL). The reaction mixture was heated at 60° C. for 3 h under inert atmosphere. The progress of the reaction was monitored by HPLC. After this period, reaction was complete. The reaction mixture was cooled to room temperature and the solvent was removed under reduced pressure. The crude product obtained was purified by preparative HPLC: Macherey Nagel column (Hilic, 5 μm, 21×250 mm) with ammonium acetate buffer solution 50 mM pH 5.3-MeCN (v/v) as eluent [isocratic 97% MeCN (3 min)], linear gradient from 97 to 80% MeCN (20 min) with a flow rate of 14 mL min$^{-1}$ and UV detection at 330 nm to give compound 41c in the form of a yellowish oil (32.7 mg, 87%). HMRS (ESI+) calculated for $C_{57}H_{55}N_6O_9$ [M+H]$^+$, m/z 967.4025 found: 967.4022. $R_t$=13.73 min (Waters XBridge RP-C18 column, 3.5 μm, 4.6×100 mm) with 0.1% aqueous solution of formic acid (pH 2-MeCN (v/v) as eluent [isocratic 5% MeCN (1 min)], linear gradient from 5 to 100% MeCN (14 min), with a flow rate of 1 mL min$^{-1}$.

Compound 41d

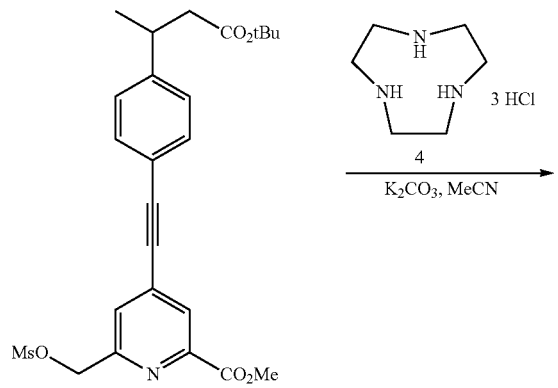

38d

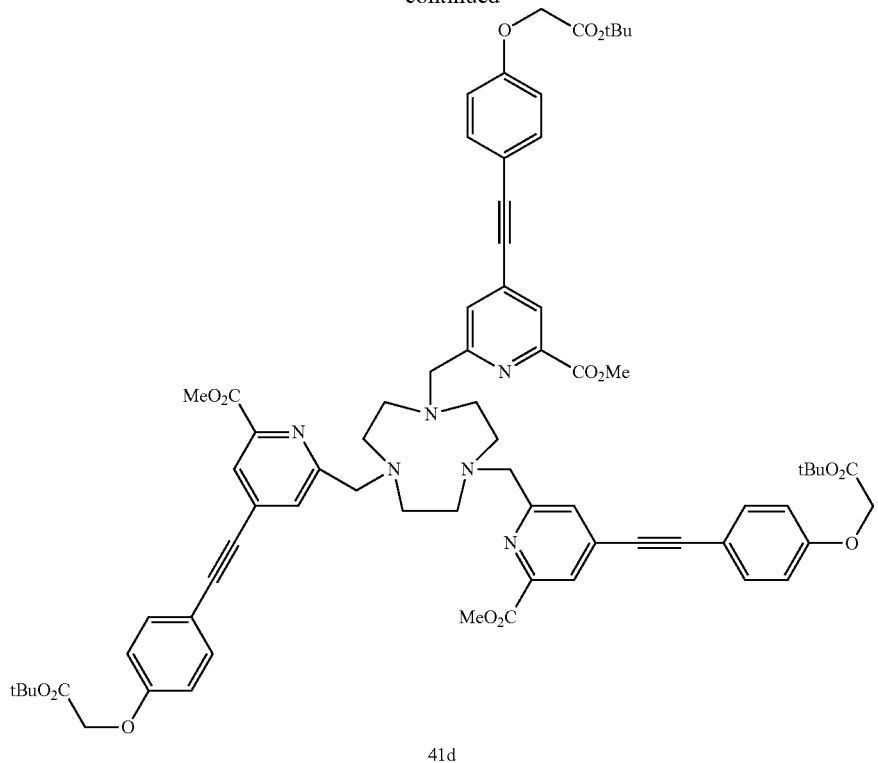

41d

Potassium carbonate (53 mg, 370 μmol) and 1,4,7-triazacyclononane 4 (14.7 mg, 62 μmol) were added under inert atmosphere to a solution of mesylated derivative 38d (88.2 mg, 190 μmol) in anhydrous acetonitrile (4 mL). The reaction mixture was heated at 60° C. for 16 h. The progress of the reaction was monitored by LC-MS. After this period, reaction was complete. The reaction mixture was cooled to room temperature and the solvent was removed under reduced pressure. Dichloromethane (30 mL) was added to the residue and the solution was washed with water (2×15 mL). The organic phase was dried over magnesium sulfate. After filtration, the solvent was removed under reduced pressure. The crude product obtained was purified by preparative HPLC: Macherey Nagel Hilic column, (5 μm, 21×250 mm) with ammonium acetate buffer solution 50 mM pH 5.3-MeCN (v/v) as eluent [isocratic 97% MeCN (3 min)], linear gradient from 97 to 80% MeCN (20 min) with a flow rate of 14 mL min$^{-1}$ and UV detection at 330 nm to give compound 41d in form (19 mg, 8%). LRMS (ESI+) calculated for $C_{72}H_{79}N_6O_{15}$ [M+H]$^+$, m/z 1267.5603. found: 1267.82. $R_t$=14.26 min (Waters XBridge RP-C18 column, 3.5 μm, 4.6×100 mm) with 0.1% aqueous solution of formic acid pH 2-MeCN (v/v) as eluent [isocratic 5% MeCN (1 min)], linear gradient from 5 to 100% MeCN (14 min), with a flow rate of 1 mL min$^{-1}$.

Compound 41e

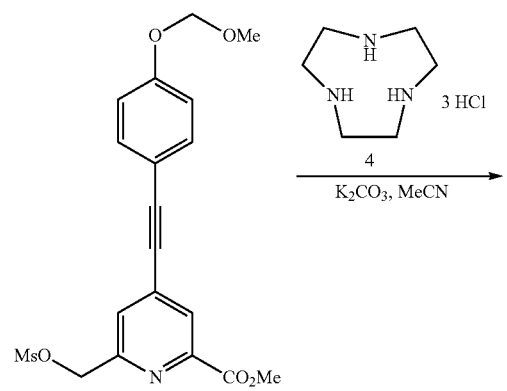

38e

-continued

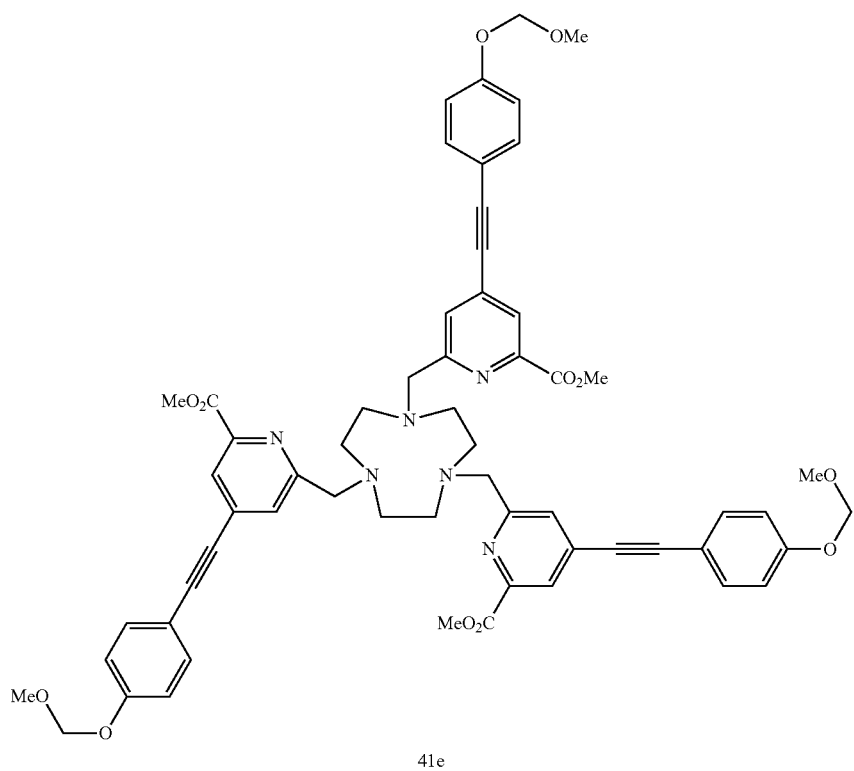

41e

Potassium carbonate (52.3 mg, 380 μmol) and 1,4,7-triazacyclononane 4 (14.5 mg, 60 μmol) were added under inert atmosphere to a solution of brominated derivative 38e (76.3 mg, 190 μmol) in anhydrous acetonitrile (5 mL). The reaction mixture was heated at 60° C. for 16 h. The progress of the reaction was monitored by LC-MS. After this period, reaction was complete. The reaction mixture was cooled to room temperature and the volume of solvent was reduced under reduced pressure to 1 mL and the reaction mixture was purified by preparative HPLC using the following gradient: Waters XBridge RP-C18 column, 5 μm, 50×150 mm) with 1% solution of trifluoroacetic acid pH 1-MeCN (v/v) as eluent [isocratic 15% MeCN (2 min), linear gradient from 15 to 100% MeCN (23 min) with a flow rate of 100 mL min$^{-1}$ and UV detection at 320 nm to give compound 41e (10.2 mg, 16%). HMRS (ESI+) calculated for $C_{60}H_{61}N_6O_{12}$ [M+H]$^+$, m/z 1057.4342. found: 1057.4341. $R_t$=12.94 min (Waters XBridge RP-C18 column, 3.5 μm, 4.6×100 mm) with 0.1% aqueous solution of formic acid (pH 2-MeCN (v/v) as eluent [isocratic 5% MeCN (1 min), linear gradient from 5 to 100% MeCN (14 min), with a flow rate of 1 mL min$^{-1}$.

Compounds 41f-g

These compounds were prepared according to the same procedure as that used for compound 41c using the corresponding precursors. Purification was carried out by the method described for compound 47b.

Compound 43c

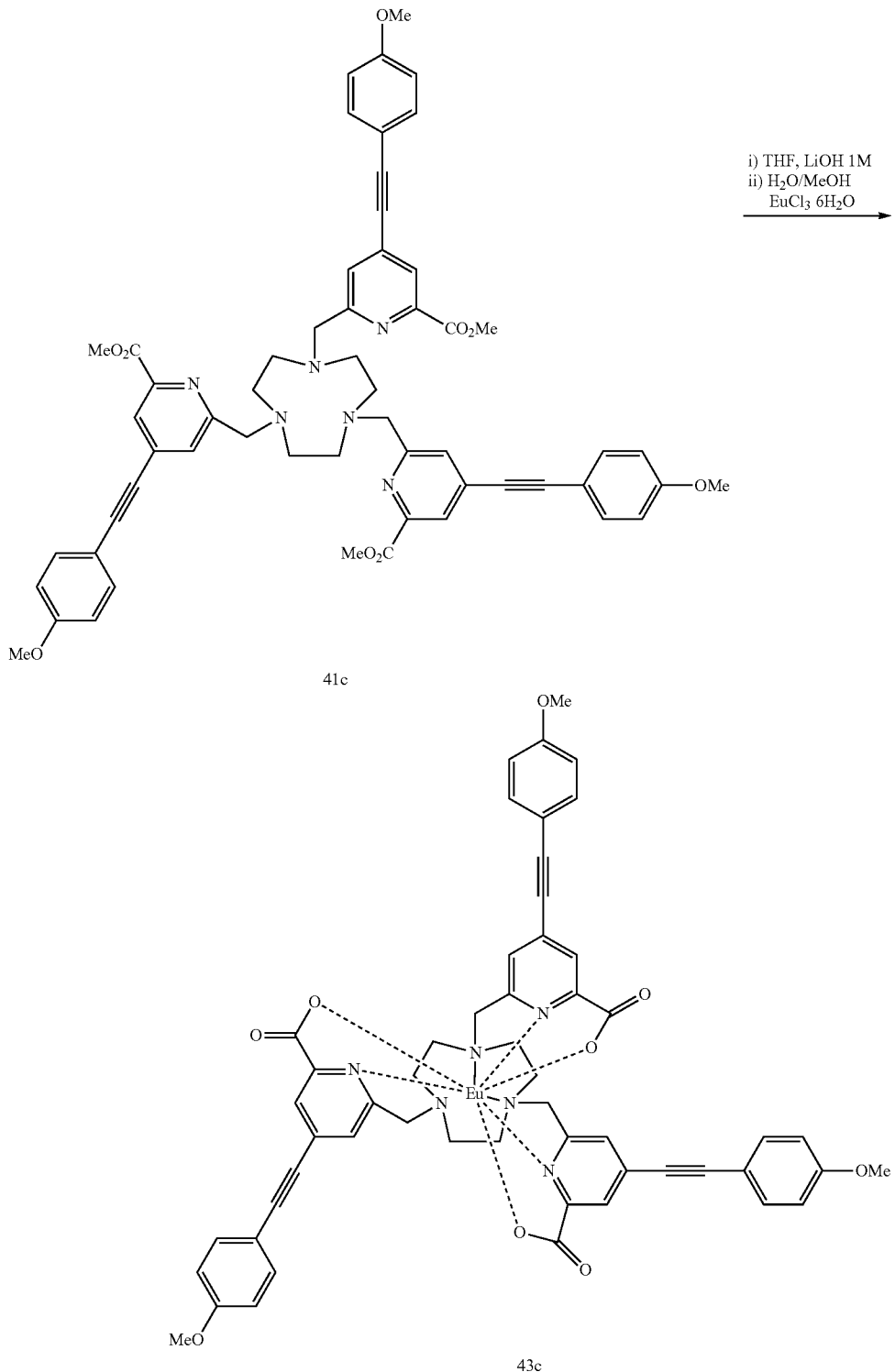

A 1 M aqueous solution of lithium hydroxide (1.5 mL) was added to a solution of ligand 41c (32.7 mg, 33.8 μmol) in tetrahydrofuran (3 mL). The solution was stirred at room temperature for 20 min. The progress of the reaction was monitored by analytical HPLC. After this time, reaction was complete. The solvent was removed under reduced pressure and then water (2 mL) and methanol (3 mL) were added to the residue. The pH of the solution was adjusted to 7 by adding hydrochloric acid (4 M). Europium chloride (36 mg, 98.1 μmol) was added to this solution. The reaction mixture was stirred at room temperature for 30 min. The progress of the reaction was monitored by LC-MS. After this time, reaction was complete. The solvent was removed under reduced pressure and then acetonitrile (4 mL) was added to the residue and this solution was purified by preparative HPLC: Macherey Nagel Hilic column, (5 μm, 21×250 mm)

with ammonium acetate buffer solution 50 mM pH 5.3-MeCN (v/v) as eluent [isocratic 97% MeCN (3 min)], linear gradient from 97 to 80% MeCN (20 min) with a flow rate of 14 mL min$^{-1}$ and UV detection at 330 nm the desired compound 43c (4.8 mg, 13%). HMRS (ESI+) calculated for $C_{54}H_{47}N_6O_9Eu$ [M+2H]$^{2+}$, m/z 537.1296 found: 537.1299. $R_t$=10.55 min (Waters XBridge RP-C18 column, 3.5 μm, 4.6×100 mm) with 0.1% aqueous solution of formic acid (pH 2-MeCN (v/v) as eluent [isocratic 5% MeCN (1 min)], linear gradient from 5 to 100% MeCN (14 min), with a flow rate of 1 mL min$^{-1}$.

Compounds 43a-b, d-g

These compounds were prepared according to the same procedure as that used for compound 43c using the corresponding precursors.

Compounds 44a-g, i, k-p

These compounds were prepared according to the same procedure as that used for compound 44h using the corresponding precursors.

Compound 44h

Potassium carbonate (44 mg, 0.321 mmol) and 1,4,7-triazacyclononane 4 (13.8 mg, 0.107 mmol) were added under inert atmosphere to a solution of mesylated derivative 40h (150 mg, 0.310 mmol) in anhydrous acetonitrile (2 mL). The reaction mixture was heated at 60° C. for 9 h. The progress of the reaction was monitored by TLC. After this period, reaction was complete. The reaction mixture was cooled to room temperature and the solvent was removed under reduced pressure. Water (10 mL) was added to the residue and the mixture was extracted with ethyl acetate (2×20 mL). The organic phases were combined and dried over magnesium sulfate. After filtration, the solvent was removed under reduced pressure. The crude product obtained was purified by silica column chromatography (dichloromethane/methanol, 0 to 20% in increments of 1%) to give compound 44h in the form of a colorless oil (43 mg, 31%). $^1$H NMR (700 MHz, CDCl$_3$) 7.96 (d J=5.5 Hz, 3H), 7.67 (bs, 3H), 7.45 (d, J=8.7 Hz, 6H), 6.87 (d, J=8.7 Hz, 6H), 4.63 (s, 6H), 4.25 (m, 6H), 4.09 (dq, J=17.3; 7.2 Hz, 3H), 3.87 (dq, J=17.3; 7.2 Hz, 3H), 3.78 (s, 9H), 3.24 (m, 12H),

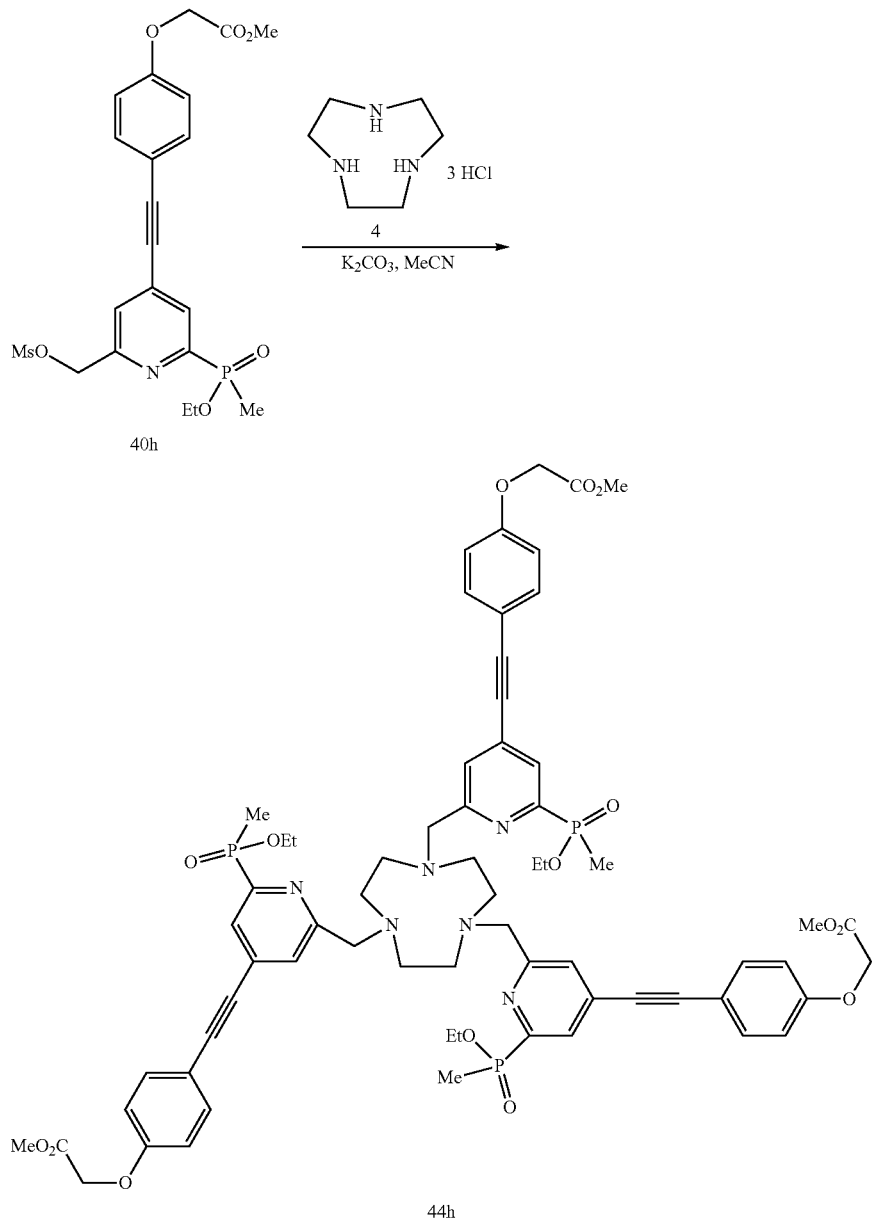

1.73 (d, J=14.9 Hz, 9H), 1.23 (t, J=7.2 Hz, 9H); $^{13}$C NMR (176 MHz, CDCl$_3$) δ: 168.9; 158.9; 157.0; 154.6 (d, J=157 Hz); 133.8; 133.4 (d, J=11 Hz); 128.2 (d, J=21 Hz); 127.7, 115.1, 115.0, 95.6, 85.3, 65.2, 61.3 (d, J=6 Hz), 60.7, 52.5, 52.2, 16.5 (d, J=4 Hz), 13.5 (d, J=104 Hz). $^{31}$P NMR (284 MHz, CDCl$_3$) δ: +39.2; m/z HMRS (ESI+) calculated for C$_{66}$H$_{76}$N$_6$O$_{15}$P$_3$ [M+H$^+$], m/z 1285.4582. found: 1285.4598. R$_f$=0.43 (silica; dichloromethane-methanol 87:13).
Compounds 46a-g, i, k-p
These compounds were prepared according to the same procedure as that used for compound 46h using the corresponding precursors.
Compound 46h
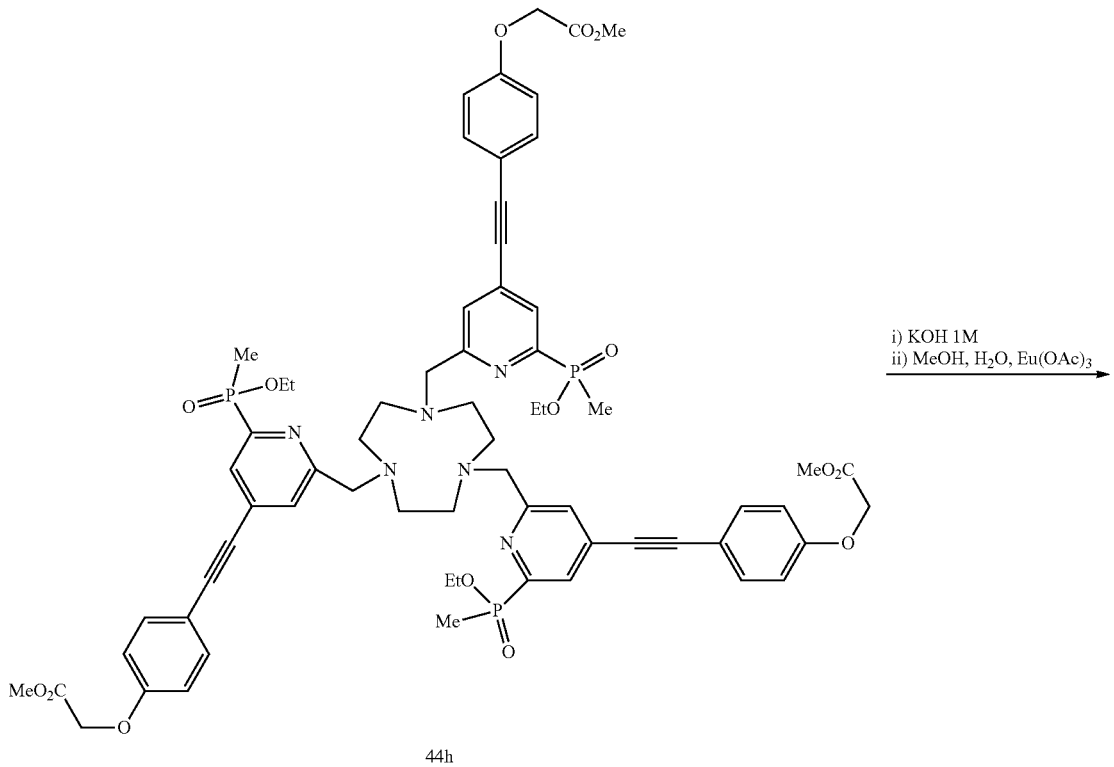
44h
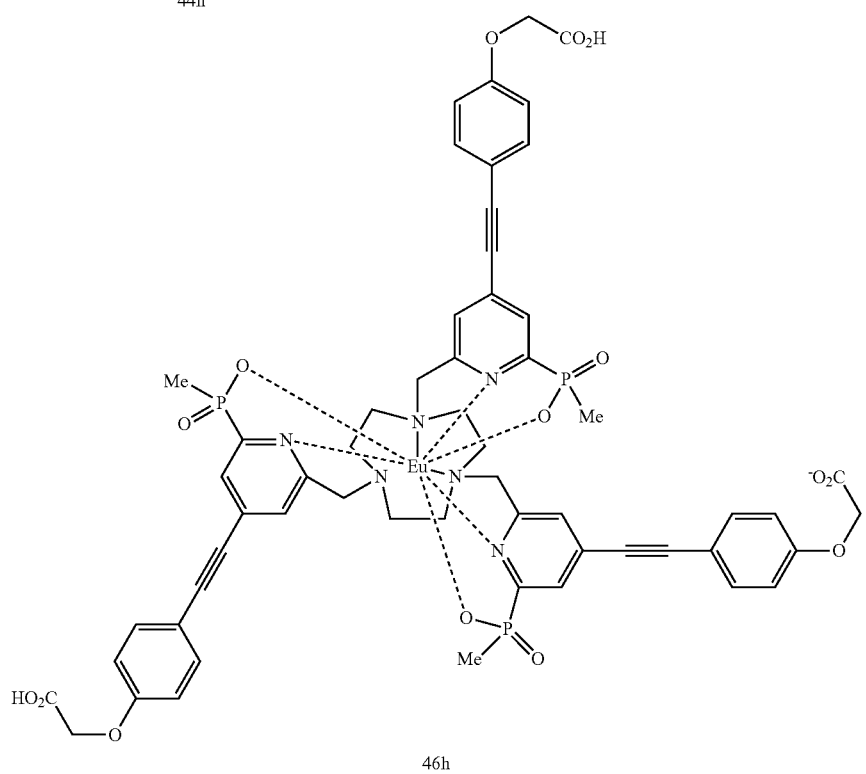
46h Potassium hydroxide (6.6 mg, 118 µmol) was added to a solution of ligand 44h (10 mg, 7.8 µmol) in a solvent mixture $CD_3OD/D_2O$ (1.5 mL, 2:1 v/v). The solution was heated at 60° C. for 18 h under inert atmosphere. The progress of the reaction was monitored by $^1H$ and $^{31}P$ NMR. After this time, reaction was complete. The solvent was removed under reduced pressure and the pH of the solution was adjusted to 7 by adding 1 M aqueous solution of hydrochloric acid. The mixture was lyophilized and the white solid obtained was dissolved in a methanol-water solvent mixture (1 mL, 1:1 v/v). Europium acetate (3 mg, 9.4 µmol) was added to this solution and the pH of the solution was adjusted to 5.8 by adding 1 M aqueous solution of hydrochloric acid. The reaction mixture was heated at 65° C. under inert atmosphere for 18 h. The reaction mixture was cooled to room temperature and the pH of the solution was adjusted to 7 by adding 1 M aqueous solution of potassium hydroxide and then was lyophilized. The crude product thus obtained was purified by semipreparative HPLC to give the desired compound 46h in the form of a white solid (4.5 mg, 45%). HMRS (ESI+) calculated for $C_{57}H_{53}N_6O_{15}P_3Eu$ [M−H], m/z 1307.1999. found: 1307.2030.

Compound 44j

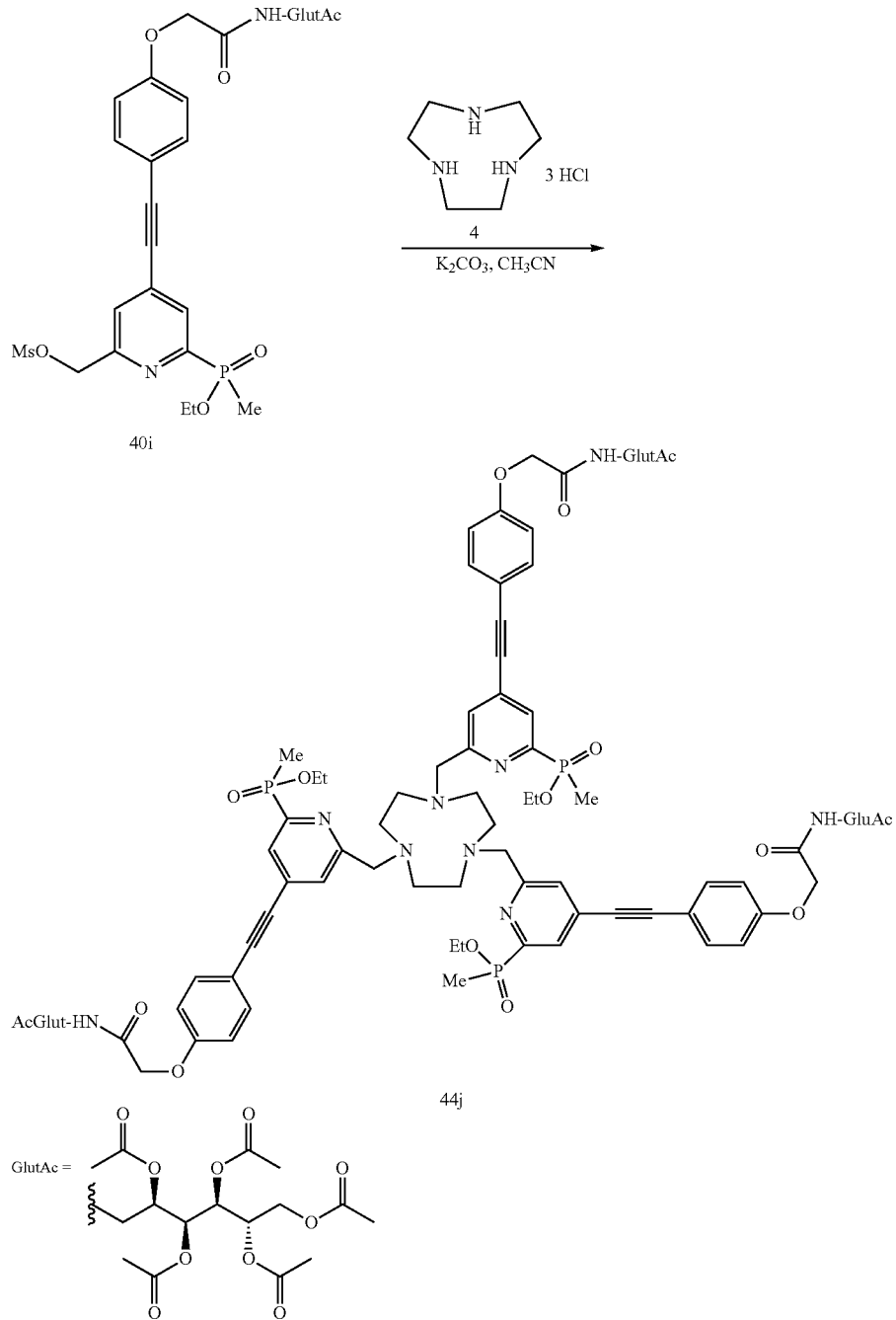

Potassium carbonate (14 mg, 96 µmol) and 1,4,7-triazacyclononane 4 (4.1 mg, 33 µmol) were added under inert atmosphere to a solution of mesylated derivative 40i (78 mg, 93 µmol) in anhydrous acetonitrile (1 mL). The reaction mixture was heated at 60° C. for 5 h under inert atmosphere. The progress of the reaction was monitored by LC-MS. After this period, reaction was complete. The reaction mixture was cooled to room temperature and the solvent was removed under reduced pressure. The potassium salts were removed by decantation and then filtration. The filtrate was evaporated under reduced pressure and the crude product obtained was purified by silica column chromatography (dichloromethane/methanol, 0 to 20% in increments of 1%) to give compound 44j in the form of a colorless oil (20 mg, 26%). $^1$H NMR (700 MHz, CDCl$_3$) δ: 8.00 (m, 3H), 7.74 (m, 3H), 7.55 (m, 3H), 7.50 (d, J=8.6 Hz, 6H), 6.93 (d, J=8.6 Hz, 6H), 5.48 (dd, J=6.4; 4.8 Hz, 3H), 5.33 (dd, J=5.8; 4.6 Hz, 3H), 5.18 (m, 3H), 5.02 (m, 3H), 4.49 (q AB, 6H), 4.25 (dd, J=12.4; 3.4 Hz, 3H), 4.11 (dd, J=12.4; 5.6 Hz, 3H), 3.95 (m, 6H), 3.87 (m, 6H), 3.55 (m, 6H), 2.93 (m, 6H), 2.69 (m, 6H), 2.12 (s, 9H), 2.09 (s, 9H), 2.06 (s, 9H), 2.05 (s, 9H), 2.02 (s, 9H), 1.74 (d, J=15.0 Hz, 9H), 1.25 (t, J=7.0 Hz, 9H); $^{13}$C NMR (176 MHz, CDCl$_3$) δ: 170.7, 170.5, 170.2, 170.0, 169.9, 168.0, 158.2, 157.0 (m 1); 154.7 (d, J=154 Hz), 134.1, 133.3, 128.3 (d, J=21 Hz), 127.9 (m 1); 115.3, 115.2, 96.3, 85.5, 70.2, 69.1 (4); 69.1 (1) 69.0; 67.3, 66.4, 61.6, 61.2, 52.0, 39.4, 20.9; 20.8 (2); 20.8 (1); 20.7; 16.6 (d, J=6 Hz); 13.6 (d, J=103 Hz); $^{31}$P NMR (284 MHz, CDCl$_3$) δ: +38.8; HMRS (ESI+) calculated for $C_{111}H_{139}N_9O_{42}P_3Na$ [M+H+Na]$^{2+}$, m/z 1192.9060 found: 1192.904. $R_f$=0.52 (silica; dichloromethane-methanol 85:15).

Compound 46j

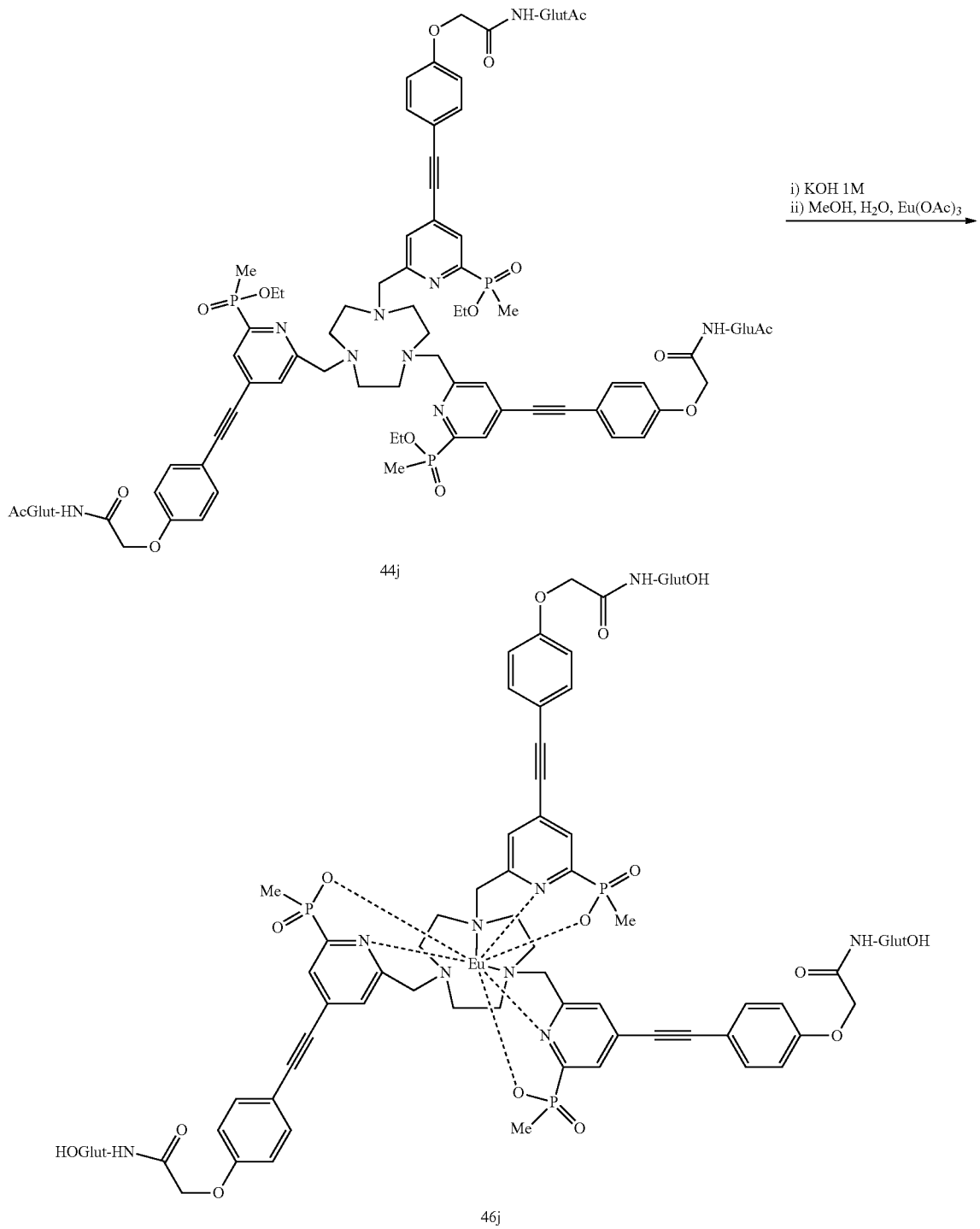

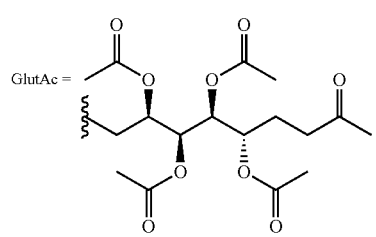

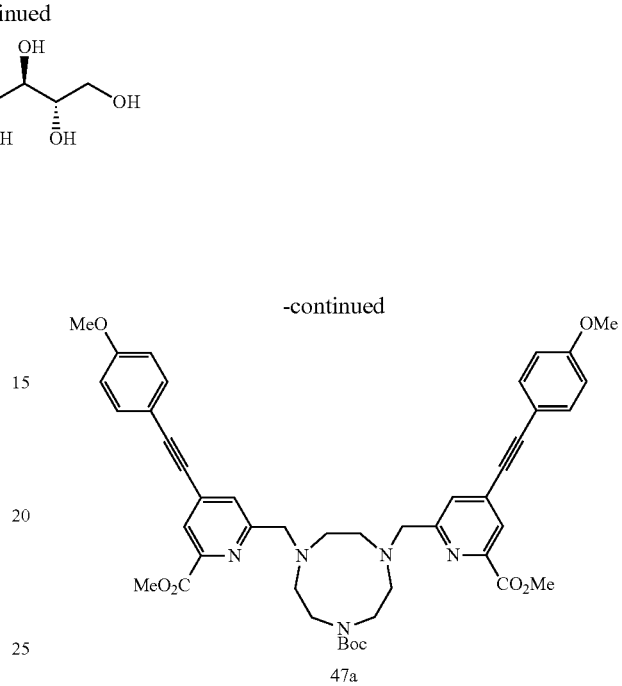

Potassium hydroxide (8 mg, 150 μmol) was added to a solution of ligand 44j (17 mg, 7.2 μmol) in a CD$_3$OD/D$_2$O solvent mixture (1.5 mL, 2:1 v/v). The solution was heated at 60° C. for 7 h under inert atmosphere. The progress of the reaction was monitored by $^1$H and $^{31}$P NMR. After this time, reaction was complete. The solvent was removed under reduced pressure and the pH of the solution was adjusted to 7 by adding 1 M aqueous solution of hydrochloric acid. The mixture was lyophilized and the white solid obtained was dissolved in a methanol-water solvent mixture (2 mL, 1:1 v/v). Europium acetate (2.8 mg, 8.6 μmol) was added to this solution. The reaction mixture was heated at 65° C. under inert atmosphere for 18 h and then it was cooled to room temperature. The suspension was centrifuged and the white solid was separated from the supernatant and then washed with water (3×5 mL). The supernatant and the filtrates were combined, neutralized with an aqueous solution of potassium hydroxide (1 M) and then lyophilized to give a white solid, which was purified by semipreparative HPLC to give the desired compound 46j in the form of a white solid (6 mg, 45%). LRMS (MALDI-TOF) calculated for C$_{57}$H$_{93}$N$_9$O$_{27}$P$_3$Eu [M+H]$^+$, m/z 1798.5. found: 1799.8.

Compound 47a

Potassium carbonate (87 mg, 640 μmol) was added under inert atmosphere to a solution of TACN monoBoc hydrochloride 7a (48 mg, 160 μmol) in anhydrous acetonitrile (20 mL). A solution of chromophore 38c (150 mg, 300 μmol) in anhydrous acetonitrile (2 mL) was added to this suspension. The mixture was heated at 65° C. for 12 h under inert atmosphere. The progress of the reaction was monitored by LC-MS. After this time, reaction was complete. The reaction mixture was cooled to room temperature. The solvent was removed under reduced pressure. The crude reaction product was purified by silica column chromatography (dichloromethane/methanol 98:2 to 80:20 in increments of 2%) to give compound 47a (95 mg, 75%). LMRS (ESI+) calculated for C$_{45}$H$_{50}$N$_5$O$_8$ [M+H]$^+$, m/z 788.3659. found: 788.78. R$_f$=0.53 (silica; dichloromethane-methanol: 90:10). R$_t$=12.89 min (Waters XBridge RP-C18 column, 3.5 μm, 4.6×100 mm) with 0.1% aqueous solution of formic acid (pH 2-MeCN (v/v) as eluent [isocratic 5% MeCN (1 min)], linear gradient from 5 to 100% MeCN (14 min), with a flow rate of 1 mL min$^{-1}$.

Compound 47b

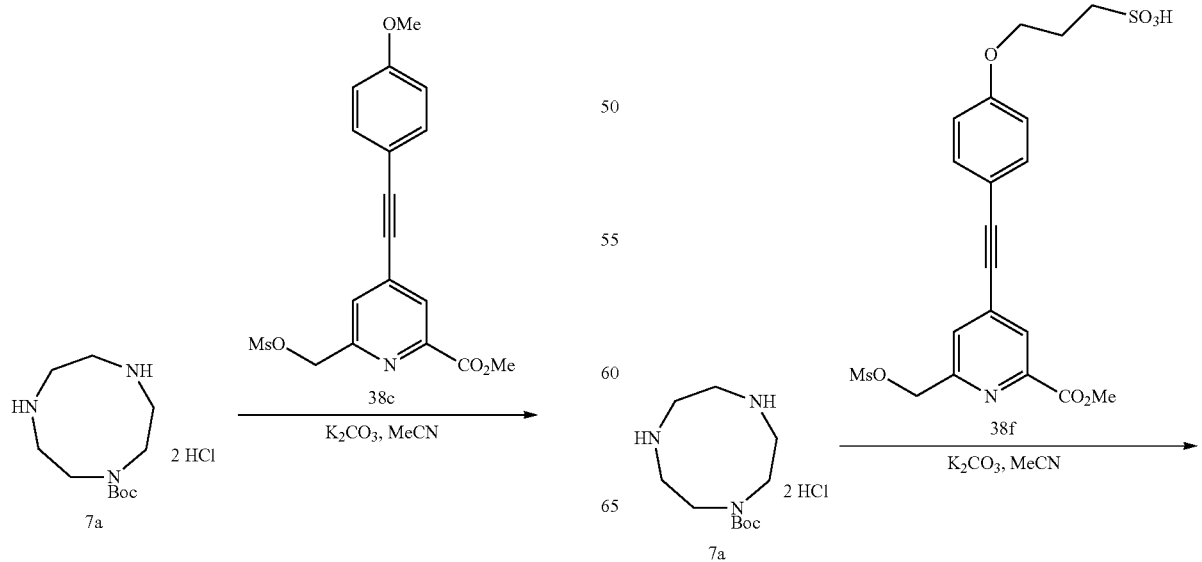

-continued

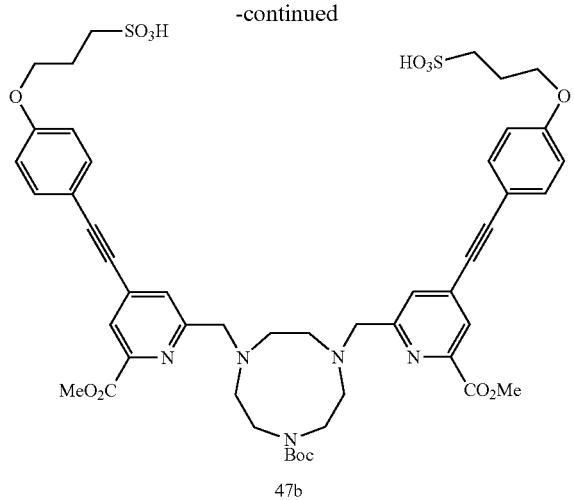

47b

Potassium carbonate (20 mg, 144 μmol) was added under inert atmosphere to a solution of TACN monoBoc hydrochloride 7a (14.6 mg, 48.3 μmol) in anhydrous acetonitrile (10 mL). A solution of chromophore 38f (41 mg, 84 μmol) in anhydrous acetonitrile (2 mL) was added to this suspension. The reaction mixture was heated at 65° C. for 2 h under inert atmosphere. The progress of the reaction was monitored by LC-MS. After this time, reaction was complete. The reaction mixture was cooled to room temperature. The solvent was removed under reduced pressure. The crude reaction product was purified by preparative HPLC using the following gradient: (Waters XBridge RP-C18 column, 5 μm, 50×150 mm) with an aqueous solution of triethylammonium acetate buffer 25 mM pH 6-MeCN (v/v) as eluent [isocratic 5% MeCN (2 min)], linear gradient from 5 to 100% MeCN (18 min) with a flow rate of 100 mL min$^{-1}$ and UV detection at 320 nm to give compound 47b in the form of a whitish solid (17.7 mg, 36%). LMRS (ESI+) calculated for $C_{49}H_{58}N_5O_{14}S_2$ [M+H]$^+$, m/z 1004.3422. found: 1004.62. R$_f$=8.12 min (Waters XBridge RP-C18 column, 3.5 μm, 4.6×100 mm) with 0.2% aqueous solution of trifluoroacetic acid (pH 1-MeCN (v/v) as eluent: linear gradient from 15 to 100% MeCN (19 min), with a flow rate of 1 mL min$^{-1}$.

Compound 47c

This compound was prepared according to the same procedure as that used for compound 47b using the corresponding precursor.

Compound 48a

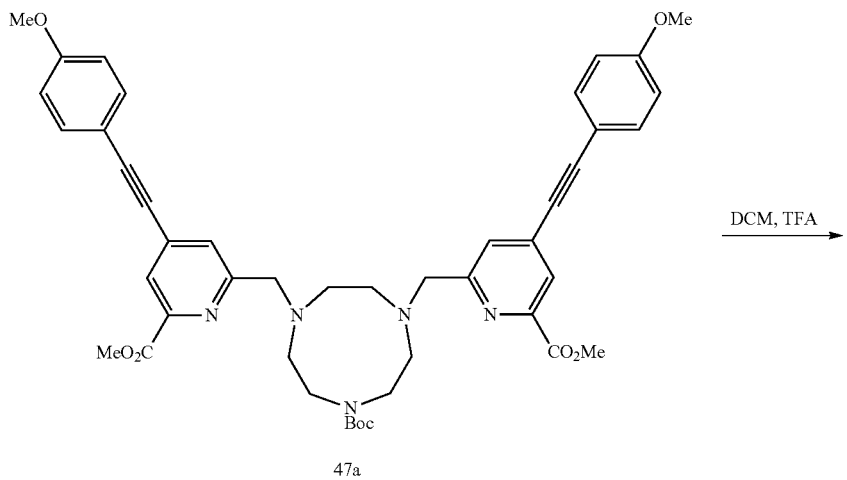

47a

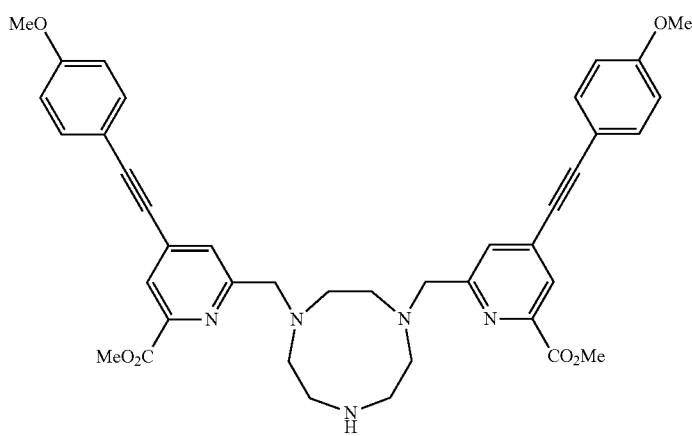

48a

Trifluoroacetic acid (0.5 mL) was added to a solution of 47a (95 mg, 120 μmol) in anhydrous dichloromethane (4 mL). The solution was stirred under argon at 5° C. for 8 h. The progress of the reaction was monitored by LC-MS. After this time, reaction was complete. This solution was washed with a saturated solution of sodium bicarbonate (2×5 mL). The organic phase was dried over magnesium sulfate, filtered and concentrated under reduced pressure. The residue was purified by preparative HPLC using the following gradient: (Waters XBridge RP-C18 column, 5 μm, 50×150 mm) with an aqueous solution of trifluoroacetic acid 0.2% pH 1-MeCN (v/v) as eluent [isocratic 15% MeCN (2 min)], linear gradient from 15 to 100% MeCN (23 min) with a flow rate of 100 mL min$^{-1}$ and UV detection at 320 nm to give compound 48a in the form of a whitish solid (44 mg, 53%). LMRS (ESI+) calculated for $C_{40}H_{42}N_5O_6$ [M+H]$^+$, m/z 688.3135 found: 688.56. $R_t$=11.01 min (Waters XBridge RP-C18 column, 3.5 μm, 4.6×100 mm) with 0.2% aqueous solution of trifluoroacetic acid (pH 1-MeCN (v/v) as eluent: linear gradient from 15 to 100% MeCN (19 min), with a flow rate of 1 mL min$^{-1}$.

Compound 48b

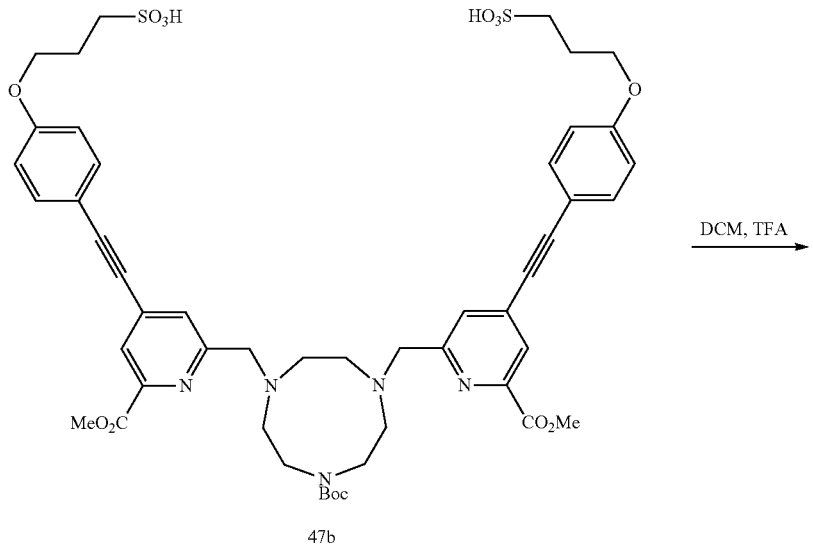

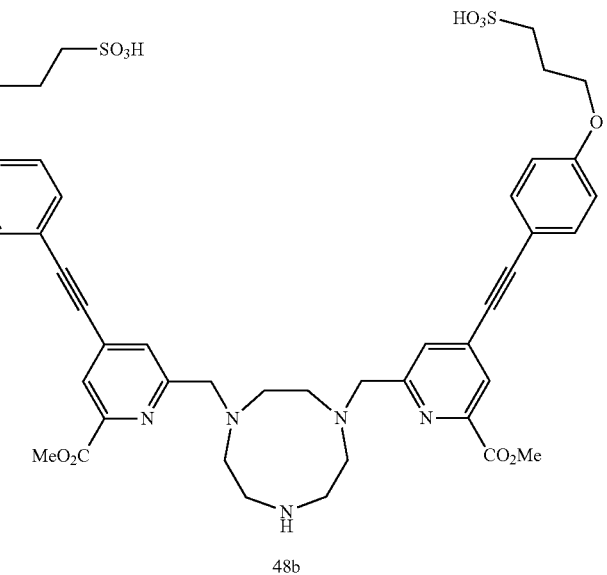

Trifluoroacetic acid (200 μL) was added to a solution of 47b (16.7 mg, 16.6 μmol) in anhydrous dichloromethane (5 mL). The solution was stirred under argon at 5° C. for 2 h and then at room temperature for 2 h. The progress of the reaction was monitored by LCMS. After this time, reaction was complete. This solution was washed with a saturated solution of sodium bicarbonate (2×5 mL). The aqueous phase was concentrated under reduced pressure. The residue was purified by preparative HPLC using the following gradient: (Waters XBridge RP-C18 column, 5 μm, 19×100 mm) with a solution of triethylammonium acetate 25 mM pH 6-MeCN (v/v) as eluent [isocratic 5% MeCN (2 min)], linear gradient from 5 to 60% MeCN (17 min)] with a flow rate of 20 mL min$^{-1}$ and UV detection at 320 nm to give compound 48b. LMRS (ESI+) calculated for $C_{44}H_{50}N_5O_{12}S_2$ [M+H]$^+$, m/z 904.2897 found: 904.61. $R_t$=6.85 mM (Waters XBridge RP-C18 column, 3.5 μm, 4.6×100 mm) with 0.1% aqueous solution of formic acid (pH 2-MeCN (v/v) as eluent [isocratic 5% MeCN (1 min)], linear gradient from 5 to 100% MeCN (14 min), with a flow rate of 1 mL min$^{-1}$.

Compound 48c

This compound was prepared according to the same procedure as that used for compound 48b using the corresponding precursor.

Compound 49a

Potassium carbonate (17 mg, 120 μmol) was added under inert atmosphere to a solution of compound 48a (22 mg, 32 μmol) in anhydrous acetonitrile (7 mL). A solution of chromophore 38a (51.8 mg, 100 μmol) in anhydrous acetonitrile (2 mL) was added to this suspension. The reaction mixture was heated at 65° C. for 2 h under inert atmosphere. The progress of the reaction was monitored by HPLC. After this time, reaction was complete. The reaction mixture was cooled to room temperature. The solvent was removed under reduced pressure. The crude reaction product was purified by preparative HPLC using the following gradient: Waters XBridge RP-C18 column, 5 μm, 50×150 mm) with an aqueous solution of trifluoroacetic acid 0.2% pH 1-MeCN (v/v) as eluent [isocratic 5% MeCN (2 min),

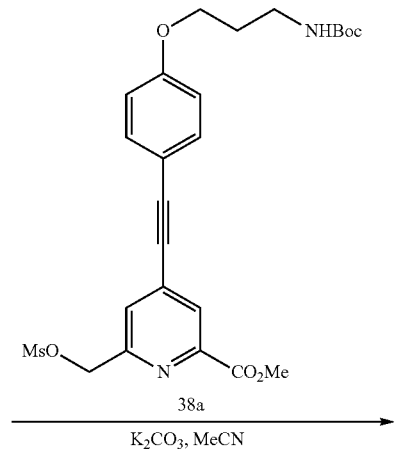

38a

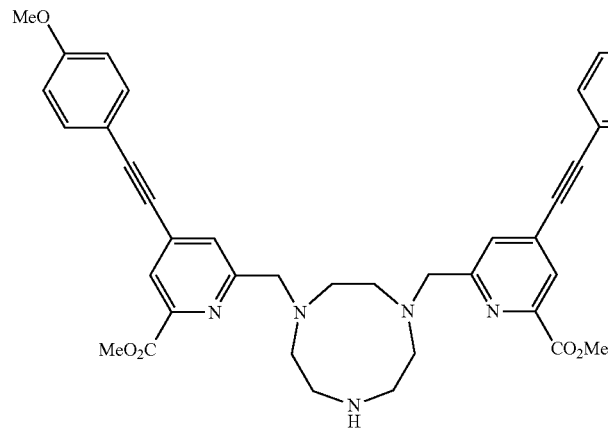

48a

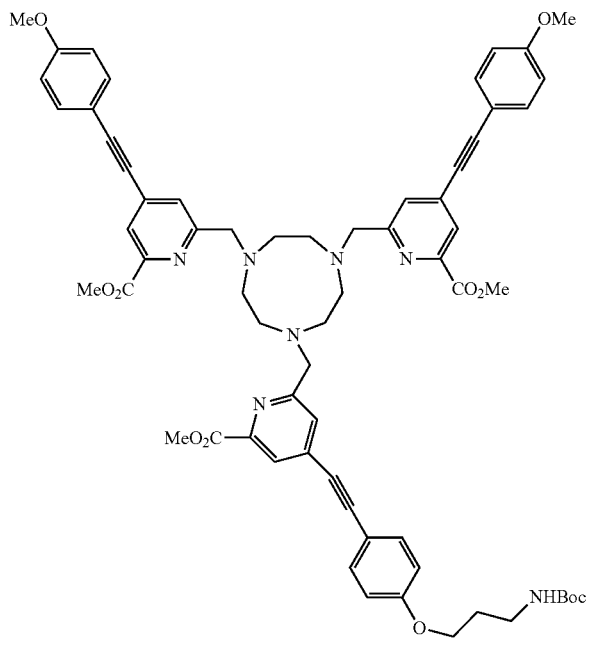

49a linear gradient from 5 to 80% MeCN (43 min) with a flow rate of 100 mL min$^{-1}$ and UV detection at 320 nm to give compound 49a in the form of a whitish solid (7.5 mg, 21%). LMRS (ESI+) calculated for $C_{64}H_{68}N_7O_{11}$ [M+H]$^+$, m/z 1110.4977. found: 1111.22. $R_t$=23.74 min (Waters XBridge RP-C18 column, 3.5 μm, 4.6×100 mm) with 0.2% aqueous solution of trifluoroacetic acid (pH 1-MeCN (v/v) as eluent: linear gradient from 5 to 80% MeCN (25 min), with a flow rate of 1 mL min$^{-1}$.

Compounds 49b-f

These compounds were prepared according to the same procedure as that used for compound 49a using the corresponding precursors.

Compound 50a

1 M lithium hydroxide (50 μmol) and pure water (100 μL) were added to a solution of methyl triester ligand 49a (1 mg, 0.901 μmol) in THF (150 μL). THF (1 mL) was added to this whitish suspension to improve solubilization. The reaction mixture was stirred at room temperature for 2 h. The progress of the reaction was monitored by HPLC. After this period, reaction was complete. The solvent was removed under reduced pressure. The reaction mixture was then taken up in pure water (500 μL) and was acidified by adding aqueous solution of hydrochloric acid (1 M) to obtain pH of the mixture between 2 and 3. The solvent was removed under reduced pressure. The residue was purified by preparative HPLC leading to the desired product in the form of an oil. Trifluoroacetic acid (150 μL) and then an additional volume of dichloromethane (2.5 mL) were added to this oil

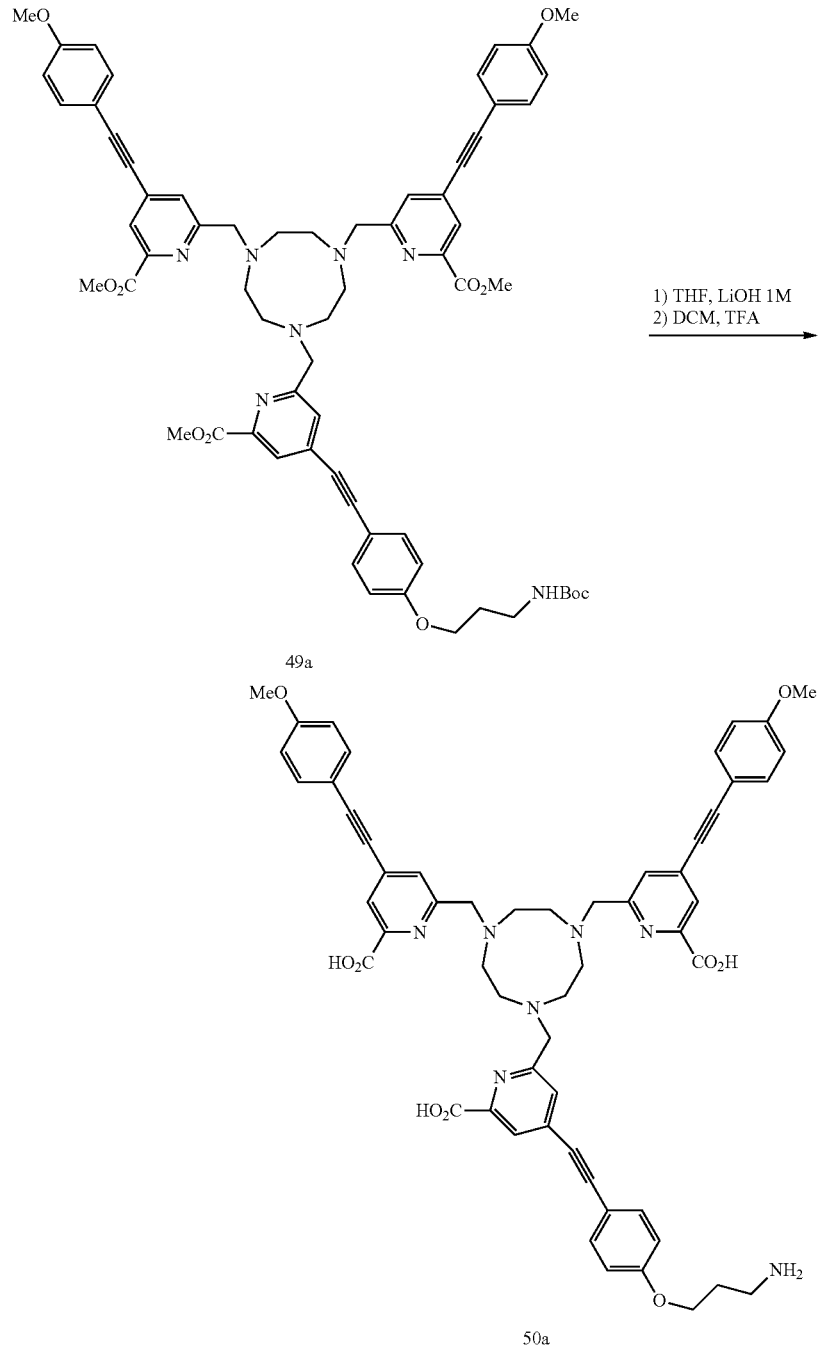

diluted in dichloromethane (0.5 mL). The reaction mixture was stirred at room temperature for 10 min. The progress of the reaction was monitored by HPLC. After this period, reaction was complete. The solvent was removed under reduced pressure to give compound 50a in the form of an oil, which was used in the next step without additional purification.

Compounds 50b-f

These compounds were prepared according to the same procedure as that used for compound 50a using the corresponding precursors.

Compound 51a

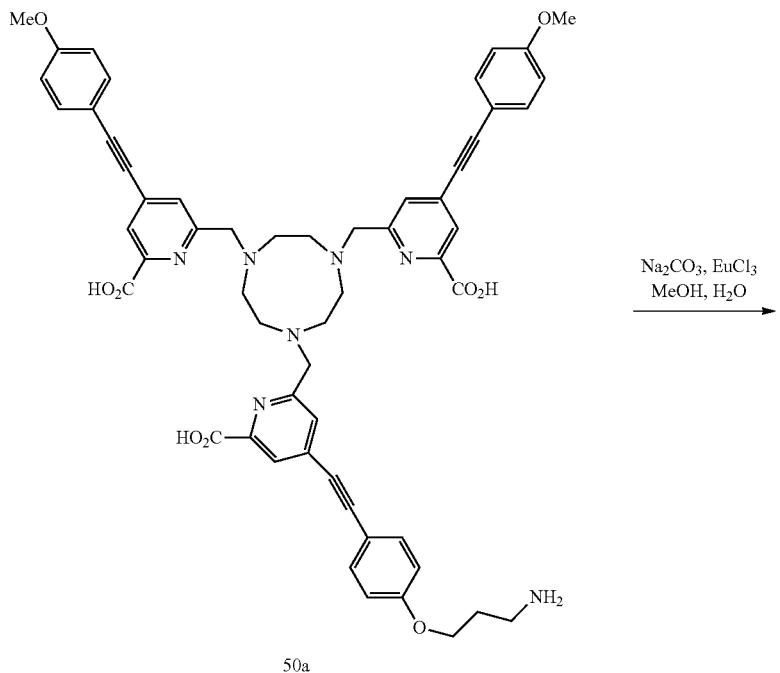

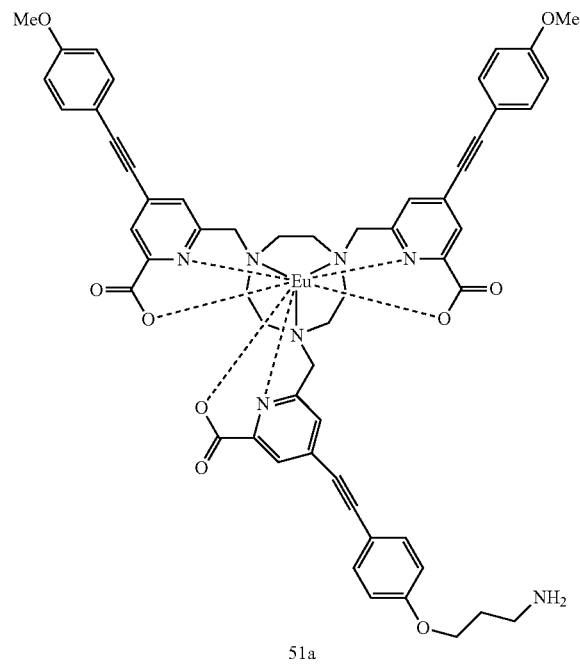

Sodium carbonate (0.53 mg, 5 µmol) and europium chloride hexahydrate (732 µg, 2 µmol) were added to a solution of ligand 50a (967 µg, 1 µmol) in methanol (1 mL) and water (0.5 mL). The reaction mixture was heated at 50° C. overnight. The progress of the reaction was monitored by analytical HPLC. After this time, reaction was complete. The reaction mixture was cooled to room temperature and then the solvent was removed under reduced pressure. The residue was purified by preparative HPLC leading to complex 51a in the form of a colorless oil (560 µmol, 56%).

Compounds 51b-f

These compounds were prepared according to the same procedure as that used for compound 51a using the corresponding precursors.

Compound 52a

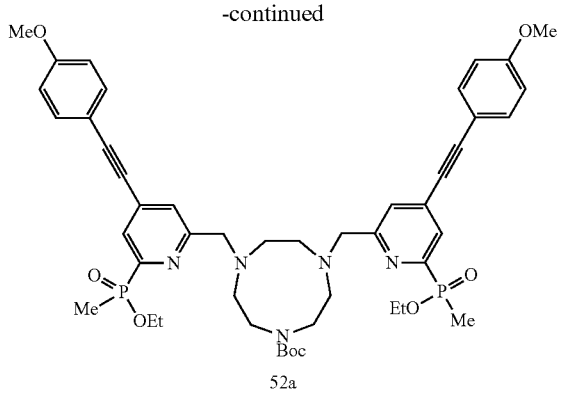

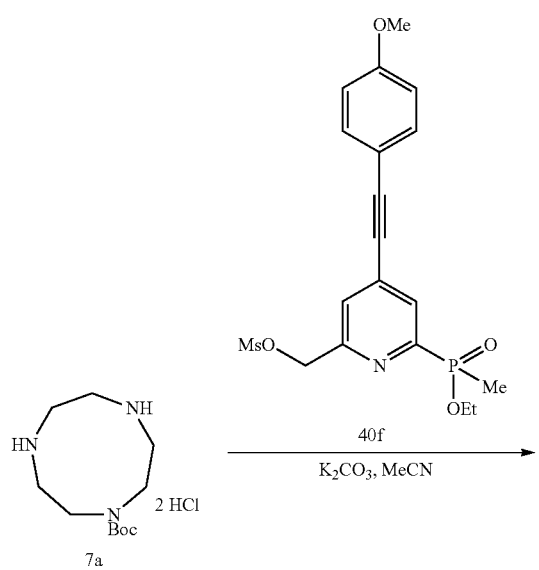

Potassium carbonate (117 mg, 850 µmol) was added under inert atmosphere to a solution of TACN monoBoc hydrochloride 7a (43 mg, 140 µmol) in anhydrous acetonitrile (5 mL). A solution of mesylated chromophore 40f (120 mg, 280 µmol) was added to this suspension. The progress of the reaction was monitored by analytical HPLC. After stirring and heating at 65° C. for 2 h, the reaction mixture was cooled to room temperature. The solvent was removed under reduced pressure. The residue was dissolved in dichloromethane (50 mL) and the resultant solution was washed with water (2×50 mL), dried over magnesium sulfate, filtered and concentrated under reduced pressure. The crude reaction product was purified by silica column chromatography (dichloromethane/methanol 100:0 to 94:6 in increments of 1%) to give compound 52a in the form of an oil (86 mg, 70%). HMRS (ESI+) calculated for $C_{47}H_{60}N_5O_8P_2$ [M+H]$^+$, m/z 884.3912. found: 884.3919. $R_f$=0.56 (silica; dichloromethane-methanol: 90:10). $R_t$=10.65 min (Waters XBridge RP-C18 column, 3.5 µm, 4.6×100 mm) with 0.1% aqueous solution of formic acid (pH 2-MeCN (v/v) as eluent [isocratic 5% MeCN (1 min)], linear gradient from 5 to 100% MeCN (14 min), with a flow rate of 1 mL min$^{-1}$.

Compounds 52b-f

These compounds were prepared according to the same procedure as that used for compound 52a using the corresponding precursors.

Compound 53a

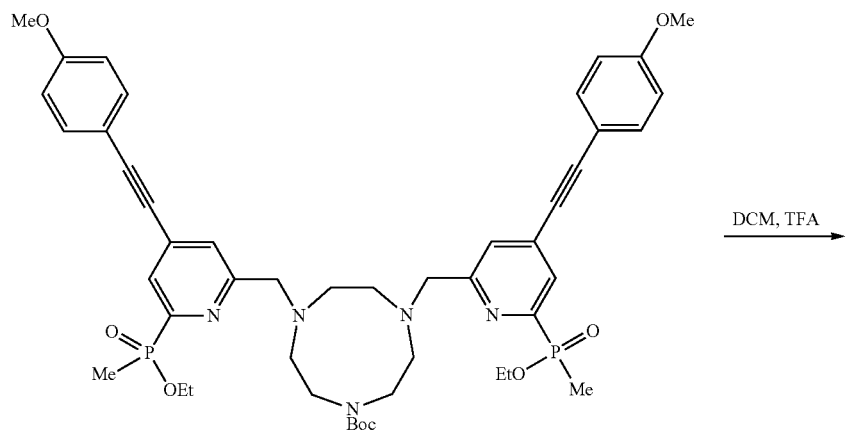

-continued

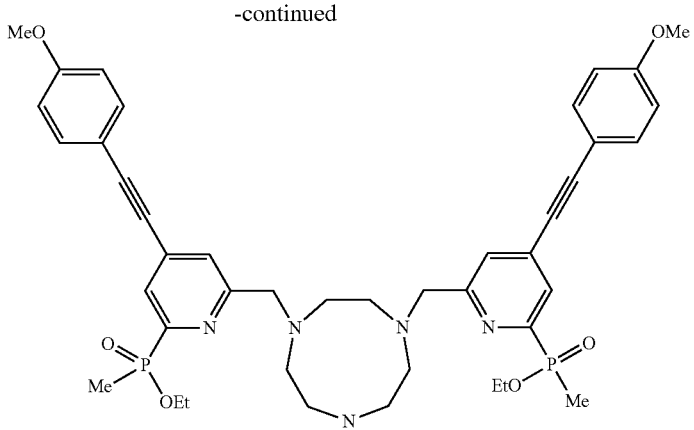

53a

Trifluoroacetic acid (0.5 mL) was added to a solution of 52a (70 mg, 0.079 mmol) in anhydrous dichloromethane (5 mL). The solution was stirred under argon at 5° C. for 2.5 h. The progress of the reaction was monitored by TLC. After this time, reaction was complete. The solvent was removed under reduced pressure and the residue was dissolved in dichloromethane (1 mL) again, and this was again removed under reduced pressure. This procedure was repeated 5 times to remove excess trifluoroacetic acid. The residue was purified by preparative HPLC using the following gradient: (Waters XBridge RP-C18 column, 5 μm, 19×100 mm) with an aqueous solution of triethylammonium acetate buffer 25 mM pH 7-MeCN (v/v) as eluent [isocratic 5% MeCN (3.5 min)], linear gradient from 5 to 100% MeCN (26.5 min) with a flow rate of 20 mL min$^{-1}$ and UV detection at 320 nm to give compound 53a (26 mg, 42%). HMRS (ESI+) calculated for $C_{42}H_{52}N_5O_6P_2$ [M+H]$^+$, m/z 784.3387. found: 784.3388. $R_t$=9.88 min (Waters XBridge RP-C18 column, 3.5 μm, 4.6×100 mm) with 0.1% aqueous solution of formic acid (pH 2-MeCN (v/v) as eluent [isocratic 5% MeCN (1 min)], linear gradient from 5 to 100% MeCN (14 min), with a flow rate of 1 mL min$^{-1}$.

Compounds 53b-f

These compounds were prepared according to the same procedure as that used for compound 53a using the corresponding precursors.

Compound 54a

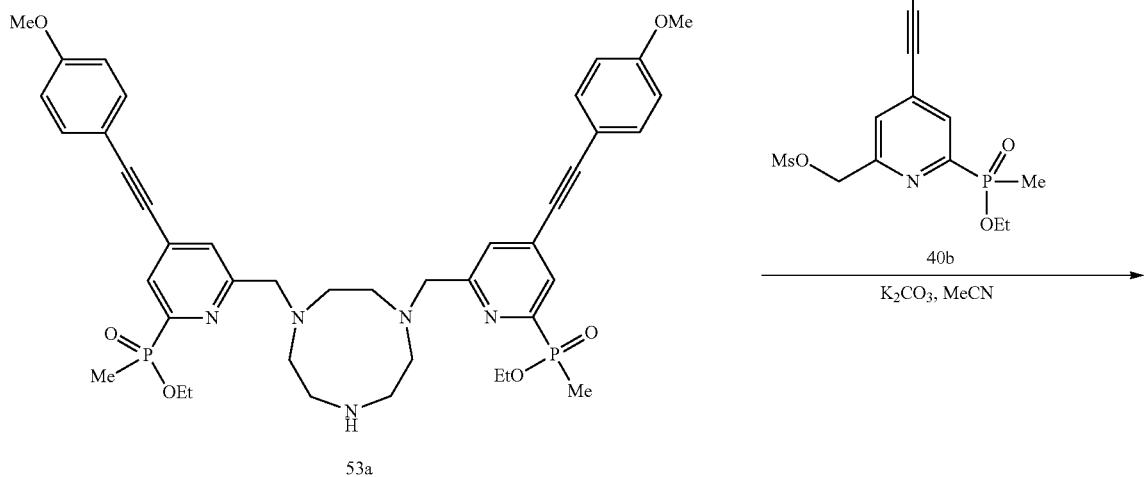

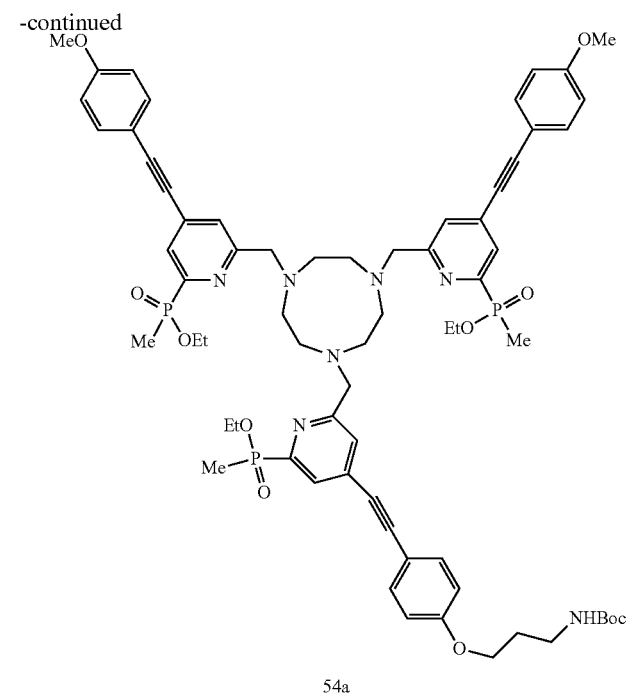

54a

Potassium carbonate (21 mg, 150 μmol) was added under inert atmosphere to a solution of dialkylated compound 53a (32 mg, 40 μmol) in anhydrous acetonitrile (5 mL). A solution of NH-Boc mesylated chromophore 40b (29 mg, 51 μmol) in anhydrous acetonitrile (5 mL) was added to this suspension. The reaction mixture was heated at 65° C. for 2.5 h. The progress of the reaction was monitored by HPLC. After this time, reaction was complete. The reaction mixture was cooled to room temperature and the solvent was removed under reduced pressure. The residue was dissolved in dichloromethane (40 mL) and was washed with water (2×40 mL), dried over magnesium sulfate, filtered and concentrated under reduced pressure. The crude reaction product was purified by HPLC on a preparative column using the following gradient: (Waters XBridge RP-C18 column, 5 μm, 19×100 mm) with an aqueous solution of triethylammonium acetate buffer 25 mM pH 7-MeCN (v/v) as eluent [isocratic 5% MeCN (3.5 min)], linear gradient from 5 to 100% MeCN (28.5 min) with a flow rate of 20 mL min$^{-1}$ and UV detection at 320 nm to give compound 54a (36 mg, 43%). HMRS (ESI+) calculated for $C_{67}H_{84}N_7O_{11}P_3$ [M+2H]$^{2+}$, m/z 627.7715. found: 627.7718. $R_t$=11.08 min (Waters XBridge RP-C18 column, 3.5 μm, 4.6×100 mm) with 0.1% aqueous solution of formic acid (pH 2-MeCN (v/v) as eluent [isocratic 5% MeCN (1 min)], linear gradient from 5 to 100% MeCN (14 min), with a flow rate of 1 mL min$^{-1}$.

Compound 54e

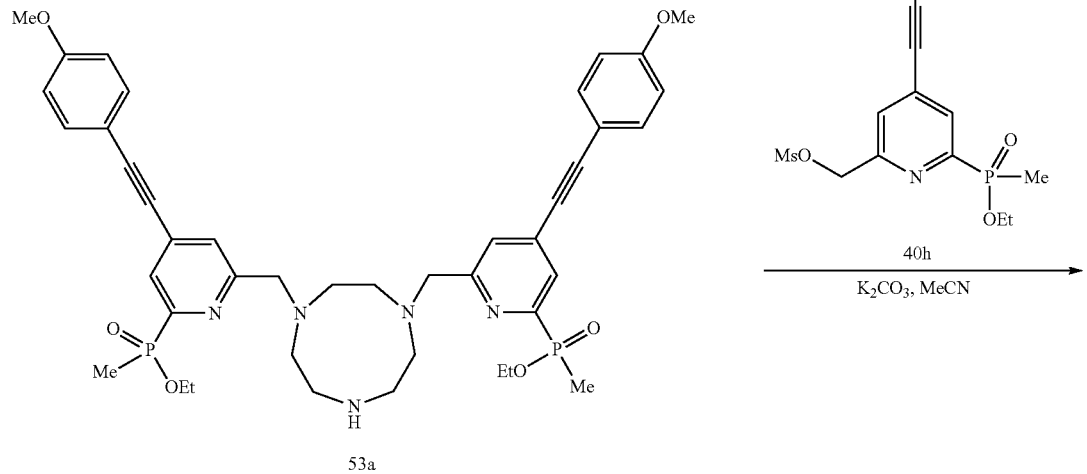

53a

-continued

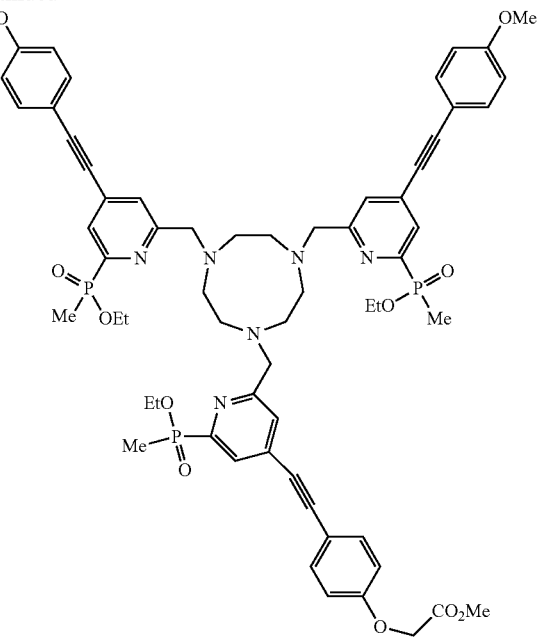

54e

Potassium carbonate (42 mg, 0.306 mmol) was added under inert atmosphere to a solution of two-arm TACN 53a (80 mg, 0.102 mmol) in anhydrous acetonitrile (4 mL). A solution of chromophore 40h (54 mg, 0.112 mmol) in anhydrous acetonitrile (2 mL) was added to this suspension. The reaction mixture was heated at 60° C. for 15 h under inert atmosphere. The progress of the reaction was monitored by HPLC. After this time, reaction was complete. The suspension was cooled to room temperature and the salts were separated by decantation. The solvent of the supernatant was removed under reduced pressure and the crude reaction product was purified by silica column chromatography (dichloromethane/methanol 0 to 20% in increments of 1%) to obtain a colorless oil corresponding to compound 54e (71 mg, 58%). $^1$H NMR (700 MHz, CDCl$_3$) δ: 7.88 (d, J=5.7 Hz, 3H), 7.52 (bs, 3H), 7.41 (d, J=8.5 Hz, 2H), 7.40 (d, J=8.6 Hz, 4H), 6.84 (d, J=8.5 Hz, 2H), 6.83 (d, J=8.6 Hz, 4H), 4.60 (s, 2H), 4.13 (m 1, 6H), 4.05 (m, 3H), 3.86 (m, 3H), 3.77 (s, 6H), 3.75 (s, 3H), 3.29 (m 1, 6H), 3.10 (m 1, 6H), 1.71 (d, J=14.9 Hz, 9H), 1.21 (t, J=7.0 Hz, 9H); $^{13}$C NMR (176 MHz, CDCl$_3$) δ 169.0, 160.8, 158.8, 156.9 (m 1); 154.2 (d, J=159 Hz); 133.8, 133.7, 133.4 (m 1); 127.9 (d, J=22 Hz); 127.4, 114.9, 114.3, 113.4, 97.1, 96.6, 85.1, 84.9, 65.1, 61.5 (d, J=6 Hz); 60.1 (bs), 55.4, 52.4, 51.3, 16.4 (d, J=6 Hz), 13.5 (d, J=104 Hz); $^{31}$P NMR (284 MHz, CDCl$_3$) δ: +39.1. HRMS (ESI+) calculated for C$_{62}$H$_{72}$N$_6$O$_{11}$P$_3$ [M+H]$^+$, m/z 1169.4470 found: 1169.4430. R$_f$=0.28 (silica; dichloromethane-methanol 90:10).

Compounds 54f, k-l, p-r

These compounds were prepared according to the same procedure as that used for compound 54e using the corresponding precursors.

Compounds 54b-d, g-j, m-p

These compounds were prepared according to the same procedure as that used for compound 54a using the corresponding precursors.

Compound 55a

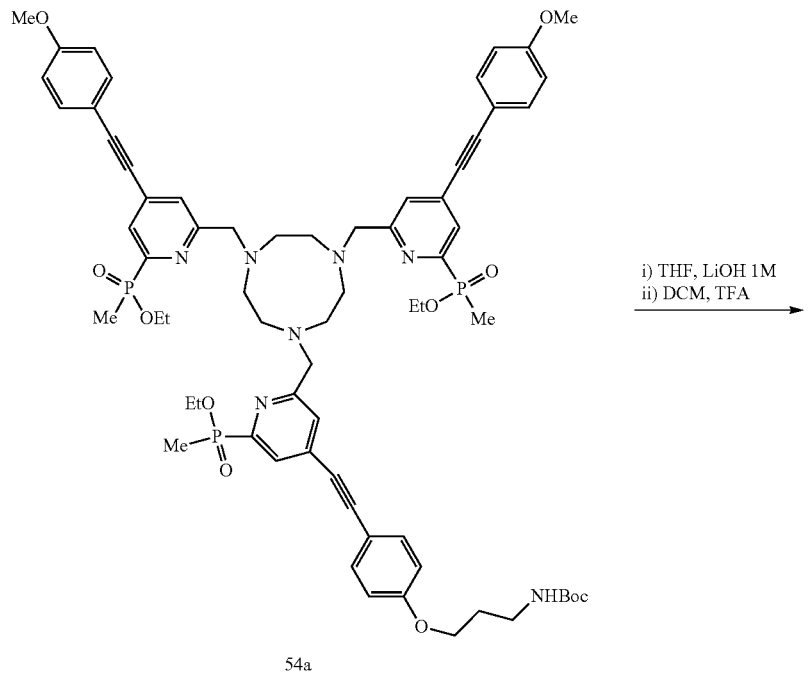

54a i) THF, LiOH 1M
ii) DCM, TFA

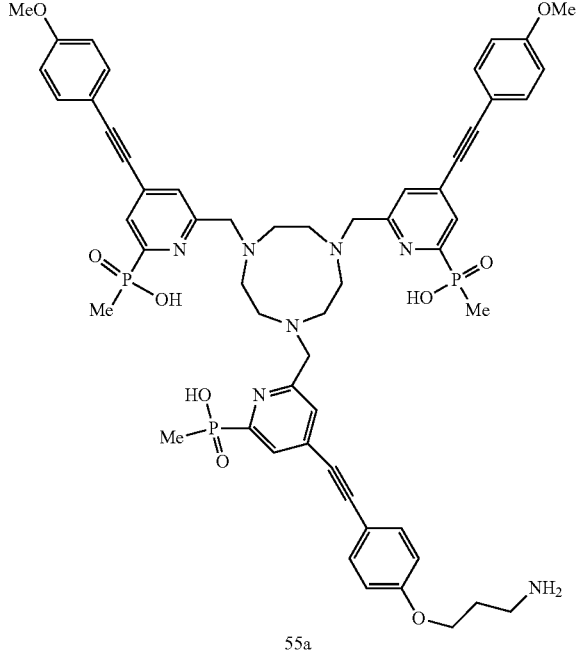

55a

Tetrahydrofuran (4 mL) and aqueous solution of lithium hydroxide (3 mL, 1 M) were added to the ligand 54a (35.6 mg, 28.4 µmol). The solution was stirred at room temperature for 2 h. The progress of the reaction was monitored by LC-MS. After this period, reaction was complete. The reaction mixture was concentrated under reduced pressure and was used in the rest of the synthesis without additional purification. LRMS (ESI+) calculated for $C_{61}H_{71}N_7O_{11}P_3$ [M+H]$^+$, m/z 1170.4424. found: 1170.99. $R_t$=9.17 min (Waters XBridge RP-C18 column, 3.5 µm, 4.6×100 mm) with 0.1% aqueous solution of formic acid (pH 2-MeCN (v/v) as eluent [isocratic 5% MeCN (1 min)], linear gradient from 5 to 100% MeCN (14 min), with a flow rate of 1 mL min$^{-1}$
Trifluoroacetic acid (1.5 mL) was added to a solution of the compound obtained previously in dichloromethane (20 mL). The solution was stirred at 5° C. for 6 h. The progress of the reaction was monitored by LC-MS. After this time, reaction was complete. The solvent was removed under reduced pressure and the residue was dissolved in dichloromethane (6 mL) again. The solvent was again removed under reduced pressure. This procedure was repeated 5 times to remove excess trifluoroacetic acid. The crude product was used in the rest of the synthesis without additional purification.

LRMS (ESI+) calculated for $C_{56}H_{63}N_7O_9P_3$ [M+H]$^+$, m/z 1070.3900. found: 1070.79. $R_t$=6.82 min (Waters XBridge RP-C18 column, 3.5 μm, 4.6×100 mm) with 0.1% aqueous solution of formic acid (pH 2-MeCN (v/v) as eluent [isocratic 5% MeCN (1 min)], linear gradient from 5 to 100% MeCN (14 min), with a flow rate of 1 mL min$^{-1}$.

Compounds 55b-d, g-j, m-p

These compounds were prepared according to the same procedure as that used for compound 55a using the corresponding precursors.

Compound 56a

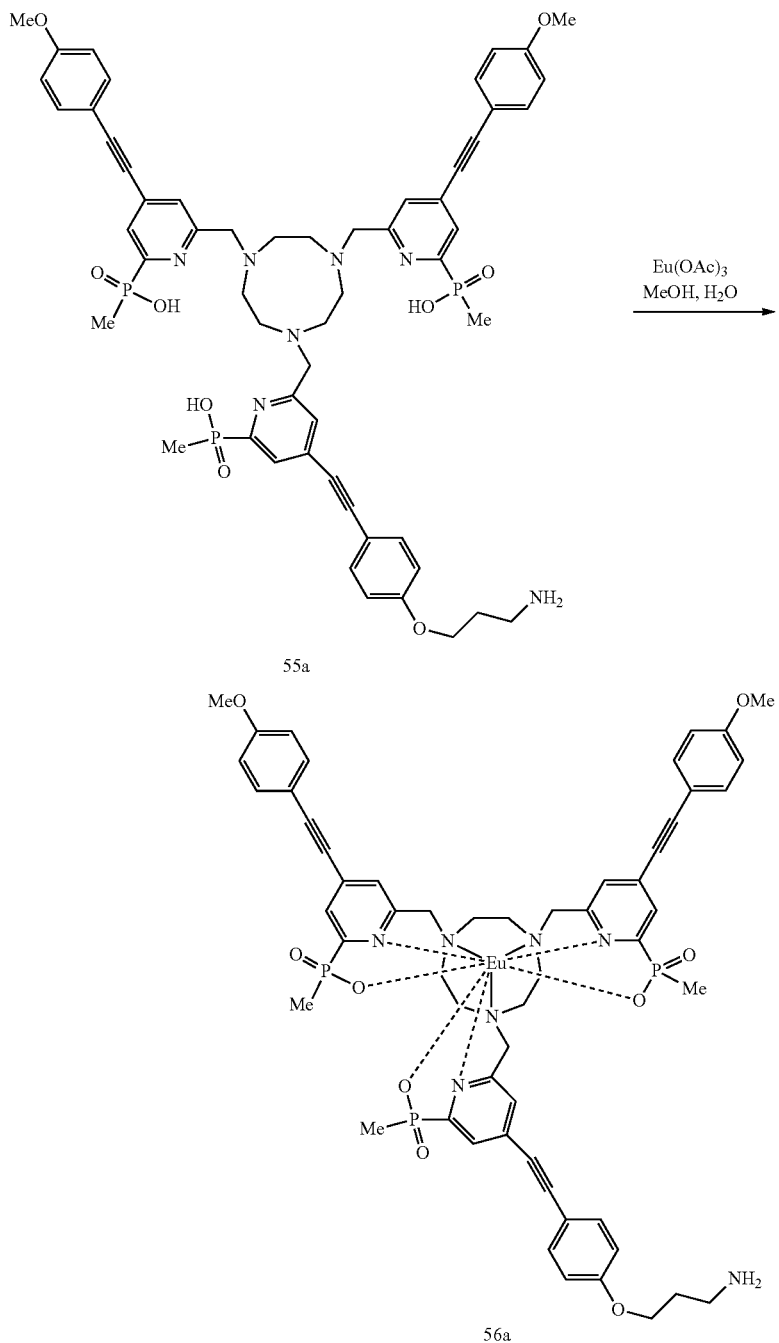

Europium chloride hexahydrate (11.1 mg, 31 µmol) was added to a solution of asymmetric three-arm TACN 55a (28.4 µmol) in methanol (15 mL) and water (2 mL). The reaction mixture was heated at 50° C. for 12 h. The progress of the reaction was monitored by LC-MS. After this time, reaction was complete. The reaction mixture was cooled to room temperature and then the solvent was removed under reduced pressure. The residue was purified by HPLC on a preparative column using the following gradient: (Waters XBridge RP-C18 column, 5 µm, 19×100 mm) with an aqueous solution of triethylammonium acetate buffer 25 mM pH 7-MeCN (v/v) as eluent [isocratic 5% MeCN (3.5 min)], linear gradient from 5 to 100% MeCN (23 min) with a flow rate of 20 mL min$^{-1}$ and UV detection at 320 nm to give compound 56a (34 mg, 98%). HMRS (ESI+) calculated for $C_{56}H_{61}EuN_7O_9P_3$ [M+2H]$^{2+}$, m/z 609.6466. found: 609.6466. $R_t$=8.08 min (Waters XBridge RP-C18 column, 3.5 µm, 4.6×100 mm) with 0.1% aqueous solution of formic acid (pH 2-MeCN (v/v) as eluent [isocratic 5% MeCN (1 min)], linear gradient from 5 to 100% MeCN (14 min), with a flow rate of 1 mL min$^{-1}$.

Compound 56e

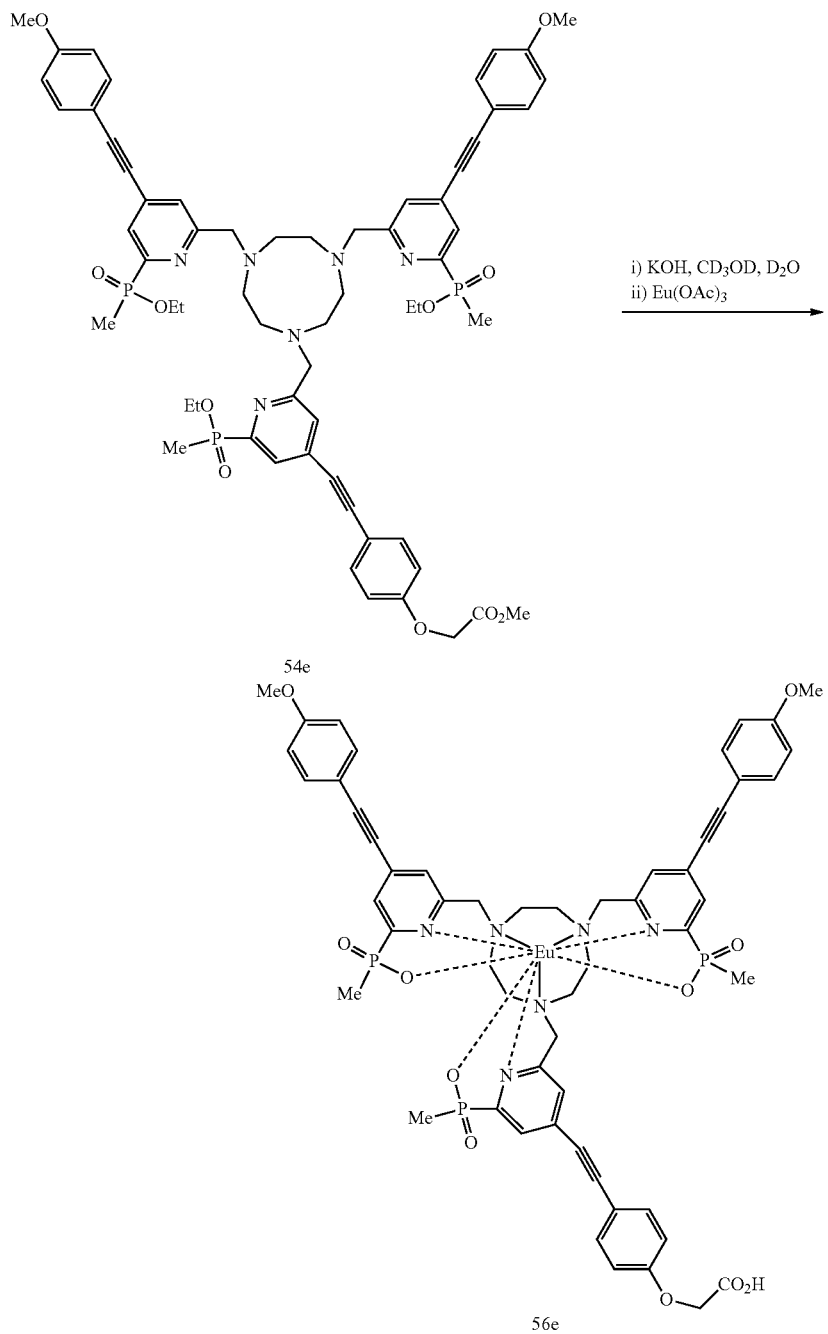

Potassium hydroxide (5 mg, 100 µmol) was added to a solution of ligand 54e (30 mg, 26 µmol) in a CD$_3$OD/D$_2$O solvent mixture (2.5 mL, 2:1 v/v). The solution was heated at 60° C. for 24 h under inert atmosphere. The progress of the reaction was monitored by $^1$H and $^{31}$P NMR. After this time, reaction was complete. The solvent was removed under reduced pressure and the pH of the solution was adjusted to 7 by adding 1 M aqueous solution of hydrochloric acid. Europium acetate (2.8 mg, 8.6 µmol) was added to this solution. The reaction mixture was heated at 65° C. under inert atmosphere for 18 h and was then cooled to room temperature. The suspension was centrifuged and the white solid was separated from the supernatant, and washed with methanol (3×2 mL). The supernatant and the filtrates were combined and concentrated under reduced pressure to give a whitish solid, which was purified by semipreparative HPLC to give the desired compound 56e in the form of a white solid (13 mg, 45%). HRMS (ESI+) calculated for $C_{55}H_{55}N_6O_{11}P_3Eu$ $[M+2H]^{2+}$, m/z 611.1220. found: 611.1247.

Compounds 56f, k-l, p-r

These compounds were prepared according to the same procedure as that used for compound 56e using the corresponding precursors.

Compounds 57a-f

These compounds were prepared according to the same procedure as that used for compound 60a using the corresponding precursors.

Compound 60a

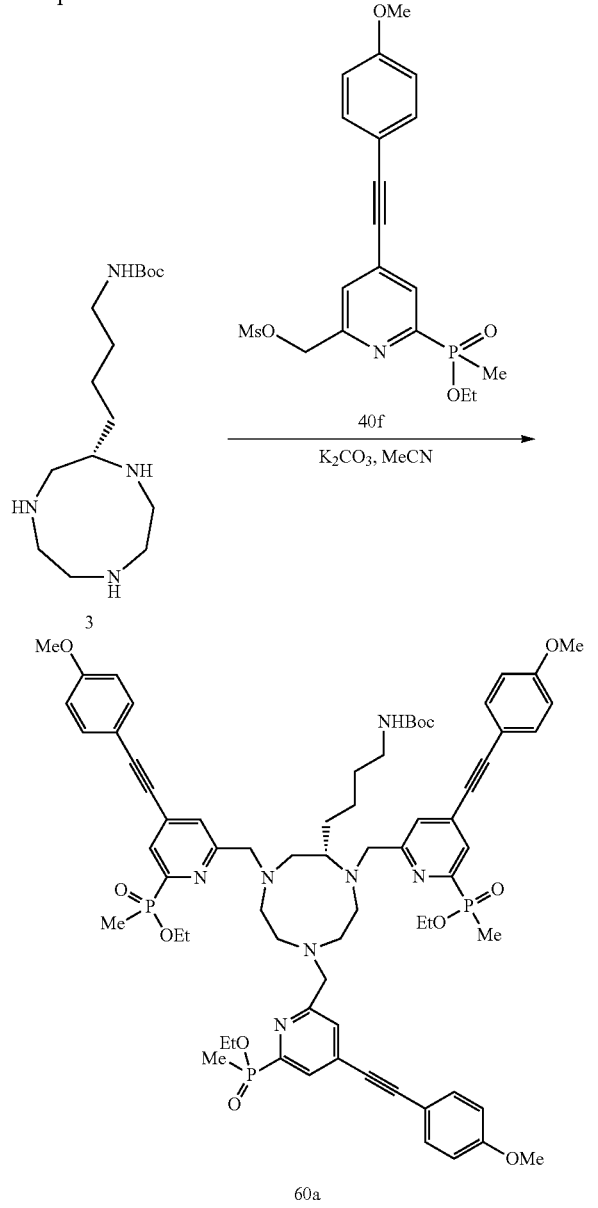

60a

Potassium carbonate (30 mg, 0.21 mmol) was added under inert atmosphere to a solution of macrocycle 3 (21 mg, 0.071 mmol) in anhydrous acetonitrile (4 mL). A solution of mesylated chromophore 40f (70 mg, 0.14 mmol) in anhydrous acetonitrile (2 mL) was added to this suspension. The mixture was heated at 60° C. for 48 h. The progress of the reaction was monitored by LC-MS. After this time the reaction was complete. The reaction mixture was cooled to room temperature. The solvent was removed under reduced pressure. The crude reaction product was purified by silica column chromatography (dichloromethane/methanol 98:2 to 80:20 in increments of 2%) to give compound 60a in the form of an oil (18 mg, 20%). $^1$H NMR (400 MHz, CDCl$_3$) δ: 7.96 (m, 3H), 7.46 (m, 9H), 6.88 (m, 6H), 5.04 (bs, 1H), 4.11-3.84 (m, 12H), 3.80 (m, 9H), 3.09-2.74 (m, 13H), 1.77-1.70 (m, 9H), 1.39 (s, 9H), 1.42-1.23 (m, 7H), 1.25 (m, 9H); $^{31}$P NMR (162 MHz, CDCl$_3$) δ: +39.2. HRMS (ESI+) calculated for $C_{69}H_{87}N_7O_{11}P_3$ $[M+H]^+$, m/z 1282.5676. found: 1282.5701. $R_f$=0.54 (silica; dichloromethane-methanol 80:20).

Compounds 58a-f

These compounds were prepared according to the same procedure as that used for compound 61a using the corresponding precursors.

Compounds 59a-f

These compounds were prepared according to the same procedure as that used for compound 62a using the corresponding precursors.

Compounds 60b-h, 60j-l

These compounds were prepared according to the same procedure as that used for compound 60a using the corresponding precursors.

Compound 60i

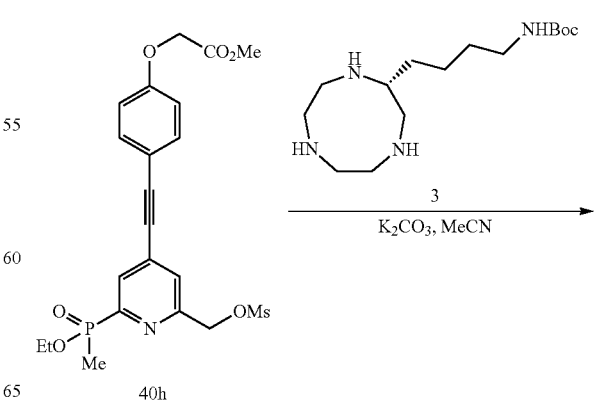

40h

-continued

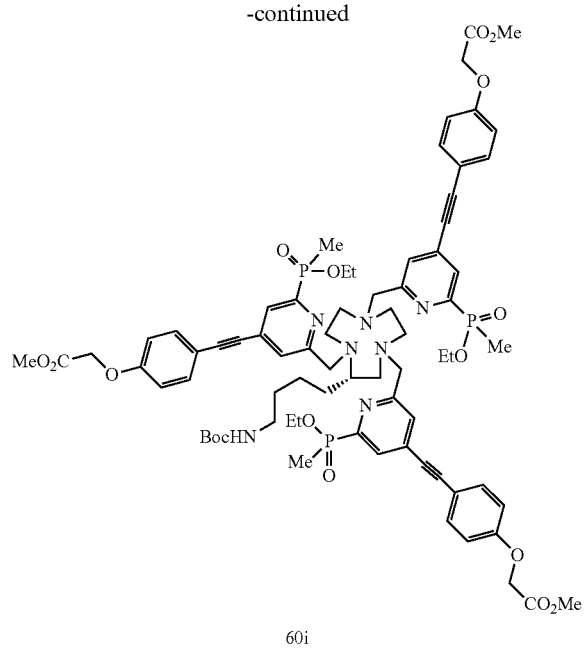

60i

The macrocycle 3 (23 mg, 0.075 mmol) and potassium carbonate (32 mg, 0.23 mmol) were added to a solution of compound 40h (105 mg, 0.22 mmol) in anhydrous acetonitrile (4 mL). The mixture was heated at 60° C. for 18 h and then cooled to room temperature. The suspended salts were removed by decantation and then the solvent was removed under reduced pressure. The residue was purified by silica column chromatography using a solvent gradient (dichloromethane-methanol, 100-0 to 80-20 in increments of 1%) to give compound 60i in the form of a yellowish oil (45 mg, 41%). $^1$H NMR (600 MHz, CDCl$_3$) δ: 7.99 (m, 3H), 7.49 (m, 9H), 6.90 (m, 6H), 5.10 (bs, 1H), 4.67 (s, 6H), 4.12-3.86 (m, 12H), 3.82 (m, 9H), 3.12-2.90 (m, 13H), 1.85-1.70 (m, 9H), 1.41 (s, 9H), 1.45-1.28 (m, 6H), 1.27 (m, 9H); $^{31}$P NMR (242 MHz, CDCl$_3$) δ: +40.4; HRMS (ESI+) calculated for $C_{75}H_{94}N_7O_{17}P_3$ [M+2H]$^{2+}$, m/z 728.7960. found: 728.7949. $R_f$=0.50 (silica; dichloromethane-methanol 80:20).

Compound 61a

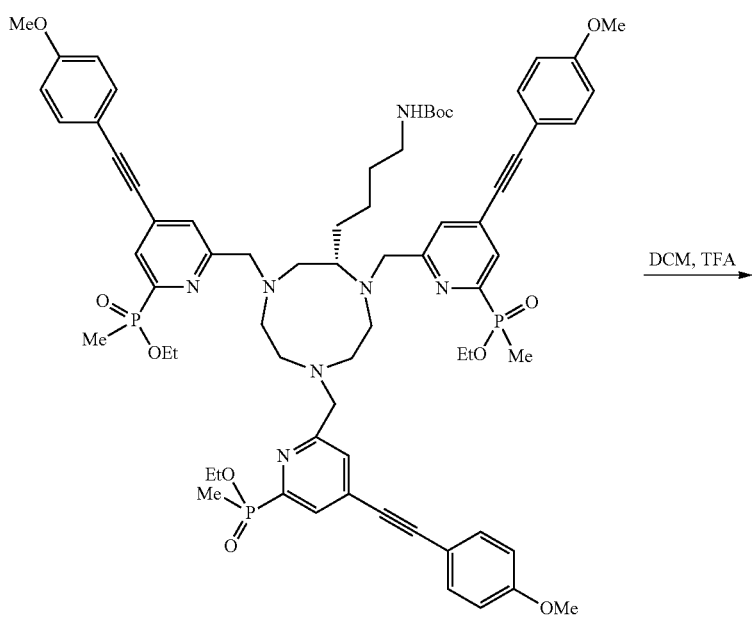

60a

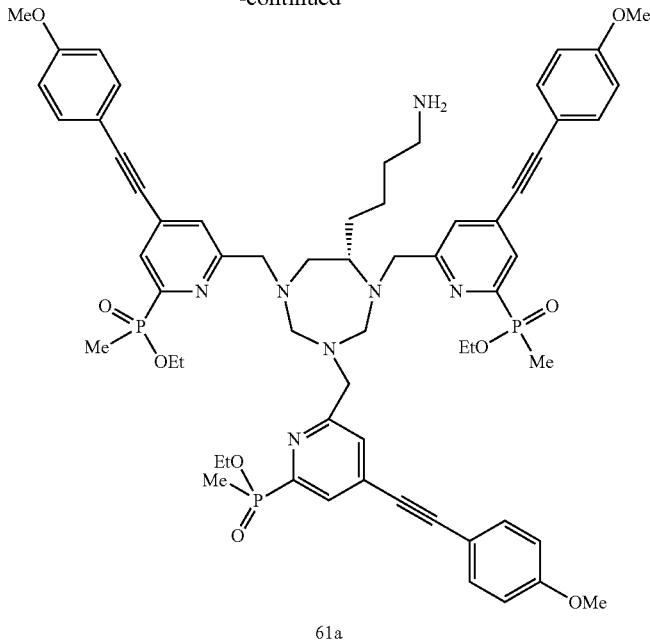

61a

Trifluoroacetic acid (0.2 mL) was added to a solution of compound 60a (12 mg, 9.4 μmol) in dichloromethane (0.8 mL), degassed for 10 min under inert atmosphere. The solution was stirred at room temperature for 15 min. The progress of the reaction was monitored by LC-MS. After this time, reaction was complete. The solvent was removed under reduced pressure to give the desired compound 61a in the form of a yellow oil (12 mg, quantitative). $^1$H NMR (400 MHz, CDCl$_3$) δ: 7.93 (m, 3H), 7.46 (m, 9H), 6.88 (m, 6H), 4.15-3.84 (m, 12H), 3.76 (m, 9H), 3.00-2.71 (m, 13H), 1.80-1.75 (m, 9H), 1.42-1.23 (m, 7H), 1.25 (m, 9H); $^{31}$P NMR (162 MHz, CDCl$_3$) δ: +39.7. HRMS (ESI+) calculated for C$_{64}$H$_{79}$N$_7$O$_9$P$_3$ [M+H]$^+$, m/z 1182.5152. found: 1182.5178.

Compounds 61b-h, 61j-l

These compounds were prepared according to the same procedure as that used for compound 61a using the corresponding precursors.

Compound 61i

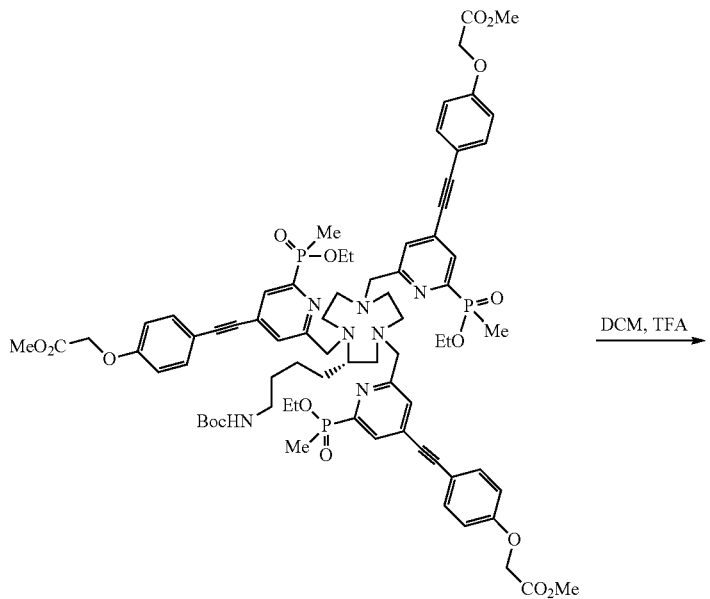

60i

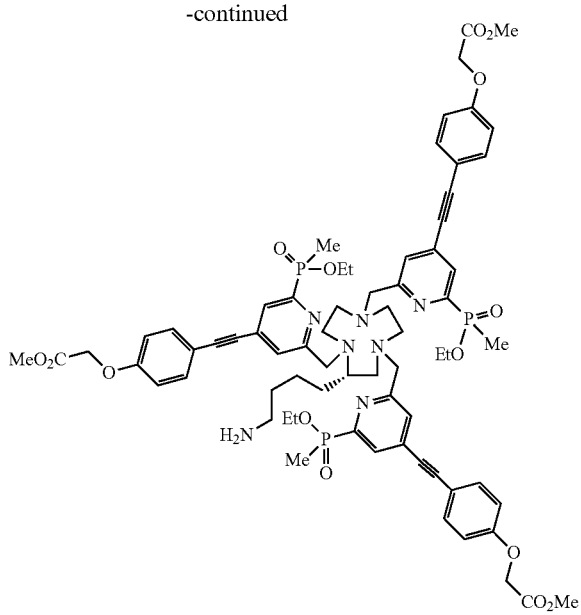

61i

Trifluoroacetic acid (0.2 mL) was added to a solution of compound 60i (30 mg, 20 μmol) in dichloromethane (1.8 mL) cooled to 4° C. and previously degassed under an argon stream for 10 min. The solution was heated to room temperature and stirred at this temperature for 15 min. The solvent was removed under reduced pressure to give a yellow oil identified as compound 61i (27 mg, quantitative).

$^1$H NMR (600 MHz, CDCl$_3$) δ: 7.91 (m, 3H), 7.51 (m, 9H), 6.92 (m, 6H), 4.67 (s, 6H), 4.16-3.97 (m, 12H), 3.81 (m, 9H), 3.12-2.90 (m, 13H), 1.89-1.75 (m, 9H), 1.45-1.32 (m, 6H), 1.29 (m, 9H); $^{31}$P NMR (242 MHz, CDCl$_3$) δ: +41.2; HRMS (ESI+) calculated for C$_{70}$H$_{85}$N$_7$O$_{15}$P$_3$ [M+H]$^+$, m/z 1356.531. found: 1356.533.

Compound 62a

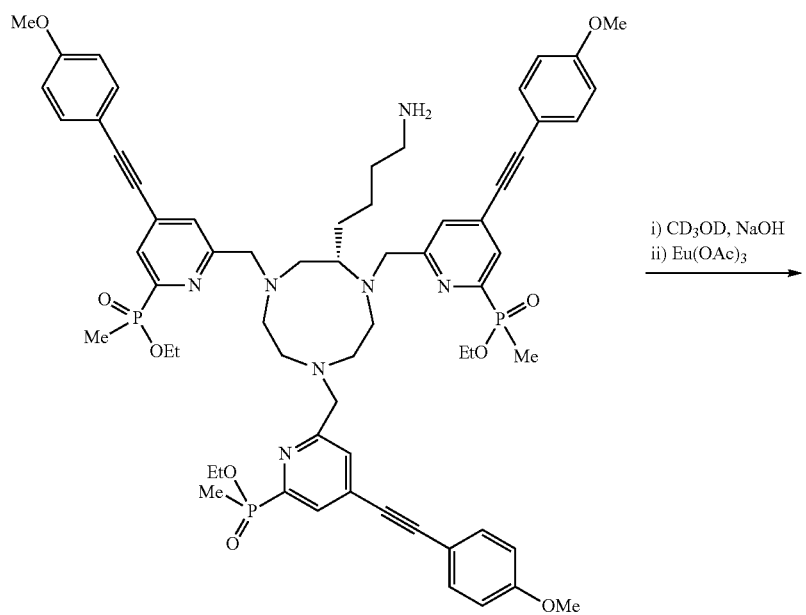

61a

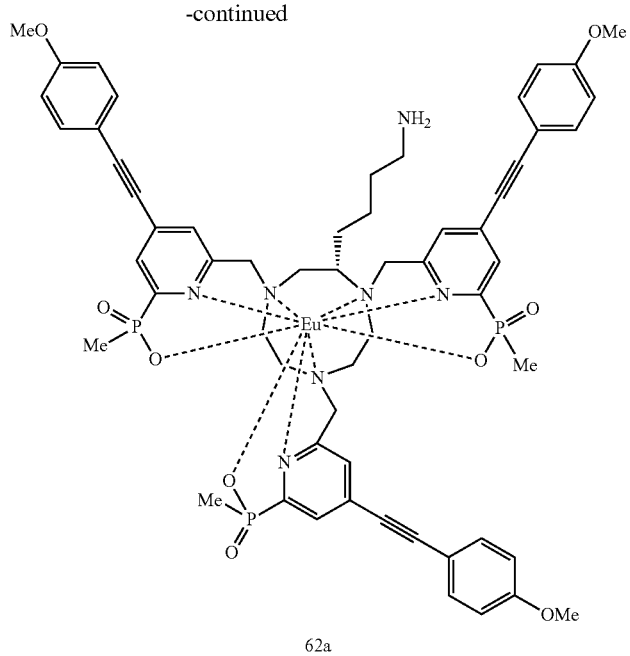

62a

A deuterated aqueous solution of sodium hydroxide (1 mL, 0.1 M) was added to a solution of ligand 61a (25 mg, 21 μmol) in $CD_3OD$ (3 mL). The solution was heated at 60° C. for 5 h under inert atmosphere. The progress of the reaction was monitored by $^1H$ and $^{31}P$ NMR. After this time, reaction was complete. The solvent was removed under reduced pressure and the pH of the solution was adjusted to 7 by adding 1 M aqueous solution of hydrochloric acid. Europium acetate (7.6 mg, 23 μmol) was added to this solution. The reaction mixture was heated at 65° C. under inert atmosphere for 12 h and was then cooled to room temperature and the solvent was removed under reduced pressure. The crude product was purified by silica column chromatography (dichloromethane-methanol-ammonia: 89.9:10:0.1) to give compound 62a in the form of a white solid (8 mg, 30%). HRMS (ESI+) calculated for $C_{58}H_{64}EuN_7O_9P_3$ $[M+H]^+$, m/z 1248.3191 found: 1248.3. $R_t$=9.69 min (Waters XBridge RP-C18 column, 3.5 μm, 4.6×100 mm) with 0.2% aqueous solution of trifluoroacetic acid (pH 1-MeCN (v/v) as eluent, linear gradient from 10 to 100% MeCN (20 min), with a flow rate of 1 mL $min^{-1}$ and UV detection at 320 nm.

Compounds 62b-h, 62j-l

These compounds were prepared according to the same procedure as that used for compound 62a using the corresponding precursors.

Compound 62i

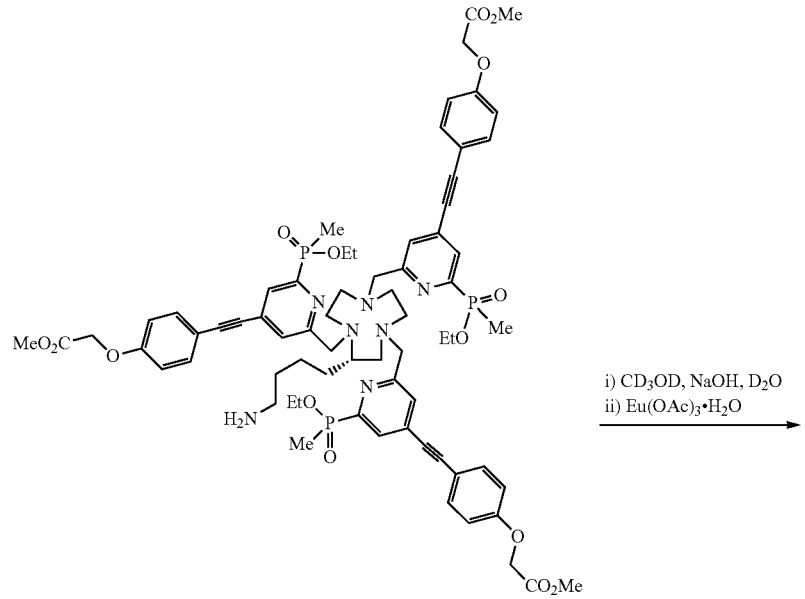

61i i) $CD_3OD$, NaOH, $D_2O$
ii) $Eu(OAc)_3 \cdot H_2O$

-continued

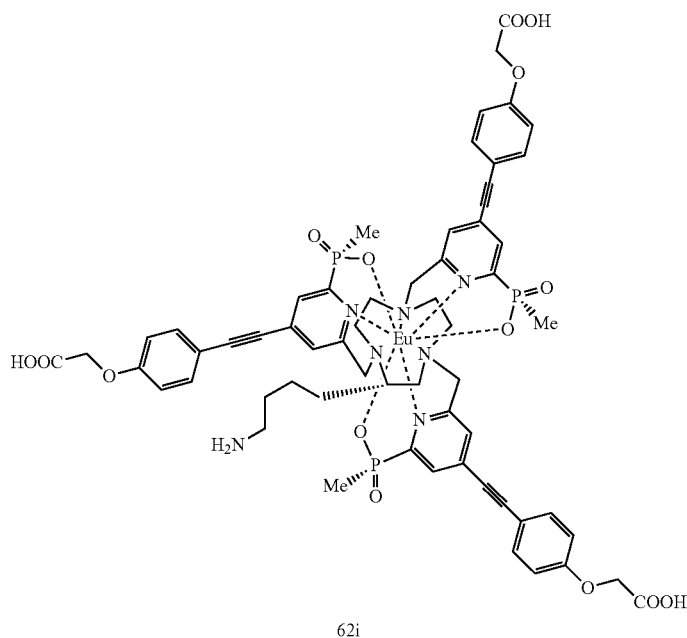

62i

A deuterated aqueous solution of sodium hydroxide (0.1 M, 1.5 mL) was added to a solution of compound 61i (27 mg, 20 µmol) in deuterated methanol (3 mL). The mixture was heated at 60° C. for 5 h and then cooled to room temperature. The pH of the solution was adjusted to 7 by adding hydrochloric acid. Europium acetate hydrate (7 mg, 21 µmol) was added to this mixture and then the solution was heated at 65° C. for 18 h under inert atmosphere. After this time, the reaction mixture was cooled to room temperature and the solvent was removed under reduced pressure. The crude product was purified by preparative HPLC to give compound 62i (11 mg, 40%); LRMS (ESI+) calculated for $C_{61}H_{65}N_7O_{15}P_3Eu$ $[M+2H]^{2+}$, m/z 690.6482 found: 690.6.

Compounds 63a-c

These compounds were prepared according to the same procedure as that used for compound 67a using the corresponding precursors.

Compounds 64a-c

These compounds were prepared according to the same procedure as that used for compound 68c using the corresponding precursors.

Compounds 66a-c

These compounds were prepared according to the same procedure as that used for compound 70c using the corresponding precursors.

Compound 67a

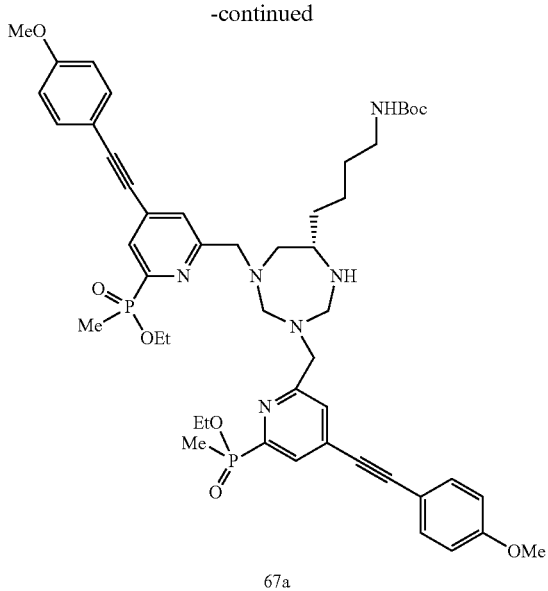

67a

Potassium carbonate (30 mg, 0.21 mmol) was added under inert atmosphere to a solution of macrocycle 3 (21 mg, 0.071 mmol) in anhydrous acetonitrile (4 mL). A solution of mesylated chromophore 40f (90 mg, 0.21 mmol) in anhydrous acetonitrile (2 mL) was added to this suspension. The mixture was heated at 60° C. for 24 h. The progress of the reaction was monitored by LC-MS. After this time, analyses showed formation of the dialkylated compound accompanied by the trialkylated compound. The reaction mixture was cooled to room temperature. The salts were separated by decantation and the supernatant was concentrated under reduced pressure. The crude reaction product was purified by silica column chromatography (dichloromethane/methanol 98:2 to 80:20 in increments of 1%) to give compound 67a in the form of an oil (14 mg, 20%). $^1$H NMR (400 MHz, CDCl$_3$) δ: 7.87 (m, 2H), 7.40 (m, 6H), 6.82 (m, 4H), 5.04 (bs, 1H), 4.09-3.98 (m, 8H), 3.75 (m, 6H), 3.08-2.60 (m, 13H), 1.82-1.69 (m, 6H), 1.35 (s, 9H), 1.51-1.20 (m, 7H), 1.22 (m, 6H); $^{31}$P NMR (162 MHz, CDCl$_3$) δ: +39.4. HRMS (ESI+) calculated for $C_{51}H_{69}N_6O_8P_2$ [M+H]$^+$, m/z 955.4652 found: 955.4622. $R_f$=0.51 (silica; dichloromethane-methanol 80:20).

Compounds 67b-f

These compounds were prepared according to the same procedure as that used for compound 67a using the corresponding precursors.

Compound 68c

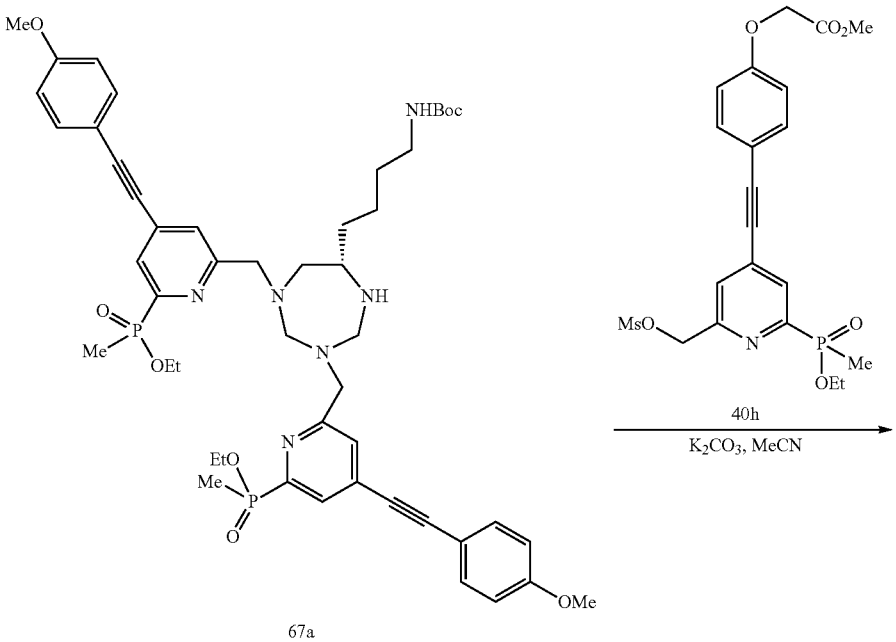

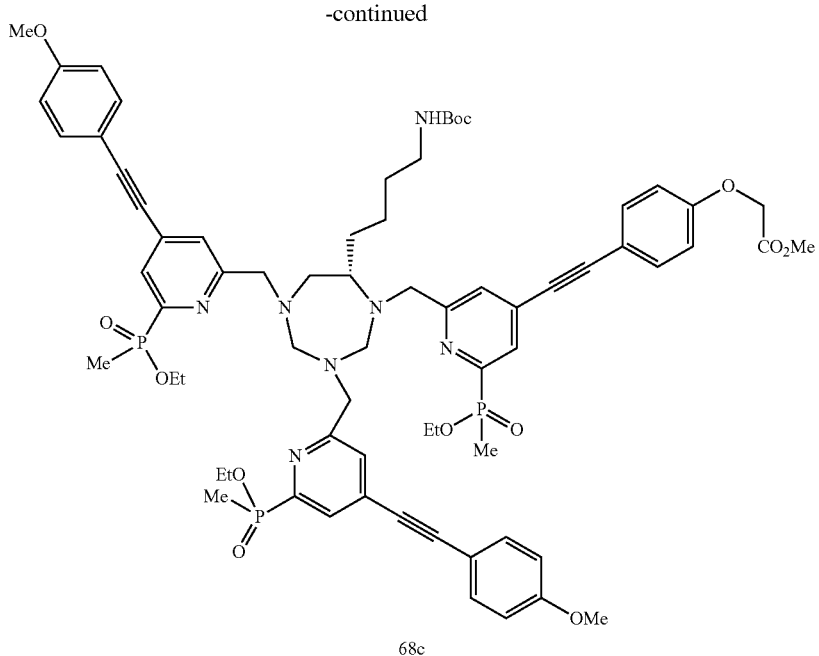

68c

Potassium carbonate (2 mg, 17 μmol) was added under inert atmosphere to a solution of two-arm TACN 67a (14 mg, 15 μmol) in anhydrous acetonitrile (0.7 mL). Chromophore 40h (8 mg, 17 μmol) was added to this suspension. The reaction mixture was heated at 60° C. for 24 h under inert atmosphere. The progress of the reaction was monitored by HPLC. After this time, reaction was complete. The suspension was cooled to room temperature and the salts were separated by decantation. The solvent of the supernatant was removed under pressure to obtain a yellow oil corresponding to compound 68c (19 mg, 95%). $^1$H NMR (700 MHz, CDCl$_3$) δ: 7.92 (m, 3H); 7.43 (m, 9H); 6.83 (m, 6H); 5.04 (bs, 1H); 4.59 (s, 2H); 4.06-3.77 (m, 12H); 3.75 (m, 9H); 3.00-2.55 (m, 13H); 1.74-1.66 (m, 9H); 1.33 (s, 9H); 1.35-1.16 (m, 6H); 1.19 (m, 9H). $^{31}$P NMR (284 MHz, CDCl$_3$) δ: +41.1. HRMS (ESI+) calculated for C$_{71}$H$_{89}$N$_7$O$_{13}$P$_3$ [M+H]$^+$, m/z 1340.5730 found: 1340.5730.

Compounds 68a-b, d-l

These compounds were prepared according to the same procedure as that used for compound 68c using the corresponding precursors.

Compound 70c

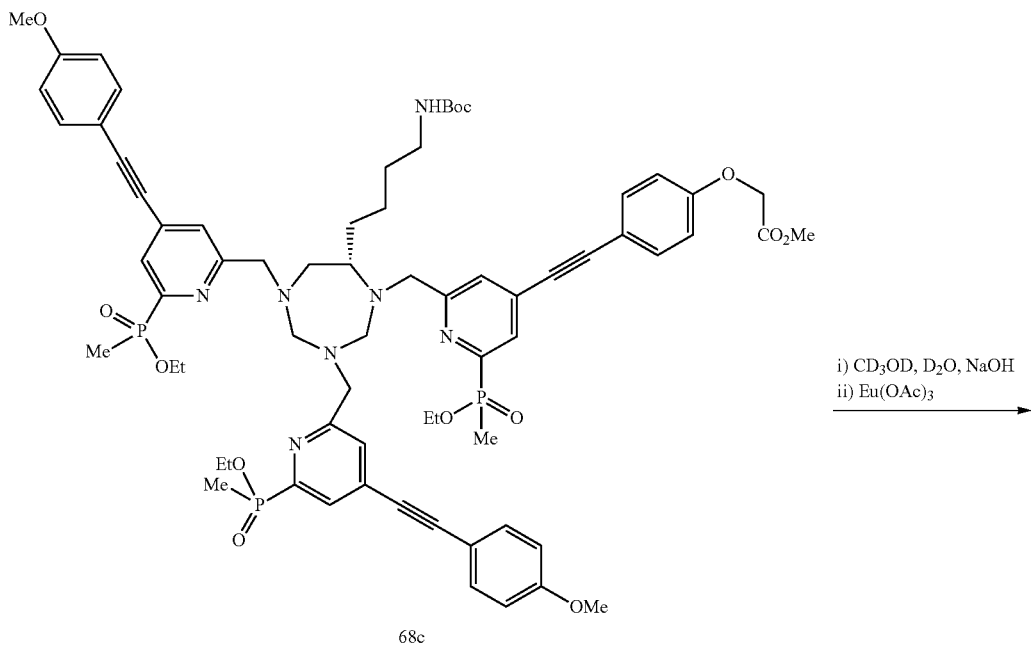

68c i) CD$_3$OD, D$_2$O, NaOH
ii) Eu(OAc)$_3$

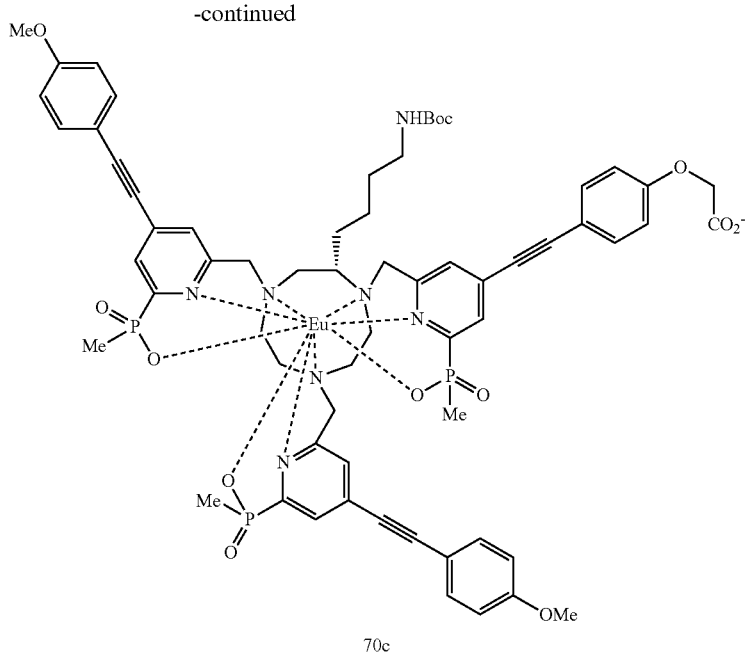

70c

A deuterated aqueous solution of sodium hydroxide (0.5 mL, 0.1 M) was added to a solution of ligand 68c (7 mg, 5.2 μmol) in CD$_3$OD (1.5 mL). The solution was heated at 60° C. for 16 h under inert atmosphere. The progress of the reaction was monitored by $^1$H and $^{31}$P NMR. After this time, reaction was complete. The solvent was removed under reduced pressure and the pH of the solution was adjusted to 7 by adding 1 M aqueous solution of hydrochloric acid. Europium acetate (1.8 mg, 5.7 μmol) was added to this solution. The reaction mixture was heated at 65° C. under inert atmosphere for 12 h and was then cooled to room temperature and the solvent was removed under reduced pressure. The crude product was purified by HPLC. LRMS (ESI+) calculated for C$_{64}$H$_{71}$EuN$_7$O$_{13}$P$_3$ [M+H]$^+$, m/z 1390.4 found: 1390.4. R$_t$=8.6 min (Waters XBridge RP-C18 column, 5 μm, 10×100 mm) with 0.1 M ammonium bicarbonate buffer solution (pH 9-MeOH (v/v) as eluent, [isocratic 10% MeOH (2 min)], linear gradient from 10 to 100% MeOH (15 min), with a flow rate of 4.4 mL min$^{-1}$ and UV detection at 330 nm.

Compounds 70a-b, d-l

These compounds were prepared according to the same procedure as that used for compound 70c using the corresponding precursors.

Compound 79

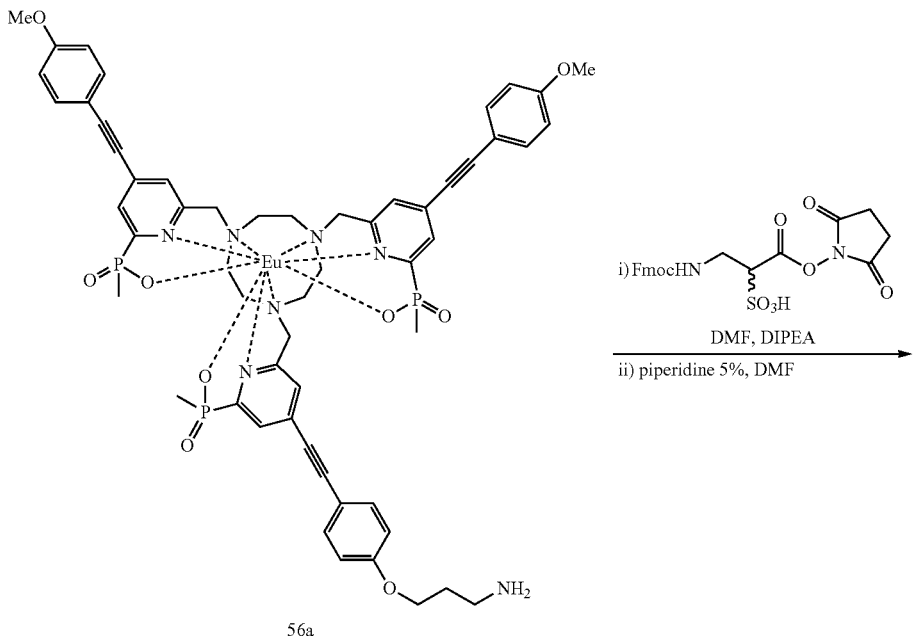

56a

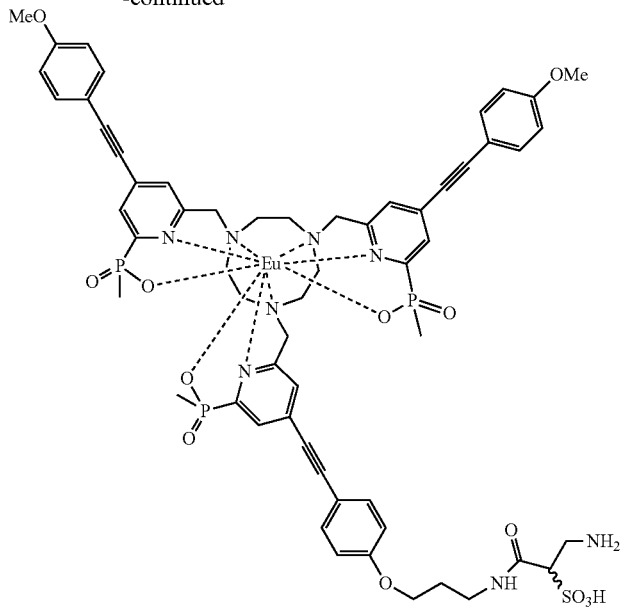
79

Diisopropylethylamine (0.2 µL, 1 µmol) was added to a solution of europium NH₂ complex 56a (500 µmol) in anhydrous dimethylformamide (200 µL). A solution of Fmoc-sulfo-β-alanine (500 µmol) in anhydrous dimethylformamide (61 µL) was added to this mixture. The mixture was stirred at room temperature for 1 h. The progress of the reaction was monitored by HPLC. After this period, reaction was complete. A 5% solution of piperidine in dimethylformamide (200 µL) was added to this mixture, and the mixture was stirred at room temperature for 30 min. The progress of the reaction was monitored by HPLC. After this time, reaction was complete. The crude reaction product was purified by preparative HPLC using the following gradient: Waters XBridge RP-C18 column, 5 nm, 19×100 mm) with 0.2% aqueous solution of trifluoroacetic acid pH 1-MeCN (v/v) as eluent [isocratic 5% MeCN (2 min), linear gradient from 5 to 100% MeCN (23 min) with a flow rate of 20 mL min$^{-1}$ and UV detection at 320 nm to give the desired product 79 (442 nmol, 88%). HRMS (ESI+) calculated for $C_{59}H_{66}EuN_8O_{13}P_3S$ [M+2H]$^{2+}$, m/z 685.1435 found: 685.1439. $R_t$=11.5 min (Waters XBridge RP-C18 column, 3.5 µm, 4.6×100 mm) with 0.2% aqueous solution of trifluoroacetic acid (pH 1-MeCN (v/v) as eluent [isocratic 5% MeCN (2 min)], linear gradient from 5 to 100% MeCN (20 min), with a flow rate of 1 mL min$^{-1}$ and UV detection at 320 nm.

Compound 80

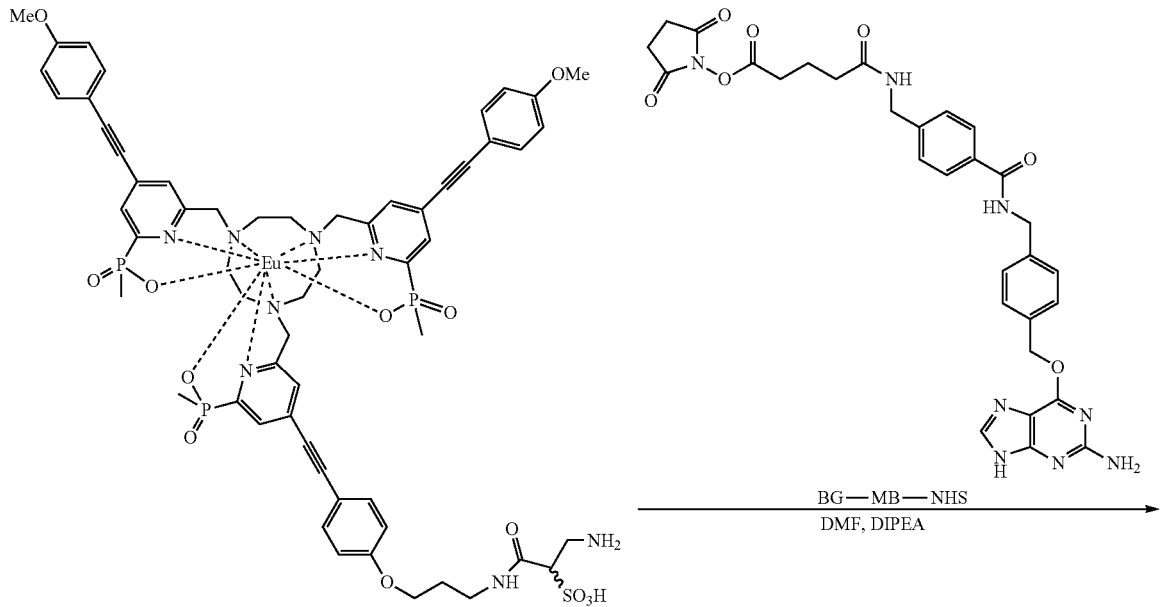
79

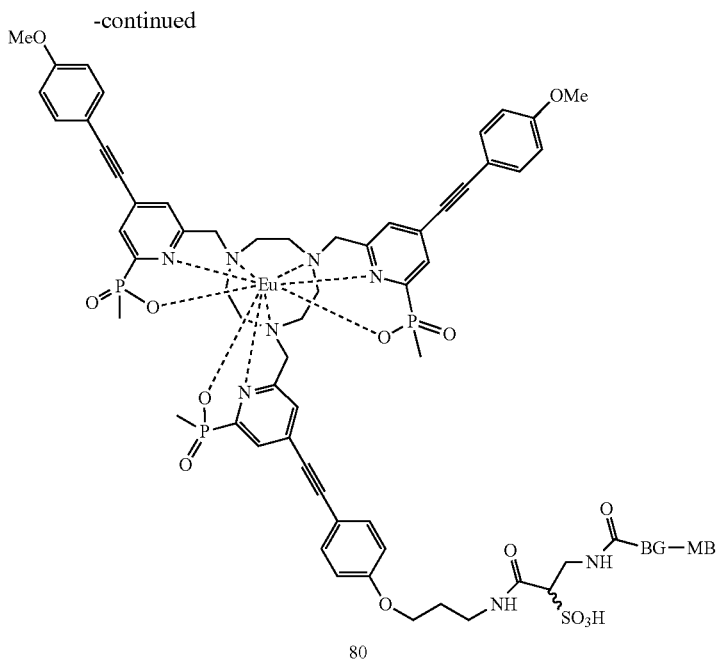

80

Diisopropylethylamine (0.3 μL, 1.72 μmol) and a solution of BG-MB-NHS in dimethylformamide (16 μL, 25 μmol) were added to a solution of europium $NH_2$ complex 79 (25 nmol) in anhydrous dimethylformamide (38 μL). The reaction is stirred at room temperature for 1 h. The progress of the reaction was monitored by HPLC. After this period, reaction was complete. The reaction mixture was purified by semipreparative HPLC using the following gradient: Waters XBridge RP-C18 column, 5 μm, 10×250 mm) with 0.2% aqueous solution of trifluoroacetic acid pH 1-MeCN (v/v) as eluent [isocratic 5% MeCN (2 min), linear gradient from 5 to 100% MeCN (23 min) with a flow rate of 5 mL min$^{-1}$ and UV detection at 320 nm to give the desired product 80 (16 nmol, 64%). LRMS (ESI+) calculated for $C_{85}H_{91}EuN_{15}O_{17}P_3S$ [M+2H]$^{2+}$, m/z 935.7432 found: 936.12. $R_t$=8.42 min (Waters XBridge RP-C18 column, 3.5 μm, 4.6×100 mm) with 0.1% aqueous solution of formic acid (pH 2-MeCN (v/v) as eluent [isocratic 5% MeCN (1 min)], linear gradient from 5 to 100% MeCN (14 min), with a flow rate of 1 mL min$^{-1}$.

Compound 81

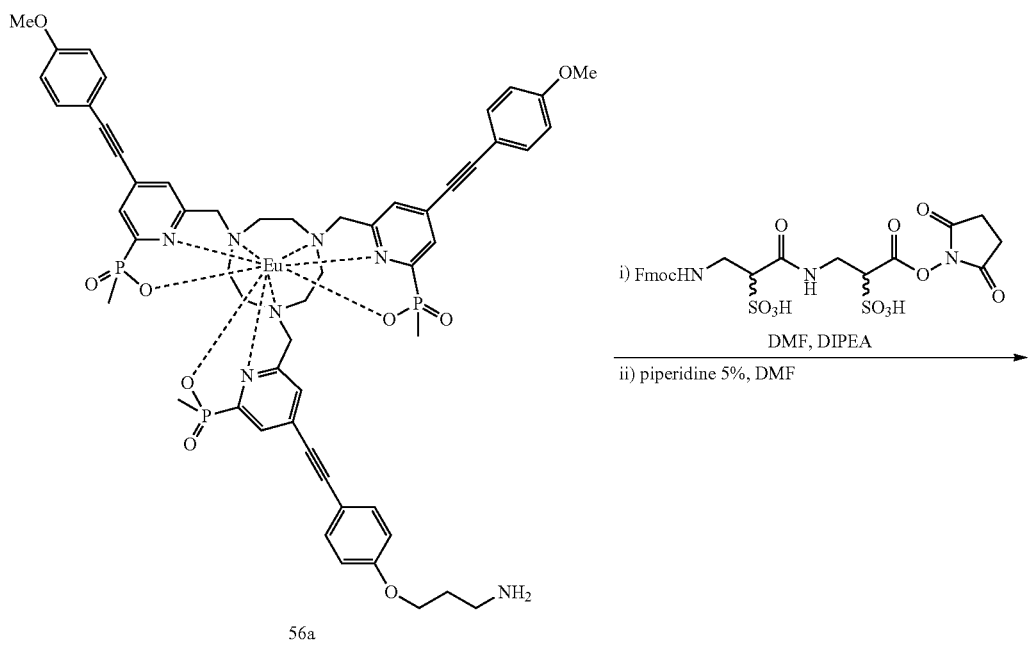

56a

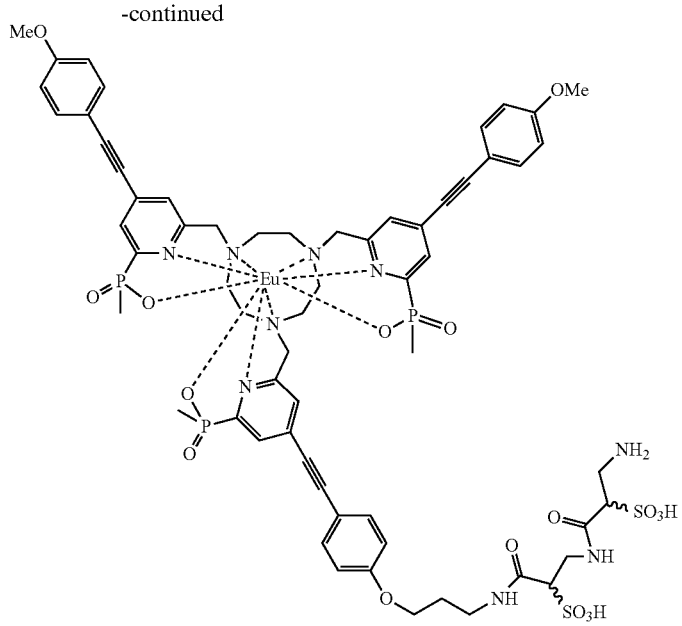

81

Diisopropylethylamine (1.7 µL) was added to a solution of europium NH$_2$ complex 56a (5 µmol) in anhydrous dimethylformamide (500 µL). A solution of N-Fmoc di-sulfo-di-β-alanine NHS (5 µmol) in anhydrous dimethylformamide (283 µL) was added to this mixture. The mixture was stirred at room temperature for 2 h. The progress of the reaction was monitored by HPLC. After this period, reaction was complete. A 5% solution of piperidine (10 µmol) in dimethylformamide (20 µL) was added to this mixture, and the mixture was stirred at room temperature for 12 h. The progress of the reaction was monitored by HPLC. After this time, reaction was complete. The crude reaction product was purified by preparative HPLC using the following gradient: Waters XBridge RP-C18 column, 5 µm, 19×100 mm) with 0.1% aqueous solution of formic acid pH 2-MeCN (v/v) as eluent [isocratic 5% MeCN (2 min), linear gradient from 5 to 100% MeCN (18 min) with a flow rate of 20 mL min$^{-1}$ and UV detection at 320 nm to give the desired product 81 (3.6 µmol, 72%). HRMS (ESI+) calculated for $C_{62}H_{71}EuN_9O_{12}P_3S_2$ [M+2H]$^{2+}$, m/z 760.6405 found: 760.6402. R$_t$=8.15 min (Waters XBridge RP-C18 column, 3.5 µm, 4.6×100 mm) with 0.1% aqueous solution of formic acid (pH 2-MeCN (v/v) as eluent [isocratic 5% MeCN (1 min)], linear gradient from 5 to 100% MeCN (14 min), with a flow rate of 1 mL min$^{-1}$.

Compound 82

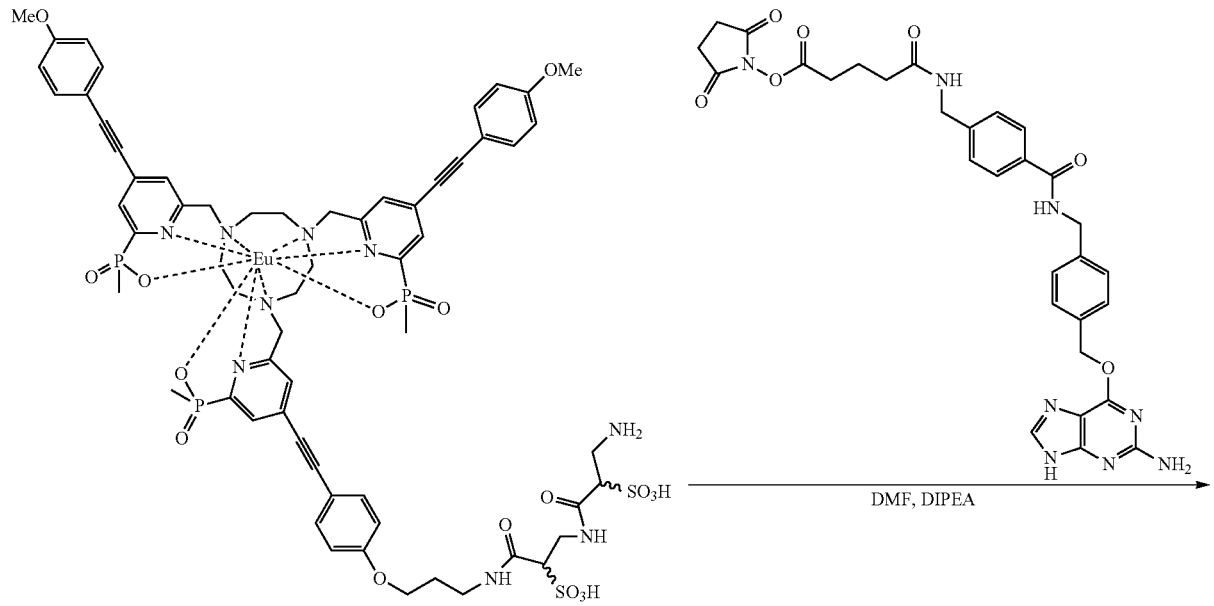

81

-continued

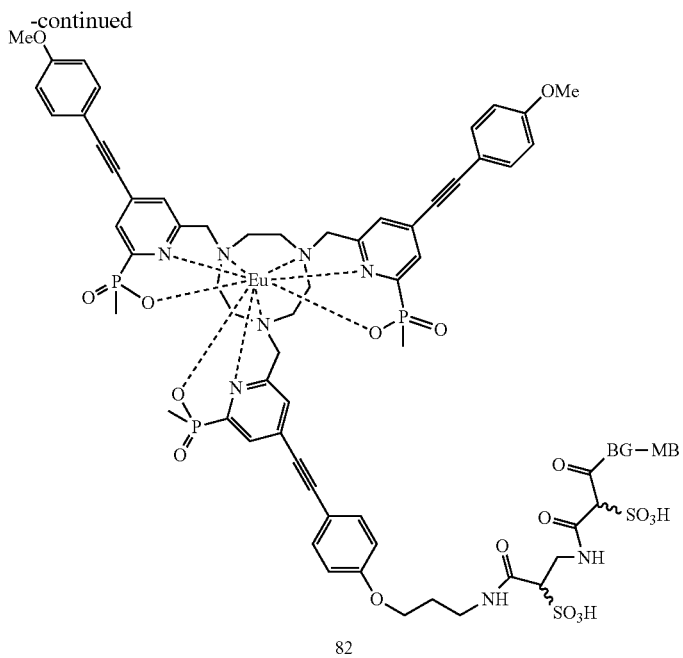

82

Diisopropylethylamine (1.5 μL) and a solution of BG-MB-NHS (200 nmol) in anhydrous dimethylformamide (100 μL) were added to a solution of europium $NH_2$ complex 81 (200 μmol) in anhydrous dimethylformamide (50 μL). The reaction is stirred at room temperature for 12 h. The progress of the reaction was monitored by HPLC. After this period, reaction was complete. The reaction mixture was purified by preparative HPLC using the following gradient: Waters XBridge RP-C18 column, 5 μm, 19×100 mm) with 0.2% aqueous solution of trifluoroacetic acid pH 1-MeCN (v/v) as eluent [isocratic 5% MeCN (2 min)], linear gradient from 5 to 100% MeCN (18 min) with a flow rate of 20 mL $min^{-1}$ and UV detection at 320 nm to give compound 82 (15 nmol, 7%). LRMS (ESI−) calculated for $C_{88}H_{92}EuN_{16}O_{21}P_3S_2$ $[M-2H]^{2-}$, m/z 1009.2245 found: 1009.29. $R_t$=11.65 min (Waters XBridge RP-C18 column, 3.5 μm, 4.6×100 mm) with 0.1% aqueous solution of formic acid (pH 2-MeCN (v/v) as eluent [isocratic 5% MeCN (2 min)], linear gradient from 5 to 100% MeCN (18 min), with a flow rate of 1 mL $min^{-1}$ and UV detection of 320 nm.

Compound 83

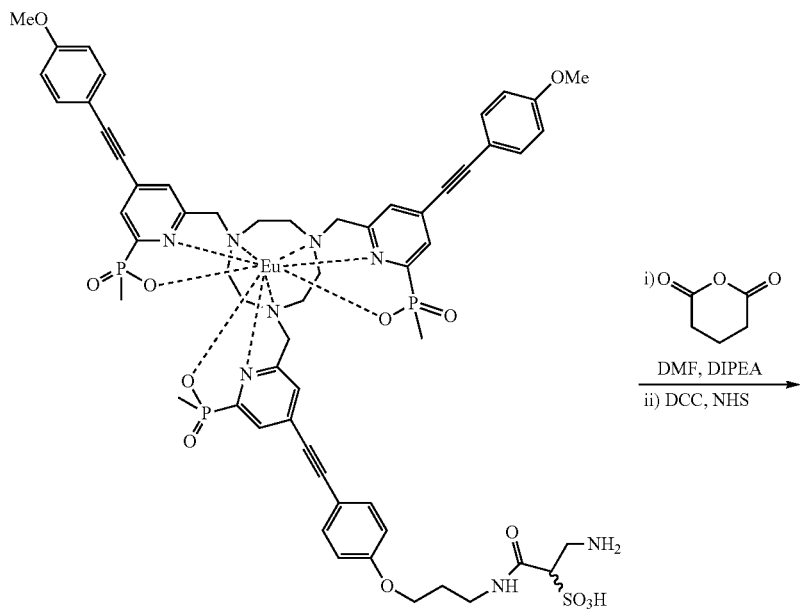

79

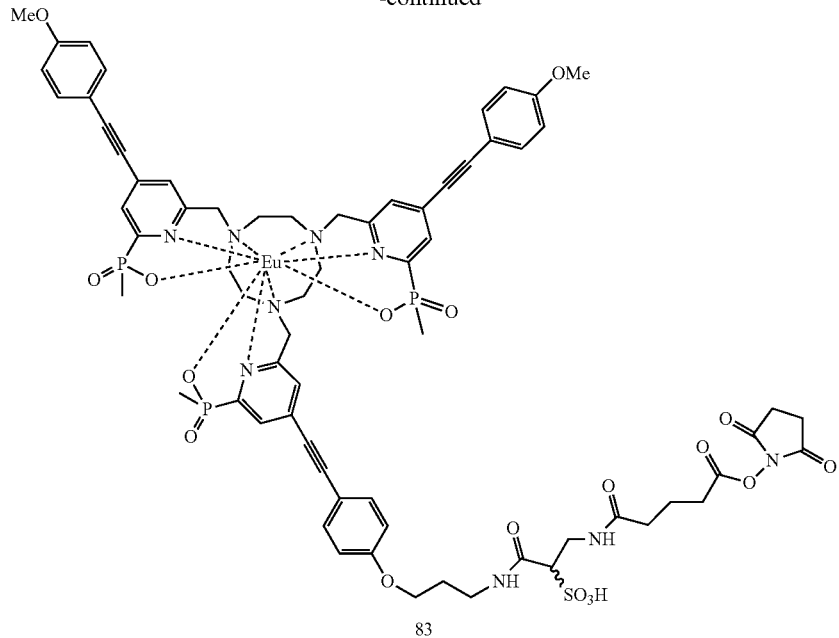

83

Diisopropylethylamine (0.3 µL) was added to a solution of europium $NH_2$ complex 79 (1 µmol) in anhydrous DMF (200 µL). Glutaric anhydride (3 µmol) was added to this mixture. The mixture was stirred at room temperature for 30 min. The progress of the reaction was monitored by HPLC. After this period, reaction was complete. The reaction mixture was purified by preparative HPLC to give the corresponding acid (668 nmol, 67%). LRMS (ESI+) calculated for $C_{64}H_{72}EuN_8O_{16}P_3S$ $[M+2H]^{2+}$, m/z 743.1606 found: 742.67. $R_t$=7.02 min (Waters XBridge RP-C18 column, 3.5 µm, 4.6×100 mm) with 0.1% aqueous solution of formic acid (pH 2-MeCN (v/v) as eluent [isocratic 5% MeCN (1 min) linear gradient from 5 to 100% MeCN (14 min), with a flow rate of 1 mL min$^{-1}$. Dicyclohexylcarbodiimide (2.2 mg, 11.4 µmol) and N-hydroxysuccinimide (1.5 mg, 13 µmol) were added to a solution of acid functionalized complex (200 nmol) in anhydrous dimethylformamide (15 µL). The reaction mixture was stirred at room temperature for 28 h. The progress of the reaction was monitored by HPLC. After this period, reaction was complete. The reaction mixture was purified directly by semipreparative HPLC to give the NHS compound 83 (69 nmol, 35%). LRMS (ESI+) calculated for $C_{68}H_{75}EuN_9O_{18}P_3S$ $[M+2H]^{2+}$, m/z 791.6688 found: 791.83. $R_t$=7.35 min (Waters XBridge RP-C18 column, 3.5 µm, 4.6×100 mm) with an aqueous solution of ammonium formate buffer 10 mM pH 4.7-MeCN (v/v) as eluent [isocratic 15% MeCN (1 min) linear gradient from 15 to 100% MeCN (14 min), with a flow rate of 1 mL min$^{-1}$.

Compound 84

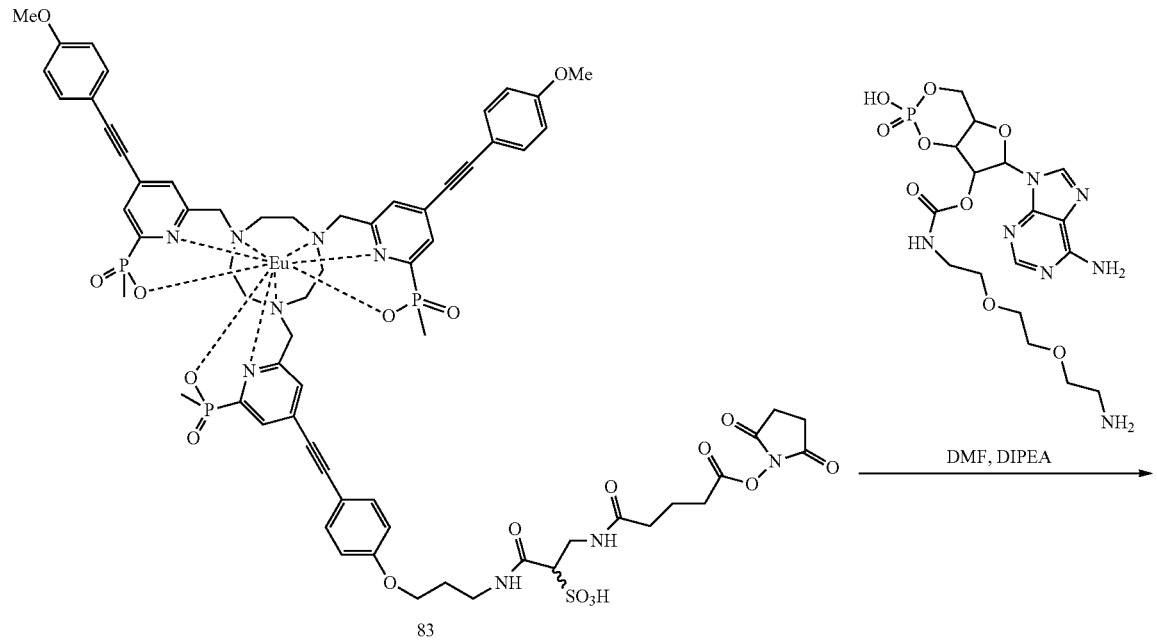

83

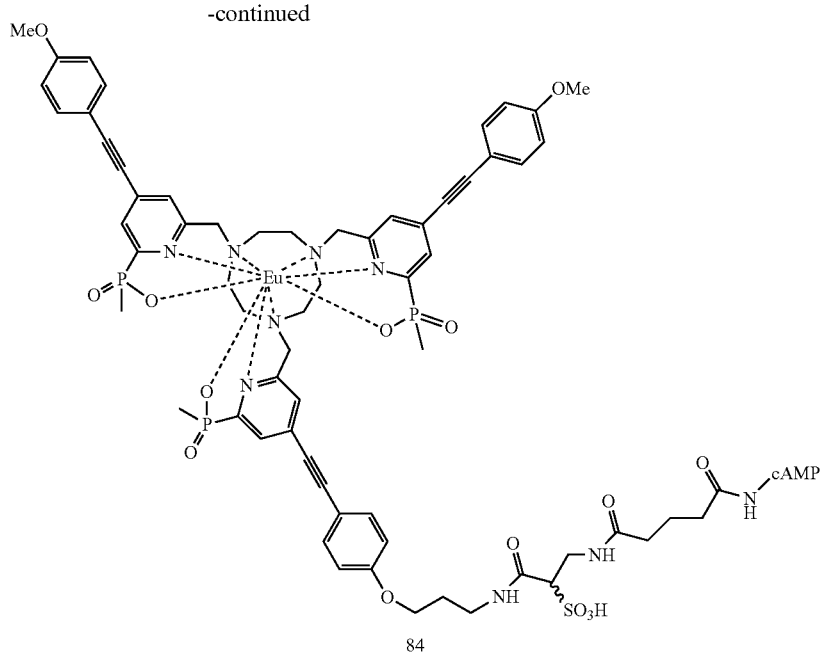

84

Diisopropylethylamine (0.9 μL) and a solution of cAMP-NH$_2$ (90 nmol) in anhydrous dimethylformamide (9 μL) were added to a solution of europium NHS complex 83 (69 nmol) in anhydrous dimethylformamide (200 μL). The reaction mixture was stirred overnight. The progress of the reaction was monitored by HPLC. The reaction mixture was purified by semipreparative HPLC using the following gradient: Waters XBridge RP-C18 column, 5 μm, 10×250 mm) with 0.2% aqueous solution of trifluoroacetic acid pH 1-MeCN (v/v) as eluent [isocratic 5% MeCN (2 min)], linear gradient from 5 to 100% MeCN (23 min) with a flow rate of 5 mL min$^{-1}$ and UV detection at 320 nm to give the desired product 84 (10 nmol, 14%). LRMS (ESI+) calculated for C$_{81}$H$_{95}$EuN$_{15}$O$_{24}$P$_4$S [M+2H]$^{2+}$, m/z 985.2279 found: 986.30. R$_t$=6.58 min (Waters XBridge RP-C18 column, 3.5 μm, 4.6×100 mm) with 0.1% aqueous solution of formic acid (pH 2-MeCN (v/v) as eluent [isocratic 5% MeCN (1 min) linear gradient from 5 to 100% MeCN (14 min), with a flow rate of 1 mL min$^{-1}$.

Compound 85

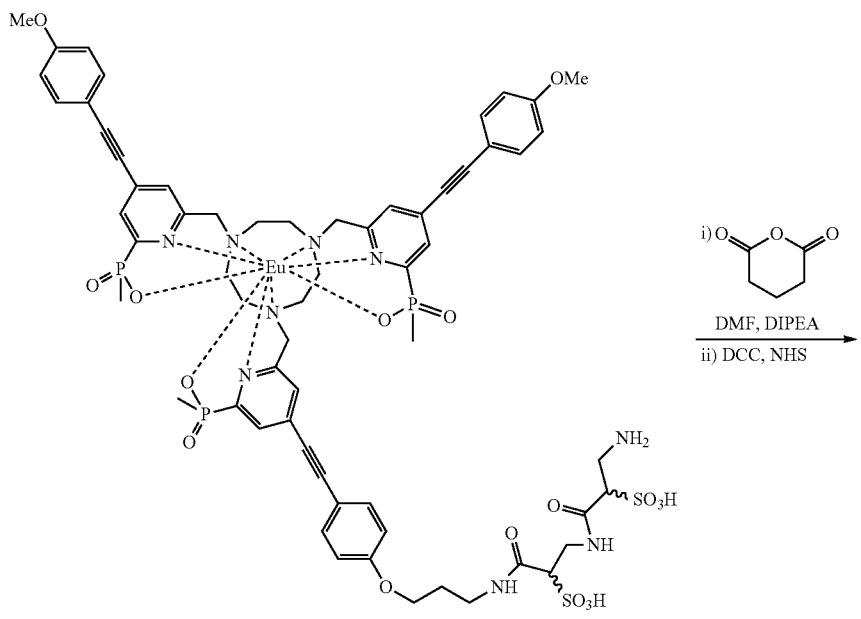

81

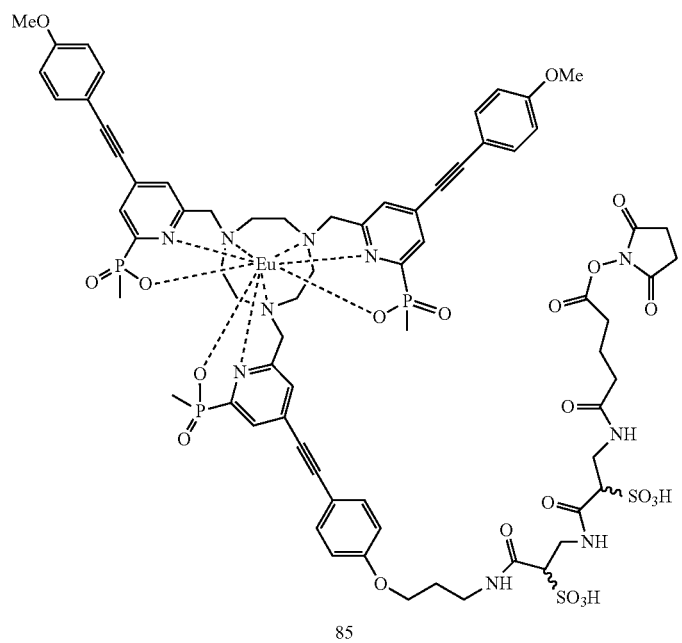

85

Diisopropylethylamine (2.6 µL, 15 µmol) was added to a solution of europium NH$_2$ complex 81 (2 µmol) in anhydrous DMF (500 µL). Glutaric anhydride (6 µmol) was added to this mixture. The mixture was stirred at room temperature for 16 h. The progress of the reaction was monitored by HPLC. After this period, reaction was complete. The reaction mixture was purified by preparative HPLC using the following gradient: Waters XBridge RP-C18 column, 5 µm, 19×100 mm) with triethylammonium acetate buffer solution 25 mM pH 5-MeCN (v/v) as eluent [isocratic 5% MeCN (2 min)], linear gradient from 5 to 100% MeCN (25 min) with a flow rate of 20 mL min$^{-1}$ and UV detection at 320 nm to give the corresponding acid (1.8 µmol, 98%). LRMS (ESI+) calculated for C$_{67}$H$_{77}$EuN$_9$O$_{20}$P$_3$S$_2$ [M+2H]$^{2+}$, m/z 818.6576 found: 818.16. R$_f$=6.73 min (Waters XBridge RP-C18 column, 3.5 µm, 4.6×100 mm) with an aqueous solution of ammonium formate buffer 10 mM pH 4.7-MeCN (v/v) as eluent [isocratic 15% MeCN (1 min)], linear gradient from 15 to 100% MeCN (14 min), with a flow rate of 1 mL min$^{-1}$. Dicyclohexylcarbodiimide (1.9 mg, 9.89 µmol) and N-hydroxysuccinimide (1.7 mg, 14.8 µmol) were added to a solution of acid complex (480 nmol) in anhydrous dimethylformamide (120 µL). The reaction mixture was stirred at room temperature for 28 h. The progress of the reaction was monitored by HPLC. After this period, reaction was complete. The reaction mixture was purified directly by preparative HPLC using the following gradient: Waters XBridge RP-C18 column, 5 µm, 19×100 mm) with triethylammonium acetate buffer solution 25 mM pH 5-MeCN (v/v) as eluent [isocratic 5% MeCN (2 min), linear gradient from 5 to 100% MeCN (25 min) with a flow rate of 20 mL min$^{-1}$ and UV detection at 320 nm to give the desired compound 85 (40 nmol, 8%). LRMS (ESI+) calculated for C$_{71}$H$_{80}$EuN$_{10}$O$_{22}$P$_3$S$_2$ [M+2H]$^{2+}$, m/z 867.1658 found: 866.60. R$_f$=6.93 min (Waters XBridge RP-C18 column, 3.5 µm, 4.6×100 mm) with an aqueous solution of ammonium formate buffer 10 mM pH 4.7-MeCN (v/v) as eluent [isocratic 15% MeCN (1 min) linear gradient from 15 to 100% MeCN (14 min), with a flow rate of 1 mL min$^{-1}$.

Compound 86

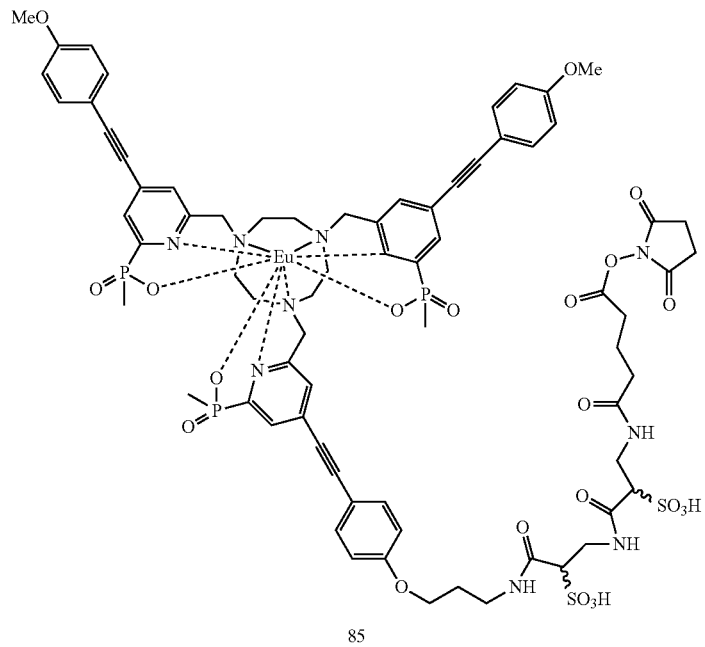
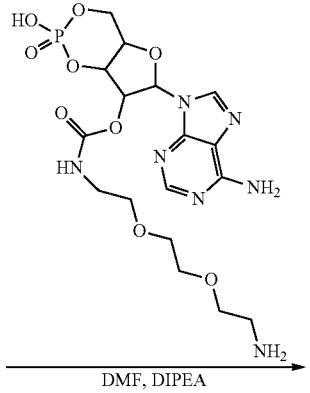

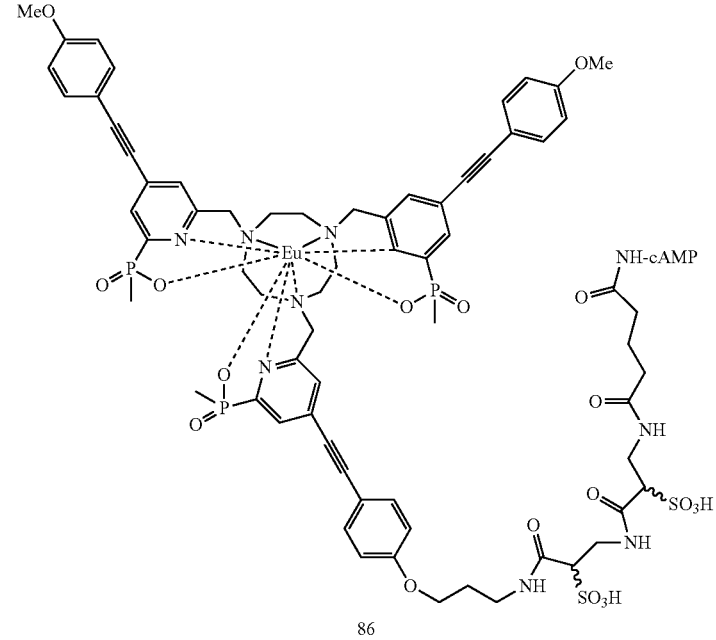

Diisopropylethylamine (0.1 µL, 575 nmol) and a solution of cAMP-NH$_2$ (50 nmol) in anhydrous dimethylformamide (4.8 µL) were added to a solution of europium NHS complex 85 (40 nmol) in anhydrous dimethylformamide (200 µL). The reaction mixture was stirred for 16 h at room temperature and under inert atmosphere. The progress of the reaction was monitored by HPLC. After this time, reaction was complete. The reaction mixture was purified by semi-preparative HPLC: Waters XBridge RP-C18 column, 5 µm, 5×150 mm) with triethylammonium acetate buffer solution 25 mM pH 5-MeCN (v/v) as eluent [isocratic 5% MeCN (2 min), linear gradient from 5 to 100% MeCN (23 min) with a flow rate of 5 mL min$^{-1}$ and UV detection at 320 nm to give the desired compound 86 (10 nmol, 25%). LRMS (ESI+) calculated for $C_{84}H_{101}EuN_{16}O_{28}P_4S_2$ [M+2H]$^{2+}$, m/z 1061.2288 found: 1062.07. R$_f$=6.33 min (Waters XBridge RP-C18 column, 3.5 µm, 4.6×100 mm) with an aqueous solution of ammonium formate buffer 10 mM pH 4.7-MeCN (v/v) as eluent [isocratic 15% MeCN (1 min) linear gradient from 15 to 100% MeCN (14 min), with a flow rate of 1 mL min$^{-1}$.

Compound 87

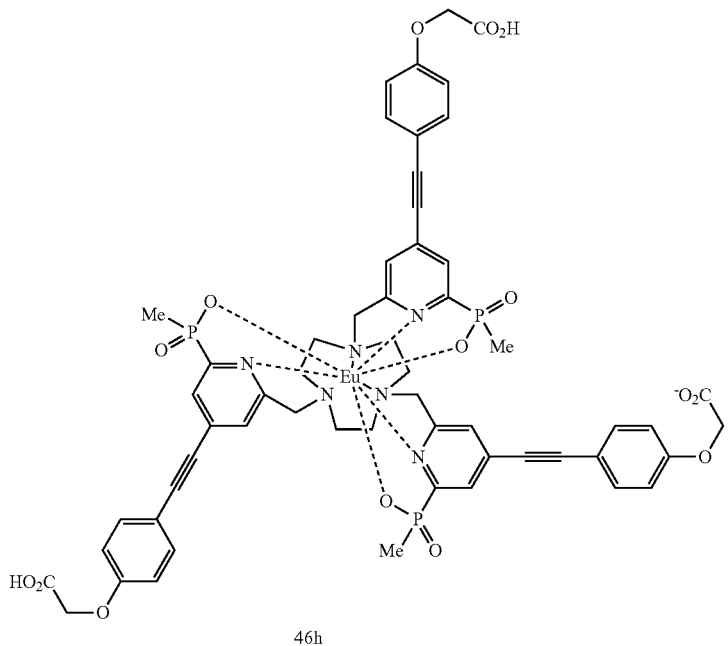

46h

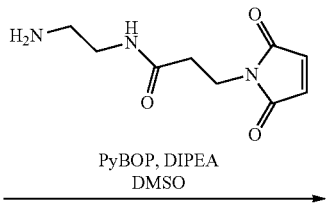

PyBOP, DIPEA
DMSO

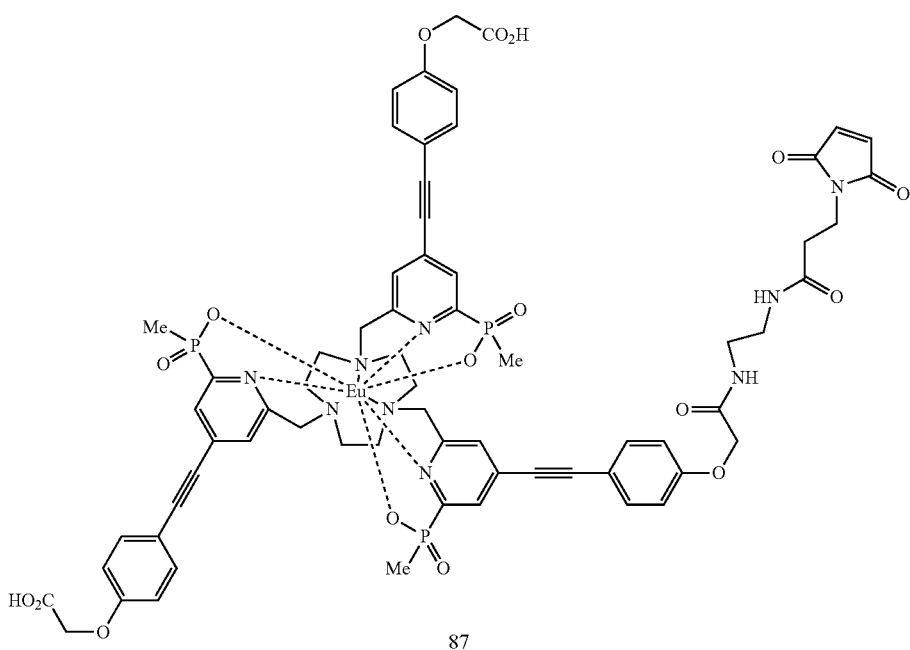

87

Benzotriazol-1-yl-oxy-tris-(dimethylamino)-phosphonium hexafluorophosphate (0.13 mg, 250 nmol) and diisopropylethylamine (0.13 μL, 760 nmol) were added to a solution of complex 46h (1 mg, 760 nmol) in anhydrous dimethylsulfoxide (50 μL). The mixture was stirred at room temperature for 5 min. A solution of maleimide derivative (0.16 mg, 760 nmol) in anhydrous dimethylsulfoxide (50 μL) was added to this solution and then the solution was stirred at room temperature under inert atmosphere for 72 h. The progress of the reaction was monitored by LCMS. After this time, reaction was complete. The reaction mixture was purified by semipreparative HPLC to give the desired product 87 (0.41 mg, 41%). HRMS (ESI+) calculated for $C_{66}H_{67}EuN_9O_{17}P_3$ $[M+2H]^{2+}$, m/z 751.6540 found: 751.6664.

Compound 88

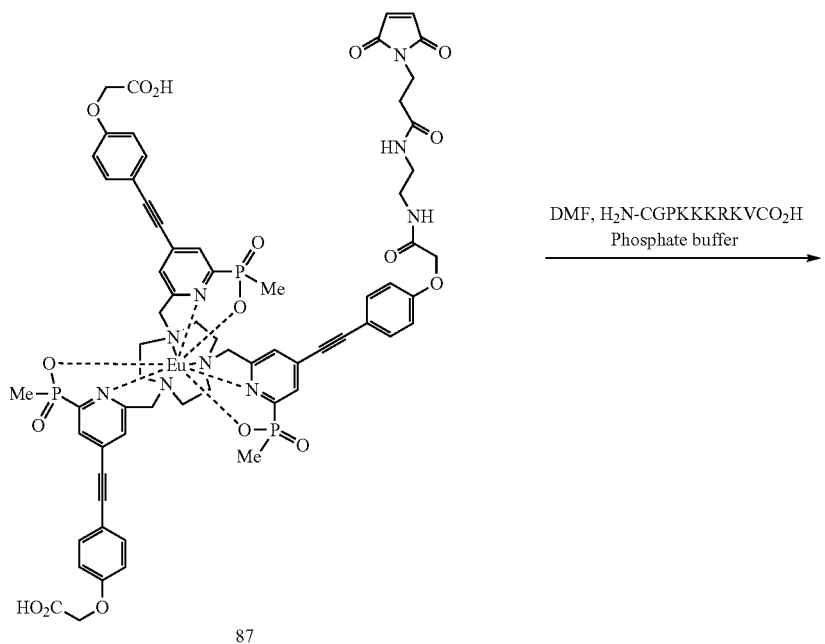

87

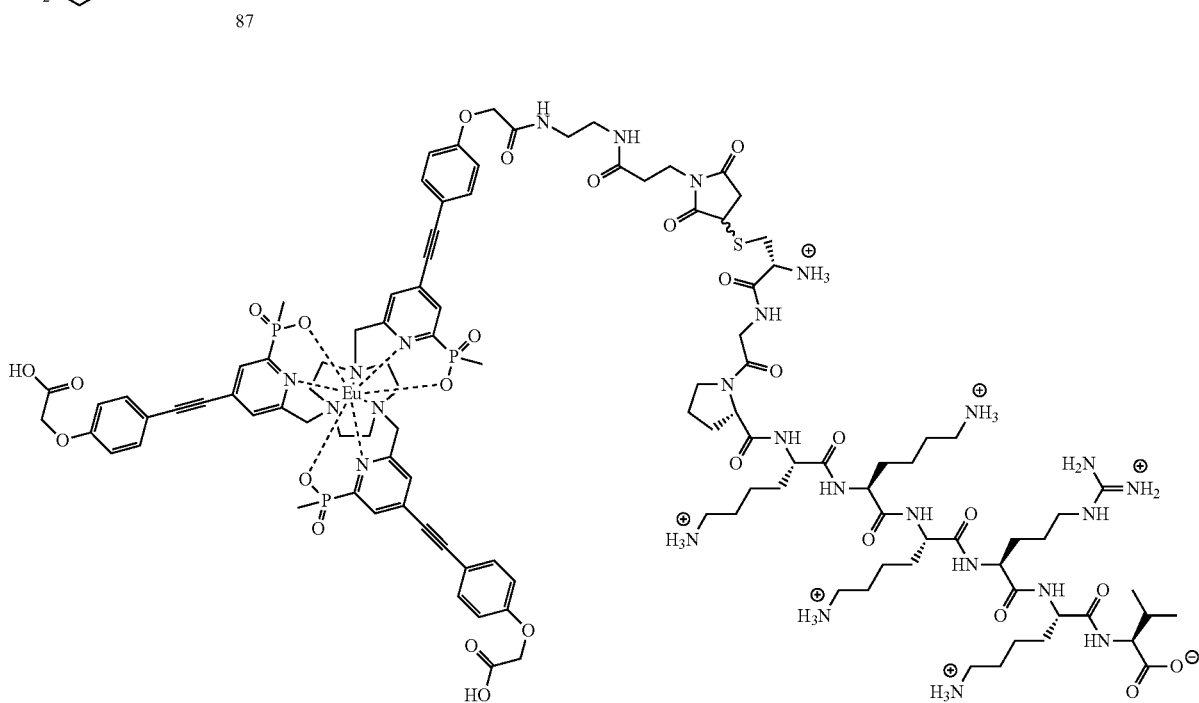

88

A solution of peptide H$_2$N-CGPKKKRKV-CO$_2$H (0.26 mg, 200 µmol) in phosphate buffer 50 mM, pH 7 (20 µL) was added to a solution of maleimide 87 (0.20 mg, 133 nmol) in anhydrous dimethylformamide (50 µL). The mixture was stirred at room temperature under inert atmosphere for 15 h. The progress of the reaction was monitored by HPLC. After this period, reaction was complete. The reaction mixture was purified by semipreparative HPLC to give the conjugate 88 (0.21 mg, 62%). HRMS (ESI+) calculated for C$_{111}$H$_{154}$EuN$_{25}$O$_{27}$P$_3$S [M]$^{3+}$, m/z 848.9871 found: 848.9963. R$_t$=9.9 min (Waters XBridge RP-C18 column, 5 µm, 10×100 mm) with 0.1% aqueous solution of formic acid (pH 2-MeOH (v/v) as eluent linear gradient from 5 to 100% MeCN (15 min), with a flow rate of 4.4 mL min$^{-1}$ and UV detection at 330 nm.

Compound 89

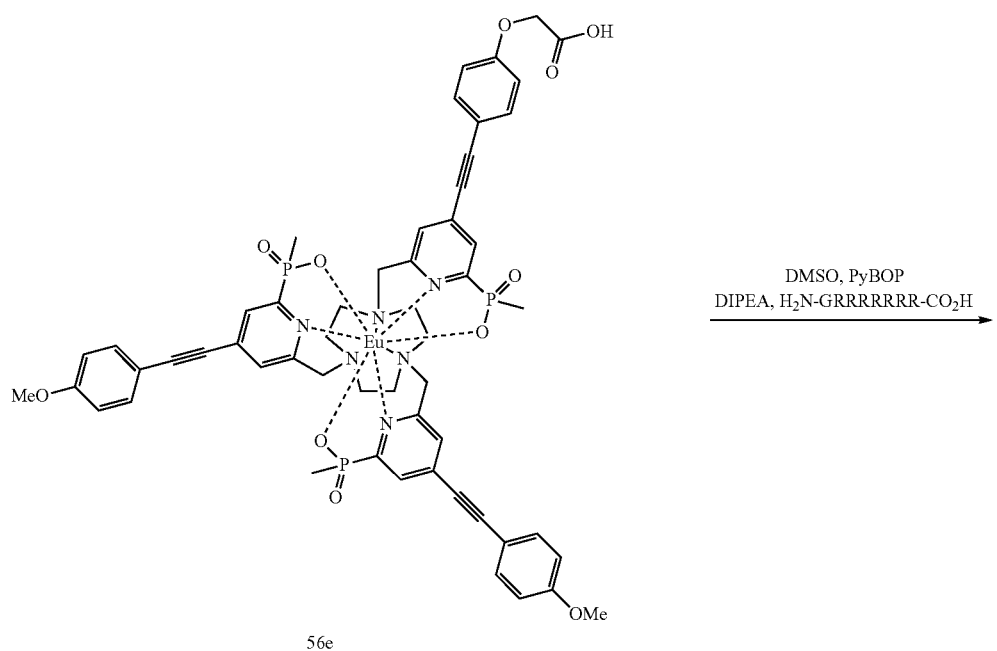

56e

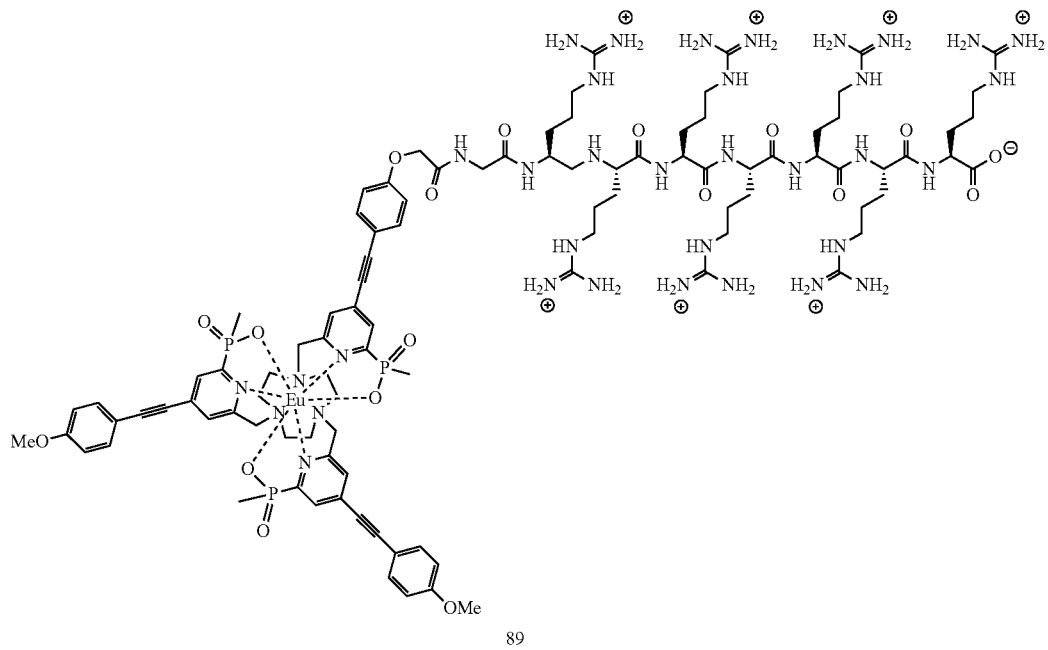

89

Benzotriazol-1-yl-oxy-tris-(dimethylamino)-phosphonium hexafluorophosphate (0.65 mg, 1.25 μmol) and diisopropylethylamine (0.3 μL, 1.65 μmol) were added to a solution of complex 56e (1 mg, 0.82 μmol) in anhydrous dimethylsulfoxide (150 μL). The mixture was stirred at room temperature for 5 min. A solution of H$_2$N-GRRRRRRR-CO$_2$H (1 mg, 0.86 μmol) in anhydrous dimethylsulfoxide (50 μL) was added to this solution, and then the solution was stirred at room temperature under inert atmosphere for 24 h. The progress of the reaction was monitored by LC-MS. After this time, reaction was complete. The reaction mixture was purified by semipreparative HPLC to give the conjugate 89 (1.2 mg, 62%). HRMS (ESI+) calculated for C$_{99}$H$_{144}$EuN$_{35}$O$_{19}$P$_3$ [M+3H]$^{3+}$, m/z 790.9940 found: 790.9938.

Compound 90

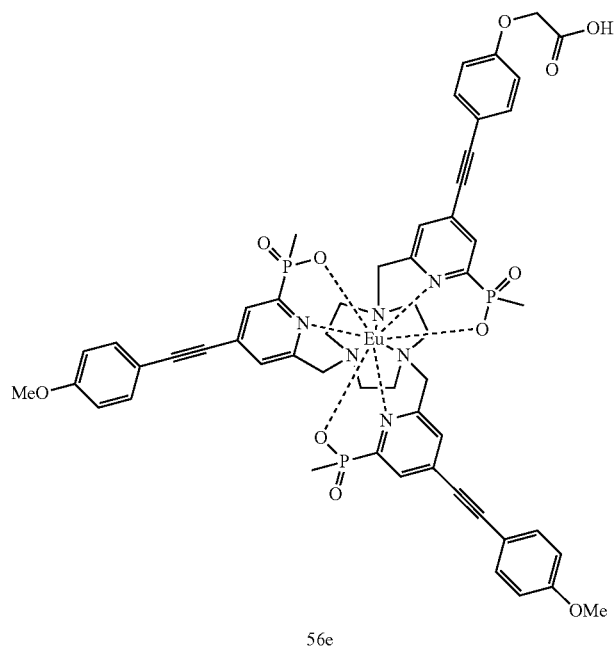

56e

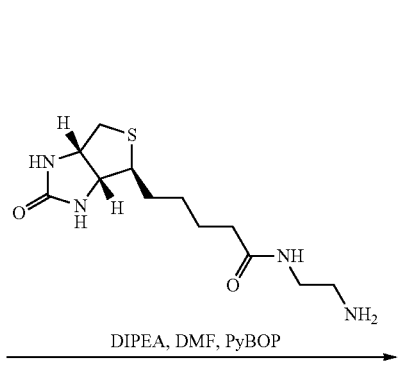

DIPEA, DMF, PyBOP

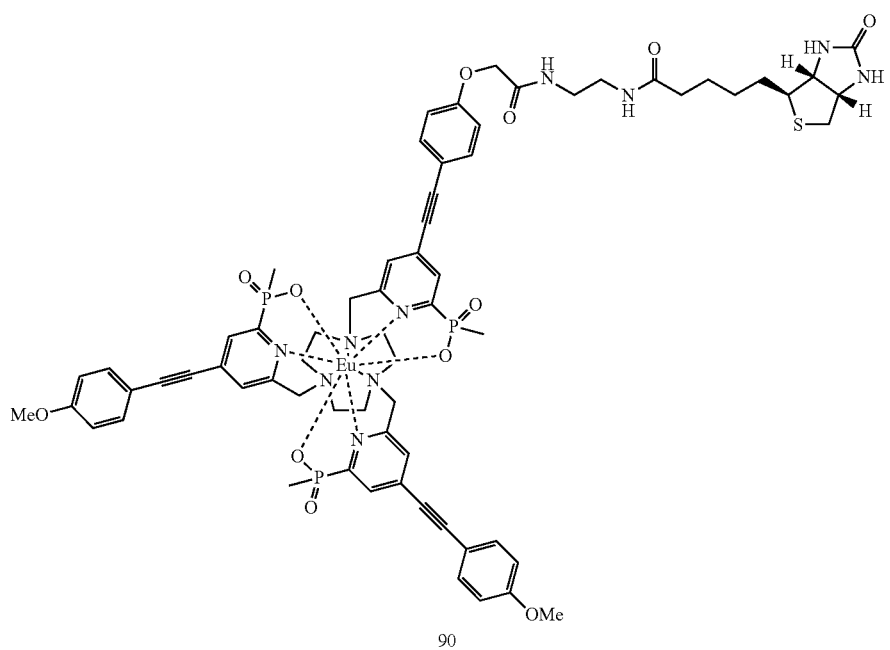

90

Benzotriazol-1-yl-oxy-tris-(dimethylamino)-phosphonium hexafluorophosphate (0.65 mg, 1.25 µmol) and diisopropylethylamine (0.3 µL, 1.65 µmol) were added to a solution of complex 56e (1 mg, 0.82 µmol) in anhydrous dimethylsulfoxide (150 µL). The mixture was stirred at room temperature for 5 min. A solution of ethylene diamine-biotin (0.35 mg, 1.23 µmol) in anhydrous dimethylformamide (50 µL) was added to this solution, and then the solution was stirred at room temperature under inert atmosphere for 3 h. The progress of the reaction was monitored by LC-MS. After this time, reaction was complete. The reaction mixture was purified by semipreparative HPLC to give the biotinylated conjugate 90 (1.0 mg, 82%). HRMS (ESI+) calculated for $C_{62}H_{76}EuN_{10}O_{12}P_3$ $[M+2H]^{2+}$, m/z 745.1899 found: 745.1907.

Compound 91

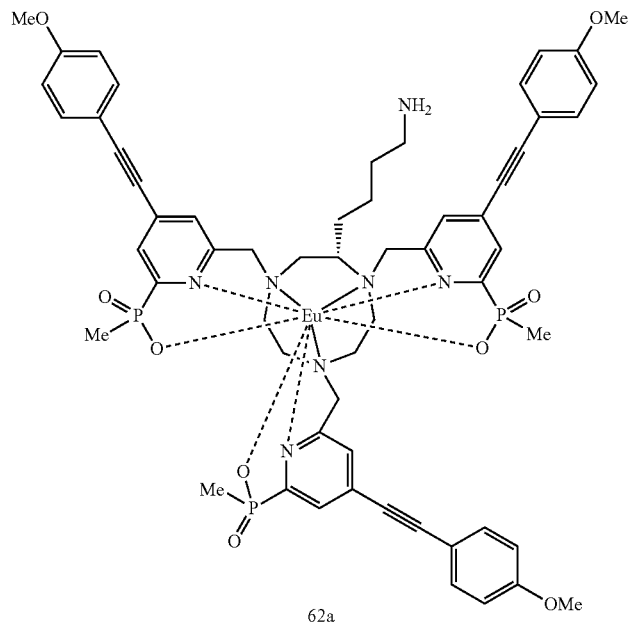

62a

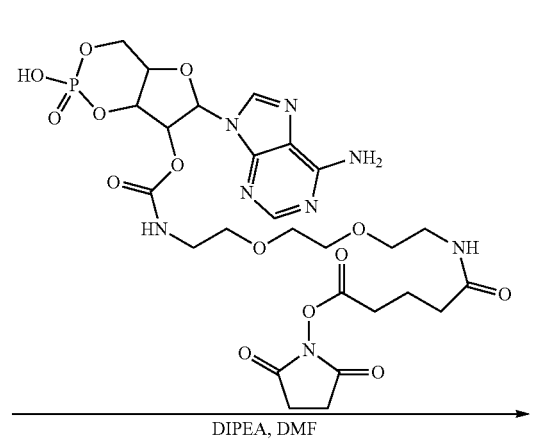

DIPEA, DMF

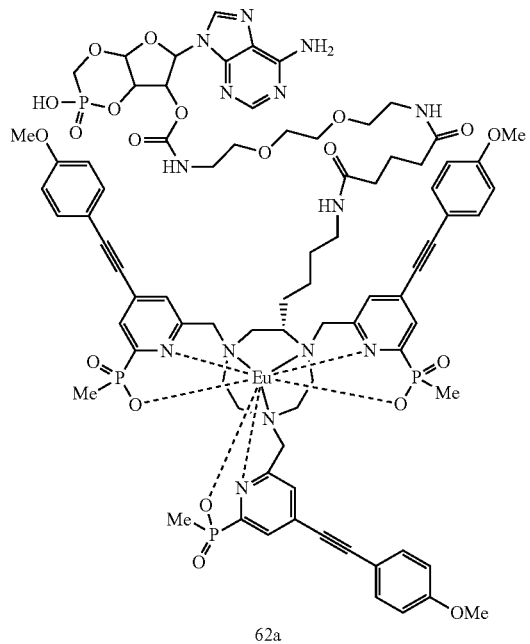

62a

Diisopropylethylamine (5 μL, 28 μmol) and a cAMP-NHS solution (250 nmol) in dimethylformamide (50 μL) were added to a solution of europium $NH_2$ complex 62a (250 nmol) in dimethylformamide (50 μL). The mixture was stirred at room temperature and under inert atmosphere for 1 h. The progress of the reaction was monitored by HPLC. After this time, reaction was complete. A 0.2% aqueous solution of trifluoroacetic acid (8 mL) was added to this solution, and this mixture was purified by preparative HPLC using the following gradient: (Waters XBridge RP-C18 column, 5 μm, 19×100 mm) with 0.2% aqueous solution of trifluoroacetic acid pH 1-MeCN (v/v) as eluent, linear gradient from 5 to 60% MeCN (19 min) with a flow rate of 20 mL min$^{-1}$ and UV detection at 320 nm to give the desired product 91 (82 nmol, 33%). LRMS (ESI+) calculated for $C_{80}H_{96}EuN_{14}O_{20}P_4$ $[M+3H]^{2+}$, m/z 924.7544 found: 924.63. $R_t$=9.10 min (Waters XBridge RP-C18 column, 3.5 μm, 4.6×100 mm) with 0.2% aqueous solution of trifluoroacetic acid (pH 1-MeCN (v/v) as eluent linear gradient from 10 to 100% MeCN (20 min), with a flow rate of 1 mL min$^{-1}$ and UV detection at 320 nm.

Compound 92

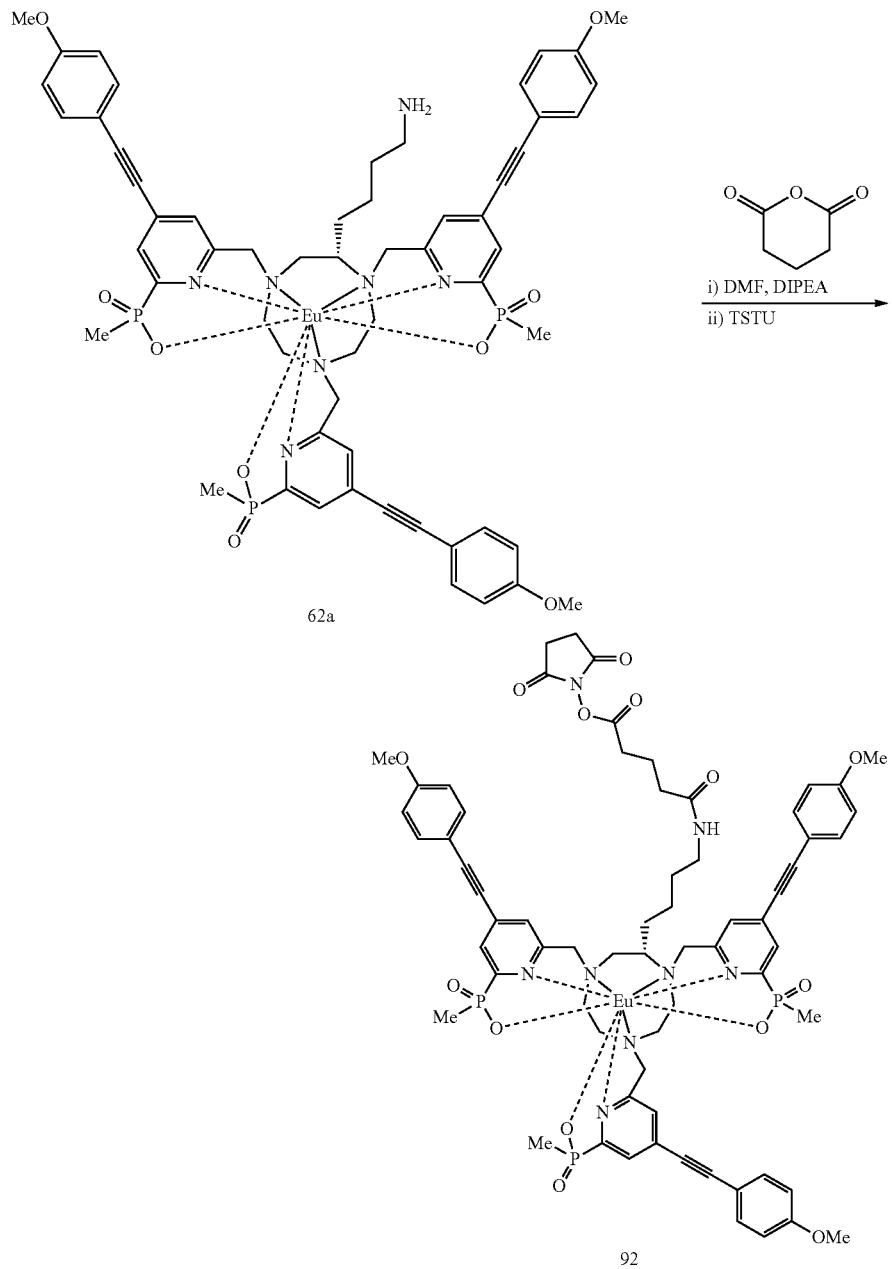

Diisopropylethylamine (4 µL, 22 µmol) was added to a solution of europium NH$_2$ complex 62a (650 nmol) in anhydrous dimethylformamide (400 µL). A solution of glutaric anhydride (780 nmol) in dimethylformamide (80 µL) was added to this mixture. The mixture was stirred at room temperature for 1 h. The progress of the reaction was monitored by HPLC. After this period, reaction was complete. A 0.1% aqueous solution of formic acid (8 mL) was added to this solution, and this mixture was purified by preparative HPLC using the following gradient: (Waters XBridge RP-C18 column, 5 µm, 19×100 mm) with 0.1% aqueous solution of formic acid pH 2-MeCN (v/v) as eluent, linear gradient from 10 to 60% MeCN (19 min) with a flow rate of 20 mL min$^{-1}$ and UV detection at 320 nm to give the desired acid (400 nmol, 61%). LRMS (ESI+) calculated for C$_{63}$H$_{70}$EuN$_7$O$_{12}$P$_3$ [M+H]$^+$, m/z 1362.3508 found: 1362.91. R$_t$=9.14 min (Waters XBridge RP-C18 column, 3.5 µm, 4.6×100 mm) with 0.1% aqueous solution of formic acid (pH 2-MeCN (v/v) as eluent linear gradient from 15 to 100% MeCN (15 min), with a flow rate of 1 mL min$^{-1}$ and UV detection at 320 nm. Diisopropylethylamine (4 µL, 22 µmol) and then O—(N-succinimidyl)-1,1,3,3-tetramethyluronium tetrafluoroborate (0.14 mg, 480 nmol) were added to a solution of acid complex (400 nmol) in anhydrous dimethylformamide (400 µL). The reaction mixture was stirred at room temperature for 15 min. The progress of the reaction was monitored by HPLC. After this period, reaction was complete. A 0.1% aqueous solution of formic acid (8 mL)

was added to this solution, and this mixture was purified by preparative HPLC using the following gradient: (Waters XBridge RP-C18 column, 5 μm, 19×100 mm) with 0.1% aqueous solution of formic acid pH 2-MeCN (v/v) as eluent, linear gradient from 10 to 60% MeCN (19 min) with a flow rate of 20 mL min$^{-1}$ and UV detection at 320 nm to give the desired NHS ester 92 (263 nmol, 65%). LRMS (ESI+) calculated for $C_{67}H_{74}EuN_8O_{14}P_3$ [M+H]$^+$, m/z 1460.3750. found: 1460.17. $R_t$=9.52 min (Waters XBridge RP-C18 column, 3.5 μm, 4.6×100 mm) with 0.1% aqueous solution of formic acid (pH 2-MeCN (v/v) as eluent linear gradient from 15 to 100% MeCN (15 min), with a flow rate of 1 mL min$^{-1}$ and UV detection at 320 nm.

Compound 93

Benzotriazol-1-yl-oxy-tris-(dimethylamino)-phosphonium hexafluorophosphate (0.2 mg, 0.37 μmol) and diisopropylethylamine (0.11 μL, 0.65 μmol) were added to a solution of complex 70c (0.35 mg, 0.25 μmol) in dimethylformamide (50 μL). The mixture was stirred at room temperature for 5 min. A solution of homotaurine (0.05 mg, 0.37 μmol) in water (10 μL) was added to this solution, and then the solution was stirred at room temperature under inert atmosphere for 16 h. The progress of the reaction was monitored by LC-MS. After this time, reaction was complete. The solvent was removed under reduced pressure. The residue was dissolved in dichloromethane (95 μL) under inert atmosphere at 4° C. and trifluoroacetic acid was added

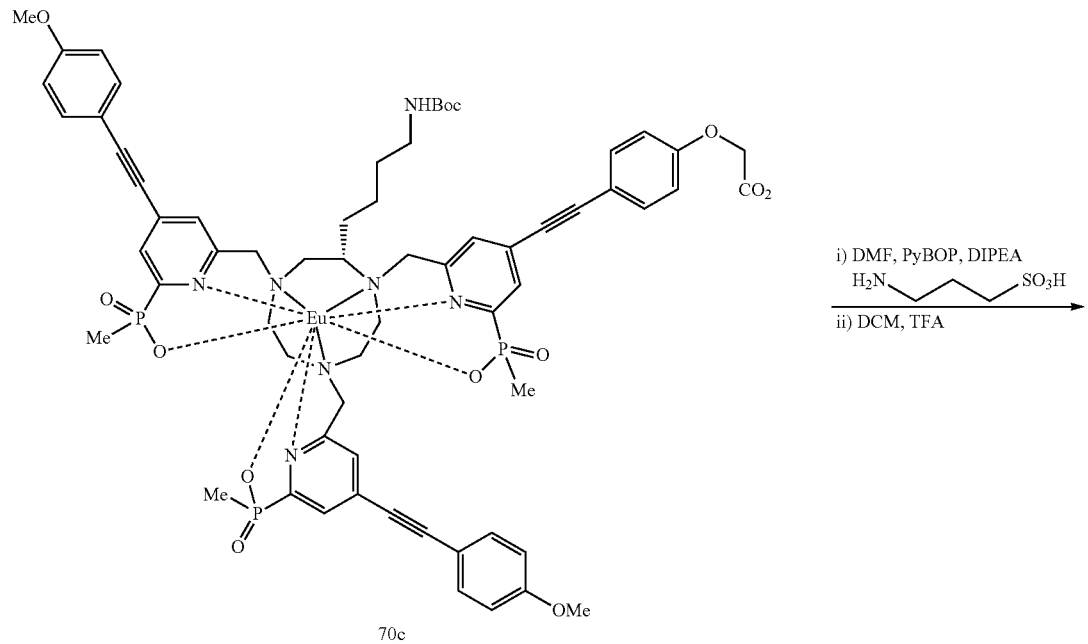

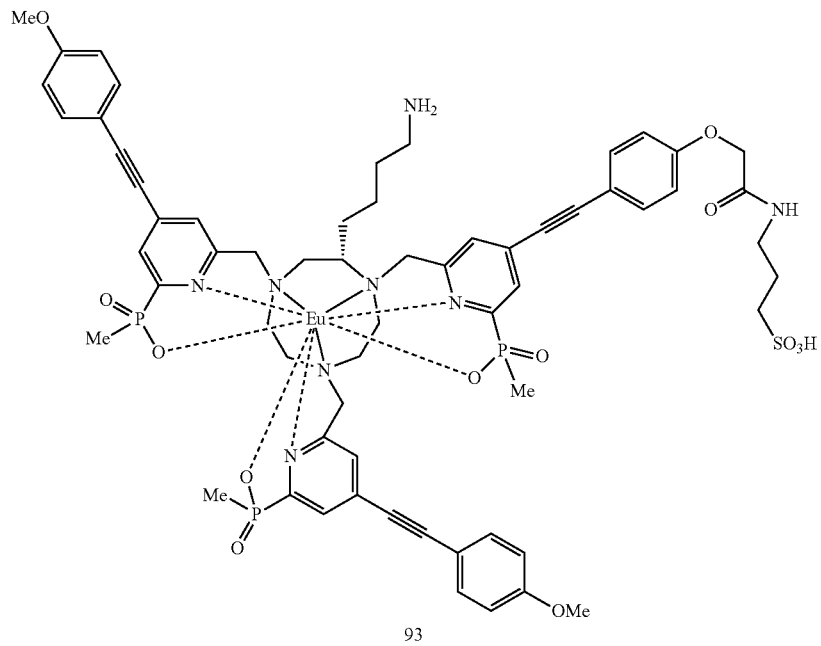

to this solution. The mixture was stirred for 20 min and then the solvent was removed under reduced pressure. The reaction mixture was purified by semipreparative HPLC to give compound 93 (0.3 mg, 85%). HRMS (ESI−) calculated for $C_{62}H_{69}EuN_8O_{13}P_3S$ [M]⁻, m/z 1409.3120 found: 1409.3110.

Compounds 95a-b

These compounds were prepared according to the same procedure as that used for compound 95c using the corresponding precursors.

Compound 95c

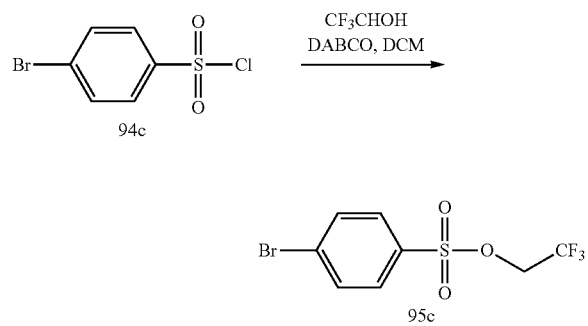

Trifluoroethanol (840 μL, 11.7 mmol) and a solution of 1,4-diazabicyclo[2.2.2]octane (1.5 g, 14.4 mmol) in dichloromethane (10 mL) were added to a solution of 4-bromobenzene-sulfonyl chloride 94c (3 g, 11.7 mmol) dissolved in dichloromethane (20 mL). A precipitate was observed. The reaction was stirred at room temperature for 1 h. A 1 M aqueous solution of sodium hydroxide (3 mL) was added to this mixture. The solution was diluted in ethyl acetate (100 mL) and washed successively with 0.5 M aqueous solution of sodium bicarbonate and then 0.1 M aqueous solution of hydrochloric acid, water and brine. The organic phase was dried over magnesium sulfate, filtered and concentrated under reduced pressure to give a white solid corresponding to compound 95c (3.4 g, 91%). M.p. 105-107° C. ¹H NMR (600 MHz, CDCl₃) δ: 7.77 (m, 4H), 4.40 (q, J=8 Hz, 2H); ¹³C NMR (151 MHz, CDCl₃) δ: 134.1; 133.1; 130.3; 129.7; 122.0 (q, J=278 Hz); 65.0 (q, J=38 Hz); ¹⁹F NMR (564 MHz, CDCl₃) δ: −74.2 (t, ³J=7.0 Hz); HRMS (ESI+) calculated for $C_8H_6O_3SBrF_3Na$ [M+Na]⁺, m/z 340.9071. found: 340.9077. $R_f$=0.58 (silica; cyclohexane-ethyl acetate 8:2).

Compounds 96a-b

These compounds were prepared according to the same procedure as that used for compound 96c using the corresponding precursors.

Compound 96c

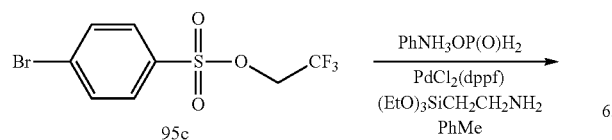

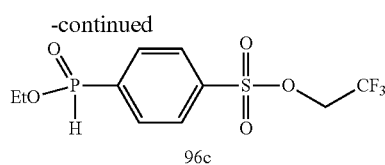

Compound 95c (1.6 g, 5 mmol) was added to a solution of anilinium hypophosphite (1 g, 6.3 mmol) in anhydrous toluene. Aminopropyltriethoxysilane (1.48 mL, 6.3 mmol) was added under inert atmosphere to this solution degassed with an argon stream for 30 min, and this solution was degassed again for an additional 30 min. Bis(Diphenylphosphino)ferrocene]palladium(II) chloride (220 mg, 0.2 mmol) was added to this solution, and the mixture was heated at 100° C. for 45 min. The progress of the reaction was monitored by phosphorus NMR. After this time, reaction was complete. The reaction mixture was cooled to room temperature and the solvent was removed under reduced pressure. 1 M hydrochloric acid solution (10 mL) was added to this residue. The aqueous phase was extracted with ethyl acetate (3×20 mL); the organic phases were combined, dried over magnesium sulfate, filtered and concentrated under reduced pressure to give an orange-colored oil corresponding to the expected compound 96c. The compound was sufficiently pure to be used in the next step without additional purification. ¹H NMR (600 MHz, CDCl₃) δ: 8.03 (m, 4H), 7.76 (d, J=576 Hz, 1H), 4.43 (q, ³J=10 Hz, 2H), 4.21 (m, 2H), 1.40 (t, ³J=7.0 Hz, 3H); ¹⁹F NMR (564 MHz, CDCl₃) δ: −74.2 (t, ³J=8 Hz); ³¹P NMR (242 MHz, CDCl₃) δ: +20.8; HRMS (ESI+) calculated for $C_{10}H_{13}O_5SF_3P$ [M+H]⁺, m/z 333.0173. found: 333.0167.

Compounds 97a-b

These compounds were prepared according to the same procedure as that used for compound 97c using the corresponding precursors.

Compound 97c

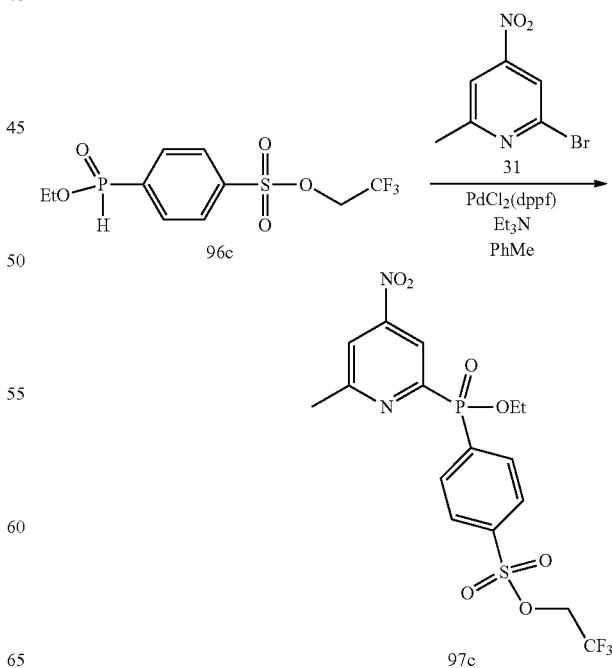

2-Bromo-6-methyl-4-nitropyridine 31 (1 g, 4.8 mmol) and freshly distilled triethylamine (2.3 mL, 16.8 mmol) were added to a solution of compound 96c (1.6 g, 4.8 mmol) in previously degassed toluene (40 mL). Bis(Diphenylphosphino)ferrocene]palladium(II) chloride (110 mg, 0.1 mmol) was added to this yellow solution, previously degassed with an argon stream for 30 min, and then the reaction mixture was heated at 120° C. for 2 h. In time, the color of the solution turned brown. The solution was cooled to room temperature and the solvent was removed under reduced pressure. The residue was purified by flash chromatography using an eluent gradient (hexane-acetate ethyl 1:3 to 1:1) to give a colorless oil corresponding to the expected compound 97c (0.9 g, 40%). $^1$H NMR (600 MHz, CDCl$_3$) δ: 8.63 (dd, J=6.5; 1.5 Hz, 1H), 8.24 (dd, J=11.5; 8.5 Hz, 2H), 8.02 (dd, J=8.5; 3 Hz, 2H), 7.79 (s, 1H), 4.42 (q, J=8 Hz, 2H), 4.27-4.09 (m, 2H), 2.74 (s, 3H), 1.40 (t, J=7 Hz, 3H); $^{13}$C NMR (151 MHz, CDCl$_3$) δ: 163.5 (d, J=21.5 Hz), 156.5 (d, J=171 Hz), 154.2 (d, J=13.5 Hz), 138.9 (d, J=3.5 Hz), 136.5 (d, J=138 Hz), 133.7 (d, J=10 Hz), 127.7 (d, J=13.5 Hz), 122.1 (q, J=281 Hz), 118.2; 118.0 (d, J=9 Hz), 64.8 (q, J=38.5 Hz), 62.9 (d, J=6.5 Hz), 24.8; 16.5 (d, J=6 Hz); $^{19}$F NMR (564 MHz, CDCl$_3$) −74.2 (t, J=7 Hz); $^{31}$P NMR (242 MHz, CDCl$_3$)+20.7; HRMS (ESI+) calculated for C$_{16}$H$_{17}$N$_2$O$_7$SF$_3$P [M+H]$^+$, m/z 469.0446. found: 469.0444. R$_f$=0.7 (silica; hexane-ethyl acetate 1:2).

Compounds 98a-b

These compounds were prepared according to the same procedure as that used for compound 98c using the corresponding precursors.

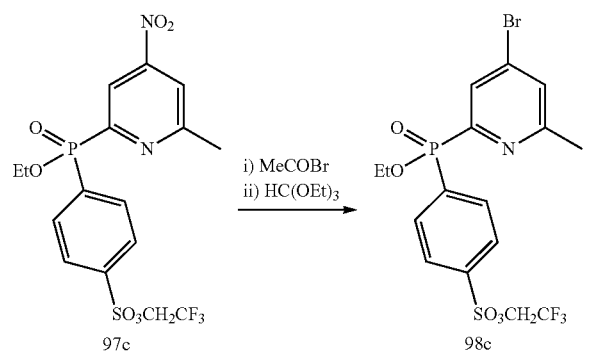

Compound 98c

Compound 97c (600 mg, 1.3 mmol) was added to a solution of acetyl bromide (3 mL, 39 mmol). The mixture was heated at 70° C. under inert atmosphere for 16 h. The brown-colored solution was cooled to room temperature and was then poured cautiously, with stirring, into methanol (30 mL) cooled to 0° C. beforehand. The solvent was removed under reduced pressure to give a slightly brown solid identified as the derivative of bromophosphinic acid. This compound, containing some unidentified impurities, was used in the rest of the synthesis without additional purification and assuming that the conversion to bromophosphinic acid derivative was quantitative. $^1$H NMR (600 MHz, CDCl$_3$) δ: 8.42 (d, J=7 Hz, 1H), 8.31 (s, 1H), 8.24 (dd, J=12.5, 8.5 Hz, 2H), 8.09 (dd, J=8.5, 2 Hz, 2H), 4.66 (q, J=8 Hz, 2H), 2.81 (s, 3H); $^{13}$C NMR (151 MHz, CDCl$_3$) δ: 158.0 (d, J=8 Hz), 151.0 (d, J=134 Hz), 143.5 (d, J=10.5 Hz), 138.9, 138.8 (d, J=155 Hz), 133.4, 133.3 (d, J=11 Hz), 131.5 (d, J=12 Hz), 128.0 (d, J=14 Hz), 122.2 (q, J=277 Hz), 65.1 (q, J=37.5 Hz), 19.0; $^{19}$F NMR (564 MHz, CDCl$_3$) −76.0 (t, J=7 Hz); $^{31}$P NMR (242 MHz, CDCl$_3$)+8.1. HRMS (ESI+) calculated for C$_{14}$H$_{13}$NO$_5$F$_3$PSBr [M+H]$^+$, m/z 473.9388. found: 473.9389. Triethylorthoformate (25 mL) was added to the bromophosphinic acid obtained previously (600 mg, 1.3 mmol) and the solution was heated at 140° C. for 16 h under inert atmosphere. After this period, the reaction mixture was cooled to room temperature and the solvent was removed under reduced pressure and the residue was purified by silica column flash chromatography using a dichloromethane-methanol (9:1) mixture of eluents to give the expected compound 98c as a yellowish oil (530 mg, 81%). $^1$H NMR (600 MHz, CDCl$_3$) δ: 8.22 (dd, J=11.5, 8.5 Hz, 2H), 8.11 (dd, J=6.5; 1.5 Hz, 1H), 8.00 (dd, J=8.5, 3 Hz, 2H), 7.45 (s, 1H), 4.40 (q, J=8 Hz, 2H), 4.23-4.08 (m, 2H), 2.54 (s, 3H), 1.37 (t, J=7.0 Hz, 3H); $^{13}$C NMR (151 MHz, CDCl$_3$) δ: 161.3 (d, J=22 Hz), 153.8 (d, J=169 Hz), 138.5 (d, J=3 Hz), 137.3 (d, J=136 Hz), 133.7, 133.6 (d, J=10 Hz), 129.2 (d, J=3 Hz), 129.0 (d, J=24 Hz), 127.5 (d, J=13 Hz), 121.7 (q, J=278 Hz), 64.8 (q, J=38.5 Hz), 62.6 (d, J=6.5 Hz), 24.3, 16.4 (d, J=6.5 Hz); $^{19}$F NMR (564 MHz, CDCl$_3$) δ: −74.2 (t, J=7 Hz); $^{31}$P NMR (242 MHz, CDCl$_3$) δ: +21.5; HRMS (ESI+) calculated for C$_{16}$H$_{17}$NO$_5$F$_3$PSBr [M+H]$^+$, m/z 501.9701. found: 501.9690. R$_f$=0.50 (silica; dichloromethane-methanol 96:4).

Compounds 99a-b

These compounds were prepared according to the same procedure as that used for compound 99c using the corresponding precursors.

Compound 99c

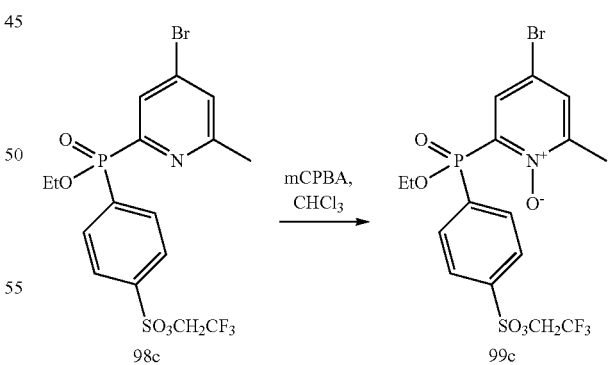

3-Chloroperbenzoic acid (365 mg, 2 mmol) was added to a solution of compound 98c (530 mg, 1 mmol) in chloroform (15 mL) 365 mg, 2 mmol) and the mixture was heated at 65° C. for 16 h. The solution was then cooled to room temperature and the solvent was removed under reduced pressure. The residue was dissolved in dichloromethane (15 mL) and washed with aqueous solution of sodium bicarbonate (0.5

M, 10 mL). The aqueous phase was extracted with dichloromethane (3×10 mL) and the organic phases were combined, dried over magnesium sulfate, filtered and then concentrated under reduced pressure to give a yellow oil identified as compound 99c (475 mg, 91%). $^1$H NMR (600 MHz, CDCl$_3$) δ: 8.25 (dd, $^3J$=13, 8.5 Hz, 2H), 8.12 (dd, $^3J$=8 Hz, $^4J$=3 Hz, 1H), 7.99 (dd, $^3J$=8.5 Hz, $^4J$=3 Hz, 2H), 7.55 (d, $^5J$=2.5 Hz, 1H), 4.40 (q, $^3J$=8 Hz, 2H), 4.26-4.16 (m, 2H), 2.37 (s, 3H), 1.40 (t, $^3J$=7.0 Hz, 3H); $^{13}$C NMR (151 MHz, CDCl$_3$) δ: 150.9, 142.8 (d, J=153 Hz), 138.7, 136.3 (d, J=151 Hz), 134.2 (d, J=11.5 Hz), 133.2 (d, J=11 Hz), 132.7, 127.4 (d, J=14.5 Hz), 124.1, 121.6 (q, J=274 Hz), 64.8 (q, J=38.5 Hz), 63.0 (d, J=6 Hz), 17.2, 16.5 (d, J=6 Hz); $^{19}$F NMR (564 MHz, CDCl$_3$) δ: −74.2 (t, $^3J$=8 Hz); $^{31}$P NMR (242 MHz, CDCl$_3$) δ: +17.2; HRMS (ESI+) calculated for C$_{16}$H$_{17}$NO$_6$F$_3$PSBr [M+H]$^+$, m/z 517.9650. found: 517.9650 R$_f$=0.49 (silica; dichloromethane-methanol 96:4).
Compounds 100a-b These compounds were prepared according to the same procedure as that used for compound 100c using the corresponding precursors.
Compound 100c under reduced pressure. The resultant aqueous solution was extracted with dichloromethane (3×30 mL). The organic phases were combined, dried over magnesium sulfate, filtered and concentrated under reduced pressure to give a colorless oil identified as compound 100c (430 mg, 91%). $^1$H NMR (600 MHz, CDCl$_3$) δ: 8.19-8.13 (m, 3H), 8.00 (dd, $^3J$=8.5 Hz, $^4J$=2.5 Hz, 2H), 7.72 (s, 1H), 6.83 (bs, 1H), 4.76 (s, 2H), 4.41 (q, $^3J$=8 Hz, 2H), 4.29-4.04 (m, 2H), 1.37 (t, $^3J$=7 Hz, 3H); $^{13}$C NMR (151 MHz, CDCl$_3$) δ: 163.1 (d, J=20.5 Hz), 152.8 (d, J=169 Hz), 139.0 (d, J=3 Hz), 136.2 (d, J=138.5 Hz), 134.6 (d, J=15 Hz), 133.5 (d, J=10.5 Hz), 130.3 (d, =23.5 Hz), 127.8 (d, J=13.5 Hz), 126.8 (d, J=3 Hz), 122.8 (q, J=274 Hz), 64.9 (q, J=38.5 Hz), 64.0, 63.2 (d, J=6.5 Hz), 16.4 (d, J=6 Hz); $^{19}$F NMR (564 MHz, CDCl$_3$) δ: −74.2 (t, $^3J$=8 Hz); $^{31}$P NMR (242 MHz, CDCl$_3$) δ: +22.1; HRMS (ESI+) calculated for C$_{16}$H$_{17}$NO$_6$F$_3$PSBr [M+H]$^+$, m/z 517.9650. found: 517.9647 R$_f$=0.56 (silica; dichloromethane-methanol 96:4).
Compounds 101a-b These compounds were prepared according to the same procedure as that used for compound 101c using the corresponding precursors.
Compound 101c

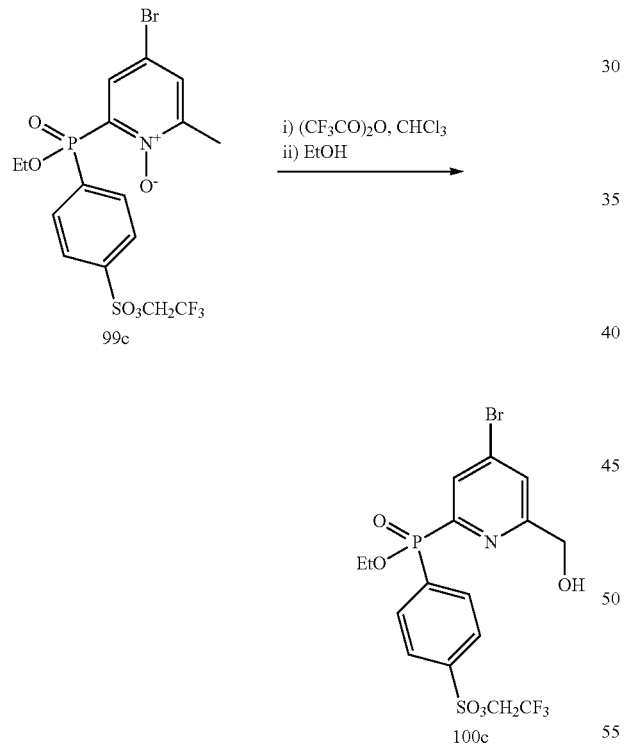

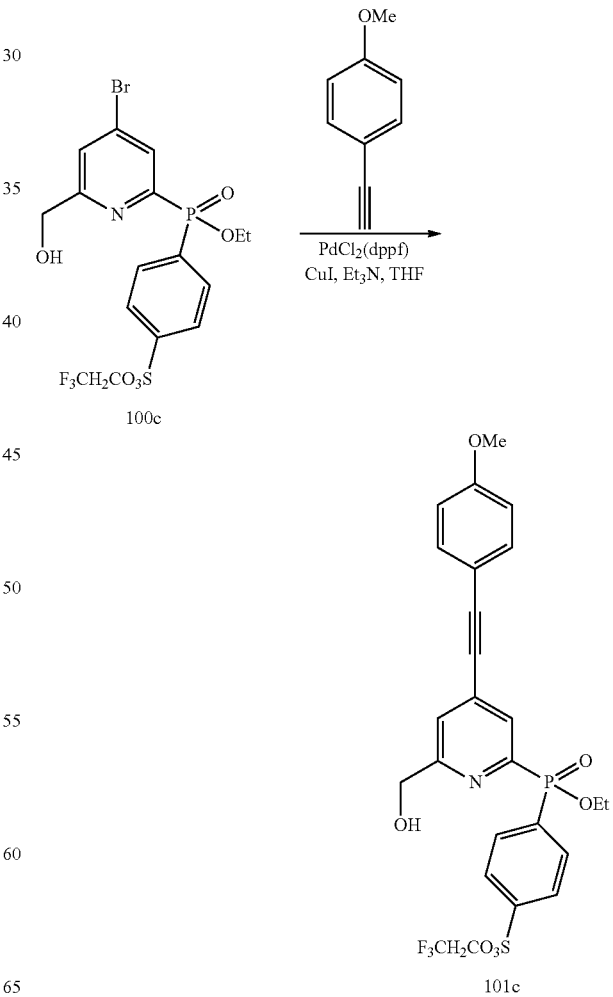

Trifluoroacetic anhydride (2.5 mL) was added to a solution of compound 99c (475 mg, 0.91 mmol) in anhydrous chloroform (20 mL). The reaction mixture was heated at 60° C. for 3 h under argon and then cooled to room temperature. The solvent was removed under reduced pressure to give an oil, which was dissolved in ethanol-water mixture (1/1, v/v), (30 mL). The solution was stirred at room temperature for 1 h and then the volume of the solution was reduced to 15 mL 4-Ethynylanisole (76 mg, 0.56 mmol) and triethylamine (1 mL) were added to a solution of compound 100c (200 mg, 0.39 mmol) dissolved in anhydrous tetrahydrofuran (2.5 mL) previously degassed under an argon stream. The mixture was degassed again and then bis(diphenylphosphino)ferrocene]palladium(II) chloride (45 mg, 0.04 mmol) and copper iodide (7 mg, 0.04 mmol) were added to this mixture. The mixture was heated at 65° C. under argon for 16 h and was then cooled to room temperature and concentrated under reduced pressure. The crude product was purified by silica column chromatography using a solvent gradient (dichloromethane-methanol 100/0 to 98/2 in increments of 0.2%) to give an orange-colored oil identified as compound 101c (153 mg, 69%) $^1$H NMR (600 MHz, CDCl$_3$) δ: 8.19 (d, $^3$J=8.5 Hz, 2H), 8.10 (s, 1H), 8.01 (d, $^3$J=7 Hz, 2H), 7.47 (m, 3H), 6.90 (d, $^3$J=8.5 Hz, 2H), 4.78 (s, 2H), 4.40 (q, $^3$J=7.5 Hz, 2H), 4.17 (m, 2H), 3.84 (s, 3H), 3.52 (bs, 1H), 1.39 (t, $^3$J=6.5 Hz, 3H); $^{13}$C NMR (151 MHz, CDCl$_3$) δ: 161.2, 160.7, 151.0 (d, J=183 Hz), 138.6, 137.4 (d, J=136 Hz), 133.7, 133.5, 133.4 (d, J=9 Hz), 128.9, 127.7 (d, J=12.5 Hz), 124.4, 121.7 (q, J=327 Hz), 114.3, 113.5, 96.7, 85.0, 64.9 (q, J=38 Hz), 64.1, 62.6, 55.4, 16.5; $^{19}$F NMR (564 MHz, CDCl$_3$) δ: −74.2 (t, J=8 Hz); $^{31}$P NMR (242 MHz, CDCl$_3$) δ: +22.5; HRMS (ESI+) calculated for C$_{25}$H$_{24}$NO$_7$F$_3$PS [M+H]$^+$, m/z 570.0963. found: 570.0973. R$_f$=0.61 (silica; dichloromethane-methanol 95:5).

Compounds 102a-b

These compounds were prepared according to the same procedure as that used for compound 102c using the corresponding precursors.

Compound 102c

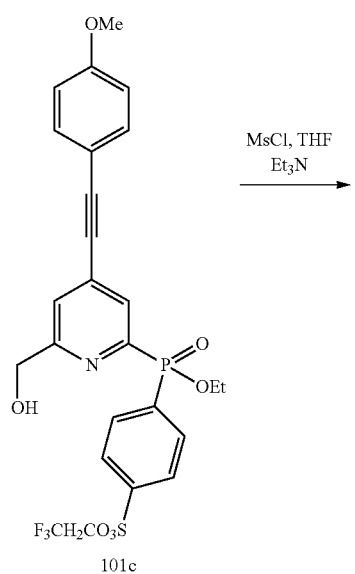

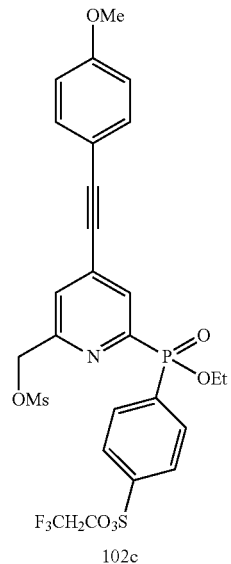

Triethylamine (0.7 mL, 0.5 mmol) was added to a solution of compound 101c (93 mg, 0.16 mmol) in anhydrous tetrahydrofuran (4 mL). The mixture was cooled to 5° C. and then methanesulfonyl chloride (19 μL, 0.24 mmol) was added to this solution, and then the solution was stirred for 30 min at the same temperature. The solvent was removed under reduced pressure, then the residue was dissolved in dichloromethane (15 mL) and the solution was washed with saturated aqueous solution of sodium chloride (10 mL). The aqueous phase was extracted again with dichloromethane (3×10 mL) and then the organic phases were combined, dried over magnesium sulfate, filtered and concentrated under reduced pressure to give a colorless oil corresponding to compound 102c (95 mg, 92%). $^1$H NMR (600 MHz, CDCl$_3$) δ: 8.22 (dd, $^3$J=11.5, 8.5 Hz, 2H), 8.17 (d, $^3$J=6.5 Hz, 1H), 8.02 (dd, $^3$J=8.5 Hz, $^4$J=2.5 Hz, 2H), 7.62 (s, 1H), 7.50 (d, $^3$J=9 Hz, 2H), 6.91 (d, $^3$J=9 Hz, 2H), 5.32 (m, 2H), 4.42 (q, $^3$J=8 Hz, 2H), 4.18 (m, 2H), 3.85 (s, 3H), 3.08 (s, 3H), 1.40 (t, $^3$J=7 Hz, 3H); $^{19}$F NMR (564 MHz, CDCl$_3$) δ: −74.1 (t, J=8 Hz); $^{31}$P NMR (242 MHz, CDCl$_3$) δ: +21.9; HRMS (ESI+) calculated for C$_{26}$H$_{26}$NO$_9$F$_3$PS$_2$ [M+H]$^+$, m/z 648.0739. found: 648.0728. R$_f$=0.75 (silica; dichloromethane-methanol 95:5).

Compounds 103a-b

These compounds were prepared according to the same procedure as that used for compound 103c using the corresponding precursors.

Compound 103c

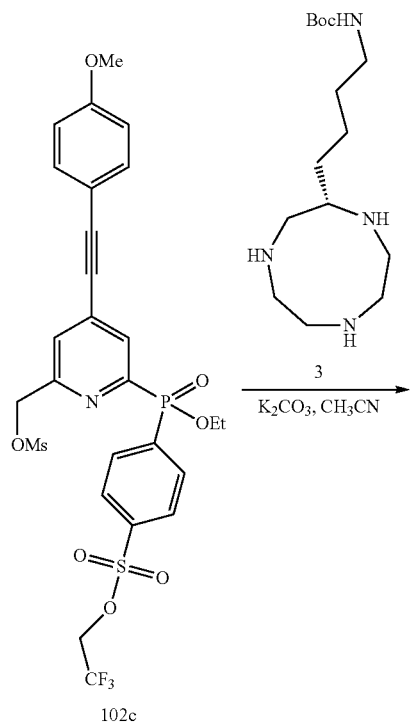

Compound 102c (95 mg, 0.15 mmol) and potassium carbonate (21 mg, 0.15 mmol) were added to a solution of macrocycle 3 (15 mg, 0.05 mmol) in anhydrous acetonitrile (2 mL). The mixture was heated at 60° C. for 16 h and was then cooled to room temperature. The suspended salts were decanted and then separated from the solution, which was then concentrated under reduced pressure. The residue was purified by preparative HPLC to give a yellow oil identified as compound 103c (32 mg, 33%). $^1$H NMR (600 MHz, CDCl$_3$) δ: 8.18 (m, 6H), 8.04 (m, 3H), 7.96 (m, 6H), 7.48 (m, 3H), 7.44 (m, 6H), 6.88 (m, 6H), 5.08 (bs, 1H), 4.40 (q, J=7.5 Hz, 6H), 4.14 (m, 6H), 3.83 (m, 15H), 3.00-2.56 (m, 13H), 1.38 (s, 9H), 1.45-1.30 (m, 6H), 1.35 (m, 9H); $^{19}$F NMR (564 MHz, CDCl$_3$) δ: −74.2 (t, J=8 Hz); $^{31}$P NMR (242 MHz, CDCl$_3$) δ: +22.6; HRMS (ESI+) calculated for C$_{90}$H$_{97}$N$_7$O$_{20}$F$_9$P$_3$S$_3$ [M+2H]$^{2+}$, m/z 977.7510. found: 977.7515.

Compounds 104a-b

These compounds were prepared according to the same procedure as that used for compound 104c using the corresponding precursors.

Compound 104c

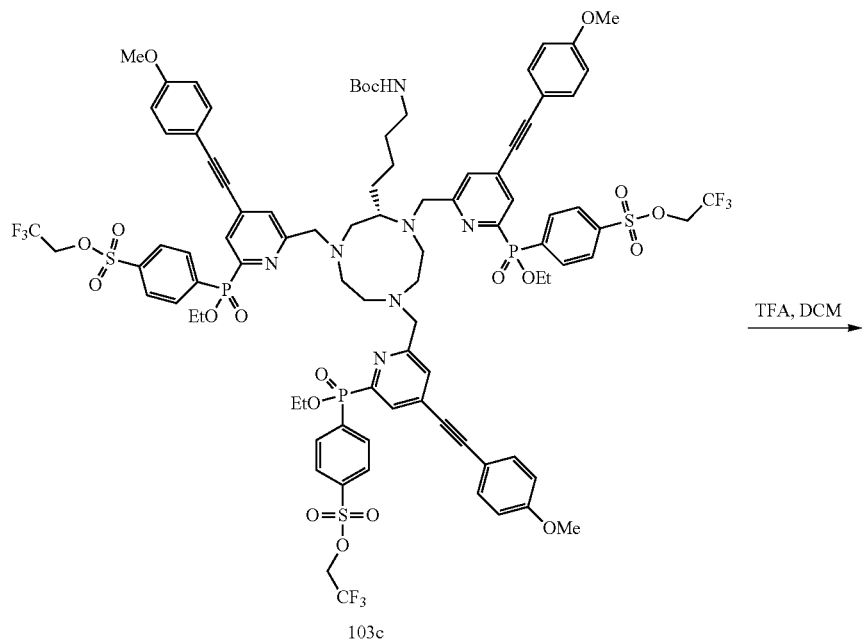

103c

TFA, DCM →

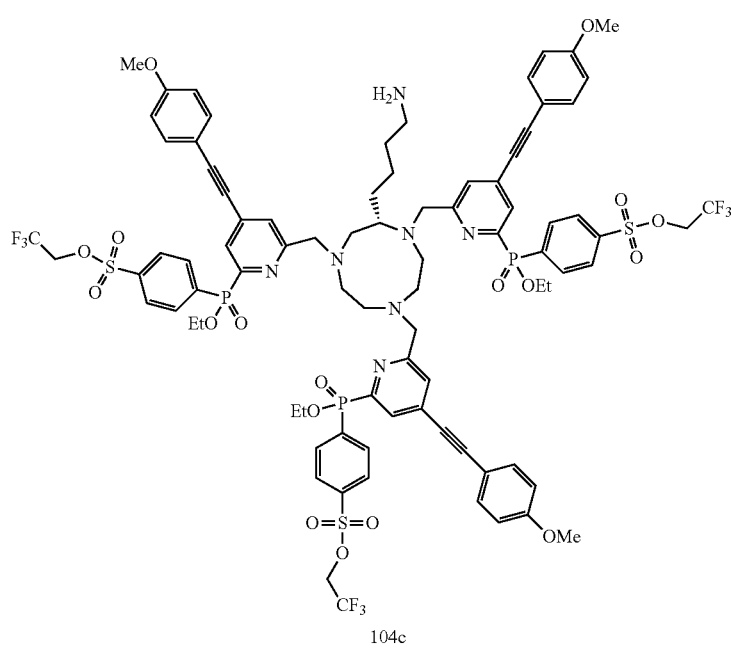

104c

Trifluoroacetic acid (0.2 mL) was added to a solution of compound 103c (30 mg, 15 µmol) in dichloromethane (1.8 mL) previously degassed with an argon stream for 10 min. The solution was stirred at room temperature for 20 min and then the solvent was removed under reduced pressure to give yellow oil identified as compound 104c (16 mg, 60%). $^1$H NMR (600 MHz, CD$_3$OD) δ: 8.11 (m, 6H), 8.04 (m, 3H), 8.01 (m, 6H), 7.61 (m, 3H), 7.57 (m, 6H), 6.93 (m, 6H), 4.65 (m, 6H), 4.17 (m, 6H), 3.96 (m, 15H), 3.82-3.60 (m, 13H), 1.61-1.47 (m, 6H), 1.46 (m, 9H); $^{19}$F NMR (564 MHz, CD$_3$OD) δ: −76.0; $^{31}$P NMR (242 MHz, CD$_3$OD) δ: +23.6; HRMS (ESI+) calculated for C$_{85}$H$_{88}$N$_7$O$_{18}$F$_9$P$_3$S$_3$ [M+H]$^+$, m/z 1854.4420. found: 1854.4370.

Compounds 105a-b

These compounds were prepared according to the same procedure as that used for compound 105c using the corresponding precursors.

Compound 105c

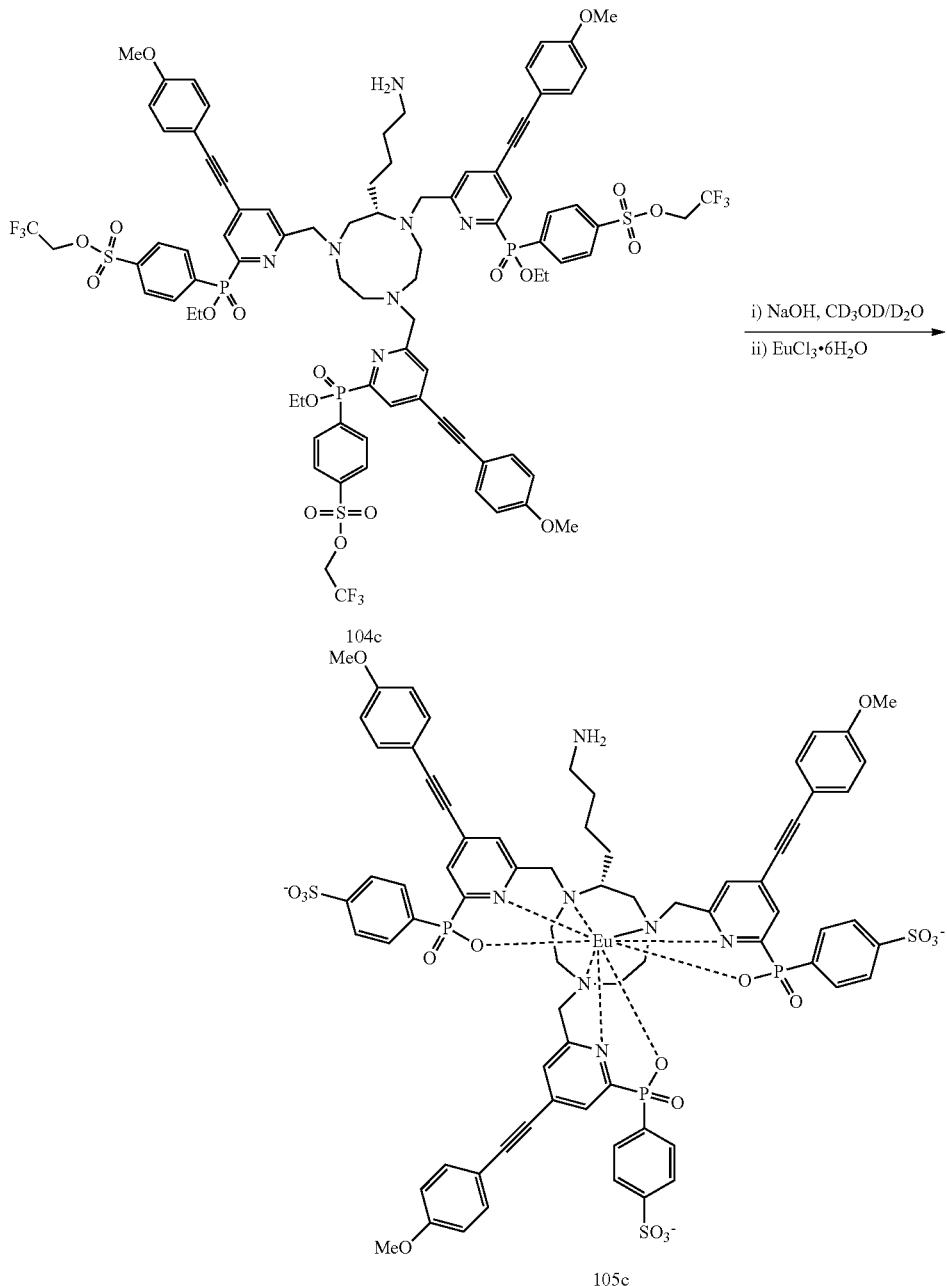

Deuterated aqueous solution of sodium hydroxide (0.1 M, 0.5 mL) was added to a solution of compound 104c (5 mg, 2.7 μmol) in deuterated methanol (1 mL). The mixture was heated at 60° C. for 3 h and then cooled to room temperature. The pH of the solution was adjusted to 7 by adding hydrochloric acid. Europium chloride hexahydrate (1 mg, 2.7 μmol) was added to this mixture and then the solution was heated at 65° C. for 18 h under inert atmosphere. After this time, the reaction mixture was cooled to room temperature and the solvent was removed under reduced pressure. The crude product was purified by preparative HPLC to give compound 105c (2.8 mg, 63%); HRMS (ESI+) calculated for $C_{73}H_{68}N_7O_{18}P_3S_3Eu$ [M+H]$^+$, m/z 1671.2380. found: 1671.2370.

Compounds 107a-b

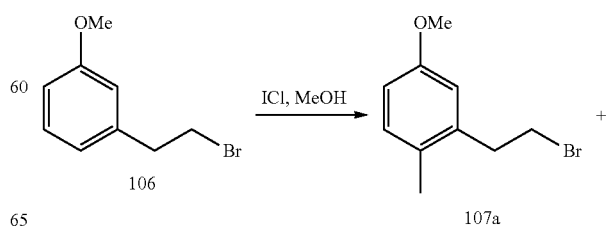

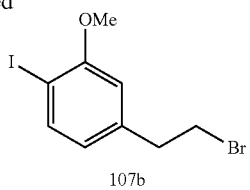

Iodine chloride (1.5 g, 9.2 mmol) was added to a solution of 2-bromo-5-methoxyphenethyl bromide 106 (1 g, 4.6 mmol) in methanol (20 mL). The reaction mixture was stirred at room temperature. After 4 h, reaction was complete. The unreacted iodine chloride was removed by a redox reaction by adding a solution of sodium metabisulfite at 10 wt % (40 mL). The solvents were evaporated under reduced pressure. The residue was solubilized in dichloromethane (30 mL). This solution was washed with a solution of sodium metabisulfite at 10 wt % (2×50 mL). The organic phase was dried over magnesium sulfate, filtered and evaporated under reduced pressure. The crude product was purified by silica column flash chromatography (cyclohexane/ethyl acetate from 0 to 50% in increments of 5%) to obtain a yellowish oil corresponding to the mixture of compound 107a and 107b in 8/2 ratio (1.22 g, 78%). 107a: $^1$H NMR (400 MHz, DMSO-$d_6$) δ: 7.70 (d, J=8.7 Hz, 1H), 7.02 (d, J=3.0 Hz, 1H), 6.66 (dd, J=8.7; 3.0 Hz, 1H), 3.74 (s, 3H), 3.65 (t, J=7.6 Hz, 2H), 3.17 (t, J=7.6 Hz, 2H); $^{13}$C NMR (100 MHz, DMSO-$d_6$) δ: 160.08, 142.67, 140.08, 116.87, 115.50, 89.58, 55.76, 43.43, 32.77. HRMS (ESI+) calculated for $C_9H_{14}BrINO$ [M+NH$_4$]$^+$, m/z: 357.9303 found: 357.9300. $R_f$=0.67 (silica; cyclohexane-ethyl acetate 1:1).

107b: $^1$H NMR (400 MHz, DMSO-$d_6$) δ: 7.67 (d, J=7.9 Hz, 1H), 6.96 (d, J=3.0 Hz, 1H), 6.66 (dd, J=7.9; 3.0 Hz, 1H), 3.82 (s, 3H), 3.74 (t, J=7.6 Hz, 2H), 3.10 (t, J=7.6 Hz, 2H).

Compounds 108a-b

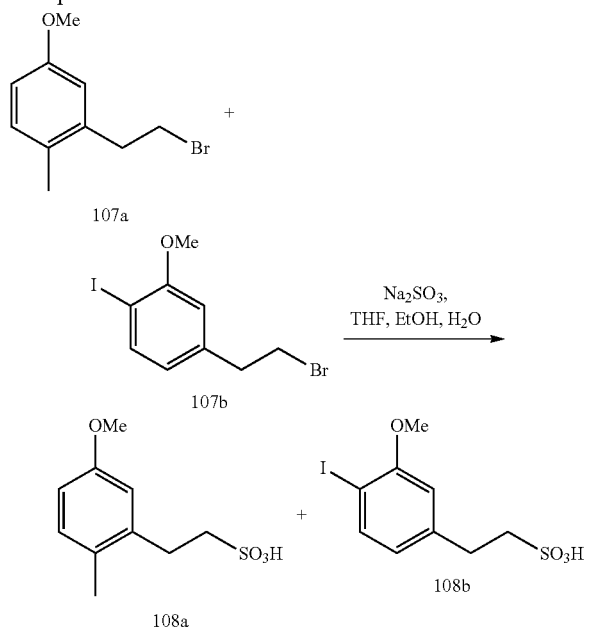

Sodium sulfite (0.93 g, 7.4 mmol) was added to a solution of iodo-5-methoxyphenethyl bromide 107a-b (1.4 g, 4.1 mmol) in a tetrahydrofuran/ethanol/water mixture in proportions 1/2/2 (150 mL). The reaction mixture was heated under reflux with magnetic stirring. After 18 h, reaction was complete. The reaction mixture was cooled to room temperature and the solvents were evaporated under reduced pressure. The crude reaction product was solubilized in methanol (100 mL), brought to the boil, and filtered hot. The filtrate was cooled to room temperature, evaporated under reduced pressure and recrystallized from methanol (50 mL) to give a white solid corresponding to the mixture of compounds 108a and 108b in 8/2 ratio (1.06 g, 71%). M.p.=282° C. (dec.). 108a: $^1$H NMR (400 MHz, DMSO-$d_6$) δ: 7.65 (d, J=8.7 Hz, 1H), 6.86 (d, J=3.0 Hz), 6.58 (dd, J=8.7; 3.0 Hz), 3.73 (s, 3H), 2.94-2.89 (m, 2H), 2.67-2.62 (m, 2H); $^{13}$C NMR (400 MHz, DMSO-$d_6$) δ: 159.67, 144.39, 139.47, 115.24, 114.36, 88.86, 55.17, 51.26, 36.57. HRMS (ESI+) calculated for $C_9H_{15}INO_4S$ [M+NH$_4$]$^+$, m/z: 359.9766 found: 359.9763. $R_f$=0.52 (silica; dichloromethane-methanol-triethylamine 85:10:5).

108b: $^1$H NMR (400 MHz, DMSO-$d_6$) δ: 7.60 (d, J=8.7 Hz, 1H), 6.86 (d, J=3.0 Hz), 6.60 (dd, J=8.7; 3.0 Hz), 3.81 (s, 3H), 2.87-2.83 (m, 2H), 2.71-2.68 (m, 2H); $^{13}$C NMR (400 MHz, DMSO-$d_6$) δ: 157.57, 143.33, 138.57, 123.53, 111.86, 82.58, 56.17, 52.61, 31.35.

Compounds 109a-b

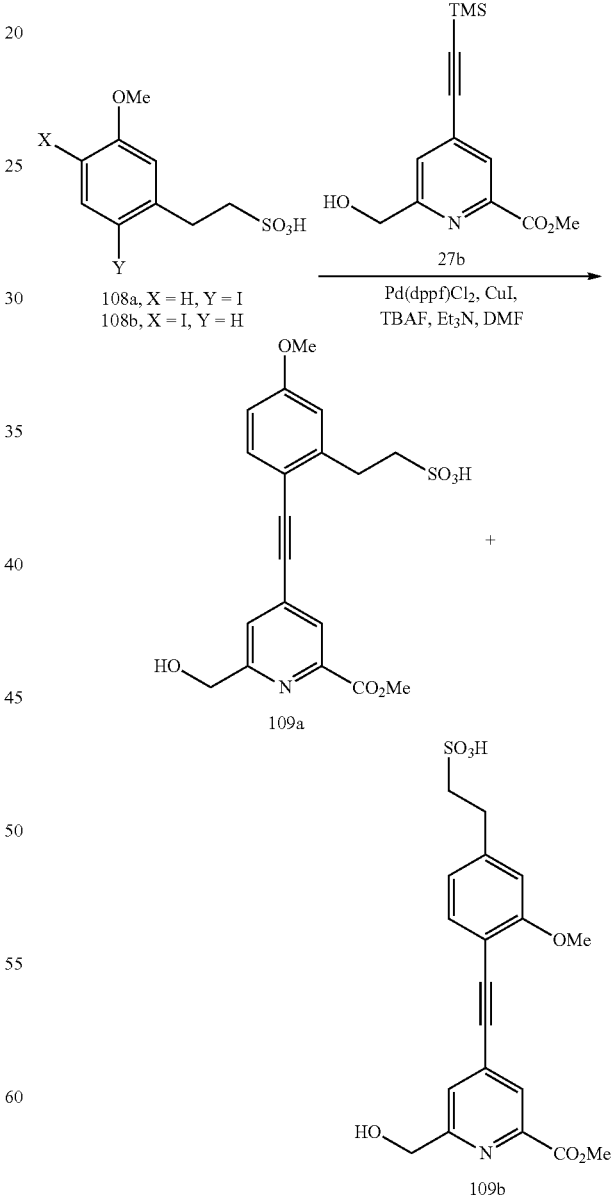

Acetylene derivative 27b (263 mg, 1 mmol) and triethylamine (12.5 mL) were added under inert atmosphere to a solution of sulfonated derivative 108a-b (1 mmol) in anhydrous dimethylformamide (25 mL). The mixture was degassed for 15 min by means of an argon stream. Then [1,1-bis(diphenylphosphino)ferrocene]dichloropalladium (II) (73.2 mg, 0.1 mmol) and copper iodide (38 mg, 0.2 mmol) were added. The reaction was heated at 75° C., with magnetic stirring, in a closed reactor, away from the light. After 4 h, reaction was complete. The reaction mixture was cooled to room temperature and the solvent was evaporated under reduced pressure. The residue was solubilized in methanol (30 mL) and calcium carbonate (200 mg, 2 mmol) was added to this solution. The mixture was stirred at room temperature for 15 min. The solution was eluted with methanol (3×50 mL) on a cartridge of cation exchange resin Porapak™Rxn CX. The fractions were combined, and the solvent was evaporated under reduced pressure. The residue was purified by preparative HPLC, separating the two isomers 109a and 109b in the form of white solids M.p.=218-221° C. 109a (77%): $^1$H NMR (400 MHz, DMSO-d$_6$) δ: 8.01 (s, 1H), 7.83 (s, 1H), 7.55 (d, J=8.5 Hz), 6.95 (d, J=2.2 Hz), 6.86 (dd, J=8.5; 2.2 Hz), 4.61 (s, 2H), 3.89 (s, 3H), 3.80 (s, 3H), 3.16-3.11 (m, 2H), 2.79-2.75 (m, 2H); $^{13}$C NMR (100 MHz, DMSO-d$_6$) δ: 164.67, 162.90, 160.51, 146.86, 145.53, 134.21, 132.76, 124.91, 124.20, 114.68, 112.47, 112.33, 93.60, 89.06, 63.70, 55.30, 51.93, 30.53. HRMS (ESI+) calculated for C$_{19}$H$_{20}$NO$_7$S [M+H]$^+$, m/z: 406.0960 found: 406.0954. R$_f$=0.45 (silica; dichloromethane-methanol-triethylamine 85:10:5).

109b (11%): $^1$H NMR (400 MHz, DMSO-d$_6$) δ: 7.90 (s, 1H), 7.72 (s, 1H), 7.47 (d, J=8.5 Hz), 7.02 (d, J=2.2 Hz), 6.87 (dd, J=8.5; 2.2 Hz), 4.64 (s, 2H), 3.90 (s, 3H), 3.89 (s, 3H), 2.96-2.91 (m, 2H), 2.75-2.71 (m, 2H).

Compound 110a

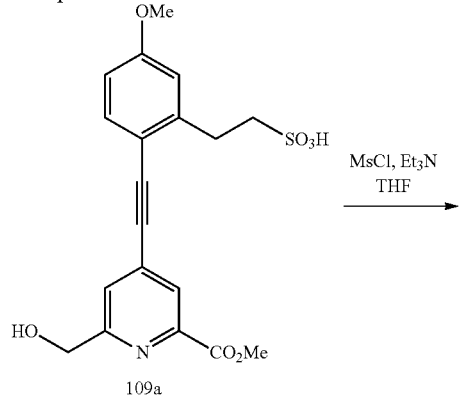

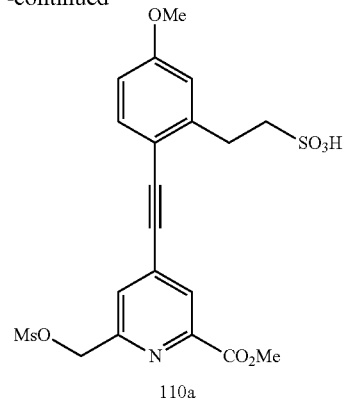

Triethylamine (102 mg, 140 μL, 1 mmol) and mesyl chloride (58.6 mg, 40 μL, 0.51 mmol) were added, under inert atmosphere and at 5° C., to a solution of alcohol derivative 109a (90 mg, 0.22 mmol) in anhydrous tetrahydrofuran (10 mL). The reaction was stirred at room temperature. After 10 min, reaction was complete. The solvent was evaporated under reduced pressure. The crude reaction product was purified by preparative HPLC to give a white solid corresponding to compound 110a (88 mg, 84%). M.p.=143-145° C. $^1$H NMR (400 MHz, DMSO-d$_6$) δ: 8.12 (s, 1H), 8.02 (s, 1H), 7.55 (d, J=8.5 Hz), 6.96 (d, J=2.5 Hz), 6.86 (dd, J=8.5; 2.5 Hz), 5.36 (s, 2H), 3.91 (s, 3H), 3.80 (s, 3H), 3.40 (s, 3H), 3.16-3.06 (m, 2H), 2.78-2.74 (m, 2H); $^{13}$C NMR (100 MHz, DMSO-d$_6$) δ: 164.89, 161.15, 155.25, 148.17, 146.60, 134.64, 133.85, 127.63, 125.96, 115.32, 112.92, 112.65, 94.98, 89.23, 71.09, 55.82, 53.14, 52.62, 37.77, 31.41. HRMS (ESI+) calculated for C$_{20}$H$_{22}$NO$_9$S$_2$ [M+H]$^+$, m/z: 484.0736 found: 484.0733. R$_f$=0.26 (silica; dichloromethane-methanol 9:1).

Compound 111a

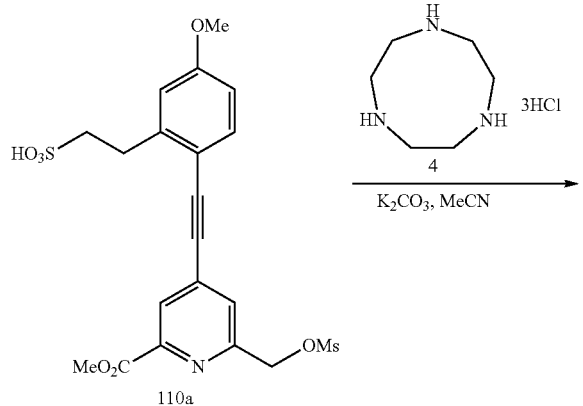

-continued

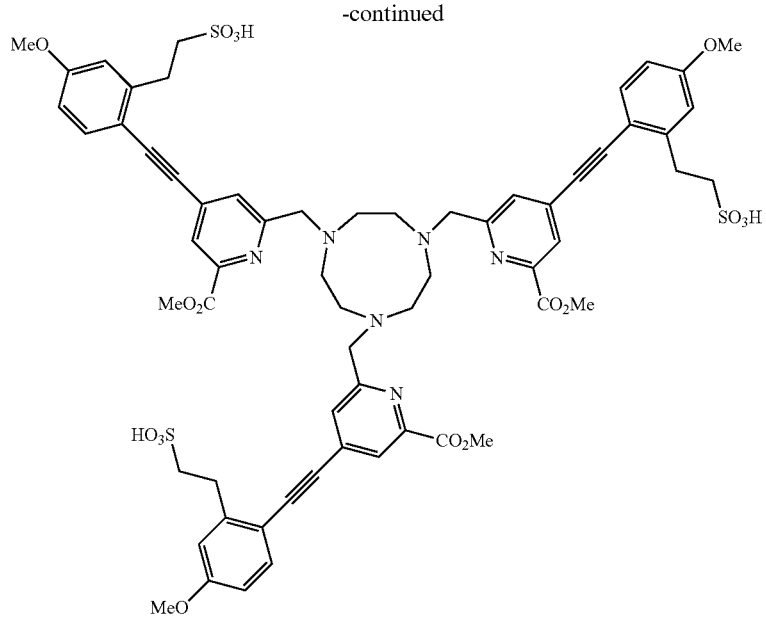

111a

Potassium carbonate (30 mg, 216 mol) was added, under inert atmosphere, to a solution of TACN in hydrochloride form 4 (8.6 mg, 36 mol) in anhydrous acetonitrile (4 mL). The reaction mixture was heated at 65° C. for 2 h, with vigorous magnetic stirring, and then the mesylated derivative 110a (69.7 mg, 144 mol) was added. After 5 h, reaction was complete. The solvent was evaporated under reduced pressure. The crude product was purified by preparative HPLC to give a white solid corresponding to compound 111a (27 mg, 58%). HRMS (ESI+) calculated for $C_{63}H_{68}N_6O_{18}S_3$ $[M+2H]^{2+}$, m/z: 646.1876. found: 646.1870.

Compound 112a

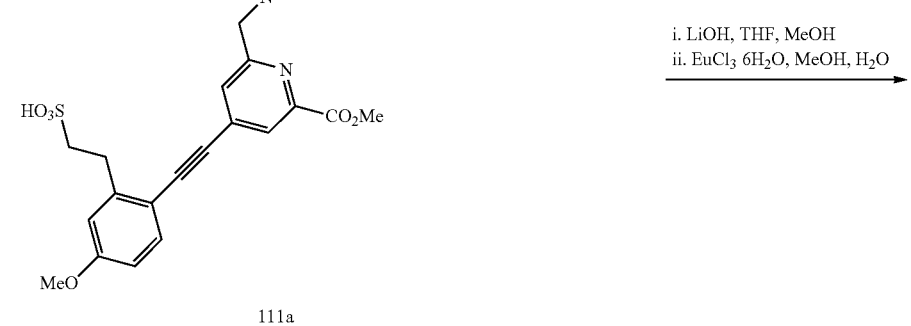

111a i. LiOH, THF, MeOH
ii. EuCl$_3$ 6H$_2$O, MeOH, H$_2$O

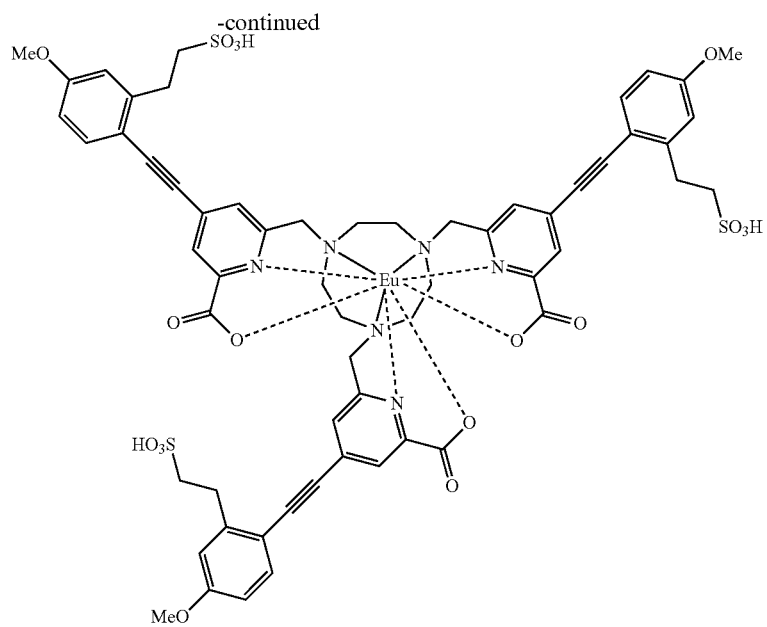

112a

A 1 M aqueous solution of lithium hydroxide (0.5 mL) was added to a solution of ligand 111a (5.8 mg, 4.5 mol) in tetrahydrofuran (1 mL). The mixture was stirred magnetically at room temperature. After 20 min, reaction was complete. The solvent was evaporated under reduced pressure and then the crude reaction product was solubilized in a mixture of methanol (1.5 mL) and pure water (1 mL). The pH of the mixture was neutralized (pH 7) by adding 1 M hydrochloric acid solution, and europium chloride hexahydrate (1.8 mg, 4.95 µmol) was added. The reaction was stirred magnetically at room temperature. After 1 h, reaction was complete. The solvent was evaporated under reduced pressure. The crude product was solubilized with a buffer solution of triethylammonium acetate pH 7 (4 mL), and then was purified by preparative HPLC. The solvent of the fractions collected was evaporated under reduced pressure. The residual triethylammonium acetate buffer was removed by successive co-evaporations using methanol/toluene mixture 1/4 (3×6 mL) to give a white solid corresponding to complex 112a (2.4 µmol, 53%). HRMS (ESI+) calculated for $C_{60}H_{59}EuN_6O_{18}S_3$ $[M+2H]^{2+}$, m/z=700.1130 found 700.1122.

Compound 113

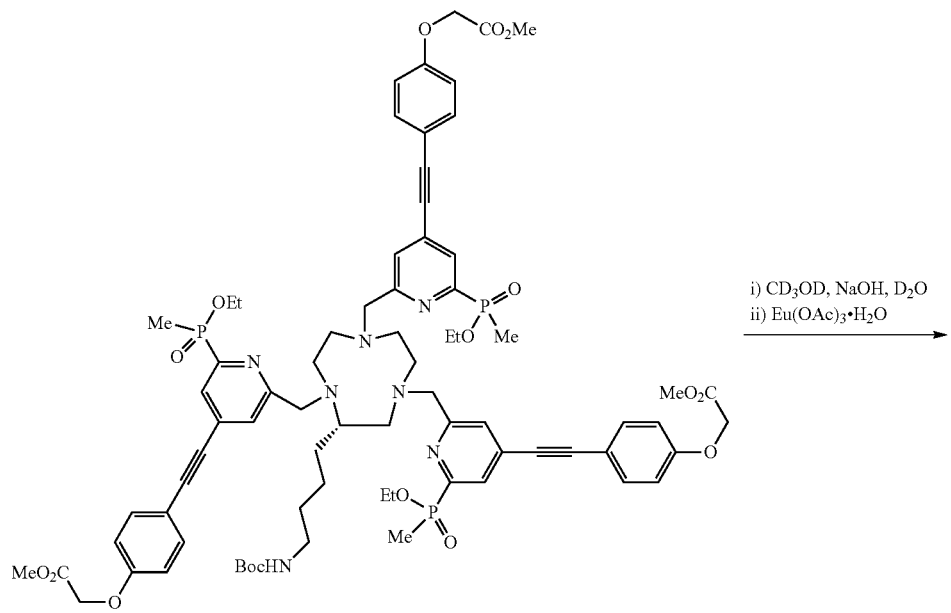

60i

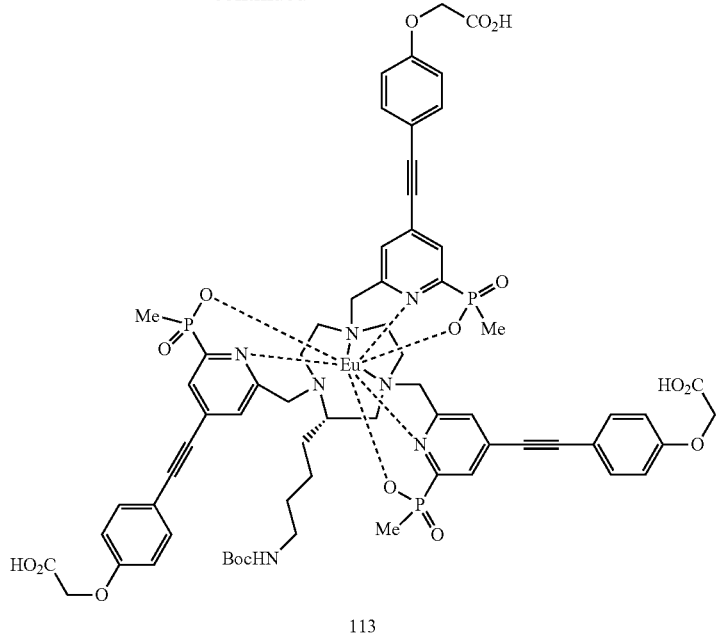

113

Deuterated aqueous solution of sodium hydroxide (0.1 M, 1 mL) was added to a solution of compound 60i (10 mg, 6.8 μmol) in deuterated methanol (2 mL). The mixture was heated at 60° C. for 5 h and then cooled to room temperature. The pH of the solution was adjusted to 7 by adding hydrochloric acid. Europium acetate hydrate (1.8 mg, 5.7 μmol) was added to this mixture, and then the solution was heated at 65° C. for 18 h under inert atmosphere. After this time, the reaction mixture was cooled to room temperature and the solvent was removed under reduced pressure. The crude product was purified by preparative HPLC to give compound 113 as a white solid (6 mg, 59%); LRMS (ESI+) calculated for $C_{68}H_{77}N_7O_{17}P_3Eu$ $[M+2H]^{2+}$, m/z 754.6900 found: 754.6905.

Compound 114

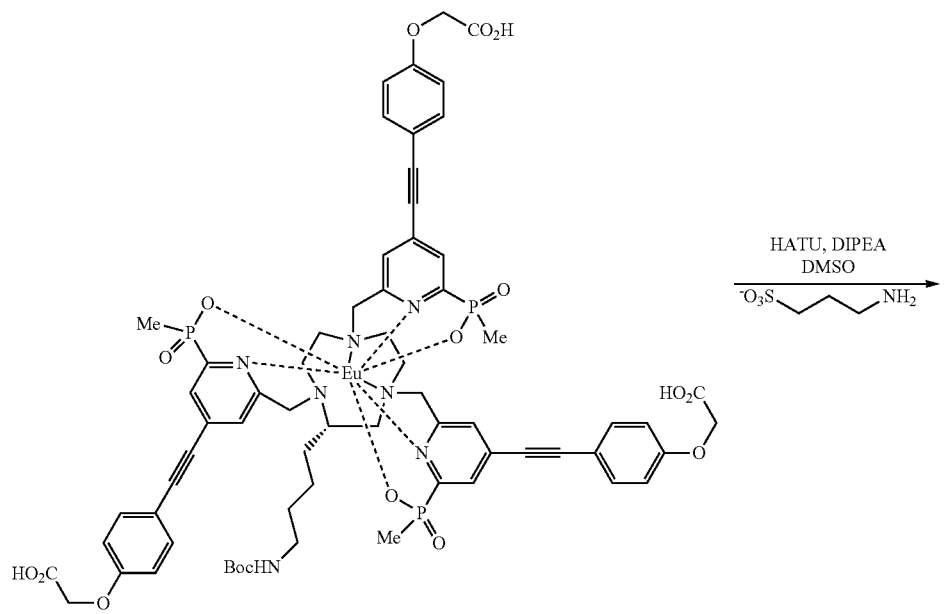

113

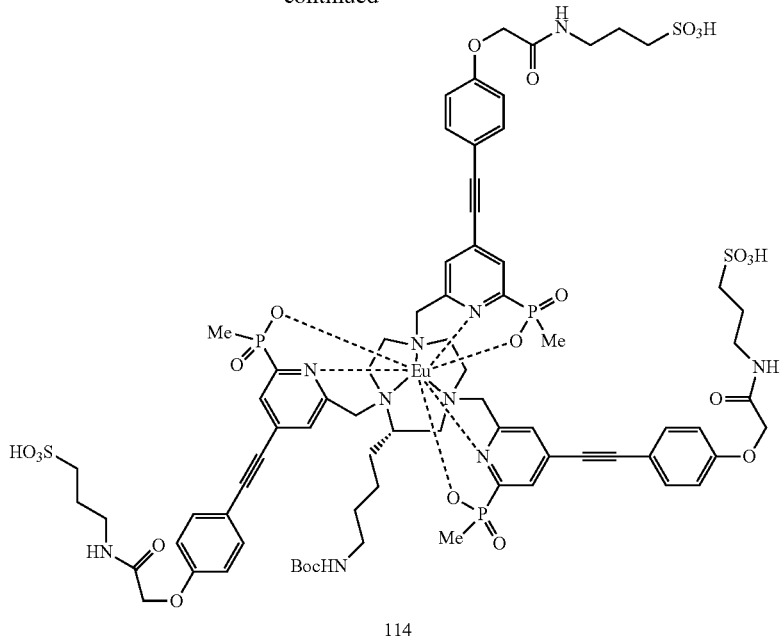

114

Homotaurine (4.0 mg, 28.8 µmol), (O-(7-azabenzotriazol-1-yl)-N,N,N',N'-tetramethyluronium hexafluorophosphate) (5.4 mg, 14.4 µmol) and diisopropylethylamine (9 µL, 48 µmol) were added successively to a solution of compound 113 (7.1 mg, 4.8 µmol) in anhydrous dimethylsulfoxide (1 mL). The mixture was stirred at room temperature for 1 h under inert atmosphere. The crude product was purified by preparative HPLC to give compound 114 in the form of a white solid (6.6 mg, 70%); HRMS (ESI+) calculated for $C_{75}H_{94}N_{10}O_{23}P_3S_3Eu$ $[M+2H]^{2+}$, m/z 922.2040 found: 922.2045.

Compound 115

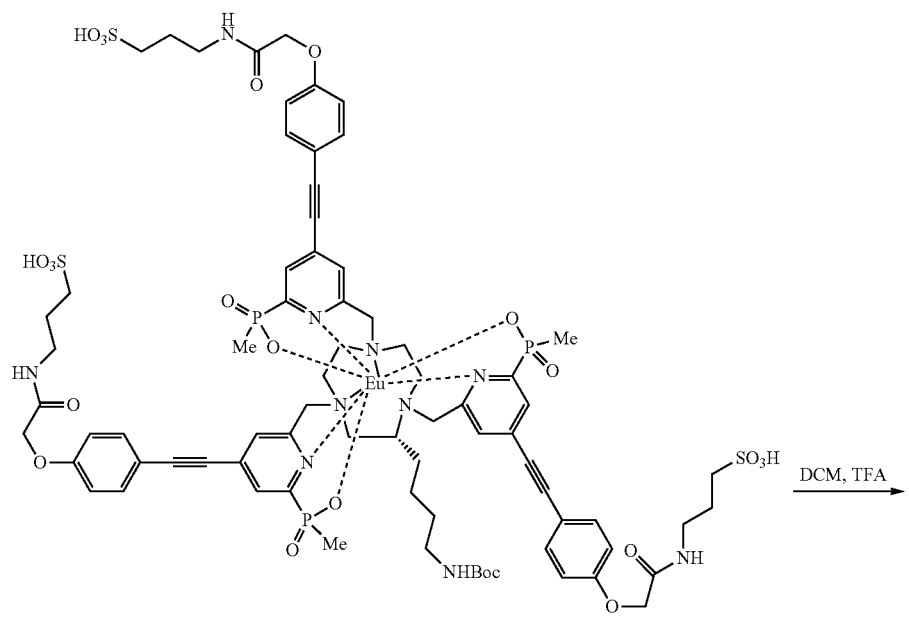

114

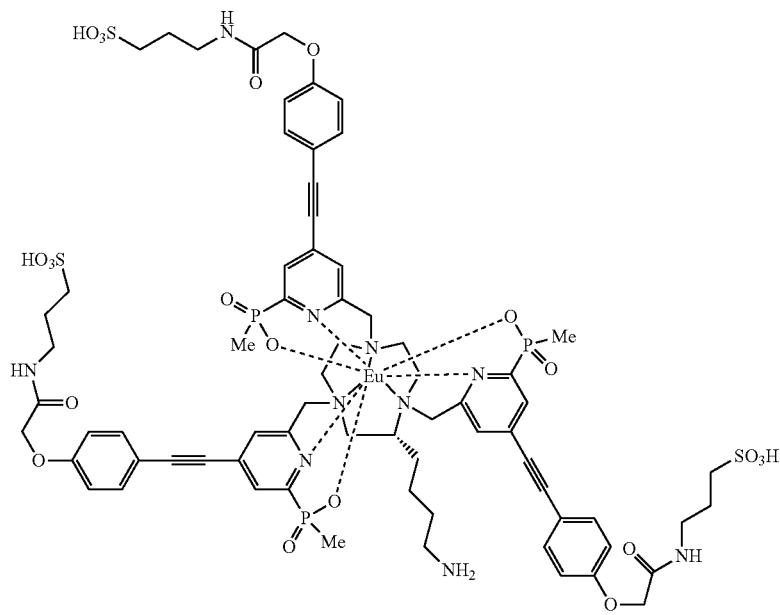

115

Trifluoroacetic acid (0.2 mL) was added to a solution of compound 114 (6.6 mg, 3.6 μmol) in dichloromethane (0.8 mL) cooled to 4° C. and previously degassed under an argon stream for 10 min. The solution is heated at room temperature and stirred at this temperature for 20 min. The solvent is removed under reduced pressure to give a yellow oil identified as compound 115 (6.4 mg, quantitative). $^1$H NMR (600 MHz, CDCl$_3$) δ: 7.91 (m, 3H), 7.51 (m, 9H), 6.92 (m, 6H), 4.67 (s, 6H), 4.16-3.97 (m, 12H), 3.81 (m, 9H), 3.12-2.90 (m, 13H), 1.89-1.75 (m, 9H), 1.45-1.32 (m, 6H), 1.29 (m, 9H); $^{31}$P NMR (242 MHz, CDCl$_3$) δ: +41.2; HRMS (ESI+) calculated for $C_{70}H_{86}EuN_{10}O_{21}P_3S_3$ [M+2H]$^{2+}$, m/z 872.1778. found: 872.1781.

Solubility and Spectroscopic Properties of the Compounds According to the Invention Log P is a measure of the differential solubility of chemical compounds in two solvents (octanol/water partition coefficient). Log P is equal to the logarithm of the ratio of the concentrations of the substance under investigation in octanol and in water. Log P=Log($C_{oct}/C_{water}$). This value ascertains the hydrophilic or hydrophobic (lipophilic) character of a molecule. In fact, if Log P is positive and very high, this expresses the fact that the molecule considered is far more soluble in octanol than in water, which reflects its lipophilic character, and vice versa. Zero or negative Log P signifies that the molecule is of a hydrophilic character. Scheme 26 shows some examples of structures of complexes for which log P is given in Table 2, as examples illustrating the good water-solubility of the compounds according to the invention.

Scheme 26: structures of the complexes in Table 2 (complexes 116-120 are not complexes according to the invention)
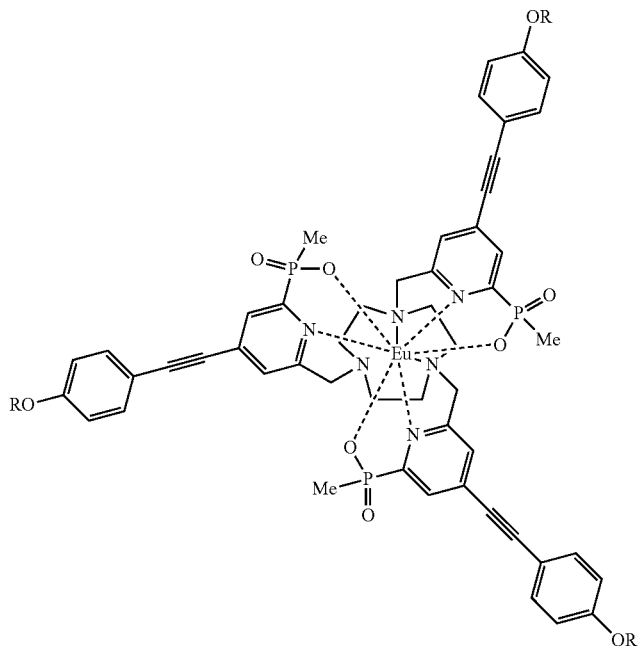
116, R = Me
46h, R = CH$_2$COO$^-$
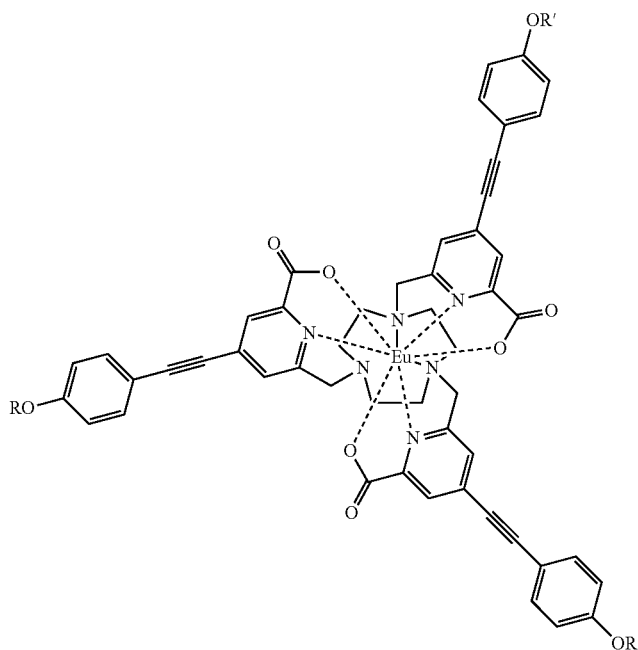
117, R = R' = (CH$_2$CH$_2$O)$_3$Me
51b, R = (CH$_2$)$_3$SO$_3^-$   R' = (CH$_2$)$_3$NH$_3^+$
118, R = (CH$_2$CH$_2$O)$_3$Me   R' = (CH$_2$)$_3$NH$_3^+$ -continued
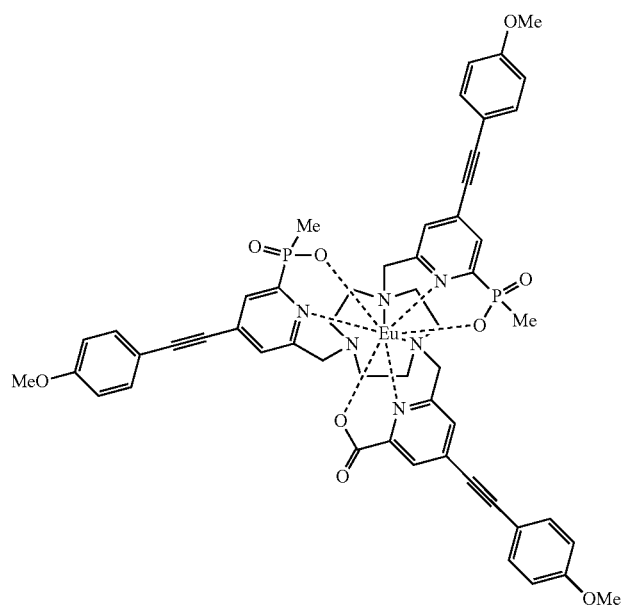
119
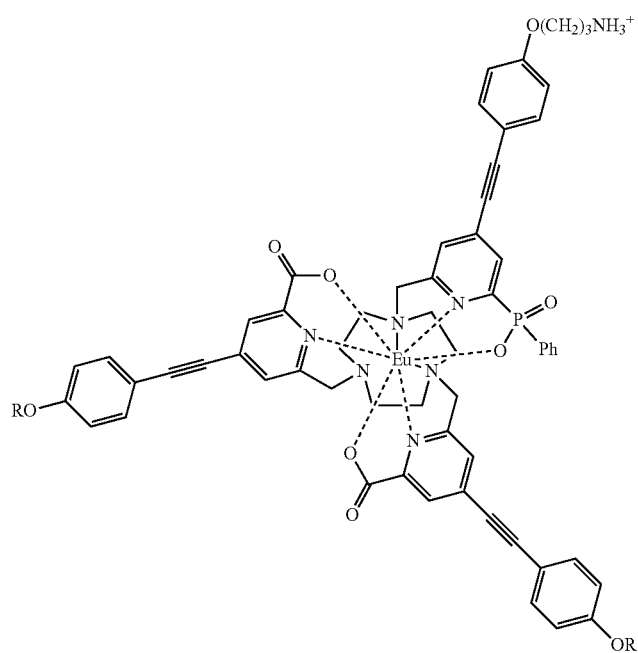
120, R = (CH₂CH₂O)₃Me -continued
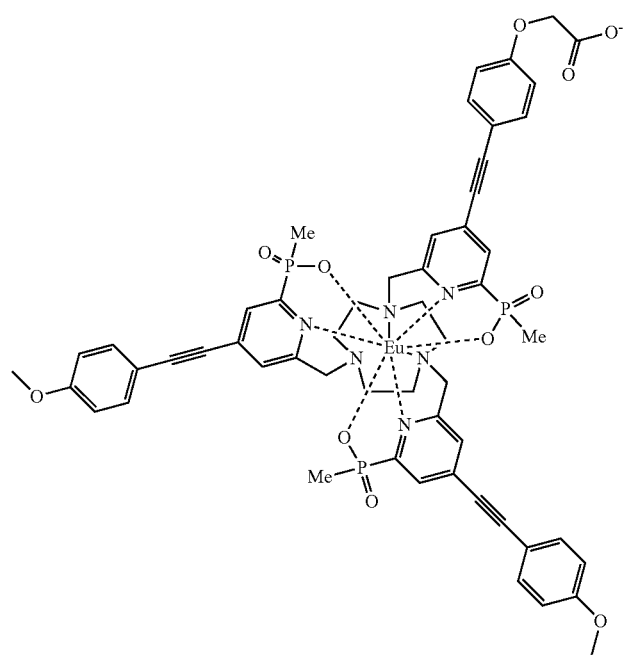
56e
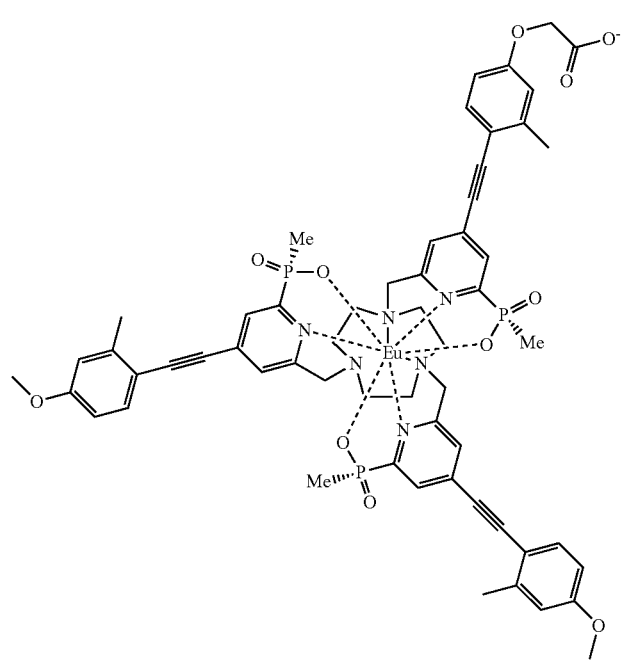
121

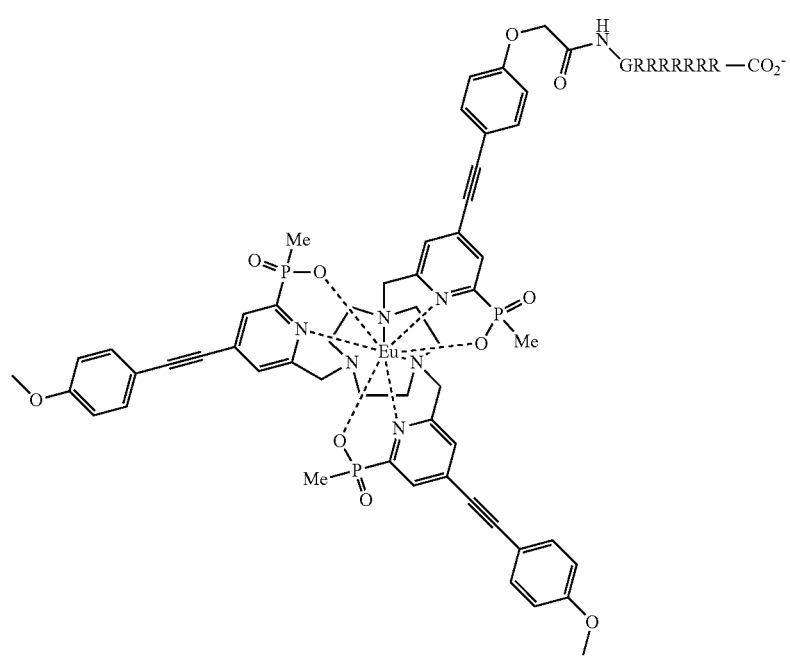

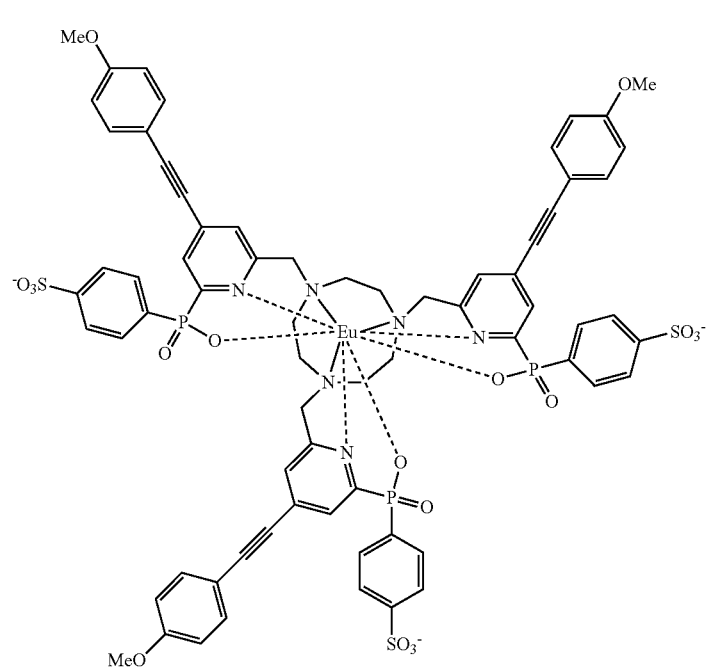

TABLE 2

| | Values of logP of the complexes in scheme 26 | | |
|---|---|---|---|
| Complexes | Complexing functions | Solubilizing function | LogP (±20%) |
| 116 | 3(Me—$PO_2^-$) | — | 1.4 |
| 117 | 3($CO_2^-$) | 3 $PEG_3$ | 1.1 |
| 118 | 3($CO_2^-$) | 2 $PEG_3$ | 0.7 |
| 119 | 1($CO_2^-$) 2(Me—$PO_2^-$) | — | 1.1 |
| 120 | 2($CO_2^-$) 1(Ph—$PO_2^-$) | 2 $PEG_3$ | 1.2 |
| 46h | 3(Me—$PO_2^-$) | 3 Carboxylates | −2.2 |

TABLE 2-continued

| | Values of logP of the complexes in scheme 26 | | |
|---|---|---|---|
| Complexes | Complexing functions | Solubilizing function | LogP (±20%) |
| 51b | 3($CO_2^-$) | 2 Sulfonates | −1.1 |
| 56e | 3(Me—$PO_2^-$) | 1 Carboxylate | 0.3 |
| 89 | 3(Me—$PO_2^-$) | Polyarginine | 0.3 |
| 105d | 3($SO_3^-$—Ph—$PO_2^-$) | 3 Sulfonates | −0.7 |
| 121 | 3(Me—$PO_2^-$) | 1 Carboxylate | 0.8 |

The complexes corresponding to structures 116-120 were described in international application WO 2013/011236. The values of Log P of the complexes according to the invention are either very close to 0 or negative, which reflects perfect solubility in aqueous buffers, in contrast to the compounds in application WO 2013/011236, some of which are also described in Chem Commun 2013, 49, 1600-1602.

Experimental Method for Determining Log P

Three equimolar solutions of europium complex were prepared in methanol. The solvent was removed under reduced pressure and the solid that remained was dissolved and stirred for 24 h in a water/octanol mixture (2:1, 1:1, 1:2), (0.9 mL) giving a total concentration of about 2 µM. After equilibration, an emission spectrum of each phase was recorded in methanol (50 µL of solution in 1 mL of methanol). For each mixture, the value of log P was calculated using the following equation:

$$\mathrm{Log}P = \mathrm{Log}\left(\frac{\int \Delta J = 2(oct)}{\int \Delta J = 2(H_2O)}\right)$$

Scheme 27: structures of the complexes in Table 3 that are not mentioned in scheme 26

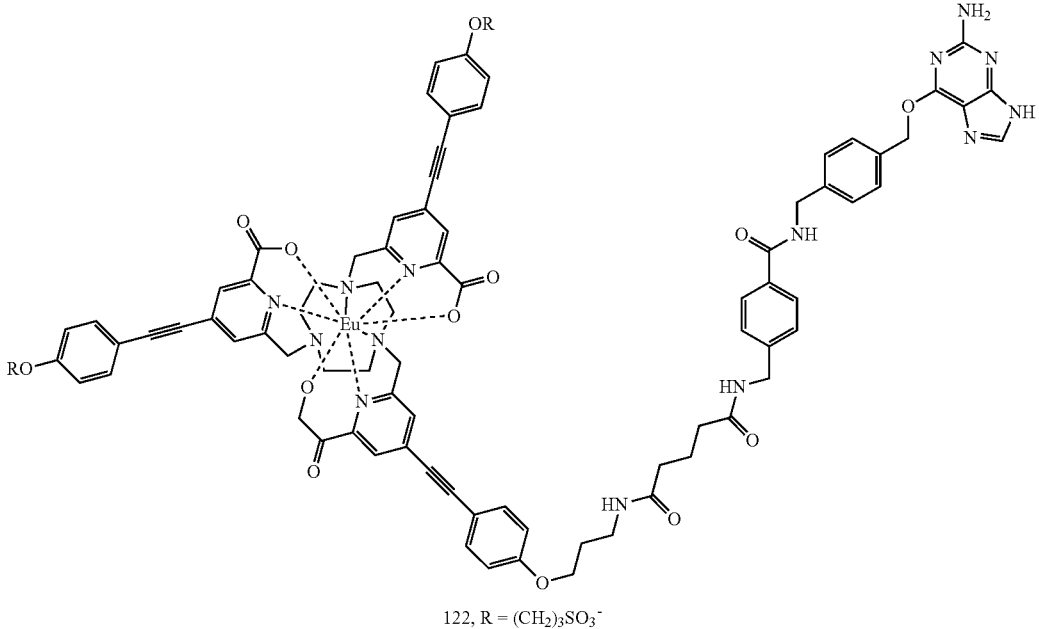

122, R = $(CH_2)_3SO_3^-$

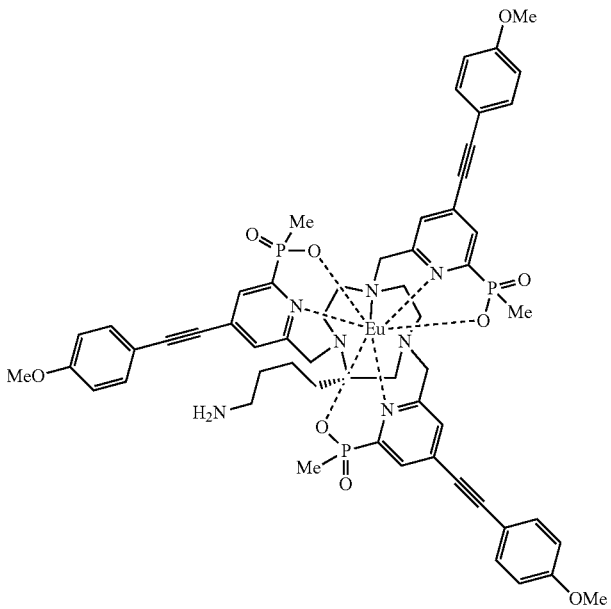

123

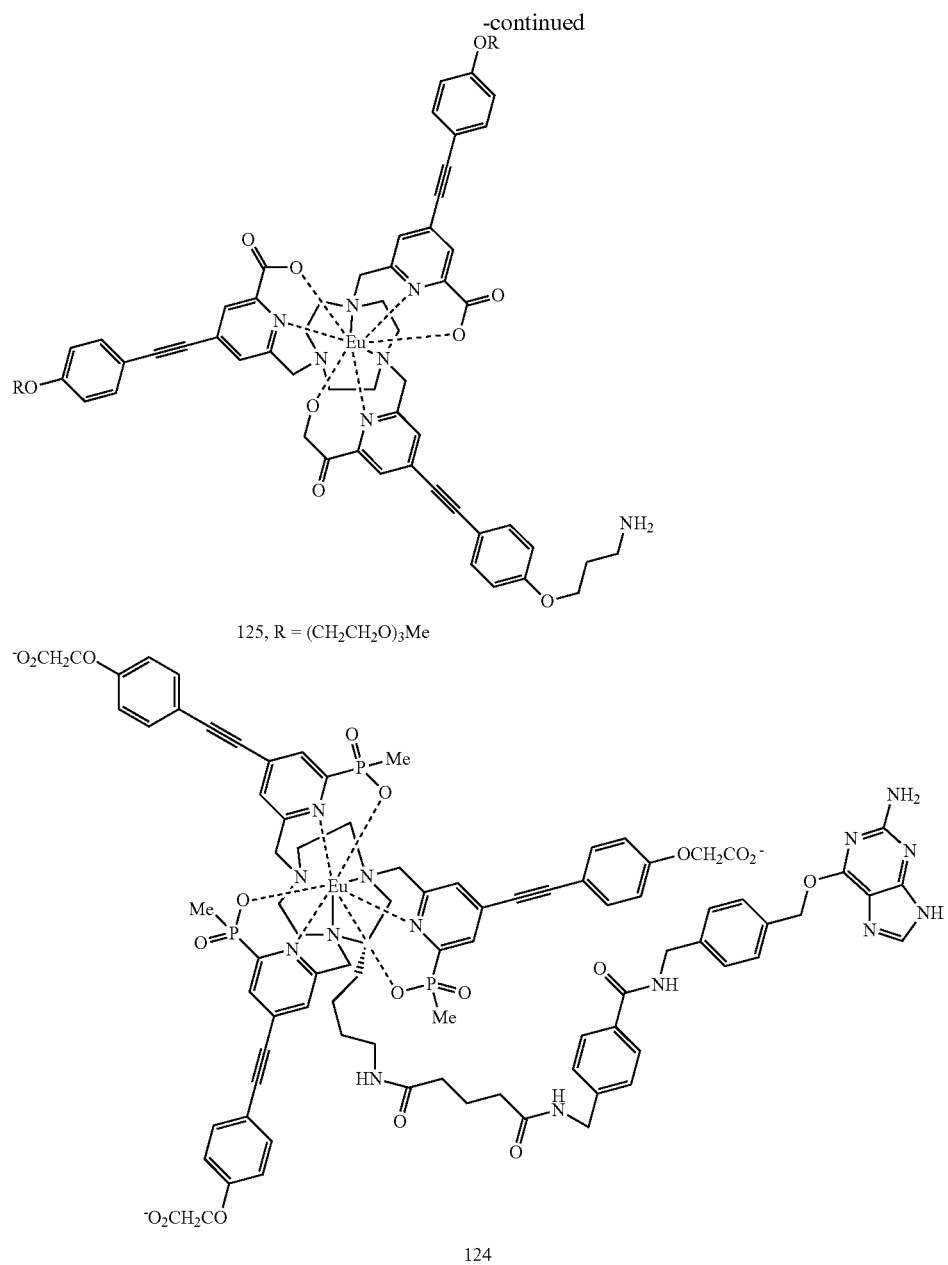
125, R = (CH₂CH₂O)₃Me
124
TABLE 3
Photophysical properties of various complexes
| Complex | λ max (nm) | Φ$_{em}$ (%) | τ$_0$ (ms) | Solvent |
|---|---|---|---|---|
| 46j | 328 | 50 | 1.07 | H₂O |
| 46h | 330 | 44 | 1.05 | H₂O |
| 51b | 339 | nd | 0.63 | Hepes buffer 50 mM, pH 7.4 |
| 56e | 330 | 49 | 1.04 | H₂O |
| 62i | 332 | 44 | 1.18 | MeOH |
| 62i | 328 | 28 | 1.05 | H₂O |
| 80 | 330 | nd | 0.96 | MeOH |
| 82 | 330 | nd | 0.98 | H₂O |
| 84 | 330 | nd | nd | H₂O |
| 86 | 330 | nd | nd | MeOH |
| 88 | 328 | 44 | 1.14 | MeOH |
| 89 | 330 | 50 | 1.12 | MeOH |
| 93 | 328 | 29 | 1.08 | H₂O |
| 105d | 332 | 31 | 1.11 | H₂O |
| 105d | 336 | 56 | 1.23 | MeOH |
| 112a | 341 | 15 | 0.69 | Hepes buffer 50 mM, pH 7.4 |
| 112a | 341 | nd | 0.78 | Hepes buffer 50 mM, pH 7.4 + 0.1% BSA |
| 115* | 329 | 16 | 1.00 | Hepes buffer 50 mM, pH 7.4 |
| 116* | 331 | 39 | 1.03 | H₂O |
| 116* | 331 | 43 | 1.18 | MeOH |
| 117* | 338 | 25 | 1.06 | MeOH |
| 121 | 342 | 55 | 1.15 | MeOH |
| 122 | 330 | nd | 0.97 | H₂O |

TABLE 3-continued

Photophysical properties of various complexes

| Complex | λ max (nm) | $\Phi_{em}$ (%) | $\tau_0$ (ms) | Solvent |
|---|---|---|---|---|
| 123 | 332 | 43 | 1.18 | MeOH |
| 124 | 328 | 14 | 1.08 | Hepes buffer 50 mM, pH 7.4 |
| 125 | 338 | nd | nd | MeOH | nd: not determined
*complexes 115, 116 and 117 are not complexes according to the invention The photophysical characteristics of some complexes are described in Table 3. All of these complexes possess the expected photophysical properties, namely a maximum absorption wavelength (λ max) between 328 and 342 nm, corresponding to nitrogen laser excitation (337 nm). The values of the quantum yields ($\Phi_{cm}$) must be considered to have a margin of error of ±15%. All these complexes have quantum yields above 10%, without adding potassium fluorides. The life-times ($\tau_0$) are at least 0.7 ms, which is favorable for FRET experiments. Finally, the complexes comprising solubilizer groups of the sulfonate or carboxylate type are highly soluble in aqueous biological buffers. The presence of charges makes complexes water-soluble that were not so initially. Unexpectedly, these charges or more broadly the solubilizing groups do not affect the photophysical properties of the europium complexes of the invention, which have a structure similar to those of complexes 115, 116 and 117 of the prior art.

The invention claimed is:

1. A complexing agent of formula (I'):

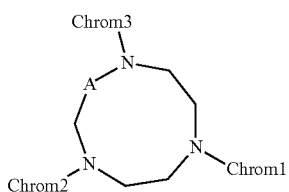

(I)

wherein:

A represents —CH$_2$— or —CH(L$_2$-G)- chrom1 and chrom2 are identical and represent a group of formula:

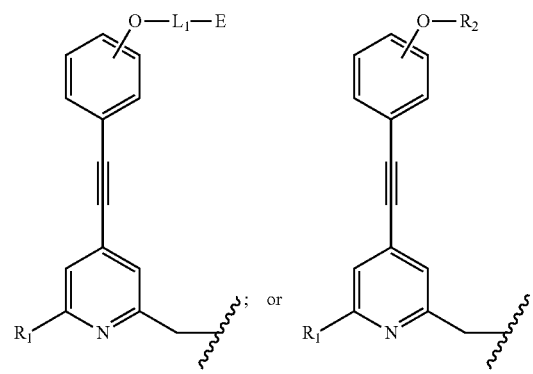

chrom3 is either identical to chrom1 and chrom2, or is a group of formula:

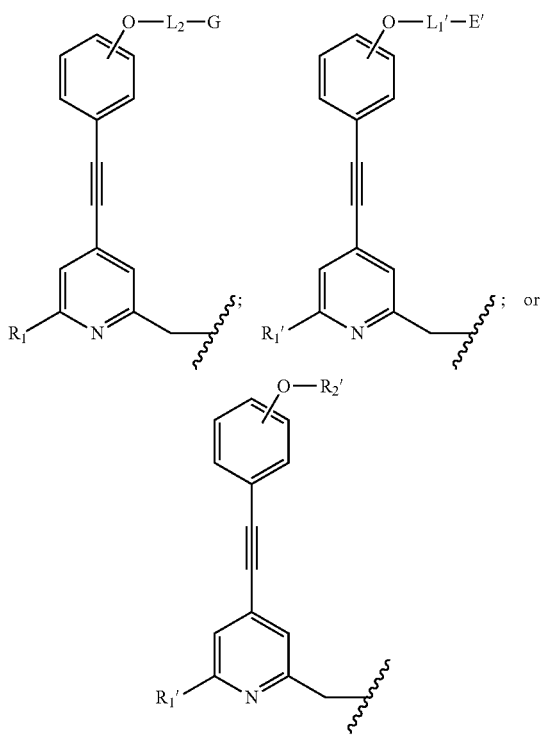

R$_2$ and R$_2$', which may be identical or different, are selected from the group consisting of: H; -Alk; -phenyl; —CH$_2$—CO—N-Alk; —CH$_2$—CO—O-Alk; —CH$_2$—CO—NH$_2$; and —CH$_2$—CO—OH;

L$_1$, L$_1$' and L$_2$ are each independently selected from the group consisting of: a covalent bond; a linear or branched C$_1$-C$_{20}$ alkylene group optionally containing one or more double or triple bonds, said alkylene group being optionally substituted with up to 3 —SO$_3$H groups; a C$_5$-C$_8$ cycloalkylene group; and a C$_6$-C$_{14}$ arylene group;

wherein the alkylene group optionally contains one or more heteroatoms selected from the group consisting of O and N, or optionally contains one or more carbamoyl groups or one or more carboxamide groups; and wherein the alkylene group, the cycloalkylene group or the arylene group is optionally substituted with one or more groups selected from the group consisting of a C$_1$-C$_8$ alkyl group, a C$_6$-C$_{14}$ aryl group, a sulfonate group and an oxo group;

E and E', which may be identical or different, are groups increasing the water-solubility of the complexing agent, selected from the group consisting of: —SO$_3$H, —PO(OH)$_2$, —COOH, —N$^+$Alk$_1$Alk$_2$Alk$_3$, and a carbohydrate residue of formula —(CHOH)$_k$—CH$_2$OH wherein k is an integer from 3 to 12;

R$_1$ and R$_1$', which may be identical or different, are selected from the group consisting of: —COOH, and —PO(OH)R$_6$, R$_6$ being selected from the group consisting of: phenyl, benzyl, methyl, ethyl, propyl, n-butyl, sec-butyl, isobutyl, and tert-butyl;

G is a reactive group selected from the group consisting of acrylamide, aldehyde, alkyl halide, anhydride, aniline, azide, aziridine, carboxylic acid, diazoalkane, haloacetamide, halotriazine, hydrazine, imido ester, isocyanate, isothiocyanate, maleimide, sulfonyl halide, thiol, ketone, amine, acid halide, succinimidyl ester, hydroxysuccinimidyl ester, hydroxysulfosuccinimidyl ester, azidonitrophenyl, azidophenyl, 3-(2-pyridyldithio)propionamide, glyoxal, triazine, and acetyl group;

Alk, Alk$_1$, Alk$_2$ and Alk$_3$, which may be identical or different, represent a (C$_1$-C$_6$)alkyl;

provided that:
when R$_1$ or R$_1$' represents a —COOH group, E or E' does not represent a —COOH group;
the complexing agent comprises at least one group E or —SO$_3$H;
when chrom1, chrom2 and chrom3 each comprise a group R$_2$ or R$_2$', A is a group —CH(L$_2$-G)- in which L$_2$ comprises at least one group —SO$_3$H.

2. The complexing agent as claimed in claim 1, wherein A is the group —CH$_2$— and chrom1, chrom2, chrom3 are identical and represent a group of formula:

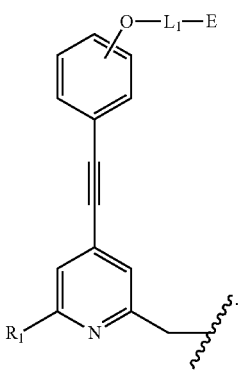

3. The complexing agent as claimed in claim 1, wherein A is the group —CH$_2$— and chrom3 is different from chrom1 and chrom2.

4. The complexing agent as claimed in claim 1, wherein A is the group —CH(L$_2$-G)- and chrom1, chrom2 and chrom3 are identical.

5. The complexing agent as claimed in claim 1, wherein A is the group —CH(L$_2$-G)- and chrom3 is different from chrom1 and chrom2.

6. The complexing agent as claimed in claim 1, wherein R$_1$ and R$_1$' represent a group —PO(OH)CH$_3$.

7. The complexing agent as claimed in claim 1, wherein E and E' when they are present, represent a group —SO$_3$H.

8. The complexing agent as claimed in claim 1, wherein R$_1$ and R$_1$' represent a group —PO(OH)R$_6$ and E and E' represent a group —SO$_3$H.

9. The complexing agent as claimed in claim 1, which comprises a group -L$_2$-G.

10. The complexing agent as claimed in claim 1, wherein L$_1$, L$_1$' and L$_2$ are each independently a group selected from the group consisting of:

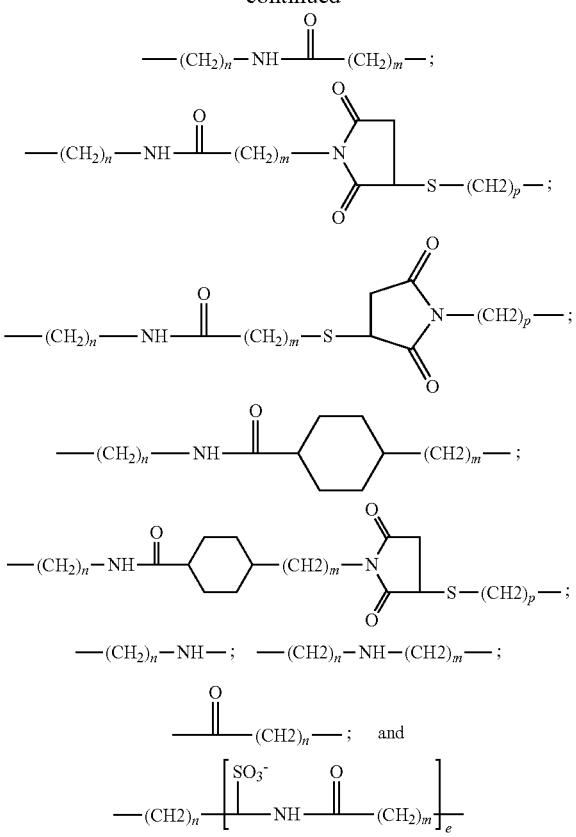

in which n, m, p, q are integers from 1 to 16, and e is an integer in the range from 1 to 6.

11. The complexing agent as claimed in claim 1, wherein when the reactive group G is present, the reactive group G is selected from the group consisting of:

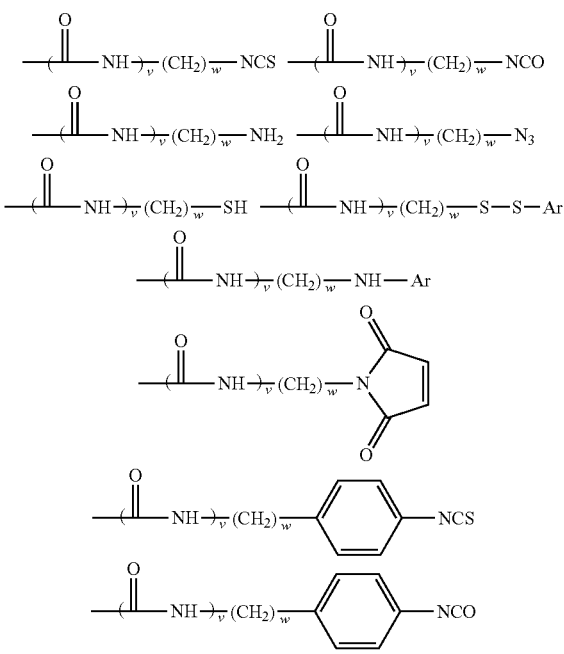

293

-continued

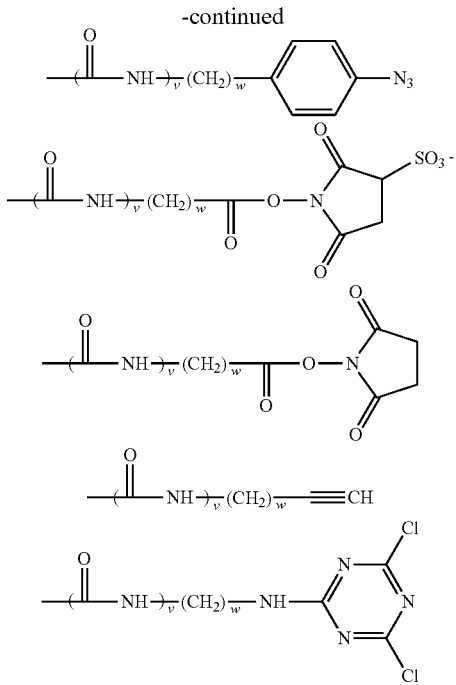

in which w varies from 0 to 8 and v is equal to 0 or 1, and Ar is a saturated or unsaturated heterocycle with 5 or 6 ring members, comprising 1 to 3 heteroatoms, optionally substituted with a halogen atom.

12. The complexing agent as claimed in claim 1, wherein the group -$L_2$-G consists of a reactive group G selected from the group consisting of: a carboxylic acid, an amine, a succinimidyl ester, a haloacetamide, a hydrazine, an isothiocyanate, a maleimide group, an aliphatic amine, and a spacer arm $L_2$ consisting of an alkylene chain comprising 1 to 5 carbon atoms or a group selected from the group consisting of:

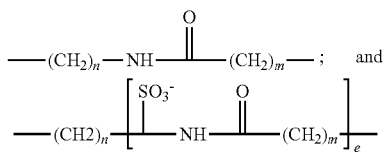

294 where n, m are integers from 1 to 16, and e is an integer in the range from 1 to 6, the group G being bound to one or other end of these divalent groups.

13. The complexing agent as claimed in claim 1, wherein $L_1$ or $L_1'$, when they are present, each independently represent an alkylene chain comprising 1 to 5 carbon atoms or a group selected from the group consisting of:

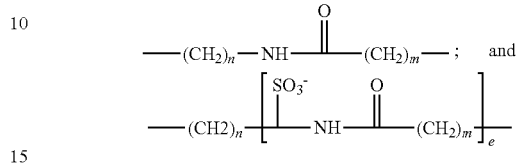

where n and m are integers from 1 to 16, and e is an integer in the range from 1 to 6, the group E or E' being bound to one or other end of these divalent groups.

14. A lanthanide complex comprising a complexing agent as claimed in claim 1 and a lanthanide.

15. The lanthanide complex as claimed in claim 14, wherein the lanthanide is selected from the group consisting of: $Eu^{3+}$, $Tb^{3+}$, $Gd^{3+}$, $Dy^{3+}$, $Nd^{3+}$, and $Er^{3+}$.

16. A conjugate between (i) a molecule of interest comprising a functional group, said molecule being selected from the group consisting of: an amino acid, a protein, a carbohydrate chain, a nucleoside, a nucleotide, an oligonucleotide, an enzyme substrate, a chloroalkane and coenzyme A, and (ii) a lanthanide complex as claimed in claim 14, wherein said lanthanide complex comprises a group -$L_2$-G, and wherein a covalent bond is formed between one or more atoms of group G and a functional group of the molecule of interest.

17. The complexing agent as claimed in claim 1, wherein A is the group —CH($L_2$-G)- and chrom1, chrom2 and chrom3 are identical.

18. The complexing agent as claimed in claim 1, wherein $R_1$ and $R_1'$ represent a group —PO(OH)$CH_3$.

19. The complexing agent as claimed in claim 1, wherein E and E' when they are present, represent a group —$SO_3H$.

20. The complexing agent as claimed in claim 1, wherein $R_1$ and $R_1'$ represent a group —PO(OH)$R_6$ and E and E' represent a group —$SO_3H$.

21. The complexing agent as claimed in claim 1, which comprises a group -$L_2$-G.

22. The conjugate as claimed in claim 16, wherein the molecule of interest is a peptide, an antibody, or a sugar.

\* \* \* \* \*